US012629002B2

(12) United States Patent
Roelle et al.

(10) Patent No.: US 12,629,002 B2
(45) Date of Patent: *May 19, 2026

(54) METHODS AND DEVICES FOR CONTROLLING A SHAPEABLE MEDICAL DEVICE

(71) Applicant: Auris Health, Inc., Redwood City, CA (US)

(72) Inventors: Matthew J. Roelle, Sunnyvale, CA (US); Neal A. Tanner, Burnet, TX (US); Robert G. Younge, Portola Valley, CA (US); Christopher R. Carlson, Menlo Park, CA (US); Federico Barbagli, San Francisco, CA (US); David Camarillo, Aptos, CA (US)

(73) Assignee: Auris Health, Inc., Santa Clara, CA (US)

( * ) Notice: Subject to any disclaimer, the term of this patent is extended or adjusted under 35 U.S.C. 154(b) by 124 days.

This patent is subject to a terminal disclaimer.

(21) Appl. No.: 18/521,817

(22) Filed: Nov. 28, 2023

(65) Prior Publication Data

US 2024/0099557 A1 Mar. 28, 2024

Related U.S. Application Data

(60) Continuation of application No. 17/340,641, filed on Jun. 7, 2021, now Pat. No. 11,857,156, which is a
(Continued)

(51) Int. Cl.
A61B 1/00 (2006.01)
A61B 1/005 (2006.01)
(Continued)

(52) U.S. Cl.
CPC ...... A61B 1/00042 (2022.02); A61B 1/00006 (2013.01); A61B 1/0016 (2013.01);
(Continued)

(58) Field of Classification Search
CPC ......... A61B 34/30; A61B 34/00; A61B 34/10; A61B 2034/301; A61M 25/0147
See application file for complete search history.

(56) References Cited

U.S. PATENT DOCUMENTS 4,745,908 A 5/1988 Wardle
5,273,025 A 12/1993 Sakiyam et al.
(Continued)

FOREIGN PATENT DOCUMENTS

CN 101147676 3/2008
CN 101222882 7/2008
(Continued)

OTHER PUBLICATIONS

Al-Ahmad, Amin, Jessica D. Grossman, and Paul J. Wang. "Early experience with a computerized robotically controlled catheter system." *Journal of Interventional Cardiac Electrophysiology* 12 (2005): 199-202.
(Continued)

*Primary Examiner* — Laura A Bouchelle
(74) *Attorney, Agent, or Firm* — FBT Gibbons LLP

(57) ABSTRACT

Systems and methods are described herein that improve control of a shapeable or steerable instrument using shape data. Additional methods include preparing a robotic medical system for use with a shapeable instrument and controlling advancement of a shapeable medical device within an anatomic path. Also described herein are methods for altering a data model of an anatomical region.

20 Claims, 70 Drawing Sheets

(a)          (b)          (c)

Related U.S. Application Data continuation of application No. 16/198,602, filed on Nov. 21, 2018, now Pat. No. 11,051,681, which is a division of application No. 14/164,961, filed on Jan. 27, 2014, now Pat. No. 10,143,360, which is a division of application No. 12/823,032, filed on Jun. 24, 2010, now Pat. No. 8,672,837.

(51) Int. Cl.

| | |
|---|---|
| *A61B 1/008* | (2006.01) |
| *A61B 34/20* | (2016.01) |
| *A61B 34/30* | (2016.01) |
| A61B 17/00 | (2006.01) |
| A61B 34/10 | (2016.01) |
| A61B 90/00 | (2016.01) |
| A61M 25/01 | (2006.01) |

(52) U.S. Cl.

CPC ............ *A61B 1/0051* (2013.01); *A61B 1/008* (2013.01); *A61B 1/009* (2022.02); *A61B 34/20* (2016.02); *A61B 34/30* (2016.02); *A61B 1/0011* (2013.01); *A61B 2017/00477* (2013.01); *A61B 2034/105* (2016.02); *A61B 2034/301* (2016.02); *A61B 2090/061* (2016.02); *A61M 25/0147* (2013.01)

(56) References Cited

U.S. PATENT DOCUMENTS

| | | | |
|---|---|---|---|
| 5,526,812 A | 6/1996 | Dumoulin et al. |
| 5,550,953 A | 8/1996 | Seraji |
| 5,831,614 A | 11/1998 | Tognazzini et al. |
| 5,935,075 A | 8/1999 | Casscells |
| 6,038,467 A | 3/2000 | De Bliek et al. |
| 6,047,080 A | 4/2000 | Chen |
| 6,059,718 A | 5/2000 | Taniguchi et al. |
| 6,063,095 A | 5/2000 | Wang et al. |
| 6,167,292 A | 12/2000 | Badano |
| 6,203,493 B1 | 3/2001 | Ben-Haim |
| 6,246,784 B1 | 6/2001 | Summers |
| 6,246,898 B1 | 6/2001 | Vesely |
| 6,332,089 B1 | 12/2001 | Acker |
| 6,425,865 B1 | 7/2002 | Salcudean et al. |
| 6,466,198 B1 | 10/2002 | Feinstein |
| 6,490,467 B1 | 12/2002 | Bucholz |
| 6,545,760 B1 | 4/2003 | Froggatt et al. |
| 6,553,251 B1 | 4/2003 | Landesmaki |
| 6,665,554 B1 | 12/2003 | Charles |
| 6,690,963 B2 | 2/2004 | Ben-Haim |
| 6,690,964 B2 | 2/2004 | Beiger et al. |
| 6,755,797 B1 | 6/2004 | Stouffer |
| 6,812,842 B2 | 11/2004 | Dimmer |
| 6,899,672 B2 | 5/2005 | Chin |
| 6,926,709 B2 | 8/2005 | Beiger et al. |
| 7,180,976 B2 | 2/2007 | Wink |
| 7,206,627 B2 | 4/2007 | Abovitz |
| 7,233,820 B2 | 6/2007 | Gilboa |
| 7,386,339 B2 | 6/2008 | Strommer et al. |
| 7,618,371 B2 | 11/2009 | Younge et al. |
| 7,697,972 B2 | 4/2010 | Verard |
| 7,756,563 B2 | 7/2010 | Higgins |
| 7,850,642 B2 | 12/2010 | Moll et al. |
| 7,901,348 B2 | 3/2011 | Soper |
| 7,935,059 B2 | 5/2011 | Younge et al. |
| 7,972,298 B2 | 7/2011 | Wallace et al. |
| 7,974,681 B2 | 7/2011 | Wallace et al. |
| 7,976,539 B2 | 7/2011 | Hlavka et al. |
| 8,021,326 B2 | 9/2011 | Moll et al. |
| 8,041,413 B2 | 10/2011 | Barbagli et al. |
| 8,050,523 B2 | 11/2011 | Younge et al. |
| 8,052,621 B2 | 11/2011 | Wallace et al. |
| 8,052,636 B2 | 11/2011 | Moll et al. |
| 8,092,397 B2 | 1/2012 | Wallace et al. |
| 8,155,403 B2 | 4/2012 | Tschirren |
| 8,190,238 B2 | 5/2012 | Moll et al. |
| 8,257,303 B2 | 9/2012 | Moll et al. |
| 8,285,364 B2 | 10/2012 | Barbagli et al. |
| 8,290,571 B2 | 10/2012 | Younge et al. |
| 8,298,135 B2 | 10/2012 | Ito et al. |
| 8,317,746 B2 | 11/2012 | Sewell et al. |
| 8,388,538 B2 | 3/2013 | Younge et al. |
| 8,388,556 B2 | 3/2013 | Wallace et al. |
| 8,391,957 B2 | 3/2013 | Carlson et al. |
| 8,394,054 B2 | 3/2013 | Wallace et al. |
| 8,409,136 B2 | 4/2013 | Wallace et al. |
| 8,409,172 B2 | 4/2013 | Moll et al. |
| 8,409,234 B2 | 4/2013 | Stahler et al. |
| 8,460,236 B2 | 6/2013 | Roelle et al. |
| 8,498,691 B2 | 7/2013 | Moll et al. |
| 8,515,215 B2 | 8/2013 | Younge et al. |
| 8,617,102 B2 | 12/2013 | Moll et al. |
| 8,672,837 B2 * | 3/2014 | Roelle .................... A61B 1/008 604/528 |
| 8,705,903 B2 | 4/2014 | Younge et al. |
| 8,801,661 B2 | 8/2014 | Moll et al. |
| 8,811,777 B2 | 8/2014 | Younge et al. |
| 8,818,143 B2 | 8/2014 | Younge et al. |
| 8,821,376 B2 | 9/2014 | Tolkowsky |
| 8,858,424 B2 | 10/2014 | Hasegawa |
| 8,864,655 B2 | 10/2014 | Ramamurthy et al. |
| 8,926,603 B2 | 1/2015 | Hlavka et al. |
| 8,929,631 B2 | 1/2015 | Pfister et al. |
| 8,974,408 B2 | 3/2015 | Wallace et al. |
| 9,014,851 B2 | 4/2015 | Wong et al. |
| 9,039,685 B2 | 5/2015 | Larkin et al. |
| 9,066,740 B2 | 6/2015 | Carlson et al. |
| 9,084,623 B2 | 7/2015 | Gomez et al. |
| 9,125,639 B2 | 9/2015 | Mathis |
| 9,138,129 B2 | 9/2015 | Diolaiti |
| 9,173,713 B2 | 11/2015 | Hart et al. |
| 9,183,354 B2 | 11/2015 | Baker et al. |
| 9,186,046 B2 | 11/2015 | Ramamurthy et al. |
| 9,186,047 B2 | 11/2015 | Ramamurthy et al. |
| 9,271,663 B2 | 3/2016 | Walker et al. |
| 9,272,416 B2 | 3/2016 | Hourtash et al. |
| 9,289,578 B2 | 3/2016 | Walker et al. |
| 9,404,734 B2 | 8/2016 | Ramamurthy et al. |
| 9,441,954 B2 | 9/2016 | Ramamurthy et al. |
| 9,457,168 B2 | 10/2016 | Moll et al. |
| 9,459,087 B2 | 10/2016 | Dunbar |
| 9,498,601 B2 | 11/2016 | Tanner et al. |
| 9,500,472 B2 | 11/2016 | Ramamurthy et al. |
| 9,500,473 B2 | 11/2016 | Ramamurthy et al. |
| 9,504,604 B2 | 11/2016 | Alvarez |
| 9,561,083 B2 | 2/2017 | Yu et al. |
| 9,603,668 B2 | 3/2017 | Weingarten et al. |
| 9,622,827 B2 | 4/2017 | Yu et al. |
| 9,629,595 B2 | 4/2017 | Walker et al. |
| 9,629,682 B2 | 4/2017 | Wallace et al. |
| 9,636,184 B2 | 5/2017 | Lee et al. |
| 9,710,921 B2 | 7/2017 | Wong et al. |
| 9,713,509 B2 | 7/2017 | Schuh et al. |
| 9,717,563 B2 | 8/2017 | Tognaccini |
| 9,726,476 B2 | 8/2017 | Ramamurthy et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |

(56) References Cited

U.S. PATENT DOCUMENTS

| | | | |
|---|---|---|---|
| 10,080,576 B2 | 9/2018 | Romo et al. |
| 10,123,755 B2 | 11/2018 | Walker et al. |
| 10,130,345 B2 | 11/2018 | Wong et al. |
| 10,136,950 B2 | 11/2018 | Schoenefeld |
| 10,136,959 B2 | 11/2018 | Mintz et al. |
| 10,143,360 B2 | 12/2018 | Roelle et al. |
| 10,143,526 B2 | 12/2018 | Walker et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,278,778 B2 | 5/2019 | State |
| 10,434,660 B2 | 10/2019 | Meyer |
| 10,464,209 B2 | 11/2019 | Ho et al. |
| 10,470,830 B2 | 11/2019 | Hill |
| 10,482,599 B2 | 11/2019 | Mintz et al. |
| 10,492,741 B2 | 12/2019 | Walker et al. |
| 10,517,692 B2 | 12/2019 | Eyre et al. |
| 10,524,866 B2 | 1/2020 | Srinivasan |
| 10,531,864 B2 | 1/2020 | Wong et al. |
| 10,539,478 B2 | 1/2020 | Lin |
| 10,555,778 B2 | 2/2020 | Ummalaneni et al. |
| 10,639,114 B2 | 5/2020 | Schuh |
| 10,667,875 B2 | 6/2020 | DeFonzo |
| 10,702,348 B2 | 7/2020 | Moll et al. |
| 10,743,751 B2 | 8/2020 | Landey et al. |
| 10,751,140 B2 | 8/2020 | Wallace et al. |
| 10,765,303 B2 | 9/2020 | Graetzel et al. |
| 10,765,487 B2 | 9/2020 | Ho |
| 10,820,954 B2 | 11/2020 | Marsot et al. |
| 10,835,153 B2 | 11/2020 | Rafii-Tari et al. |
| 10,850,013 B2 | 12/2020 | Hsu |
| 11,051,681 B2 | 7/2021 | Roelle et al. |
| 2001/0021843 A1 | 9/2001 | Bosselmann et al. |
| 2001/0039421 A1 | 11/2001 | Heilbrun |
| 2002/0065455 A1 | 5/2002 | Ben-Haim et al. |
| 2002/0077533 A1 | 6/2002 | Bieger et al. |
| 2002/0120188 A1 | 8/2002 | Brock et al. |
| 2003/0105603 A1 | 6/2003 | Hardesty |
| 2003/0125622 A1 | 7/2003 | Schweikard |
| 2003/0181809 A1 | 9/2003 | Hall et al. |
| 2003/0195664 A1 | 10/2003 | Nowlin et al. |
| 2004/0047044 A1 | 3/2004 | Dalton |
| 2004/0072066 A1 | 4/2004 | Cho et al. |
| 2004/0097806 A1 | 5/2004 | Hunter et al. |
| 2004/0186349 A1 | 9/2004 | Ewers |
| 2004/0249267 A1 | 12/2004 | Gilboa |
| 2004/0263535 A1 | 12/2004 | Birkenbach et al. |
| 2005/0027397 A1 | 2/2005 | Niemeyer |
| 2005/0060006 A1 | 3/2005 | Pflueger |
| 2005/0085714 A1 | 4/2005 | Foley et al. |
| 2005/0107679 A1 | 5/2005 | Geiger |
| 2005/0143649 A1 | 6/2005 | Minai et al. |
| 2005/0143655 A1 | 6/2005 | Satoh |
| 2005/0182295 A1 | 8/2005 | Soper et al. |
| 2005/0182319 A1 | 8/2005 | Glossop |
| 2005/0193451 A1 | 9/2005 | Quistgaard et al. |
| 2005/0197557 A1 | 9/2005 | Strommer et al. |
| 2005/0256398 A1 | 11/2005 | Hastings |
| 2005/0272975 A1 | 12/2005 | McWeeney et al. |
| 2006/0004286 A1 | 1/2006 | Chang |
| 2006/0013523 A1 | 1/2006 | Childers et al. |
| 2006/0015096 A1 | 1/2006 | Hauck et al. |
| 2006/0025668 A1 | 2/2006 | Peterson |
| 2006/0058643 A1 | 3/2006 | Florent |
| 2006/0084860 A1 | 4/2006 | Geiger |
| 2006/0095066 A1 | 5/2006 | Chang |
| 2006/0098851 A1 | 5/2006 | Shoham et al. |
| 2006/0100061 A1* | 5/2006 | Welter .................. B60W 10/04 477/167 |
| 2006/0100610 A1 | 5/2006 | Wallace et al. |
| 2006/0149134 A1 | 7/2006 | Soper et al. |
| 2006/0173290 A1 | 8/2006 | Lavallee et al. |
| 2006/0184016 A1 | 8/2006 | Glossop |
| 2006/0200026 A1 | 9/2006 | Wallace et al. |
| 2006/0209019 A1 | 9/2006 | Hu |
| 2006/0258935 A1 | 11/2006 | Pile-Spellman et al. |
| 2006/0258938 A1 | 11/2006 | Hoffman et al. |
| 2007/0013336 A1 | 1/2007 | Nowlin et al. |
| 2007/0032826 A1 | 2/2007 | Schwartz |
| 2007/0055128 A1 | 3/2007 | Glossop |
| 2007/0055144 A1 | 3/2007 | Neustadter |
| 2007/0073136 A1 | 3/2007 | Metzger |
| 2007/0083193 A1 | 4/2007 | Werneth |
| 2007/0123748 A1 | 5/2007 | Meglan |
| 2007/0135803 A1 | 6/2007 | Belson |
| 2007/0135886 A1 | 6/2007 | Maschke |
| 2007/0156019 A1 | 7/2007 | Larkin et al. |
| 2007/0161857 A1 | 7/2007 | Durant et al. |
| 2007/0167743 A1 | 7/2007 | Honda |
| 2007/0167801 A1 | 7/2007 | Webler et al. |
| 2007/0208252 A1 | 9/2007 | Makower |
| 2007/0253599 A1 | 11/2007 | White et al. |
| 2007/0265503 A1 | 11/2007 | Schlesinger et al. |
| 2007/0269001 A1 | 11/2007 | Maschke |
| 2007/0293721 A1 | 12/2007 | Gilboa |
| 2007/0299353 A1 | 12/2007 | Harley et al. |
| 2008/0027464 A1 | 1/2008 | Moll et al. |
| 2008/0071140 A1 | 3/2008 | Gattani |
| 2008/0079421 A1 | 4/2008 | Jensen |
| 2008/0082109 A1 | 4/2008 | Moll et al. |
| 2008/0103389 A1 | 5/2008 | Begelman et al. |
| 2008/0118118 A1 | 5/2008 | Berger |
| 2008/0118135 A1 | 5/2008 | Averbach |
| 2008/0123921 A1 | 5/2008 | Gielen et al. |
| 2008/0140087 A1 | 6/2008 | Barbagli et al. |
| 2008/0147089 A1 | 6/2008 | Loh |
| 2008/0161681 A1 | 7/2008 | Hauck |
| 2008/0183064 A1 | 7/2008 | Chandonnet |
| 2008/0183068 A1 | 7/2008 | Carls et al. |
| 2008/0183073 A1 | 7/2008 | Higgins et al. |
| 2008/0183188 A1 | 7/2008 | Carls et al. |
| 2008/0201016 A1 | 8/2008 | Finlay |
| 2008/0207997 A1 | 8/2008 | Higgins et al. |
| 2008/0212082 A1 | 9/2008 | Froggatt et al. |
| 2008/0218770 A1 | 9/2008 | Moll et al. |
| 2008/0221425 A1 | 9/2008 | Olson et al. |
| 2008/0243142 A1 | 10/2008 | Gildenberg |
| 2008/0255505 A1 | 10/2008 | Carlson et al. |
| 2008/0262297 A1 | 10/2008 | Gilboa |
| 2008/0275349 A1 | 11/2008 | Halperin |
| 2008/0275367 A1 | 11/2008 | Barbagli et al. |
| 2008/0287963 A1 | 11/2008 | Rogers et al. |
| 2008/0300478 A1 | 12/2008 | Zuhars et al. |
| 2008/0306490 A1 | 12/2008 | Lakin et al. |
| 2008/0312501 A1 | 12/2008 | Hasegawa et al. |
| 2009/0012533 A1 | 1/2009 | Barbagli et al. |
| 2009/0024141 A1 | 1/2009 | Stahler et al. |
| 2009/0030307 A1 | 1/2009 | Govari |
| 2009/0054729 A1 | 2/2009 | Mori |
| 2009/0076476 A1 | 3/2009 | Barbagli et al. |
| 2009/0137952 A1 | 5/2009 | Ramamurthy et al. |
| 2009/0138025 A1 | 5/2009 | Stahler et al. |
| 2009/0149867 A1 | 6/2009 | Glozman |
| 2009/0209817 A1 | 8/2009 | Averbuch |
| 2009/0227861 A1 | 9/2009 | Ganatra |
| 2009/0228020 A1 | 9/2009 | Wallace et al. |
| 2009/0248036 A1 | 10/2009 | Hoffman et al. |
| 2009/0259230 A1 | 10/2009 | Khadem |
| 2009/0262109 A1 | 10/2009 | Markowitz et al. |
| 2009/0292166 A1 | 11/2009 | Ito |
| 2009/0295797 A1 | 12/2009 | Sakaguchi |
| 2010/0008555 A1 | 1/2010 | Trumer |
| 2010/0030061 A1 | 2/2010 | Canfield |
| 2010/0039506 A1 | 2/2010 | Sarvestani et al. |
| 2010/0041949 A1 | 2/2010 | Tolkowsky |
| 2010/0054536 A1 | 3/2010 | Huang |
| 2010/0113852 A1 | 5/2010 | Sydora |
| 2010/0114115 A1 | 5/2010 | Schlesinger et al. |
| 2010/0121139 A1 | 5/2010 | OuYang |
| 2010/0160733 A1 | 6/2010 | Gilboa |
| 2010/0161022 A1 | 6/2010 | Tolkowsky |
| 2010/0161129 A1 | 6/2010 | Costa et al. |

(56)                    References Cited

U.S. PATENT DOCUMENTS

| | | |
|---|---|---|
| 2010/0225209 A1 | 9/2010 | Goldberg |
| 2010/0240989 A1 | 9/2010 | Stoianovici |
| 2010/0290530 A1 | 11/2010 | Huang et al. |
| 2010/0292565 A1 | 11/2010 | Meyer |
| 2010/0298641 A1 | 11/2010 | Tanaka |
| 2010/0328455 A1 | 12/2010 | Nam et al. |
| 2010/0331856 A1 | 12/2010 | Carlson et al. |
| 2011/0015648 A1 | 1/2011 | Alvarez et al. |
| 2011/0054303 A1 | 3/2011 | Barrick |
| 2011/0092808 A1 | 4/2011 | Shachar |
| 2011/0152880 A1 | 6/2011 | Alvarez et al. |
| 2011/0184238 A1 | 7/2011 | Higgins |
| 2011/0234780 A1 | 9/2011 | Ito |
| 2011/0238082 A1 | 9/2011 | Wenderow |
| 2011/0238083 A1 | 9/2011 | Moll et al. |
| 2011/0245665 A1 | 10/2011 | Nentwick |
| 2011/0248987 A1 | 10/2011 | Mitchell |
| 2011/0249016 A1 | 10/2011 | Zhang |
| 2011/0257480 A1 | 10/2011 | Takahashi |
| 2011/0270273 A1 | 11/2011 | Moll et al. |
| 2011/0276179 A1 | 11/2011 | Banks et al. |
| 2011/0295247 A1 | 12/2011 | Schlesinger et al. |
| 2011/0295248 A9 | 12/2011 | Wallace et al. |
| 2011/0295267 A1 | 12/2011 | Tanner et al. |
| 2011/0295268 A1 | 12/2011 | Roelle et al. |
| 2011/0319910 A1 | 12/2011 | Roelle et al. |
| 2012/0046521 A1 | 2/2012 | Hunter et al. |
| 2012/0056986 A1 | 3/2012 | Popovic |
| 2012/0059248 A1 | 3/2012 | Noising |
| 2012/0062714 A1 | 3/2012 | Liu |
| 2012/0065481 A1 | 3/2012 | Hunter |
| 2012/0069167 A1 | 3/2012 | Liu et al. |
| 2012/0071782 A1 | 3/2012 | Patil et al. |
| 2012/0082351 A1 | 4/2012 | Higgins |
| 2012/0116253 A1 | 5/2012 | Wallace et al. |
| 2012/0120305 A1 | 5/2012 | Takahashi |
| 2012/0165656 A1 | 6/2012 | Montag |
| 2012/0172712 A1 | 7/2012 | Bar-Tal |
| 2012/0191079 A1 | 7/2012 | Moll et al. |
| 2012/0209069 A1 | 8/2012 | Popovic |
| 2012/0209293 A1 | 8/2012 | Carlson |
| 2012/0215094 A1 | 8/2012 | Rahimian et al. |
| 2012/0219185 A1 | 8/2012 | Hu |
| 2012/0289777 A1 | 11/2012 | Chopra |
| 2012/0289783 A1 | 11/2012 | Duindam et al. |
| 2012/0302869 A1 | 11/2012 | Koyrakh |
| 2013/0060146 A1 | 3/2013 | Yang et al. |
| 2013/0085330 A1 | 4/2013 | Ramamurthy et al. |
| 2013/0085331 A1 | 4/2013 | Ramamurthy et al. |
| 2013/0085333 A1 | 4/2013 | Ramamurthy et al. |
| 2013/0090528 A1 | 4/2013 | Ramamurthy et al. |
| 2013/0090530 A1 | 4/2013 | Ramamurthy |
| 2013/0090552 A1 | 4/2013 | Ramamurthy et al. |
| 2013/0144116 A1 | 6/2013 | Cooper et al. |
| 2013/0165945 A9 | 6/2013 | Roelle |
| 2013/0190741 A1 | 7/2013 | Moll et al. |
| 2013/0204124 A1 | 8/2013 | Duindam |
| 2013/0225942 A1 | 8/2013 | Holsing |
| 2013/0243153 A1 | 9/2013 | Sra |
| 2013/0246334 A1 | 9/2013 | Ahuja |
| 2013/0259315 A1 | 10/2013 | Angot et al. |
| 2013/0303892 A1 | 11/2013 | Zhao |
| 2013/0345718 A1 | 12/2013 | Crawford |
| 2014/0058406 A1 | 2/2014 | Tsekos |
| 2014/0072192 A1 | 3/2014 | Reiner |
| 2014/0114180 A1 | 4/2014 | Jain |
| 2014/0142591 A1 | 5/2014 | Alvarez et al. |
| 2014/0148673 A1 | 5/2014 | Bogusky |
| 2014/0148808 A1 | 5/2014 | Inkpen et al. |
| 2014/0180063 A1 | 6/2014 | Zhao |
| 2014/0235943 A1 | 8/2014 | Paris |
| 2014/0243849 A1 | 8/2014 | Saglam |
| 2014/0257746 A1 | 9/2014 | Dunbar et al. |
| 2014/0261453 A1 | 9/2014 | Carlson |
| 2014/0264081 A1 | 9/2014 | Walker et al. |
| 2014/0275988 A1 | 9/2014 | Walker et al. |
| 2014/0276033 A1 | 9/2014 | Brannan |
| 2014/0276594 A1 | 9/2014 | Tanner et al. |
| 2014/0276937 A1 | 9/2014 | Wong et al. |
| 2014/0296655 A1 | 10/2014 | Akhbardeh et al. |
| 2014/0296657 A1 | 10/2014 | Izmirli |
| 2014/0309527 A1 | 10/2014 | Namati et al. |
| 2014/0309649 A1 | 10/2014 | Alvarez et al. |
| 2014/0343416 A1 | 11/2014 | Panescu |
| 2014/0350391 A1 | 11/2014 | Prisco et al. |
| 2014/0357984 A1 | 12/2014 | Wallace et al. |
| 2014/0364739 A1 | 12/2014 | Liu |
| 2014/0364870 A1 | 12/2014 | Alvarez et al. |
| 2015/0051482 A1 | 2/2015 | Liu et al. |
| 2015/0051592 A1 | 2/2015 | Kintz |
| 2015/0054929 A1 | 2/2015 | Ito et al. |
| 2015/0057498 A1 | 2/2015 | Akimoto |
| 2015/0073266 A1 | 3/2015 | Brannan |
| 2015/0119638 A1 | 4/2015 | Yu et al. |
| 2015/0133963 A1 | 5/2015 | Barbagli |
| 2015/0141808 A1 | 5/2015 | Elhawary |
| 2015/0141858 A1 | 5/2015 | Razavi |
| 2015/0142013 A1 | 5/2015 | Tanner et al. |
| 2015/0164594 A1 | 6/2015 | Romo et al. |
| 2015/0164596 A1 | 6/2015 | Romo |
| 2015/0223725 A1 | 8/2015 | Engel |
| 2015/0223765 A1 | 8/2015 | Chopra |
| 2015/0223897 A1 | 8/2015 | Kostrzewski et al. |
| 2015/0223902 A1 | 8/2015 | Walker et al. |
| 2015/0255782 A1 | 9/2015 | Kim et al. |
| 2015/0265087 A1 | 9/2015 | Park |
| 2015/0265359 A1 | 9/2015 | Camarillo |
| 2015/0265368 A1 | 9/2015 | Chopra |
| 2015/0275986 A1 | 10/2015 | Cooper |
| 2015/0287192 A1 | 10/2015 | Sasaki |
| 2015/0297133 A1 | 10/2015 | Jouanique-Dubuis et al. |
| 2015/0305650 A1 | 10/2015 | Hunter |
| 2015/0313503 A1 | 11/2015 | Seibel et al. |
| 2015/0335480 A1 | 11/2015 | Alvarez et al. |
| 2015/0374956 A1 | 12/2015 | Bogusky |
| 2016/0000302 A1 | 1/2016 | Brown |
| 2016/0000414 A1 | 1/2016 | Brown |
| 2016/0000520 A1 | 1/2016 | Lachmanovich |
| 2016/0001038 A1 | 1/2016 | Romo et al. |
| 2016/0008033 A1 | 1/2016 | Hawkins et al. |
| 2016/0067009 A1 | 3/2016 | Ramamurthy et al. |
| 2016/0111192 A1 | 4/2016 | Suzara |
| 2016/0128992 A1 | 5/2016 | Hudson |
| 2016/0183841 A1 | 6/2016 | Duindam et al. |
| 2016/0199134 A1 | 7/2016 | Brown et al. |
| 2016/0206389 A1 | 7/2016 | Miller |
| 2016/0213432 A1 | 7/2016 | Flexman |
| 2016/0228032 A1 | 8/2016 | Walker et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0314710 A1 | 10/2016 | Jarc |
| 2016/0331469 A1 | 11/2016 | Hall et al. |
| 2016/0360947 A1 | 12/2016 | Lida |
| 2016/0372743 A1 | 12/2016 | Cho et al. |
| 2016/0374541 A1 | 12/2016 | Agrawal et al. |
| 2017/0007337 A1 | 1/2017 | Dan |
| 2017/0023423 A1 | 1/2017 | Jackson |
| 2017/0055851 A1 | 3/2017 | Al-Ali |
| 2017/0079725 A1 | 3/2017 | Hoffman |
| 2017/0079726 A1 | 3/2017 | Hoffman |
| 2017/0086929 A1 | 3/2017 | Moll et al. |
| 2017/0100199 A1 | 4/2017 | Yu et al. |
| 2017/0119413 A1 | 5/2017 | Romo |
| 2017/0119481 A1 | 5/2017 | Romo et al. |
| 2017/0119484 A1 | 5/2017 | Tanner et al. |
| 2017/0165011 A1 | 6/2017 | Bovay et al. |
| 2017/0172673 A1 | 6/2017 | Yu et al. |
| 2017/0189118 A1 | 7/2017 | Chopra |
| 2017/0202627 A1 | 7/2017 | Sramek et al. |
| 2017/0209073 A1 | 7/2017 | Sramek et al. |
| 2017/0209224 A1 | 7/2017 | Walker et al. |
| 2017/0215808 A1 | 8/2017 | Shimol et al. |
| 2017/0215969 A1 | 8/2017 | Zhai et al. |

(56)　　References Cited

U.S. PATENT DOCUMENTS

| | | |
|---|---|---|
| 2017/0215978 A1 | 8/2017 | Wallace et al. |
| 2017/0238807 A9 | 8/2017 | Veritkov et al. |
| 2017/0258366 A1 | 9/2017 | Tupin |
| 2017/0290631 A1 | 10/2017 | Lee et al. |
| 2017/0296032 A1 | 10/2017 | Li |
| 2017/0296202 A1 | 10/2017 | Brown |
| 2017/0303941 A1 | 10/2017 | Eisner |
| 2017/0325896 A1 | 11/2017 | Donhowe |
| 2017/0333679 A1 | 11/2017 | Jiang |
| 2017/0340241 A1 | 11/2017 | Yamada |
| 2017/0340396 A1 | 11/2017 | Romo et al. |
| 2017/0348067 A1 | 12/2017 | Krimsky |
| 2017/0360508 A1 | 12/2017 | Germain et al. |
| 2017/0367782 A1 | 12/2017 | Schuh et al. |
| 2018/0025666 A1 | 1/2018 | Ho et al. |
| 2018/0055576 A1 | 3/2018 | Koyrakh |
| 2018/0055582 A1 | 3/2018 | Krimsky |
| 2018/0098690 A1 | 4/2018 | Iwaki |
| 2018/0177383 A1 | 6/2018 | Noonan et al. |
| 2018/0177556 A1 | 6/2018 | Noonan et al. |
| 2018/0214011 A1 | 8/2018 | Graetzel et al. |
| 2018/0217734 A1 | 8/2018 | Koenig et al. |
| 2018/0221038 A1 | 8/2018 | Noonan et al. |
| 2018/0221039 A1 | 8/2018 | Shah |
| 2018/0240237 A1 | 8/2018 | Donhowe et al. |
| 2018/0250083 A1 | 9/2018 | Schuh et al. |
| 2018/0263714 A1 | 9/2018 | Kostrzewski |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0286108 A1 | 10/2018 | Hirakawa |
| 2018/0289243 A1 | 10/2018 | Landey et al. |
| 2018/0289431 A1 | 10/2018 | Draper et al. |
| 2018/0308232 A1 | 10/2018 | Gliner |
| 2018/0308247 A1 | 10/2018 | Gupta |
| 2018/0325499 A1 | 11/2018 | Landey et al. |
| 2018/0333044 A1 | 11/2018 | Jenkins |
| 2018/0360435 A1 | 12/2018 | Romo |
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0046814 A1 | 2/2019 | Senden et al. |
| 2019/0066314 A1 | 2/2019 | Abhari |
| 2019/0086349 A1 | 3/2019 | Nelson |
| 2019/0110839 A1 | 4/2019 | Rafii-Tari et al. |
| 2019/0142519 A1 | 5/2019 | Siemionow et al. |
| 2019/0151148 A1 | 5/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0287673 A1 | 9/2019 | Michihata |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0078103 A1 | 3/2020 | Duindam |
| 2020/0085516 A1 | 3/2020 | DeFonzo |
| 2020/0093549 A1 | 3/2020 | Chin |
| 2020/0093554 A1 | 3/2020 | Schuh |
| 2020/0100845 A1 | 4/2020 | Julian |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0155084 A1 | 5/2020 | Walker |
| 2020/0170630 A1 | 6/2020 | Wong |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |
| 2020/0352420 A1 | 11/2020 | Graetzel |
| 2020/0360183 A1 | 11/2020 | Alvarez |
| 2020/0367726 A1 | 11/2020 | Landey et al. |
| 2020/0367981 A1 | 11/2020 | Ho et al. |
| 2020/0375678 A1 | 12/2020 | Wallace |
| 2020/0405317 A1 | 12/2020 | Wallace |
| 2020/0405411 A1 | 12/2020 | Draper et al. |
| 2020/0405419 A1 | 12/2020 | Mao |
| 2020/0405420 A1 | 12/2020 | Purohit |
| 2020/0405423 A1 | 12/2020 | Schuh |
| 2020/0405424 A1 | 12/2020 | Schuh |
| 2020/0405434 A1 | 12/2020 | Schuh |
| 2020/0406002 A1 | 12/2020 | Romo |
| 2021/0007819 A1 | 1/2021 | Schuh |
| 2021/0008341 A1 | 1/2021 | Landey et al. |
| 2021/0353129 A1 | 11/2021 | Roelle et al. |

FOREIGN PATENT DOCUMENTS

| | | |
|---|---|---|
| CN | 102316817 | 1/2012 |
| CN | 102458295 | 5/2012 |
| CN | 102946801 | 2/2013 |
| CN | 102973317 | 3/2013 |
| CN | 103705307 | 4/2014 |
| CN | 103735313 | 4/2014 |
| CN | 103813748 | 5/2014 |
| CN | 104758066 | 7/2015 |
| CN | 105559850 | 5/2016 |
| CN | 105559886 | 5/2016 |
| CN | 105611881 | 5/2016 |
| CN | 106455908 | 2/2017 |
| CN | 106821498 | 6/2017 |
| CN | 104931059 | 9/2018 |
| EP | 3025630 | 6/2016 |
| KR | 20140009359 | 1/2014 |
| KR | 101713676 | 3/2017 |
| RU | 2569699 C2 | 11/2015 |

(56)          References Cited

FOREIGN PATENT DOCUMENTS

| WO | WO 2005/087128 | 9/2005 |
| WO | WO 2006/051523 | 5/2006 |
| WO | WO 2006/099056 | 9/2006 |
| WO | WO 2009/097461 | 6/2007 |
| WO | WO 2013/116140 | 8/2013 |
| WO | WO 2014/058838 | 4/2014 |
| WO | WO 2015/089013 | 6/2015 |
| WO | WO 2016/077419 | 5/2016 |
| WO | WO 2016/203727 | 12/2016 |
| WO | WO 2017/030916 | 2/2017 |
| WO | WO 2017/036774 | 3/2017 |
| WO | WO 2017/048194 | 3/2017 |
| WO | WO 2017/066108 | 4/2017 |
| WO | WO 2017/146890 | 8/2017 |
| WO | WO 2017/167754 | 10/2017 |

OTHER PUBLICATIONS

Bell, Charreau S., et al. "Six DOF motion estimation for teleoperated flexible endoscopes using optical flow: A comparative study." *2014 IEEE International Conference on Robotics and Automation (ICRA)*. IEEE, 2014.
Ciuti, Gastone, et al. "Intra-operative monocular 3D reconstruction for image-guided navigation in active locomotion capsule endoscopy." *2012 4th IEEE Ras & EMBS International Conference on Biomedical Robotics and Biomechatronics (BioRob)*. IEEE, 2012.
Duncan, Roger. "Sensing Shape: Fiber-Bragg-grating sensor arrays monitor shape at a high resolution." *Spie's OE Magazine* (2005): 18-21.
Fallavollita, Pascal. "Acquiring multiview c-arm images to assist cardiac ablation procedures." *EURASIP Journal on Image and Video Processing* 2010 (2010): 1-10.
Froggatt, Mark, and Jason Moore. "High-spatial-resolution distributed strain measurement in optical fiber with Rayleigh scatter." *Applied optics* 37.10 (1998): 1735-1740.
Gutiérrez, Luis F., et al. "A practical global distortion correction method for an image intensifier based x-ray fluoroscopy system." *Medical physics* 35.3 (2008): 997-1007.
Haigron, Pascal, et al. "Depth-map-based scene analysis for active navigation in virtual angioscopy." *IEEE Transactions on Medical Imaging* 23.11 (2004): 1380-1390.
Hansen Medical, Inc. 2005, System Overview, product brochure, 2 pp., dated as available at http://hansenmedical.com/system.aspx on Jul. 14, 2006 (accessed Jun. 25, 2019, using the internet archive way back machine).
Hansen Medical, Inc. Bibliography, product brochure, 1 p., dated as available at http://hansenmedical.com/bibliography.aspx on Jul. 14, 2006 (accessed Jun. 25, 2019, using the internet archive way back machine).
Hansen Medical, Inc. dated 2007, Introducing the Sensei Robotic Catheter System, product brochure, 10 pages.
Hansen Medical, Inc. dated 2009, Sensei X Robotic Catheter System, product brochure, 5 pp.
Hansen Medical, Inc. Technology Advantages, product brochure, 1 p., dated as available at http://hansenmedical.com/advantages.aspx on Jul. 13, 2006 (accessed Jun. 25, 2019, using the internet archive way back machine).
http://www.sjmprofessional.com-Products-US-Mapping-and-Visualization-EnSite-Velocity.aspx.
Kiraly, Atilla P., et al. "Three-dimensional human airway segmentation methods for clinical virtual bronchoscopy." *Academic radiology* 9.10 (2002): 1153-1168.
Kiraly, Atilla P., et al. "Three-dimensional path planning for virtual bronchoscopy." *IEEE Transactions on Medical Imaging* 23.11 (2004): 1365-1379.
Konen, W., M. Scholz, and S. Tombrock. "The VN project: endoscopic image processing for neurosurgery." Computer Aided Surgery 3.3 (1998): 144-148.

Kumar, Atul, et al. "Stereoscopic visualization of laparoscope image using depth information from 3D model." *Computer methods and programs in biomedicine* 113.3 (2014): 862-868.
Livatino, Salvatore, et al. "Stereoscopic visualization and 3-D technologies in medical endoscopic teleoperation." *IEEE Transactions on Industrial Electronics* 62.1 (2014): 525-535.
Luó, Xióngbiāo, et al. "Modified hybrid bronchoscope tracking based on sequential monte carlo sampler: Dynamic phantom validation." *Computer Vision—ACCV 2010: 10th Asian Conference on Computer Vision, Queenstown, New Zealand, Nov. 8-12, 2010, Revised Selected Papers, Part III 10*. Springer Berlin Heidelberg, 2011.
Marrouche, Nassir F., et al. "Preliminary human experience using a novel robotic catheter remote control." *Heart Rhythm* 2.5 (2005): S63.
Mayo Clinic, Robotic Surgery, https://www.mayoclinic.org/tests-procedures/robotic-surgery/about/pac-20394974?p=1, downloaded from the internet on Jul. 12, 2018, 2 pages.
Mourgues, Fabien, Eve Coste-Maniere, and CHIR Team www.inria. fr/chir. "Flexible calibration of actuated stereoscopic endoscope for overlay in robot assisted surgery." *Medical Image Computing and Computer-Assisted Intervention—MICCAI 2002: 5th International Conference Tokyo, Japan, Sep. 25-28, 2002 Proceedings, Part I 5*. Springer Berlin Heidelberg, 2002.
Nadeem, Saad, and Arie Kaufman. "Depth reconstruction and computer-aided polyp detection in optical colonoscopy video frames." *arXiv preprint arXiv: 1609.01329* (2016).
Oh, Seil, et al. "Novel robotic catheter remote control system: Safety and accuracy in delivering RF lesions in all 4 cardiac chambers." *Heart Rhythm* 2.5 (2005): S277-S278.
Point Cloud, Sep. 10, 2010, Wikipedia, 2 pages.
Racadio, John M., et al. "Live 3D guidance in the interventional radiology suite." *American Journal of Roentgenology* 189.6 (2007): W357-W364.
Reddy, Vivek Y., et al. "Porcine pulmonary vein ablation using a novel robotic catheter control system and real-time integration of CT imaging with electroanatomical mapping." *Heart Rhythm* 2.5 (2005): S121.
Ren, Hongliang, et al. "Multisensor data fusion in an integrated tracking system for endoscopic surgery." *IEEE Transactions on Information Technology in Biomedicine* 16.1 (2011): 106-111.
Sato, Masaaki, Tomonori Murayama, and Jun Nakajima. "Techniques of stapler-based navigational thoracoscopic segmentectomy using virtual assisted lung mapping (VAL-MAP)." *Journal of thoracic disease* 8.Suppl 9 (2016): S716.
Shen, Mali, Stamatia Giannarou, and Guang-Zhong Yang. "Robust camera localisation with depth reconstruction for bronchoscopic navigation." *International journal of computer assisted radiology and surgery* 10 (2015): 801-813.
Shi, Chaoyang, et al. "Simultaneous catheter and environment modeling for trans-catheter aortic valve implantation." *2014 IEEE/RSJ International Conference on Intelligent Robots and Systems*. IEEE, 2014.
Slepian, dated 2010, Robotic Catheter Intervention: the Hansen Medical Sensei Robot Catheter System, PowerPoint presentation, 28 pages.
Solheim, Ole, et al. "Navigated resection of giant intracranial meningiomas based on intraoperative 3D ultrasound." *Acta neurochirurgica* 151 (2009): 1143-1151.
Solomon, Stephen B., et al. "Three-dimensional CT-guided bronchoscopy with a real-time electromagnetic position sensor: a comparison of two image registration methods." *Chest* 118.6 (2000): 1783-1787.
Song, Kai-Tai, and Chun-Ju Chen. "Autonomous and stable tracking of endoscope instrument tools with monocular camera." *2012 IEEE/ASME International Conference on Advanced Intelligent Mechatronics (AIM)*. IEEE, 2012.
Vemuri, Anant Suraj, et al. "Interoperative biopsy site relocalization in endoluminal surgery." *IEEE Transactions on Biomedical Engineering* 63.9 (2015): 1862-1873.
Verdaasdonk, R. M., et al. "Effect of microsecond pulse length and tip shape on explosive bubble formation of 2.78 μm Er,Cr;YSGG and 2.94 μm Er:YAG laser." *Proceedings of SPIE*, vol. 8221, 12.

(56)     References Cited

OTHER PUBLICATIONS

Wilson, Emmanuel, et al. "A buyer's guide to electromagnetic tracking systems for clinical applications." *Medical imaging 2008: visualization, image-guided procedures, and modeling.* vol. 6918. SPIE, 2008.

Yip, Michael C., et al. "Tissue tracking and registration for image-guided surgery." *IEEE transactions on medical imaging* 31.11 (2012): 2169-2182.

Zhou, Jin, et al. "Synthesis of stereoscopic views from monocular endoscopic videos." *2010 IEEE Computer Society Conference on Computer Vision and Pattern Recognition—Workshops.* IEEE, 2010.

Extended European Search Report dated Jul. 28, 2017, for Application No. 11799017.6.

* cited by examiner

Figure 3: Overview block diagram showing the basic existing catheter control topology.

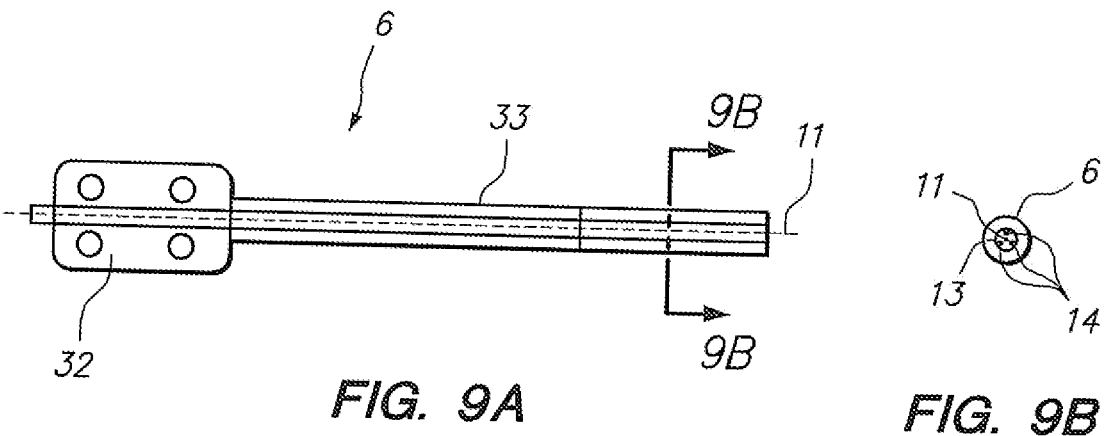
FIG. 9A
FIG. 9B
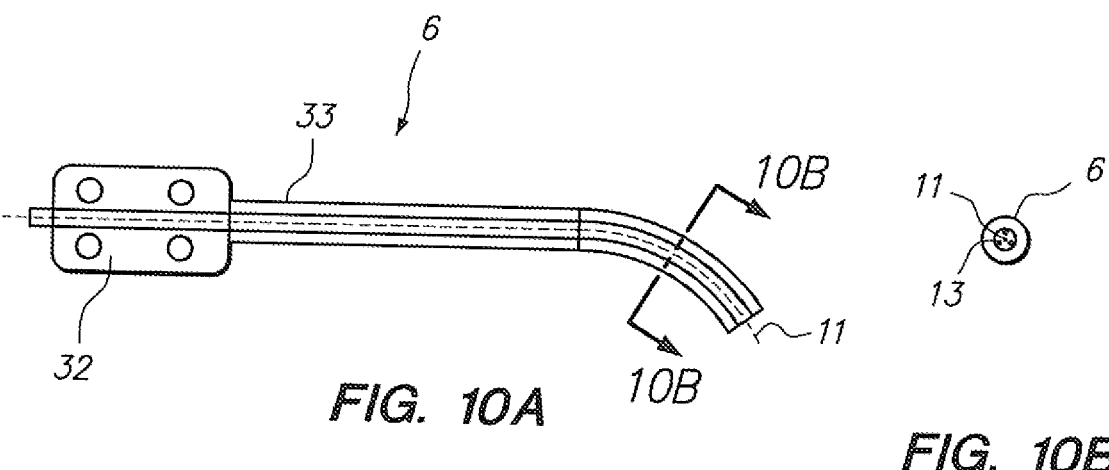
FIG. 10A
FIG. 10B
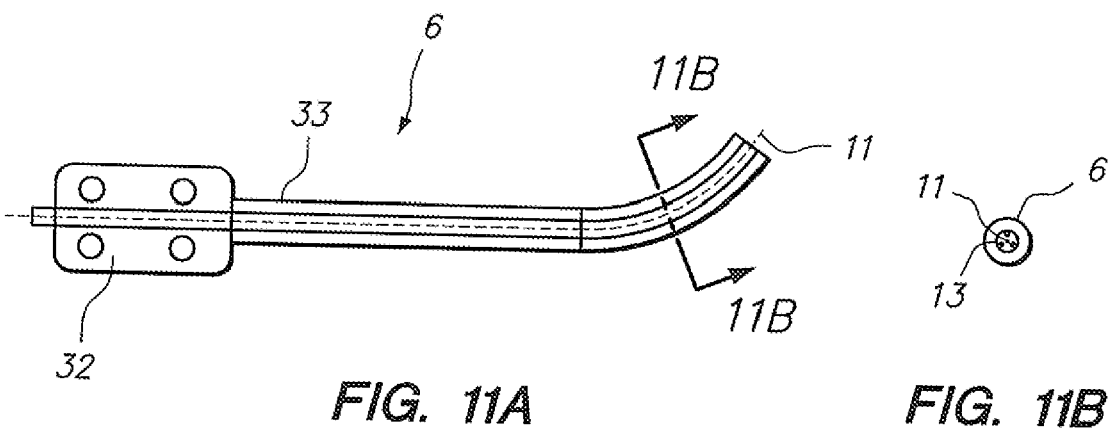
FIG. 11A
FIG. 11B

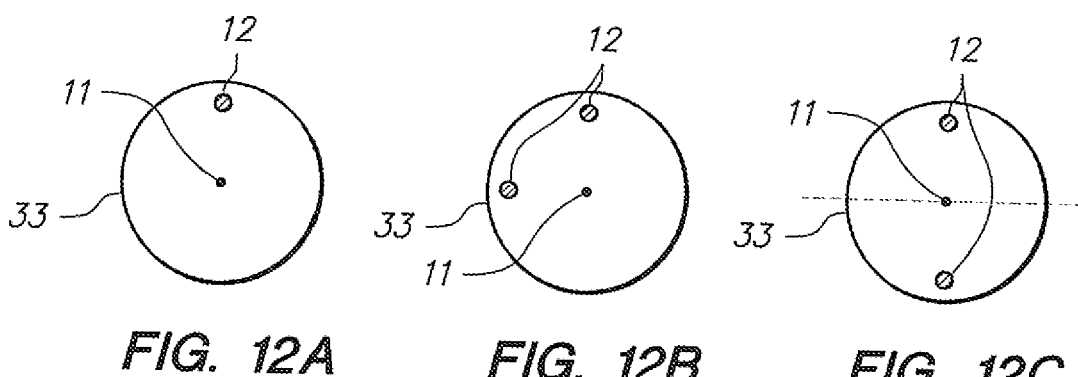
*FIG. 12A*          *FIG. 12B*          *FIG. 12C*
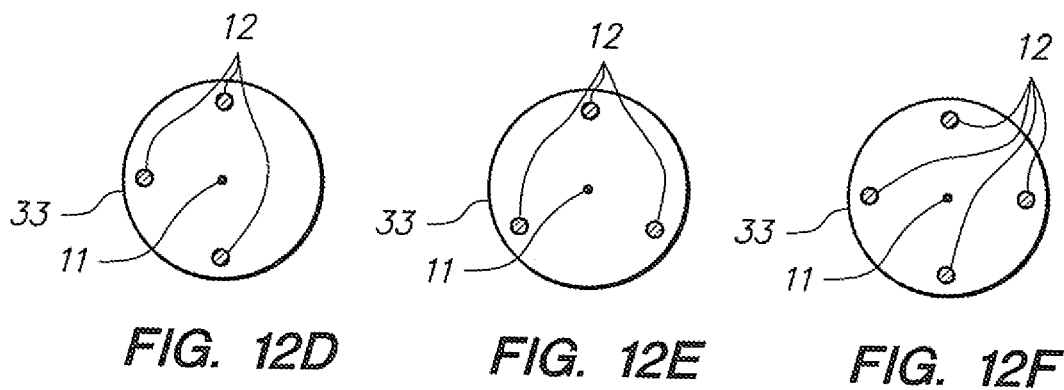
*FIG. 12D*          *FIG. 12E*          *FIG. 12F*
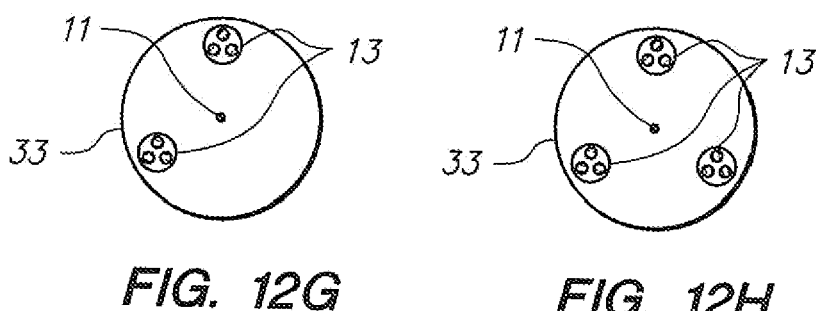
*FIG. 12G*          *FIG. 12H*

Figure 16D:
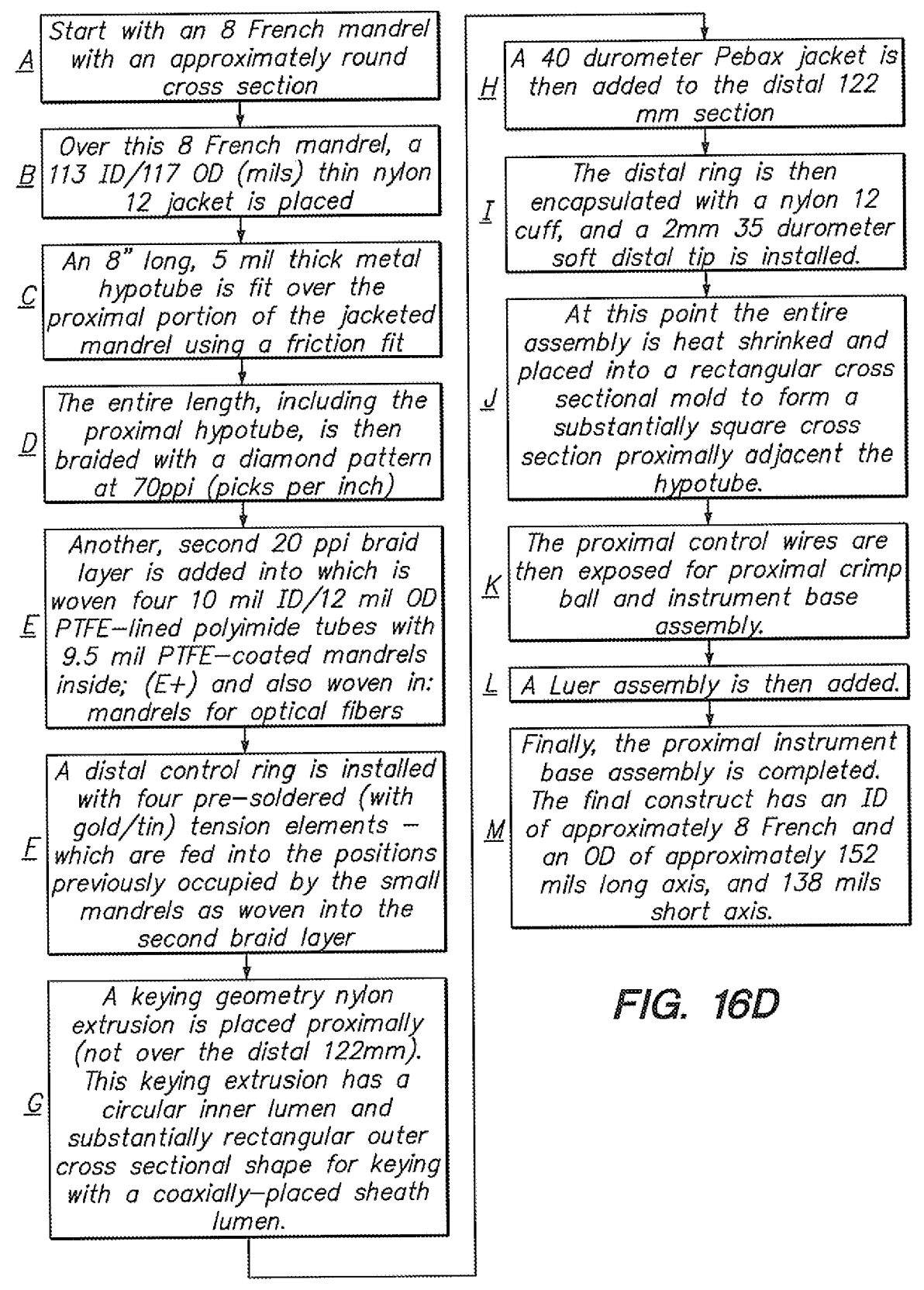

A | Start with an 8 French mandrel with an approximately round cross section

B | Over this 8 French mandrel, a 113 ID/117 OD (mils) thin nylon 12 jacket is placed C | An 8" long, 5 mil thick metal hypotube is fit over the proximal portion of the jacketed mandrel using a friction fit D | The entire length, including the proximal hypotube, is then braided with a diamond pattern at 70ppi (picks per inch)

E | Another, second 20 ppi braid layer is added into which is woven four 10 mil ID/12 mil OD PTFE-lined polyimide tubes with 9.5 mil PTFE-coated mandrels inside; (E+) and also woven in: mandrels for optical fibers F | A distal control ring is installed with four pre-soldered (with gold/tin) tension elements — which are fed into the positions previously occupied by the small mandrels as woven into the second braid layer G | A keying geometry nylon extrusion is placed proximally (not over the distal 122mm). This keying extrusion has a circular inner lumen and substantially rectangular outer cross sectional shape for keying with a coaxially-placed sheath lumen.

H | A 40 durometer Pebax jacket is then added to the distal 122 mm section

I | The distal ring is then encapsulated with a nylon 12 cuff, and a 2mm 35 durometer soft distal tip is installed.

J | At this point the entire assembly is heat shrinked and placed into a rectangular cross sectional mold to form a substantially square cross section proximally adjacent the hypotube.

K | The proximal control wires are then exposed for proximal crimp ball and instrument base assembly.

L | A Luer assembly is then added.

M | Finally, the proximal instrument base assembly is completed. The final construct has an ID of approximately 8 French and an OD of approximately 152 mils long axis, and 138 mils short axis.

Figure 17G-1:
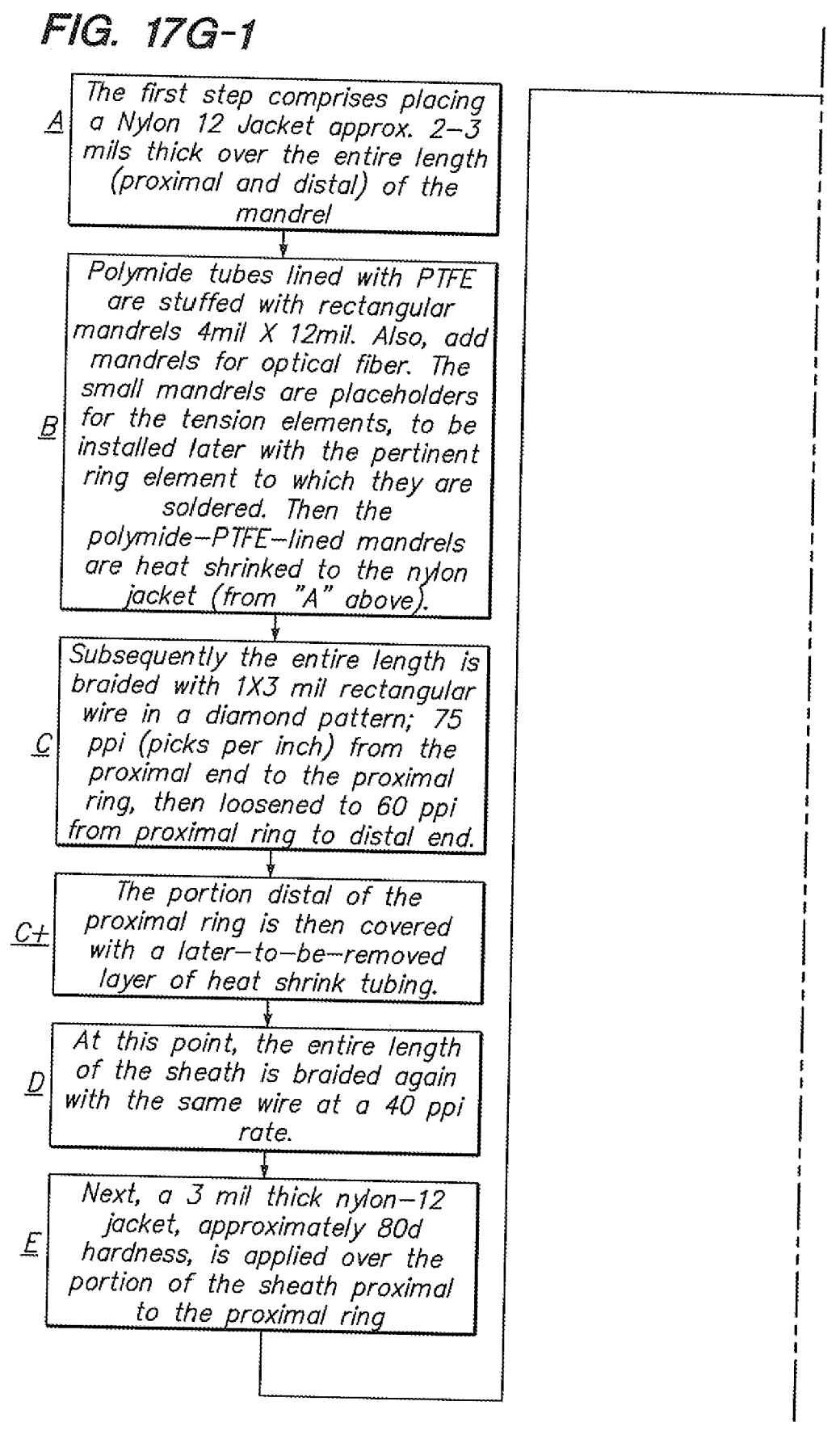

A | The first step comprises placing a Nylon 12 Jacket approx. 2-3 mils thick over the entire length (proximal and distal) of the mandrel B | Polymide tubes lined with PTFE are stuffed with rectangular mandrels 4mil X 12mil. Also, add mandrels for optical fiber. The small mandrels are placeholders for the tension elements, to be installed later with the pertinent ring element to which they are soldered. Then the polymide—PTFE—lined mandrels are heat shrinked to the nylon jacket (from "A" above).

C | Subsequently the entire length is braided with 1X3 mil rectangular wire in a diamond pattern; 75 ppi (picks per inch) from the proximal end to the proximal ring, then loosened to 60 ppi from proximal ring to distal end.

C+ | The portion distal of the proximal ring is then covered with a later—to—be—removed layer of heat shrink tubing.

D | At this point, the entire length of the sheath is braided again with the same wire at a 40 ppi rate.

E | Next, a 3 mil thick nylon—12 jacket, approximately 80d hardness, is applied over the portion of the sheath proximal to the proximal ring

FIG. 17G-2

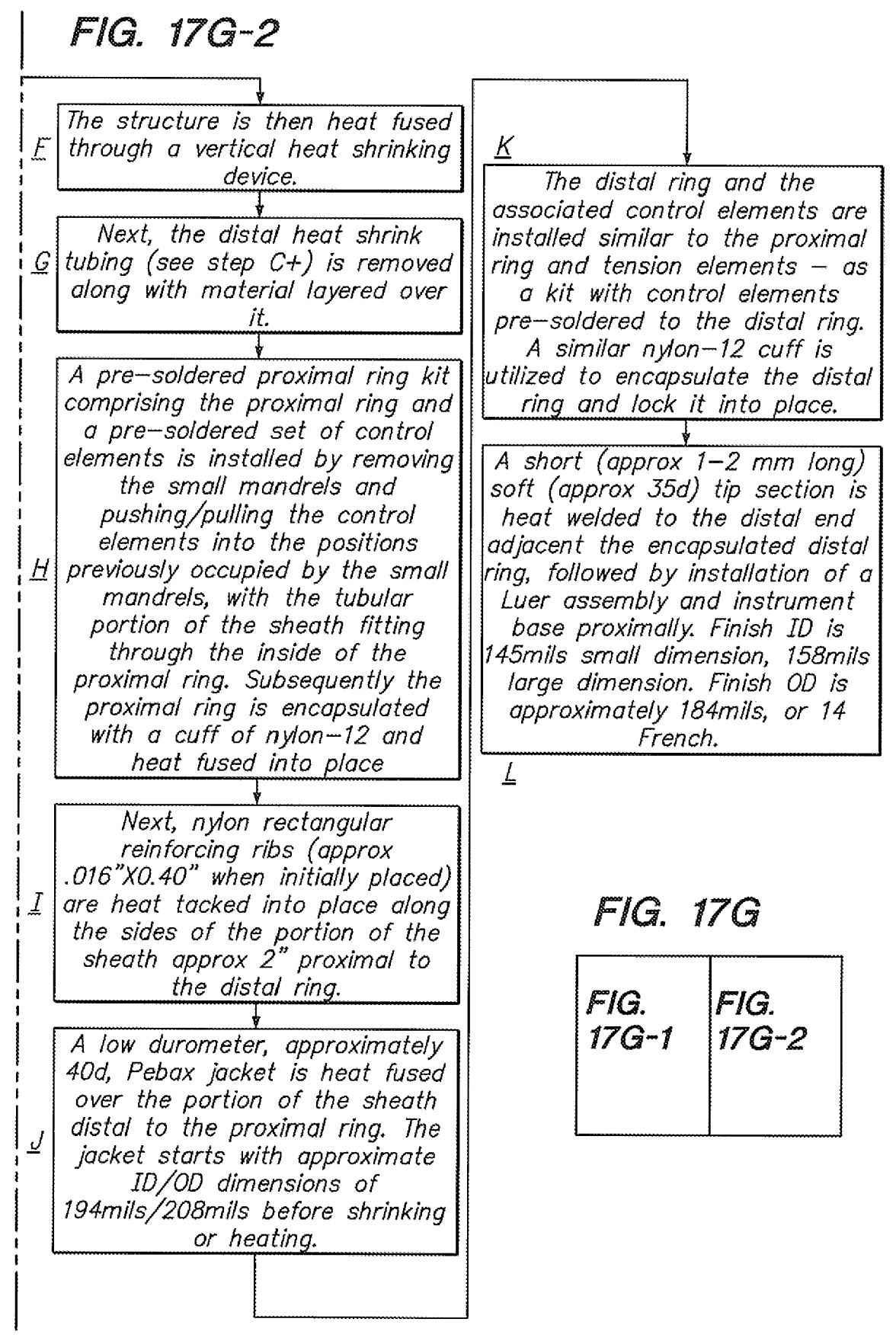

E | The structure is then heat fused through a vertical heat shrinking device.

G | Next, the distal heat shrink tubing (see step C+) is removed along with material layered over it.

H | A pre-soldered proximal ring kit comprising the proximal ring and a pre-soldered set of control elements is installed by removing the small mandrels and pushing/pulling the control elements into the positions previously occupied by the small mandrels, with the tubular portion of the sheath fitting through the inside of the proximal ring. Subsequently the proximal ring is encapsulated with a cuff of nylon-12 and heat fused into place

I | Next, nylon rectangular reinforcing ribs (approx .016"X0.40" when initially placed) are heat tacked into place along the sides of the portion of the sheath approx 2" proximal to the distal ring.

J | A low durometer, approximately 40d, Pebax jacket is heat fused over the portion of the sheath distal to the proximal ring. The jacket starts with approximate ID/OD dimensions of 194mils/208mils before shrinking or heating.

K | The distal ring and the associated control elements are installed similar to the proximal ring and tension elements — as a kit with control elements pre-soldered to the distal ring. A similar nylon-12 cuff is utilized to encapsulate the distal ring and lock it into place.

L | A short (approx 1-2 mm long) soft (approx 35d) tip section is heat welded to the distal end adjacent the encapsulated distal ring, followed by installation of a Luer assembly and instrument base proximally. Finish ID is 145mils small dimension, 158mils large dimension. Finish OD is approximately 184mils, or 14 French.

FIG. 17G

| FIG. 17G-1 | FIG. 17G-2 |
|---|---|

90

308

310

312

314

Forward Kinematics:
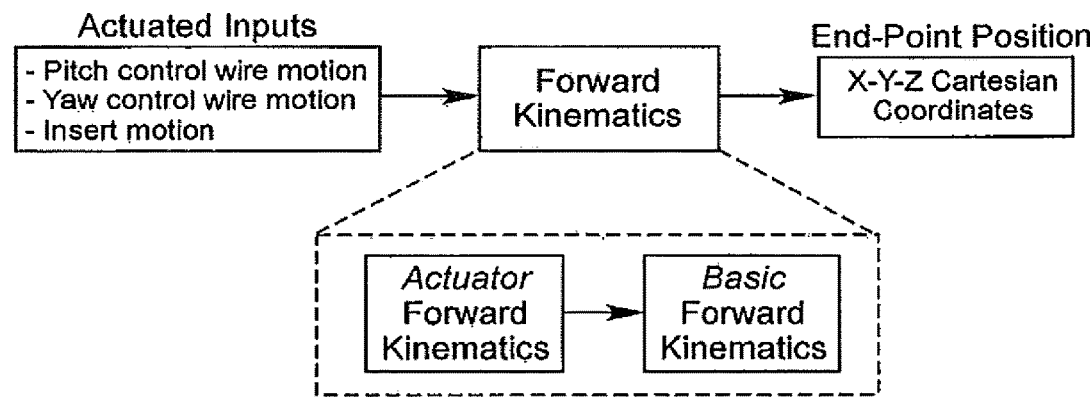
Inverse Kinematics:
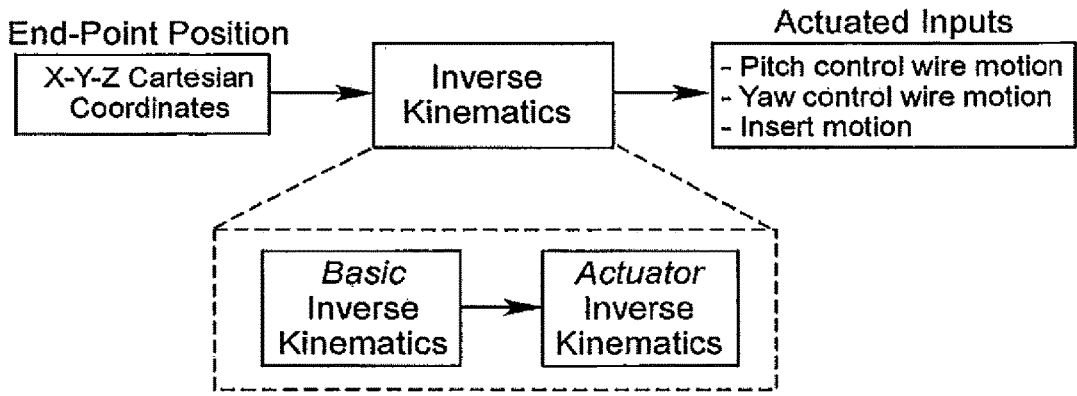
*FIG. 48*

| Information Needed → / To Estimate ↓ | Shape | Tissue Contact | Tip position | Tip orientation | Device model | Base orientation | Base position | Distal Force | 3D environment model | Wire tension |
|---|---|---|---|---|---|---|---|---|---|---|
| Shape | | | X | X | X | X | X | | | |
| Tissue Contact | | | X | | | | | o¹ | X | |
| Tip position | X | | | | | X | X | | | |
| Tip orientation | X | | | | | X | | | | |
| Device model | X | X | | | | | | | | |
| Base orientation | X | | | X | | | | | | |
| Base position | X | | X | X | | | | | | |
| Distal Force | X | X | | | X | | | | | |
| 3D environment model | | X | | | | | | | X | |
| Wire tension | X | | | | X | | | | | |

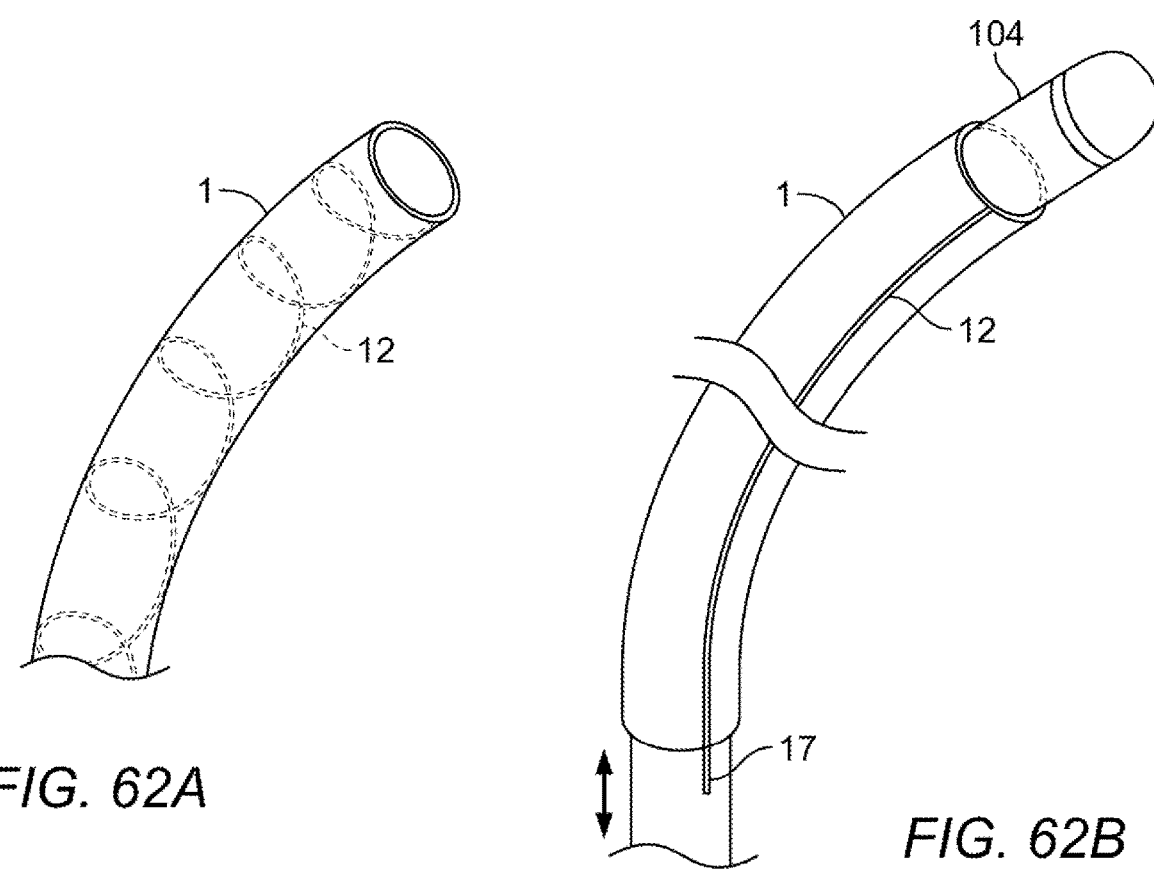
*FIG. 62A*
*FIG. 62B*
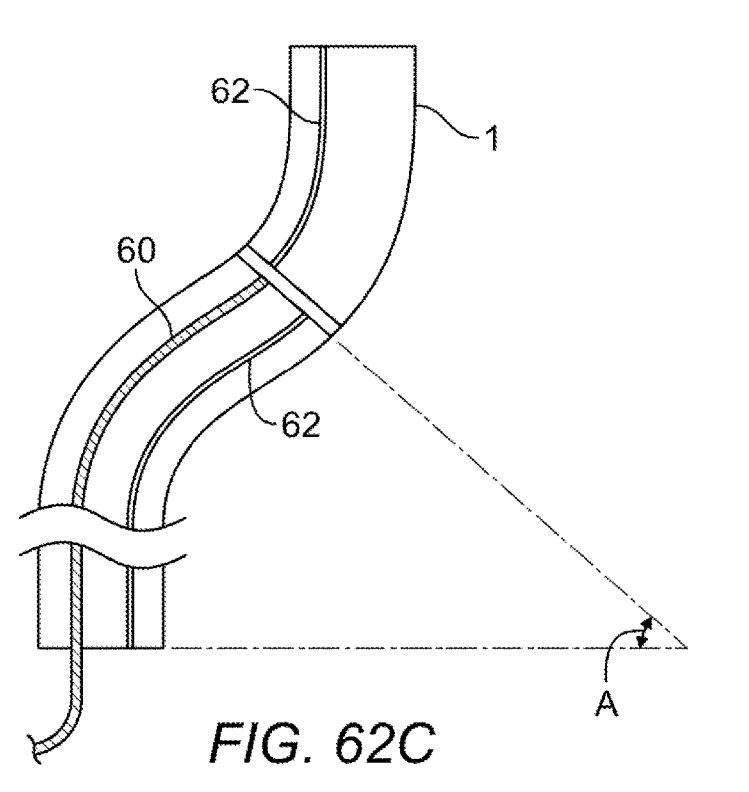
*FIG. 62C*

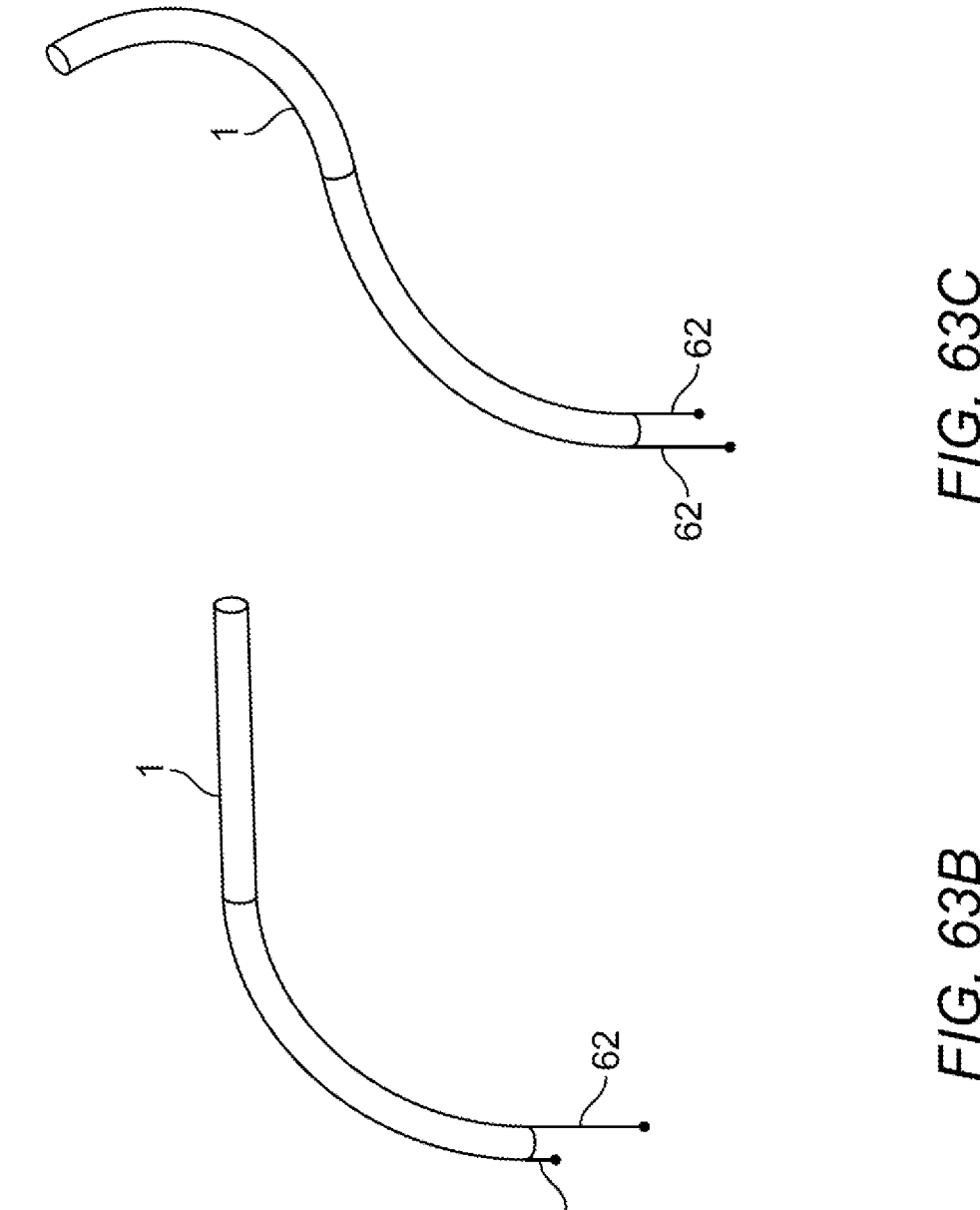
*FIG. 63C*
*FIG. 63B*
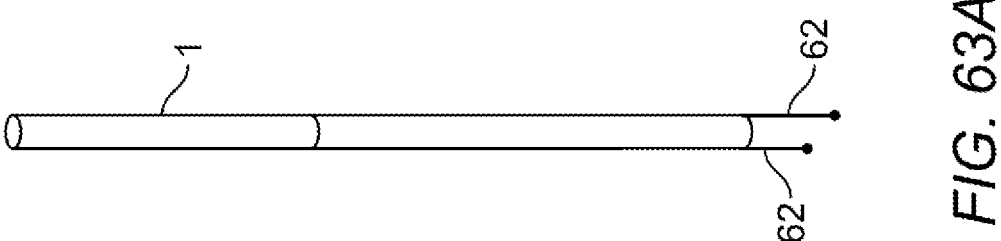
*FIG. 63A*

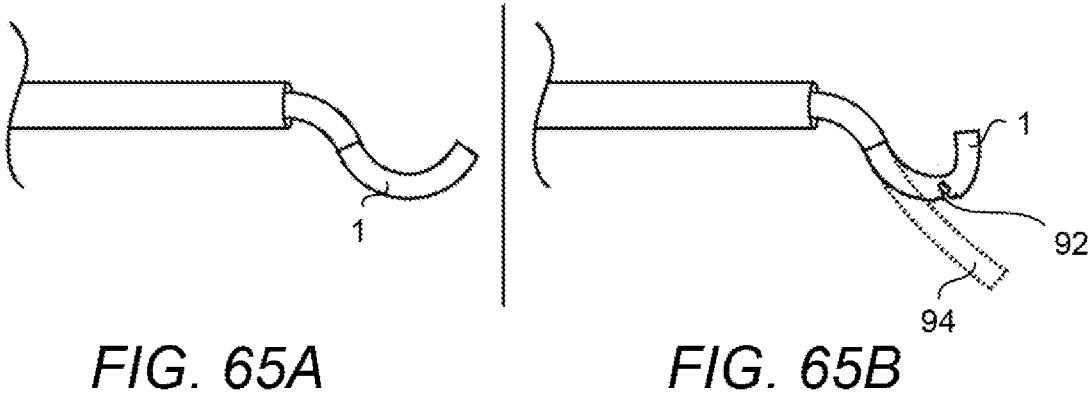
*FIG. 65A*          *FIG. 65B*
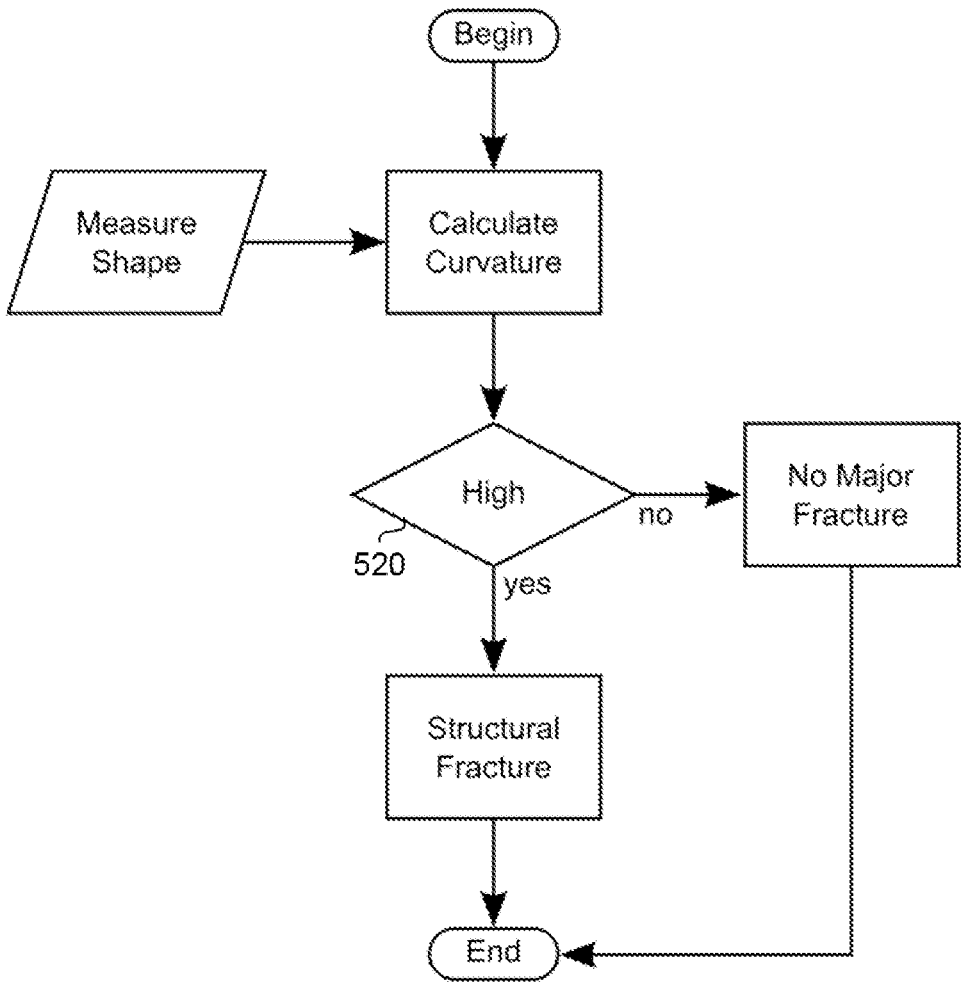
*FIG. 65C*

METHODS AND DEVICES FOR CONTROLLING A SHAPEABLE MEDICAL DEVICE

CROSS-REFERENCE TO RELATED APPLICATIONS

This application is a continuation of U.S. patent application Ser. No. 17/340,641, filed Jun. 7, 2021, published as 2021/0353129, and issued as U.S. Pat. No. 11,857,156, entitled "METHODS AND DEVICES FOR CONTROL-LING A SHAPEABLE MEDICAL DEVICE," which is a continuation of U.S. patent application Ser. No. 16/198,602, filed Nov. 21, 2018, and issued as U.S. Pat. No. 11,051,681 entitled "METHODS AND DEVICES FOR CONTROL-LING A SHAPEABLE MEDICAL DEVICE," which is a divisional of U.S. patent application Ser. No. 14/164,961, filed Jan. 27, 2014, and issued as U.S. Pat. No. 10,143,360 entitled "METHODS AND DEVICES FOR CONTROL-LING A SHAPEABLE MEDICAL DEVICE", which is a divisional of U.S. patent application Ser. No. 12/823,032, filed Jun. 24, 2010, and issued as U.S. Pat. No. 8,672,837, entitled "METHODS AND DEVICES FOR CONTROL-LING A SHAPEABLE MEDICAL DEVICE," the entire disclosures of all of which are expressly incorporated by reference herein for all purposes.

FIELD OF THE INVENTION

The invention relates generally to medical instruments, such as elongate steerable instruments for minimally-invasive intervention or diagnosis, and more particularly to a method, system, and apparatus for sensing or measuring the shape or position and shape of one or more parts of a shapeable elongate medical instrument.

BACKGROUND

Currently known minimally invasive procedures for diagnosis and treatment of medical conditions use shapeable instruments, such as steerable devices, flexible catheters or more rigid arms or shafts, to approach and address various tissue structures within the body. Hereafter, such devices are referred to as "shapeable" instruments. Such a term can include steerable devices, flexible devices, devices having one or more pre-determined shapes (such as an articulating device that locks into a particular shape). For various reasons, it is highly valuable to be able to determine the 3-dimensional spatial position of portions of such shapeable instruments relative to other structures, such as the operating table, other instruments, or pertinent anatomical tissue structures. Such information can be used for a variety of reasons, including, but not limited to improve device control; to improve mapping of the region; to adapt control system parameters (whether kinematic and/or solid mechanic parameters); to estimate, plan and/or control reaction forces of the device upon the anatomy; and/or to even monitor the system characteristics for determination of mechanical problems. Alternatively, or in combination, shape information can be useful to simply visualize the tool with respect to the anatomy or other regions whether real or virtual.

Conventional systems can be improved by incorporating shape information into the control of the medical device. To better understand such improvements a discussion of the concept of shape might be useful. Most generally, shape can include geometric information about an object without information of location, scale or rotation. While the discussion focuses on the use of robotics to control a shapeable device, the concepts disclosed herein can be applied to any robotic, automated, or machine assisted control of a medical device.

Shape can be important for improved control of shapeable devices. In the field of discrete robotics, joint positions are used extensively to describe relative positions of connected articulating members. In the case of a shapeable instrument being advanced by a robotic or other system, there are effectively infinite joints with multiple degrees of freedom. Instead of just knowing the scalar or vector configuration of a joint, the shape of a shapeable section is needed and must be either inferred or measured.

A machine that controls a shapeable medical device carries force and flexure continuously through sections with some degree of smoothness in one or more path derivatives. The shape of these sections can provide valuable information. However, purely defined shape excludes location, rotation and scaling of a body. Shape as described hereafter generally includes shape with scale. Thus, with the shape, the relative position and orientation of any two points on the shape are known. For example, as shown in FIG. 1A, if the shape S of shapeable instrument 1 is known and coordinates are known or assigned for q, relative coordinates and orientation may also be assigned for q' in the reference frame of q. In other words, knowing the shape allows for all point in the body to be defined relative to a reference frame in the body. To reiterate, the reference frame or point is on the shapeable instrument rather than on the actual robot or controlling device.

Without shape measurement, other information must be used to control a shapeable device. However, such control is subject to error by multiple sources. FIG. 1B shows an example of an overview block diagram of a basic topology used for controlling devices without shape feedback. The left side of the diagram (or the Desired/Master side) describes the desired behavior of the catheter (sometimes also referred to as virtual side). The right side of the diagram (referred to as the real, actual, or slave side) describes the behavior of the actual physical catheter. Both sides provide a description of the catheter into at least three levels: tip position (task space), catheter configuration (configuration or joint space), and tendon displacements (actuator space).

FIG. 1B also illustrates a typical control flow for a basic catheter control. The operator enters a command to designate a desired tip position for the device via some input mechanism (a master input device, computer software, or other user interface, etc.). Next, one or more inverse kinematic algorithms compute a desired catheter configuration in order to achieve the commanded tip position. The inverse kinematic algorithm can be varied depending on the construction of the shapeable device. The desired catheter configuration is then fed to one or more catheter mechanics algorithm to compute the positioning element displacements necessary to achieve the desired catheter configuration. These positioning element commands are then provided to the robots control algorithms (or in some cases actuators in the robot that interface with positioning elements in the shapeable element).

Based upon the applied positioning element displacements, the actual (physical) catheter mechanics including any constraints and obstructions acting on the catheter determine the real configuration or shape that the shapeable device achieves. This is illustrated on the right (slave/actual) side of FIG. 1B. This real catheter configuration/shape determines the real catheter tip position. These kinematic relationships of the physical device are represented in the figure with a forward kinematics block (50). Assuming that the operator is observing the catheter tip through some sort of visualization (fluoro, endoscopy, etc.), the operator can then use this visual feedback to make corrections to the commanded tip position. However, this form of feedback is based on the human operator's perception and skill, which vary between individuals, not to mention that an individual's perception of the feedback can vary during a procedure or over a number of procedures.

To generate the control inputs, the system must calculate inverse kinematics and translate to configuration space. These mathematical operations are essentially inverted by the physical system in actuating the device, subject to disturbances such as interference with the environment.

In many conventional systems, the catheter (or other shapeable instrument) is controlled in an open-loop manner as shown in FIG. IC. In this type of open loop control model, the shape configuration command comes in to the beam mechanics, is translated to beam moments and forces, then is translated to tendon tensions given the actuator geometry, and finally into tendon displacement given the entire deformed geometry. However, there are numerous reasons why the assumed motion of the catheter will not match the actual motion of the catheter, one important factor is the presence of unanticipated or unmodeled constraints imposed by the patient's anatomy.

Clearly, the presence of unanticipated or unmodeled portions of the anatomy affects the behavior and therefore kinematics of the shapeable instrument. This affect will often alter any mapping between configuration or shape and task space or endpoint for the instrument. FIG. 1D shows a basic example of this situation. When a section of a shapeable instrument articulates without encountering an obstruction (from "a" to "b"), the tip of the instrument (1) moves along an arc that is now oriented largely vertically. When the instrument (1) encounters an environmental constraint (49), the constraint (49) limits the movement of the tip of the instrument (1) in a tighter arc. In most cases, the controller that issues signals to direct the instrument (1) does not account for the presence of this constraint (49), so any inverse kinematic analysis assumes that the instrument (1) is in the shape depicted in B while in reality is in the altered shape depicted in "c".

Accordingly, a control system that directs shapeable instruments can command joint configurations that can achieve a desired tip position. However, the presence of modeling inaccuracies and environment interaction causes a differential between the actual position from that intended. A simple tip position can quantify this error, but addressing the source of the error requires the additional information regarding the shapeable instrument. Data defining the actual or real shape of the instrument can provide much of this information.

Conventional technologies such as electromagnetic position sensors, available from providers such as the Biosense Webster division of Johnson & Johnson, Inc., can be utilized to measure 3-dimensional spatial position but may be limited in utility for elongate medical instrument applications due to hardware geometric constraints, electromagnetivity issues, etc.

It is well known that by applying the Bragg equation (wavelength=2*d*sin(theta)) to detect wavelength changes in reflected light, elongation in a diffraction grating pattern positioned longitudinally along a fiber or other elongate structure may be be determined. Further, with knowledge of thermal expansion properties of fibers or other structures which carry a diffraction grating pattern, temperature readings at the site of the diffraction grating may be calculated.

"Fiberoptic Bragg grating" ("FBG") sensors or components thereof, available from suppliers such as Luna Innovations, Inc., of Blacksburg, Virginia, Micron Optics, Inc., of Atlanta, Georgia, LxSix Photonics, Inc., of Quebec, Canada, and Ibsen Photonics A/S, of Denmark, have been used in various applications to measure strain in structures such as highway bridges and aircraft wings, and temperatures in structures such as supply cabinets.

The use of such technology in shapeable instruments is disclosed in commonly assigned U.S. patent application Ser. No. 11/690,116, published as U.S. Pub. No. 2007/0265503 on Nov. 15, 2007, now abandoned; Ser. No. 11/176,598, published as U.S. Pub. No. 2006/0100610 on May 11, 2006, now abandoned; Ser. No. 12/012,795, published as U.S. Pub. No. 2008/0218770 on Sep. 11, 2008, now abandoned; Ser. No. 12/106,254, issued as U.S. Pat. No. 8,050,523 on Nov. 1, 2011; and Ser. No. 12/507,727, published as U.S. Pub. No. 2010/0114115 on May 6, 2010, now abandoned. Such technology is also described in U.S. Provisional application Nos: 60/785,001; 60/788,176; 60/678,097; 60/677,580; 60/600,869; 60/553,029; 60/550,961; 60/644,505. The entirety of each of the above applications is incorporated by reference herein. Related disclosures of systems and methods for controlling a shapeable instrument can be found U.S. Ser. No. 12/822,876, filed Jun. 24, 2010, issued as U.S. Pat. No. 8,460,236 on Jun. 11, 2013, the entirety of which is incorporated by reference.

There remains a need to apply the information gained by the spatial information or shape and applying this information to produce improved device control or improved modeling when directing a robotic or similar device. There also remains a need to apply such controls to medical procedures and equipment.

SUMMARY OF THE INVENTION

The systems, methods, and devices described herein include a robotic medical system for controlling a shapeable instrument within an anatomical region. The systems, methods, and devices described herein incorporate shape measurement and apply the measured information as feedback for controlling of the shapeable member or for performing other tasks related to controlling the instrument (e.g., improving a map or a model of the anatomy or region).

The shapeable medical instruments, in most variations described herein, include any steerable devices, flexible catheters or more rigid arms or shafts whether such devices are used to access a region for advancement of a treatment device, or any actual shapeable treatment device. A shapeable device as used herein include includes flexible, steerable, or otherwise positionable devices that are advanced to various tissue structures within the body. Such devices can assume a shaped configuration via manipulation or steering. Moreover, shapeable devices include those flexible devices that conform to anatomic or other obstructions. In many variations, shapeable instruments include a working end and one or more positioning elements that move the shapeable instrument. In one example, the positioning elements comprise control elements such as tendons wires, or other mechanical structures that are moved by one or more actuators to affect a shape or reposition the shapeable instrument. Unless specifically used to indicate a particular device, the term catheter is one example of a shapeable instrument.

In a first variation, the robotic medical system comprises a medical system for controlling a shapeable instrument within an anatomical region, where the shapeable instrument includes at least a working section and one or more positioning elements that move the shapeable instrument.

One variation of the system includes a controller including a master input device, where the controller generates a position control signal in response to the master input device to position the working section at a desired position; one or more actuators operatively coupleable to the one or more positioning elements, where the actuators manipulate the positioning elements based on the position control signal to drive at least a first portion of the shapeable instrument to position the working section toward the desired position; a localization system configured to obtain a plurality of localized shape data from the first portion of the shapeable instrument; and where the controller generates a signal based upon a differential between the localized shape data and a desired configuration of the first portion of the shapeable instrument. The desired configuration of the first portion can include a desired position of the first portion or the desired position of the working section. Alternatively, or in combination, the desired configuration of the first portion comprises a desired shape of the first portion.

The localization system can determine a position of the working section from the plurality of localized shape data. In another variation, the desired configuration of the first portion comprises a desired position of the first portion and where controller generates the signal based upon the differential between the position of the working section and the desired position of the working section. The controller of the robotic medical system can be configured to derive a position of the working section from a kinematic model of the shapeable instrument.

A variation of the robotic medical system includes a localization system that determines a shape of the first portion of the shapeable instrument from the plurality of localized shape data. The desired configuration of the first portion can comprises a desired shape of the first portion and where controller generates the signal based upon the differential between the shape of the first portion and the desired shape of the first portion. In another variation, the localization system also determines a position of the working section from the plurality of localized shape data, and where the desired configuration of the first portion also includes a desired position of the first portion.

In another variation, the controller generates the signal also based upon the differential between a desired position of the first portion and the position of the first portion.

The robotic medical system can also include a controller that is configured to feed the signal to the actuators such that the actuators manipulate one or more of the positioning elements using the signal to position the working section or the first portion of the shapeable instrument.

In one variation, the localization system comprises a fiber optic localization system configured to supply the plurality of localization data. Furthermore, the shapeable instrument can include at least one optic fiber and where the localization system is configured to measure a plurality of data of Rayleigh scatter of the optic fiber. The Rayleigh scatter data can be used to supplement or supply the localization data.

The localization system can comprises a system selected from the group consisting of a plurality of positioning sensors, a vision system, a plurality of strain sensors. In another variation, the localization system can comprise an electromagnetic localization system and where the shapeable instrument includes at least one electromagnetic coil. In yet another variation, the localization system can comprise an impedance based localization system and where the shapeable instrument includes at least one sensor, where the system further includes at least one electrode where the impedance based localization system determines a voltage gradient between the sensor and the electrode. However, any number of localization systems can be employed with the robotic medical system as described herein.

The robotic medical system described herein can also include a control configured to generate the position control feed signal using an inverse kinematic model of the shapeable instrument. The controller can generate the position control signal to maximize a probability of achieving a prescribed shape or position by optimizing a cost function subject to a set of constraints based upon a model and a measurement estimate. For example, the model can be selected from the group consisting of a kinematic and solid mechanic model and the measurement projection can be selected from the group consisting of a shape, a strain, and a projection (e.g., a fluoroscopic projection, etc.).

In one variation, the controller can use the signal to alter at least one parameter of the inverse kinematic model of the shapeable instrument to produce an improved inverse kinematic model of the shapeable instrument. Furthermore, the controller can modify the position control signal using the improved kinematic model.

The robotic medical system described herein can also be configured such that the actuators alter a force applied to one or more of the positioning elements based on the signal to reposition the working section or the first portion of the shapeable instrument.

In yet another variation, the robotic medical system can be further configured to measure an axial deformation of the shapeable member, and where the controller further generates the signal based on the axial deformation of the shapeable member.

In variations of the robotic medical system the controller can be configured to determine an applied force on the first portion of the shapeable instrument using a shape of the first portion of the shapeable instrument, the position control signal and at least one characteristic of the shapeable instrument. The controller can further use one or more actuators to reposition the portion of the shapeable instrument to reduce the applied force.

In another variation, when the robotic medical system generates the signal, the controller can trigger an operator alert signal alarm to the master input device. The operator signal can cause a haptic effect on the master input device for feedback. In some variations, the controller triggers the operator alert signal only if the signal is greater than a pre-determined level. Any number of safety measures can be employed when the controller triggers the operator alert signal. For example, the controller can be configured to stop movement of the shapeable instrument; the controller can be configured to reverse movement of the shapeable instrument; and/or the controller can be configured to increase a force required to operate the master input device.

The controller of the robotic medical system described herein can be configured to further determine a calculated curvature from the real shape and compares the calculated curvature to a pre-determined curvature to assess a fracture of the shapeable element.

The present disclosure also includes methods for controlling a shapeable instrument within an anatomical region using a robotic medical system. For example, the method can include operatively coupling one or more actuators to one or more positioning elements of a shapeable instrument where the one or more positioning elements are adapted to move the shapeable instrument and where the actuators manipulate the positioning elements; advancing the shapeable instrument to the anatomical region, where the shapeable instrument includes a working section; generating a position control signal in response to position the working section at a desired position; obtaining a plurality of localized shape data of a first portion of the shapeable instrument using a localization system; and controlling the actuators using the position control signal to manipulate the positioning control elements to drive at least the first portion of the shapeable instrument to position the working section toward the desired position, where the controller generates a signal based upon a differential between the localized shape data and a desired configuration of the first portion of the shapeable instrument.

The methods described herein can also permit tracking of a device through an anatomic path using shape information of the device. For instance, one method includes controlling advancement of a shapeable medical device within an anatomic path. Such variation includes identifying a reference shape of one or more portions of the shapeable medical device; advancing the shapeable medical device along the anatomic path; obtaining a plurality of localization data to determine a real shape of at least the one or more portions of the shapeable instrument when advanced along the anatomic path; and monitoring advancement of the shapeable medical device by determining a differential between the real shape and the reference shape of the one or more portions.

In addition, the method of controlling advancement of the medical device can further comprise controlling advancement of the shapeable medical device if the differential between the real shape and the reference shape of the one or more portions is greater than a threshold value.

In one variation controlling the advancement of the shapeable medical device comprises reversing the shapeable medical device along the anatomic path until the differential between the real shape and the reference shape decreases. In another variation, controlling the advancement of the shapeable medical device comprises slowing advancement of the shapeable medical device along the anatomic path until the differential between the real shape and the reference shape decreases. Another variation controlling the advancement of the shapeable medical device comprises advancing a guide device from the shapeable medical device within the anatomic path and subsequently advancing the shapeable medical device along the guide track. In additional variations controlling the advancement of the shapeable medical device comprises stopping the shapeable medical device and withdrawing a proximal end of the shapeable medical device until the differential between the real shape and the reference shape decreases.

The disclosure also includes method for reduced model control. One such method includes altering a data model of an anatomical region. For example, such a method can include advancing a shapeable instrument relative to the anatomical region, the shapeable instrument comprising one or more positioning elements that alter a shape of a first portion of the shapeable instrument obtaining a plurality of localization data to determine a real shape of the first portion of the shapeable instrument; correlating the real shape of the first portion of the shapeable instrument against a desired shape of the first portion to determine a data model of an anatomic feature affecting the real shape of at least the first portion of the shapeable instrument; and updating the data model with the data model of the anatomic feature.

The method described above can further comprise measuring at least one force on at least one positioning element and where correlating the real shape of the first portion of the shapeable instrument includes assessing the force on the at least one positioning element to determine the data model of the anatomic feature affecting the real shape of at least the first portion of the shapeable instrument. The methods can further include cycling movement of the shapeable instrument by advancing and retracting the shapeable instrument, and where obtaining the localization data occurs after advancing the shapeable instrument.

The methods described herein can repositioning the shapeable instrument to maintain a historical database of real shapes, where the historical database comprises a plurality of active spaces through which the shapeable instrument moved and a plurality of void spaces through which the shapeable instrument did not move, and determining a location of an atomic feature using the plurality of void spaces.

The present disclosure also include methods of preparing a robotic medical system for use with a shapeable instrument, where the shapeable instrument includes a working end and one or more positioning elements that move the shapeable instrument. A variation of this method includes obtaining a plurality of localization data to determine a real shape of at least the first portion of the shapeable instrument; pretensioning the shapeable instrument by incrementally actuating at least one of the actuators to determine a zero displacement point of the actuator after which the shapeable instrument moves from the real shape; providing the zero displacement point to a controller including a master input device, where the controller adds the first displacement point to at least one actuation command where the actuation command manipulates one or more of the positioning elements to reposition the working end or the first portion of the shapeable instrument and where the first displacement point compensates for slack in the shapeable element.

In one example, a shapeable instrument comprises an elongate instrument body; an optical fiber coupled in a constrained manner to the elongate instrument body, the optical fiber is in communication with one or more optical gratings; and a detector operably coupled to a proximal end of the optical fiber and configured to detect respective light signals reflected by the one or more optical gratings. The system further includes a controller operatively coupled to the detector, wherein the controller is configured to determine a geometric configuration of at least a portion of the shapeable instrument based on a spectral analysis of the detected reflected portions of the light signals. Variations of the devices, systems and methods described herein can employ Bragg Fiber gratings as mentioned above. However, additional variations of the devices, systems and method contained in this disclosure can employ any number of optical gratings.

The systems, methods, and devices described herein can also employ alternate means to obtain information regarding shape of the device. For example, such alternate means includes, but is not limited to positioning sensors, a vision system, a plurality of strain sensors.

By way of non-limiting example, a shapeable instrument can be robotically controlled, or manually controlled with automated assistance. In some variations, the shapeable instrument includes a reference reflector coupled to the optical fiber in an operable relationship with the one or more optical gratings. In yet additional embodiments, the detector comprises a frequency domain reflectometer. The optical fiber can include multiple fiber cores, each core including one or more optical gratings. The optical fiber (or each fiber core of a multi-core optical fiber) can optionally comprise a plurality of paced apart optical gratings.

In another variation, a localization system as described herein can use measurement of Rayleigh scatter in the optical fiber. Measurement of Rayleigh scatter can be used to measure strain in the fiber. Such information can be used as an alternate mode of obtaining shape data. Alternatively, Rayleigh scatter can be combined with other localization systems to supplement or improve the localized shape data.

When single mode optical fiber is drawn there can be slight imperfections that result in index of refraction variations along the fiber core. These variations result in a small amount of backscatter that is called Rayleigh scatter. Changes in strain or temperature of the optical fiber cause changes to the effective length of the optical fiber. This change in the effective length results in variation or change of the spatial position of the Rayleigh scatter points. Cross correlation techniques can measure this change in the Rayleigh scattering and can extract information regarding the strain. These techniques can include using optical frequency domain reflectometer techniques in a manner that is very similar to that associated with low reflectivity fiber gratings. A more complete discussion of these methods can be found in M. Froggatt and J. Moore, "High-spatial-resolution distributed strain measurement in optical fiber with Rayleigh scatter", Applied Optics, Vol. 37, p. 1735, 1998 the entirety of which is incorporated by reference herein.

Methods and devices for calculating birefringence in an optical fiber based on Rayleigh scatter as well as apparatus and methods for measuring strain in an optical fiber using the spectral shift of Rayleigh scatter can be found in PCT Publication No. WO2006099056 filed on Mar. 9, 2006 and U.S. Pat. No. 6,545,760 filed on Mar. 24, 2000 both of which are incorporated by reference herein. Birefringence can be used to measure axial strain and/or temperature in a waveguide. Using Rayleigh scatter to determine birefringence rather than Bragg gratings offers several advantages. First, the cost of using Rayleigh scatter measurement is less than when using Bragg gratings. Rayleigh scatter measurement permits birefringence measurements at every location in the fiber, not just at predetermined locations. Since Bragg gratings require insertion at specific measurement points along a fiber, measurement of Rayleigh scatter allows for many more measurement points. Also, the process of physically "writing" a Bragg grating into an optical fiber can be time consuming as well as compromises the strength and integrity of the fiber. Such drawbacks do not occur when using Rayleigh scatter measurement.

In various embodiments, the optical fiber may be substantially encapsulated in a wall of the elongate instrument body. Alternatively, the elongate instrument body may define an interior lumen, wherein the optical fiber is disposed in the lumen. Further alternatively, the optical fiber may be disposed in an embedded lumen in a wall of the elongate instrument body.

In various embodiments, the elongate instrument body has a neutral axis of bending, and the optical fiber is coupled to the elongate instrument body so as to be substantially aligned with the neutral axis of bending when the elongate instrument body is in a substantially unbent configuration, and to move relative to the neutral axis of bending as the elongate instrument body undergoes bending. In other embodiments, the optical fiber is coupled to the elongate instrument body so as to be substantially aligned with the neutral axis of bending regardless of bending of the elongate instrument body. In still further embodiments, the optical fiber is coupled to the elongate instrument body so as to remain substantially parallel to, but not aligned with, the neutral axis of bending regardless of bending of the elongate instrument body.

Shape feedback can be used directly along with system models in both control for task-space (e.g., the distal end) and/or configuration-space (the elongate portion). The configuration can be extended over time to plan for the environment, for example to track the shape inside a vessel. On the other hand, a control architecture uses less device models instead relying on the information rich shape feedback.

Shape feedback can also be used in device kinematics. Shape provides a measurement of the real kinematics of a device. Kinematic parameters may be estimated using the shape measurement. Extending that concept, shape measurement can be used to adapt the kinematic model by several methods as described herein. Moreover, a real measured shape may be displayed to a system operator in addition to or in lieu of an idealized virtual shape.

Moving beyond the geometry of the device, the physical properties of the device materials, its solid mechanics, make up a fourth area. Addressing a specific challenge for elongate flexible devices, shape can be used to measure axial deformation. Shape can also be used to pretension actuating tendons or control elements. More generally, real device shape may be compared with model expectation to adapt real model parameters or estimate a state of health based on degradation of material properties.

Shape data can further assist in estimation and control of reaction force between the device and environment. Deflection of measured shape from the predicted free shape belies application of external forces. Estimates of these forces may be used to navigate the environment or if an environment model is available, plan a navigation path.

In another variation, use of data from shape feedback can be used to detect mechanical failures of the shapeable instrument. Such feedback allows a mechanism for detecting, displaying, and handling mechanical fractures. Basic diagnosis is extended with an active secondary diagnostic to test potential fractures, redundant sensors for model-based diagnosis and shape sensor diagnostics.

Other and further embodiments, objects and advantages of the invention will become apparent from the following detailed description when read in view of the accompanying figures.

BRIEF DESCRIPTION OF THE DRAWINGS

FIGS. 9A-9B illustrate top and cross sectional views of an elongate instrument such as a catheter having a multi-fiber structure with optical gratings.

FIGS. 10A-10B illustrate top and cross sectional views of an elongate instrument such as a catheter having a multi-fiber structure with optical gratings.

FIGS. 11A-11B illustrate top and cross sectional views of an elongate instrument such as a catheter having a multi-fiber structure with optical gratings.

FIGS. 12A-12H illustrate cross sectional views of elongate instruments with various fiber positions and configurations.

FIGS. 16A-16D illustrates integration of an optical fiber sensing system to a robotically-controlled guide catheter configuration.

FIGS. 17A-F, 17G-1 and 17G-2 illustrate integration of an optical fiber sensing system to a robotically-controlled sheath catheter configuration; where FIGS. 17A-F illustrate exemplary sheath instrument integrations, and FIGS. 17G-1 and 17G-2 each depict an integration to build the exemplary sheath instrument integrations shown in FIGS. 17A-17F.

FIGS. 29-32 illustrate the manipulation of control or positioning elements that adjust the kinematics of a catheter in accordance with various embodiments, with FIG. 29A illustrating a catheter with tension placed upon a bottom control element, and FIG. 29B illustrating an end view of the catheter of FIG. 29A.

FIG. 48 illustrates forward kinematics and inverse kinematics in accordance with some embodiments.

FIGS. 62A to 62C illustrate examples of use of a fiber or other element to measure compression along an axis of a shapeable instrument.

FIGS. 63A to 63C illustrate examples of initial slack in positioning elements of a shapeable instrument.

FIGS. 65A and 65B illustrate a normal shape of an instrument and possible failure modes.

FIG. 65C shows an example of a block diagram to assess fracture.

DETAILED DESCRIPTION

Figure 2A:
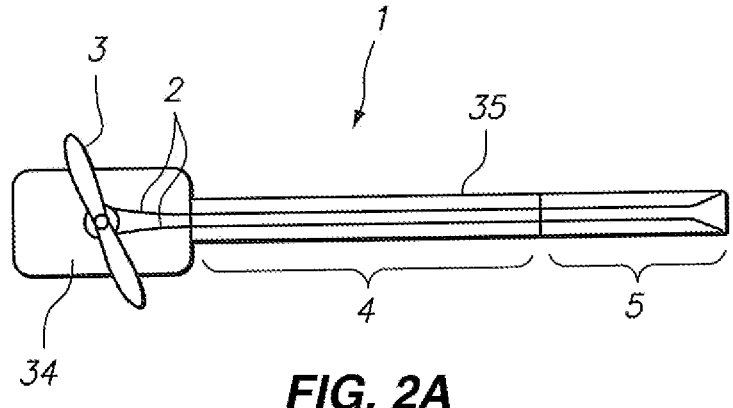
FIG. 2A illustrates an example of an elongate instrument such as a conventional manually operated catheter.

Referring to FIG. 2A, a conventional manually-steerable catheter (1) is depicted. Pullwires (2) may be selectively tensioned through manipulation of a handle (3) on the proximal portion of the catheter structure to make a more flexible distal portion (5) of the catheter bend or steer controllably. The handle (3) may be coupled, rotatably or slidably, for example, to a proximal catheter structure (34) which may be configured to be held in the hand, and may be coupled to the elongate portion (35) of the catheter (1). A more proximal, and conventionally less steerable, portion (4) of the catheter may be configured to be compliant to loads from surrounding tissues (for example, to facilitate passing the catheter, including portions of the proximal portion, through tortuous pathways such as those formed by the blood vessels), yet less steerable as compared with the distal portion (5).

Figure 1A:
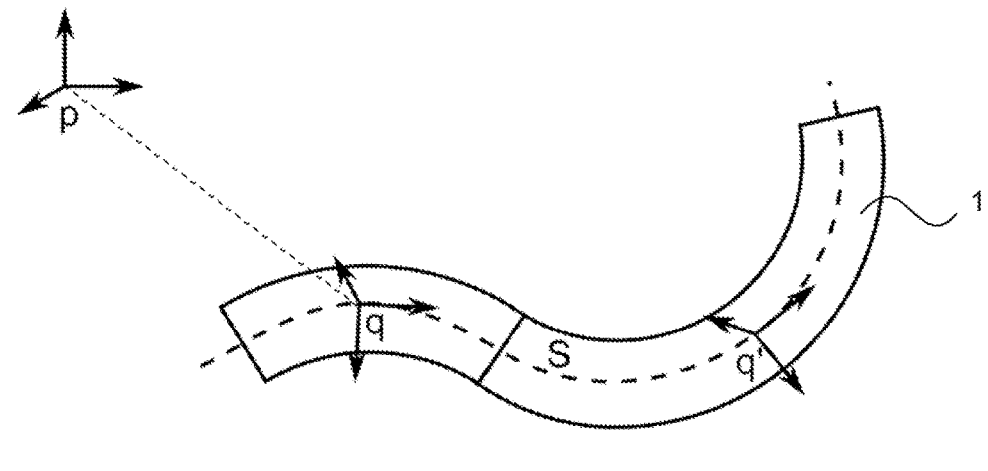
FIG. 1A shows a general diagram to demonstrate the ability to determine coordinates along a known shape.
Figure 1B:
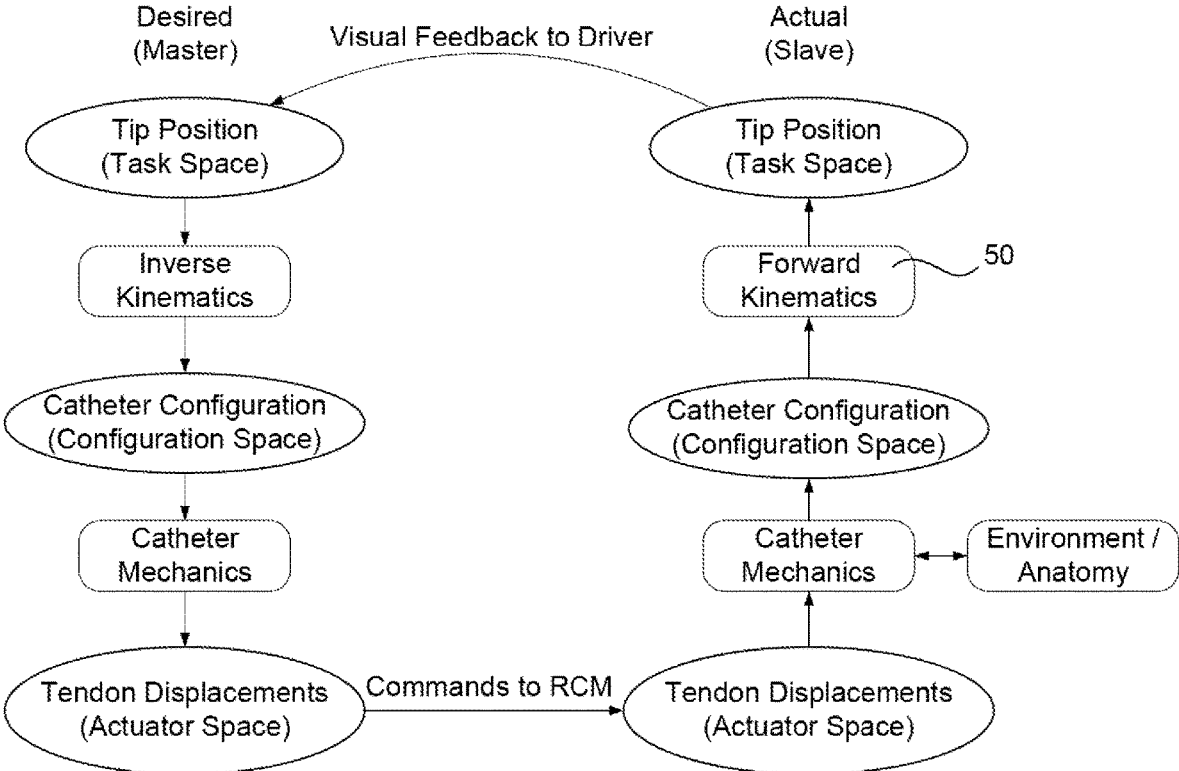
FIG. 1B shows an example of an overview block diagram of a basic topology used for controlling devices without shape feedback.
Figures 1C, 1D:
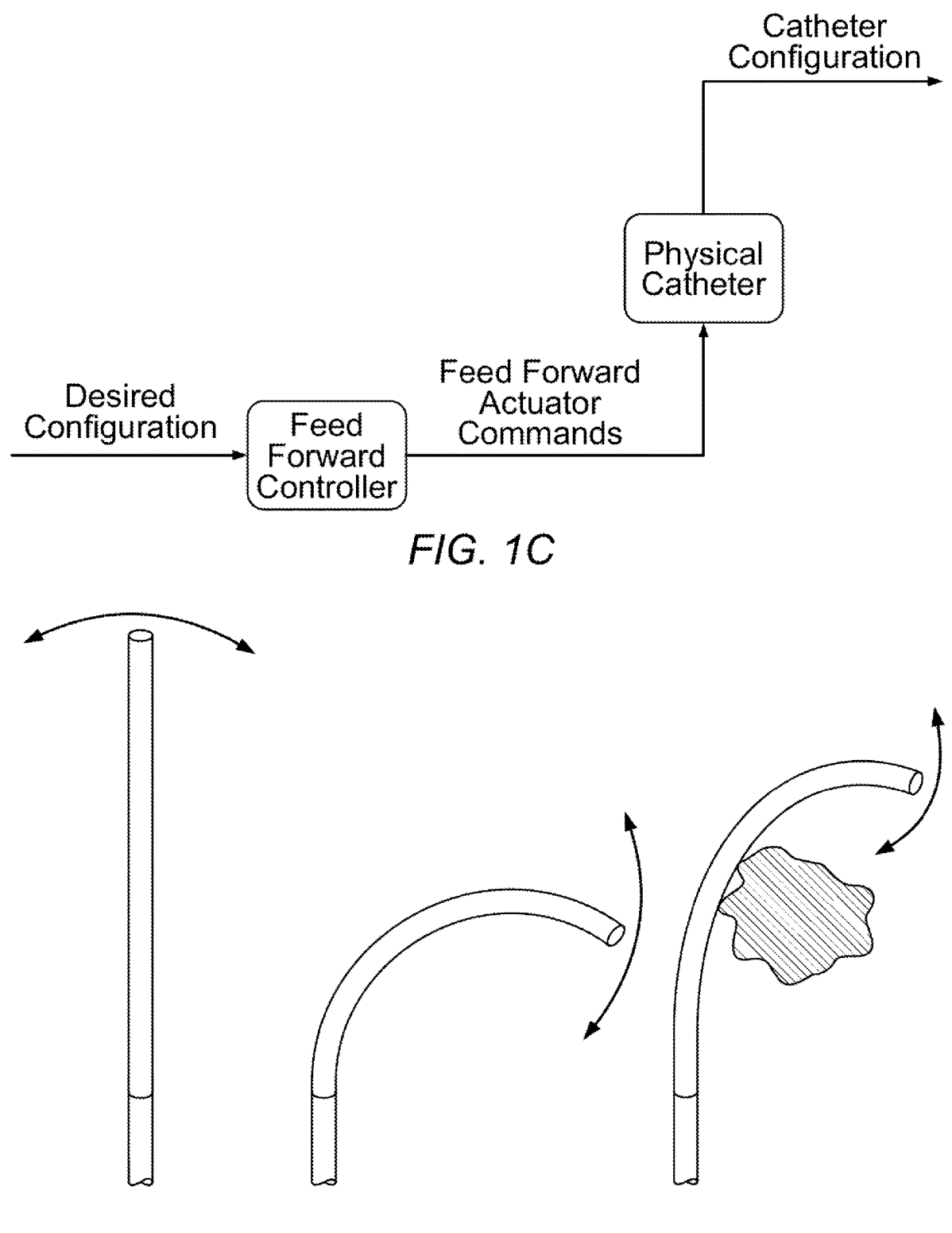
FIG. 1C illustrates a conventional open loop control model.
FIG. 1D shows an example of a shapeable instrument articulating in free space and when engaging an environmental constraint.
Figure 2B:
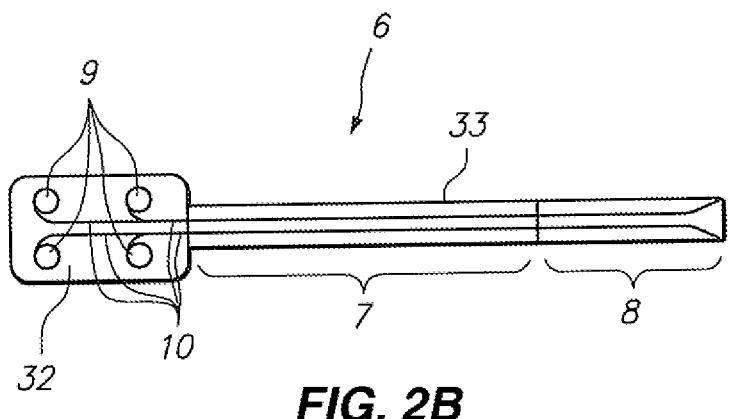
FIG. 2B illustrates another example of an elongate instrument such as a robotically-driven steerable catheter.

Referring to FIG. 2B, a robotically-driven steerable catheter (6), has some similarities with the manually-steerable catheter (1) of FIG. 1 in that it has pullwires or similar control elements (10) associated distally with a more flexible section (8) configured to steer or bend when the control elements (10) are tensioned in various configurations, as compared with a less steerable proximal portion (7) configured to be stiffer and more resistant to bending or steering. The control elements can be flexible tendons, or other mechanical structures that allow for steering or deflection of the catheter (6). The depicted embodiment of the robotically-driven steerable catheter (6) comprises proximal axles or spindles (9) configured to primarily interface not with fingers or the hand, but with an electromechanical instrument driver configured to coordinate and drive, with the help of a computer, each of the spindles (9) to produce precise steering or bending movement of the catheter (6). The spindles (9) may be rotatably coupled to a proximal catheter structure (32) which may be configured to mount to an electromechanical instrument driver apparatus, such as that described in the aforementioned U.S. patent application Ser.

No. 11/176,598, published as U.S. Pub. No. 2006/0100610 on May 11, 2006, now abandoned, and may be coupled to the elongate portion (33) of the catheter (6).

Each of the embodiments depicted in FIGS. 2A and 2B may have a working lumen (not shown) located, for example, down the central axis of the catheter body, or may be without such a working lumen. If a working lumen is formed by the catheter structure, it may extend directly out the distal end of the catheter, or may be capped or blocked by the distal tip of the catheter. It is highly useful in many procedures to have precise information regarding the position of the distal tip of such catheters or other elongate instruments, such as those available from suppliers such as the Ethicon Endosurgery division of Johnson & Johnson, or Intuitive Surgical Corporation. The examples and illustrations that follow are made in reference to a robotically-steerable catheter such as that depicted in FIG. 2B, but as would be apparent to one skilled in the art, the same principles may be applied to other elongate instruments, such as the manually-steerable catheter depicted in FIG. 1, or other elongate instruments, highly flexible or not, from suppliers such as the Ethicon Endosurgery division of Johnson & Johnson, Inc., or Intuitive Surgical, Inc.

Figure 3A:
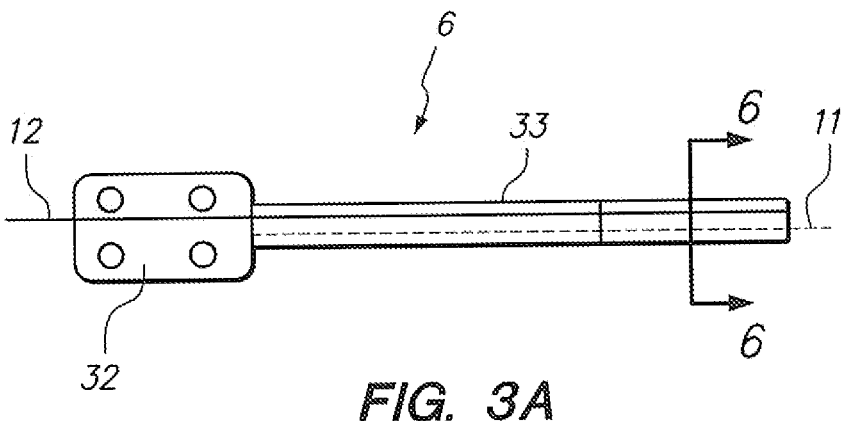
FIGS. 3A-3C illustrate implementations of an optical fiber with various optical gratings to an elongate instrument such as a robotically-steerable catheter.
Figure 3B:
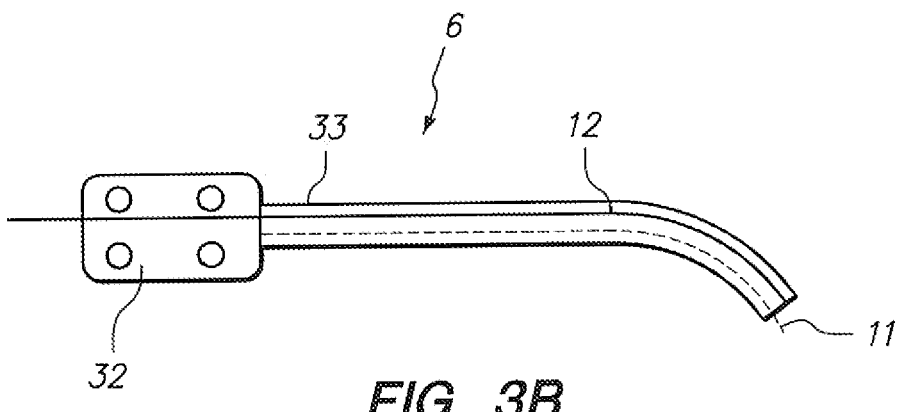
Figure 3C:
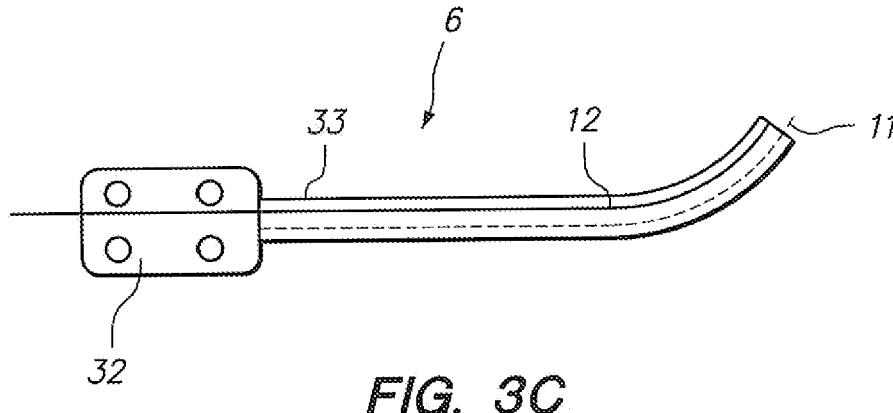
Figures 4A, 4B, 4C, 4D:
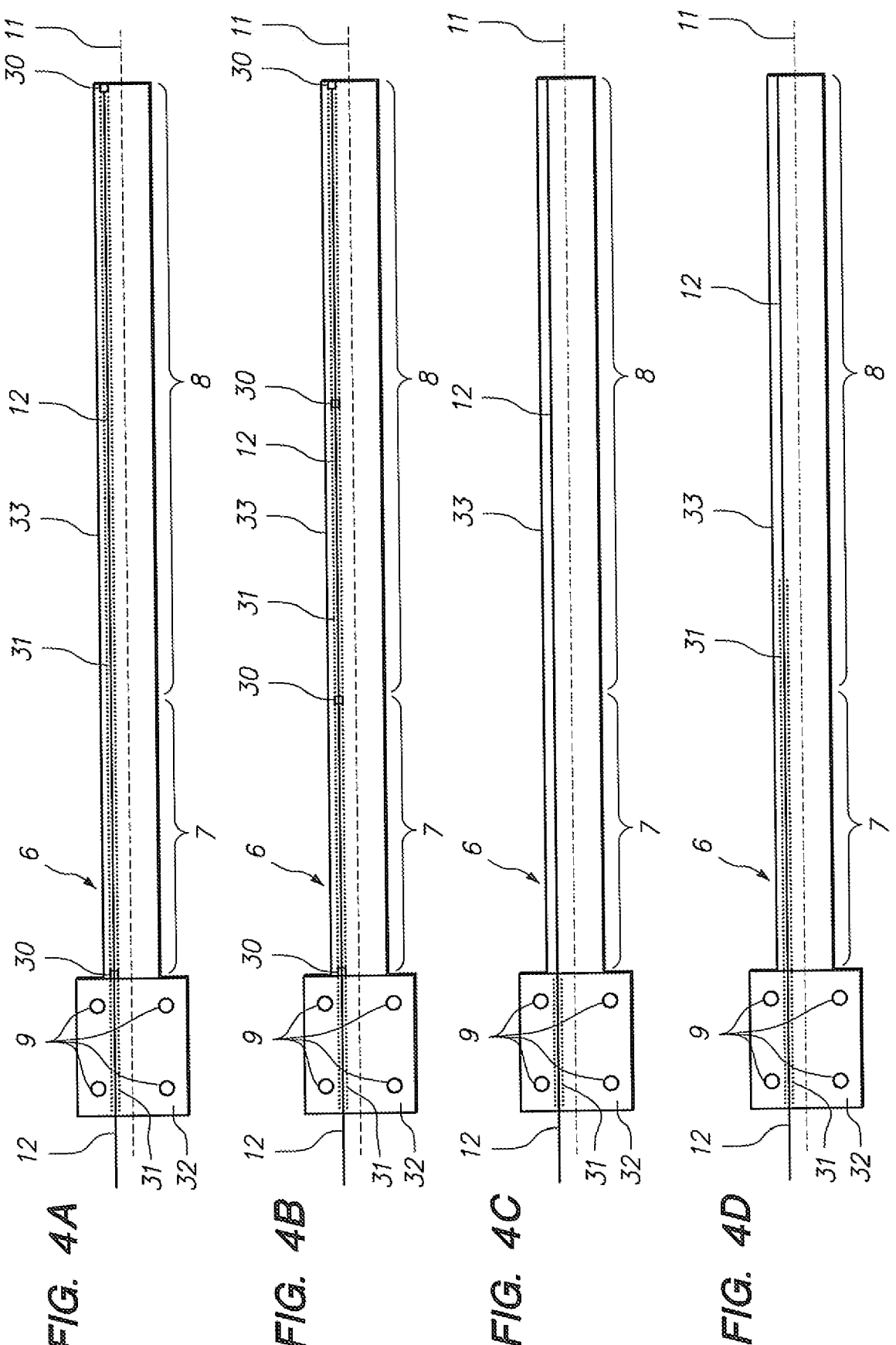
FIGS. 4A-4D illustrate implementations of an optical fiber with a grating to an elongate instrument such as a robotically-steerable catheter.

Referring to FIGS. 3A-3C, a robotically-steerable catheter (6) is depicted having an optical fiber (12) positioned along one aspect of the wall of the catheter (6). The fiber is not positioned coaxially with the neutral axis of bending (11) in the bending scenarios depicted in FIGS. 3B and 3C. Indeed, with the fiber (12) attached to, or longitudinally constrained by, at least two different points along the length of the catheter (6) body (33) and unloaded from a tensile perspective relative to the catheter body in a neutral position of the catheter body (33) such as that depicted in FIG. 3A, the longitudinally constrained portion of the fiber (12) would be placed in tension in the scenario depicted in FIG. 3B, while the longitudinally constrained portion of the fiber (12) would be placed in compression in the scenario depicted in FIG. 3C. Such relationships are elementary to solid mechanics, but may be applied as described herein with the use of an optical fiber grating to assist in the determination of deflection of an elongate instrument. As noted above, the optical fiber grating can comprise a Bragg grating Referring to FIGS. 4A-5D, several different embodiments are depicted. Referring to FIG. 4A, a robotic catheter (6) is depicted having a fiber (12) deployed through a lumen (31) which extends from the distal tip of the distal portion (8) of the catheter body (33) to the proximal end of the proximal catheter structure (32). In one embodiment a broadband reference reflector (not shown) is positioned near the proximal end of the fiber in an operable relationship with the optical grating wherein an optical path length is established for each reflector/grating relationship comprising the subject fiber grating sensor configuration; additionally, such configuration also comprises a reflectometer (not shown), such as a frequency domain reflectometer, to conduct spectral analysis of detected reflected portions of light waves.

Constraints (30) may be provided to prohibit axial or longitudinal motion of the fiber (12) at the location of each constraint (30). Alternatively, the constraints (30) may only constrain the position of the fiber (12) relative to the lumen (31) in the location of the constraints (30). For example, in one variation of the embodiment depicted in FIG. 4A, the most distal constraint (30) may be configured to disallow longitudinal or axial movement of the fiber (12) relative to the catheter body (33) at the location of such constraint (30), while the more proximal constraint (30) may merely act as a guide to lift the fiber (12) away from the walls of the lumen

15

(31) at the location of such proximal constraint (30). In another variation of the embodiment depicted in FIG. 4A, both the more proximal and more distal constraints (30) may be configured to disallow longitudinal or axial movement of the fiber (12) at the locations of such constraints, and so on. As shown in the embodiment depicted in FIG. 4A, the lumen (31) in the region of the proximal catheter structure (32) is without constraints to allow for free longitudinal or axial motion of the fiber relative to the proximal catheter structure (32). Constraints configured to prohibit relative motion between the constraint and fiber at a given location may comprise small adhesive or polymeric welds, interference fits formed with small geometric members comprising materials such as polymers or metals, locations wherein braiding structures are configured with extra tightness to prohibit motion of the fiber, or the like. Constraints configured to guide the fiber (12) but to also allow relative longitudinal or axial motion of the fiber (12) relative to such constraint may comprise small blocks, spheres, hemispheres, etc. defining small holes, generally through the geometric middle of such structures, for passage of the subject fiber (12).

The embodiment of FIG. 4B is similar to that of FIG. 4A, with the exception that there are two additional constraints (30) provided to guide and/or prohibit longitudinal or axial movement of the fiber (12) relative to such constraints at these locations. In one variation, each of the constraints is a total relative motion constraint, to isolate the longitudinal strain within each of three "cells" provided by isolating the length of the fiber (12) along the catheter body (33) into three segments utilizing the constraints (30). In another variation of the embodiment depicted in FIG. 4B, the proximal and distal constraints (30) may be total relative motion constraints, while the two intermediary constraints (30) may be guide constraints configured to allow longitudinal or axial relative motion between the fiber (12) and such constraints at these intermediary locations, but to keep the fiber aligned near the center of the lumen (31) at these locations.

Referring to FIG. 4C, an embodiment similar to those of FIGS. 4A and 4B is depicted, with the exception that entire length of the fiber that runs through the catheter body (33) is constrained by virtue of being substantially encapsulated by the materials which comprise the catheter body (33). In other words, while the embodiment of FIG. 4C does have a lumen (31) to allow free motion of the fiber (12) longitudinally or axially relative to the proximal catheter structure (32), there is no such lumen defined to allow such motion along the catheter body (33), with the exception of the space naturally occupied by the fiber as it extends longitudinally through the catheter body (33) materials which encapsulate it.

FIG. 4D depicts a configuration similar to that of FIG. 4C with the exception that the lumen (31) extends not only through the proximal catheter structure (32), but also through the proximal portion (7) of the catheter body (33); the distal portion of the fiber (12) which runs through the distal portion of the catheter body (33) is substantially encapsulated and constrained by the materials which comprise the catheter body (33).

Figures 5A, 5B, 5C, 5D:
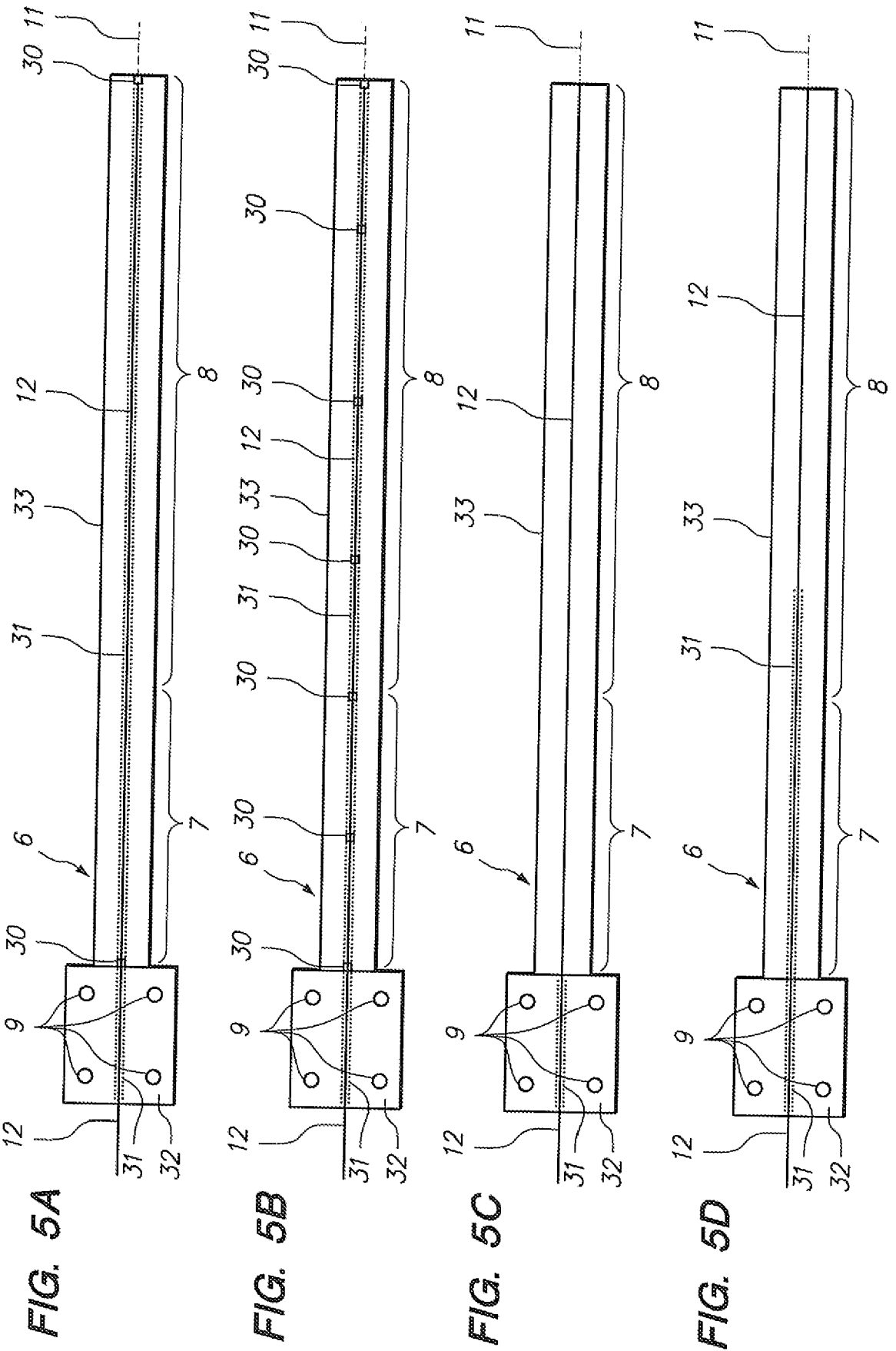
FIGS. 5A-D illustrate implementation of an optical fiber with a grating to an elongate instrument as a robotically-steerable catheter.

FIGS. 5A-5D depict embodiments analogous to those depicted in FIGS. 4A-D, with the exception that the fiber (12) is positioned substantially along the neutral axis of bending (11) of the catheter body (33), and in the embodiment of FIG. 5B, there are seven constraints (30) as opposed to the three of the embodiment in FIG. 4B.

Figure 6:
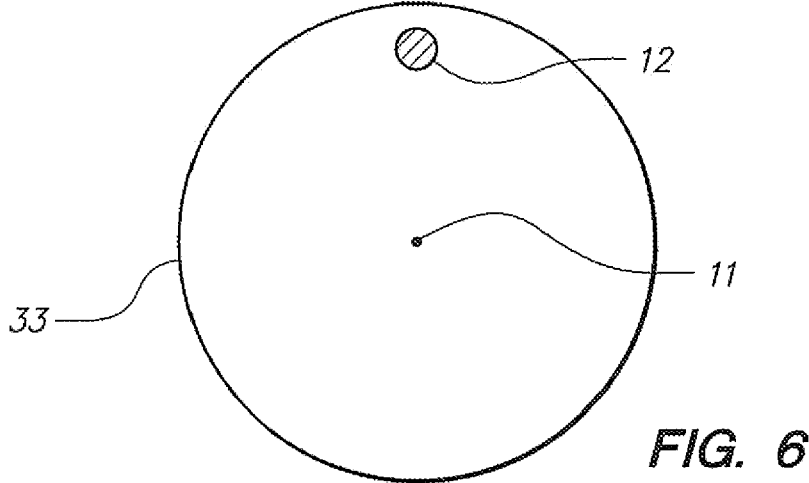
FIG. 6 illustrates a cross sectional view of an elongate instrument such as a catheter including an optical fiber with optical gratings.

Referring to FIG. 6, a cross section of a portion of the catheter body (33) of the configuration depicted in FIG. 4C

Figure 7:
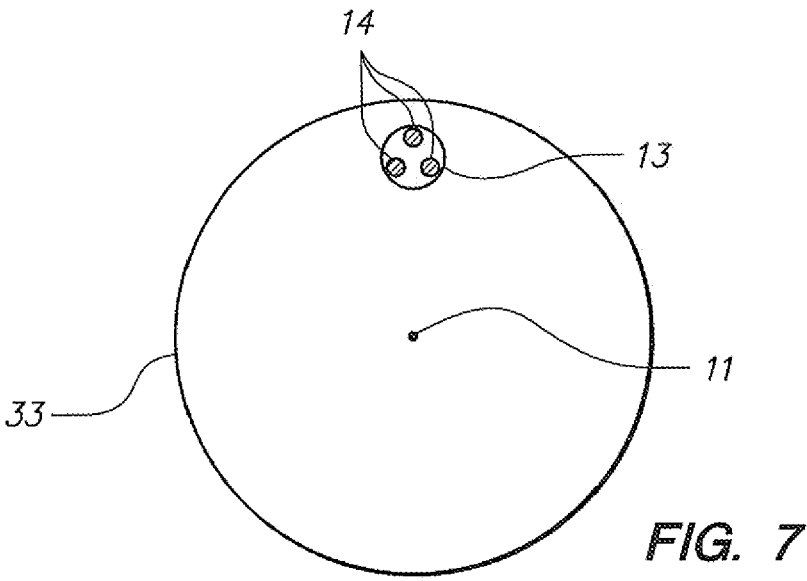
FIG. 7 illustrates a cross sectional view of an elongate instrument such as a catheter including a multi-fiber optical grating configuration.
Figure 8:
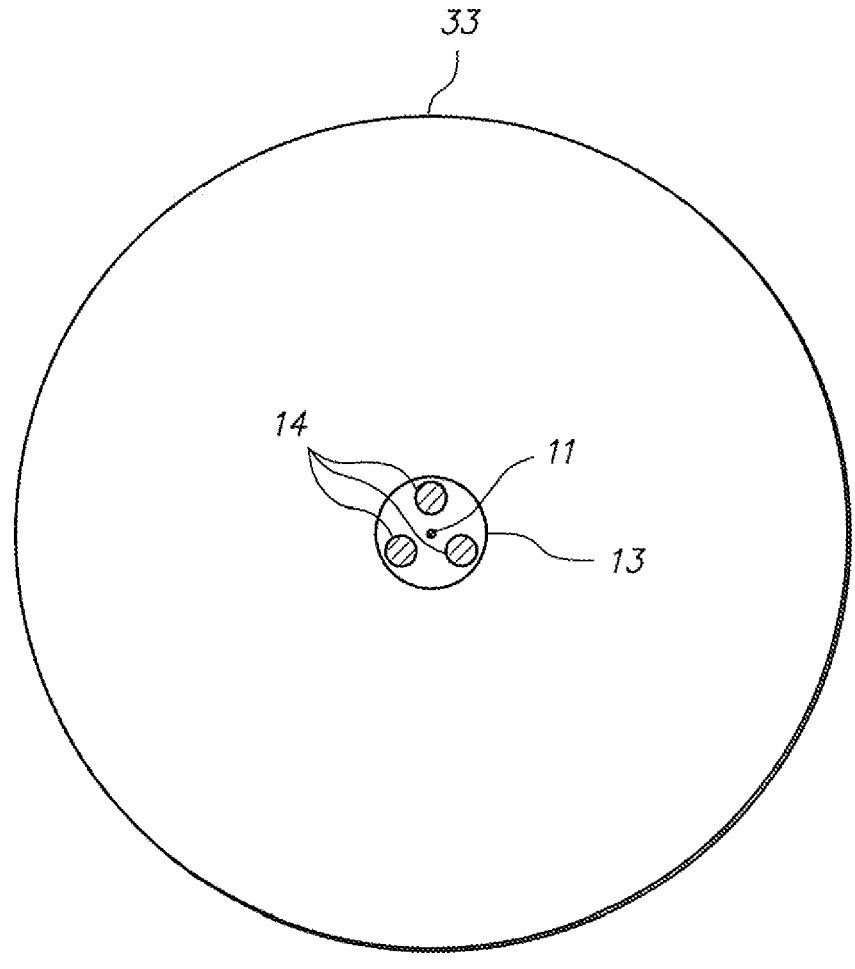
FIG. 8 illustrates a cross sectional view of an elongate instrument such as a catheter including a multi-fiber grating configuration.

16 is depicted, to clearly illustrate that the fiber (12) is not placed concentrically with the neutral axis (11) of bending for the sample cross section. FIG. 7 depicts a similar embodiment, wherein a multi-fiber bundle (13), such as those available from Luna Technologies, Inc., is positioned within the wall of the catheter rather than a single fiber as depicted in FIG. 6, the fiber bundle (13) comprising multiple, in this embodiment three, individual (e.g., smaller) fibers or fiber cores (14). When a structure such as that depicted in FIG. 7 is placed in bending in a configuration such as that depicted in FIG. 3B or 3C, the most radially outward (from the neutral axis of bending (11)) of the individual fibers (14) experiences more compression or tension than the more radially inward fibers. Alternatively, in an embodiment such as that depicted in FIG. 8, which shows a cross section of the catheter body (33) portion a configuration such as that depicted in FIG. 5C, a multi-fiber bundle (13) is positioned coaxially with the neutral axis of bending (11) for the catheter (6), and each of three individual fibers (14) within the bundle (13) will experience different degrees of tension and/or compression in accordance with the bending or steering configuration of the subject catheter, as would be apparent to one skilled in the art. For example, referring to FIGS. 9A and 9B (a cross section), at a neutral position, all three individual fibers (14) comprising the depicted bundle (13) may be in an unloaded configuration. With downward bending, as depicted in FIGS. 10A and 10B (a cross section), the lowermost two fibers comprising the bundle (13) may be configured to experience compression, while the uppermost fiber experiences tension. The opposite would happen with an upward bending scenario such as that depicted in FIGS. 11A and 11B (cross section).

Indeed, various configurations may be employed, depending upon the particular application, such as those depicted in FIGS. 12A-12H. For simplicity, each of the cross sectional embodiments of FIGS. 12A-12H is depicted without reference to lumens adjacent the fibers, or constraints (i.e., each of the embodiments of FIGS. 12A-12H are depicted in reference to catheter body configurations analogous to those depicted, for example, in FIGS. 4C and 5C, wherein the fibers are substantially encapsulated by the materials comprising the catheter body (33); additional variations comprising combinations and permutations of constraints and constraining structures, such as those depicted in FIGS. 4A-5D, are within the scope of this invention. FIG. 12A depicts an embodiment having one fiber (12). FIG. 12B depicts a variation having two fibers (12) in a configuration capable of detecting tensions sufficient to calculate three-dimensional spatial deflection of the catheter portion. FIG. 12C depicts a two-fiber variation with what may be considered redundancy for detecting bending about a bending axis such as that depicted in FIG. 12C. FIGS. 12D and 12E depict three-fiber configurations configured for detecting three-dimensional spatial deflection of the subject catheter portion. FIG. 12F depicts a variation having four fibers configured to accurately detect three-dimensional spatial deflection of the subject catheter portion. FIGS. 12G and 12H depict embodiments similar to 12B and 12E, respectively, with the exception that multiple bundles of fibers are integrated, as opposed to having a single fiber in each location. Each of the embodiments depicted in FIGS. 12A-12H, each of which depicts a cross section of an elongate instrument comprising at least one optical fiber, may be utilized to facilitate the determination of bending deflection, torsion, compression or tension, and/or temperature of an elongate instrument. Such relationships may be clarified in reference to FIGS. 13, 14A, and 14B.

In essence, the 3-dimensional position of an elongate member may be determined by determining the incremental curvature experienced along various longitudinal sections of such elongate member. In other words, if you know how much an elongate member has curved in space at several points longitudinally down the length of the elongate member, you can determine the position of the distal portion and more proximal portions in three-dimensional space by virtue of the knowing that the sections are connected, and where they are longitudinally relative to each other. Towards this end, variations of embodiments such as those depicted in FIGS. 12A-12H may be utilized to determine the position of a catheter or other elongate instrument in 3-dimensional space. To determine local curvatures at various longitudinal locations along an elongate instrument, fiber optic grating analysis may be utilized.

Figure 13:
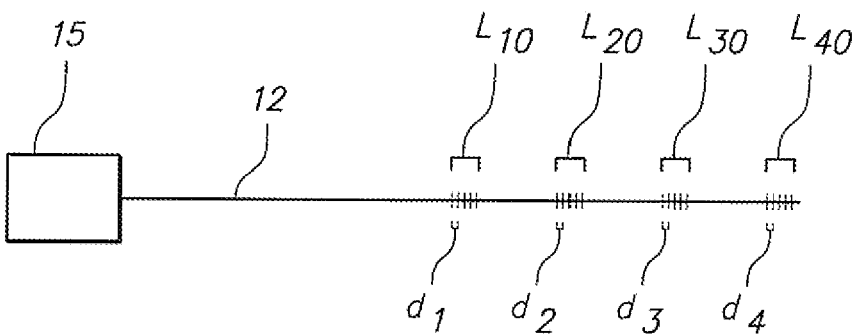
FIG. 13 illustrates an optical fiber sensing system with optical gratings.

Referring to FIG. 13, a single optical fiber (12) is depicted having four sets of diffraction gratings, each of which may be utilized as a local deflection sensor. Such a fiber (12) may be interfaced with portions of an elongate instrument, as depicted, for example, in FIGS. 12A-12H. A single detector (15) may be utilized to detect and analyze signals from more than one fiber. With a multi-fiber configuration, such as those depicted in FIGS. 12B-12H, a proximal manifold structure may be utilized to interface the various fibers with one or more detectors. Interfacing techniques for transmitting signals between detectors and fibers are well known in the art of optical data transmission. The detector is operatively coupled with a controller configured to determine a geometric configuration of the optical fiber and, therefore, at least a portion of the associated elongate instrument (e.g., catheter) body based on a spectral analysis of the detected reflected light signals. Further details are provided in Published US Patent Application 2006/0013523, now abandoned, the contents of which are fully incorporated herein by reference.

In the single fiber embodiment depicted in FIG. 13, each of the diffraction gratings has a different spacing (d1, d2, d3, d4), and thus a proximal light source for the depicted single fiber and detector may detect variations in wavelength for each of the "sensor" lengths (L10. L20, L30, L40). Thus, given determined length changes at each of the "sensor" lengths (L10, L20, L30, L40), the longitudinal positions of the "sensor" lengths (L10, L20, L30, 140), and a known configuration such as those depicted in cross section in FIGS. 12A-12H, the deflection and/or position of the associated elongate instrument in space may be determined. One of the challenges with a configuration such as that depicted in FIG. 13 is that a fairly broad band emitter and broad band tunable detector must be utilized proximally to capture length differentiation data from each of the sensor lengths, potentially compromising the number of sensor lengths that may be monitored, etc. Regardless, several fiber (12) and detector (15) configurations such as that depicted in FIG. 13 may comprise embodiments such as those depicted in FIGS. 12A-12H to facilitate determination of three-dimensional positioning of an elongate medical instrument.

Figure 14A:
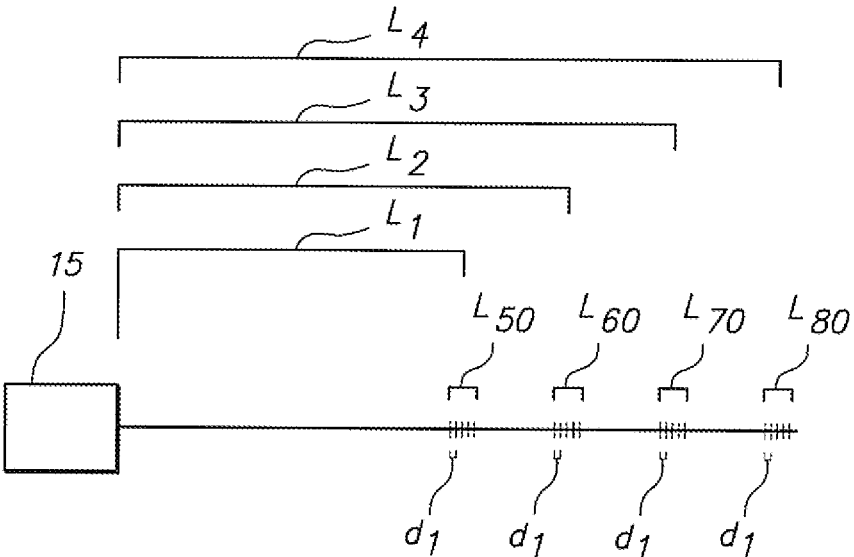
FIGS. 14A-14B illustrates an optical fiber sensing system with optical gratings.

In another embodiment of a single sensing fiber, depicted in FIG. 14A, various sensor lengths (L50, L60, L70, L80) may be configured to each have the same grating spacing, and a more narrow band source may be utilized with some sophisticated analysis, as described, for example, in "Sensing Shape—Fiber-Bragg-grating sensor arrays monitor shape at high resolution," SPIE's OE Magazine, September, 2005, pages 18-21, incorporated by reference herein in its entirety, to monitor elongation at each of the sensor lengths given the fact that such sensor lengths are positioned at different positions longitudinally (L1, L2, L3, L4) away from the proximal detector (15). In another (related) embodiment, depicted in FIG. 14B, a portion of a given fiber, such as the distal portion, may have constant gratings created to facilitate high-resolution detection of distal lengthening or shortening of the fiber. Such a constant grating configuration would also be possible with the configurations described in the aforementioned scientific journal article.

Figure 14B:
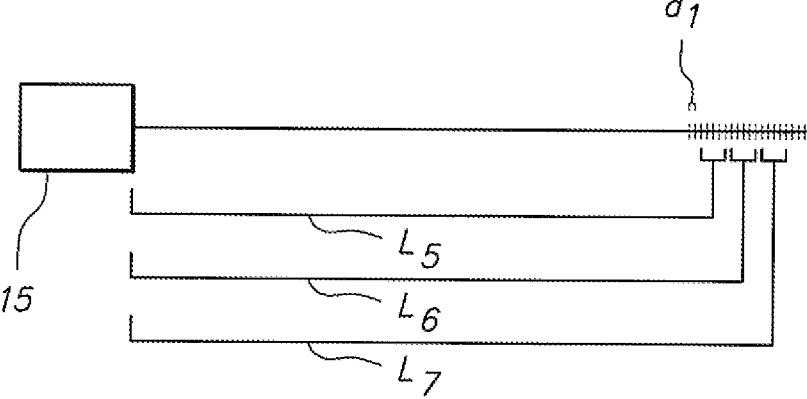
Figure 15A:
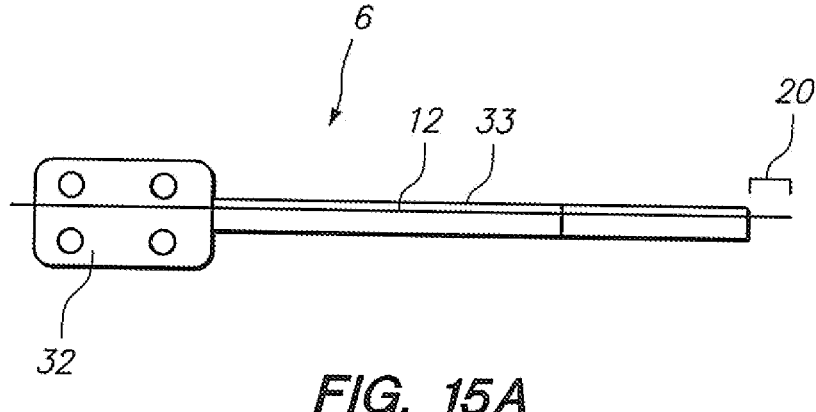
FIGS. 15A-15B illustrate optical fiber sensing system configurations with optical gratings.
Figure 15B:
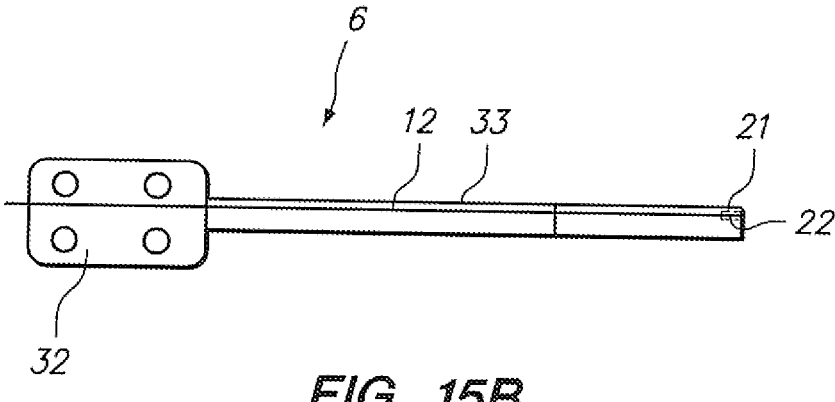

Referring to FIGS. 15A and 15B, temperature may be sensed utilizing Fiber-Bragg grating sensing in embodiments similar to those depicted in FIGS. 13 and 14A-B. Referring to FIG. 15A, a single fiber protrudes beyond the distal tip of the depicted catheter (6) and is unconstrained, or at least less constrained, relative to other surrounding structures so that the portion of the depicted fiber is free to change in length with changes in temperature. With knowledge of the thermal expansion and contraction qualities of the small protruding fiber portion, and one or more Bragg diffraction gratings in such protruding portion, the changes in length may be used to extrapolate changes in temperature and thus be utilized for temperature sensing. Referring to FIG. 15B, a small cavity (21) or lumen may be formed in the distal portion of the catheter body (33) to facilitate free movement of the distal portion (22) of the fiber (12) within such cavity (21) to facilitate temperature sensing distally without the protruding fiber depicted in FIG. 15A.

As will be apparent to those skilled in the art, the fibers in the embodiments depicted herein will provide accurate measurements of localized length changes in portions of the associated catheter or elongate instrument only if such fiber portions are indeed coupled in some manner to the nearby portions of the catheter or elongate instrument. In one embodiment, it is desirable to have the fiber or fibers intimately coupled with or constrained by the surrounding instrument body along the entire length of the instrument, with the exception that one or more fibers may also be utilized to sense temperature distally, and may have an unconstrained portion, as in the two scenarios described in reference to FIGS. 15A and 15B. In one embodiment, for example, each of several deflection-sensing fibers may terminate in a temperature sensing portion, to facilitate position determination and highly localized temperature sensing and comparison at different aspects of the distal tip of an elongate instrument. In another embodiment, the proximal portions of the fiber(s) in the less bendable catheter sections are freely floating within the catheter body, and the more distal/bendable fiber portions intimately coupled, to facilitate high-precision monitoring of the bending within the distal, more flexible portion of the catheter or elongate instrument.

Figure 16A:
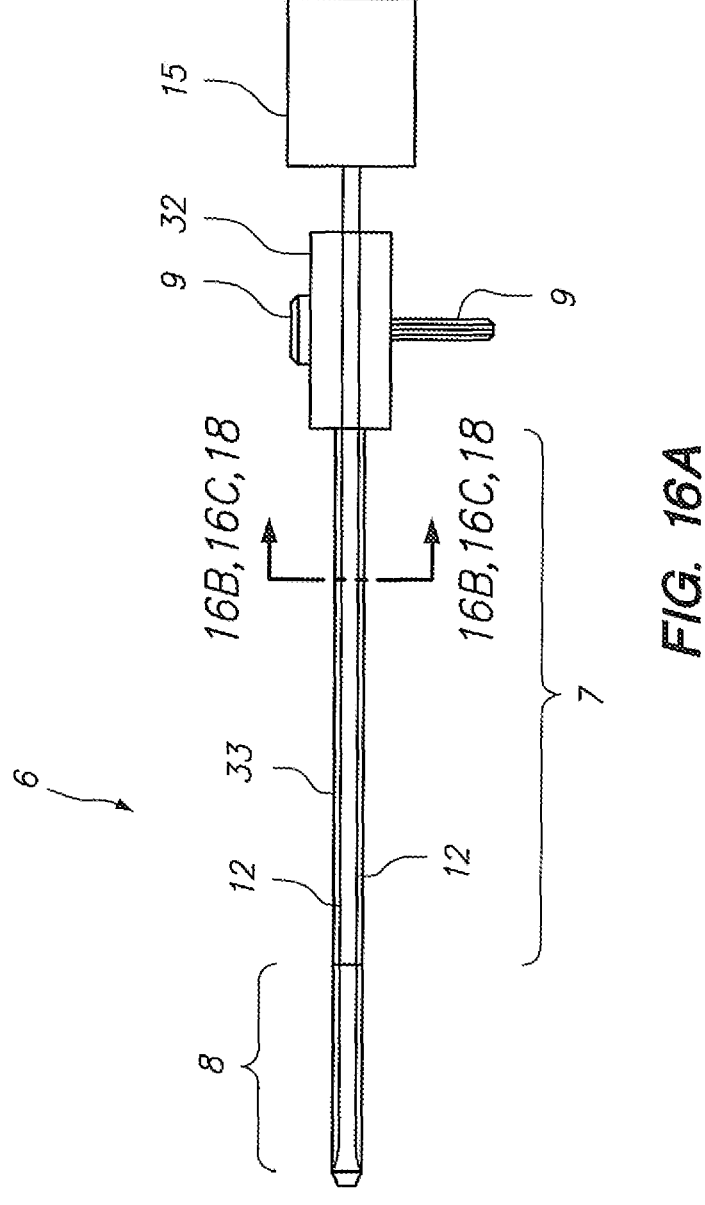
Figure 16B:
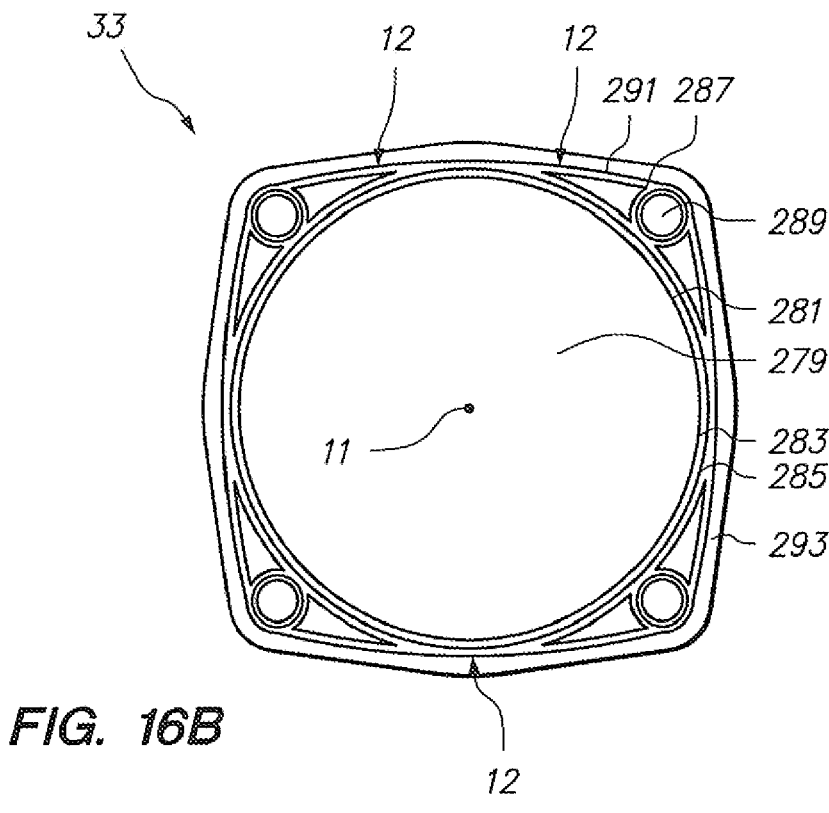
Figure 16C:
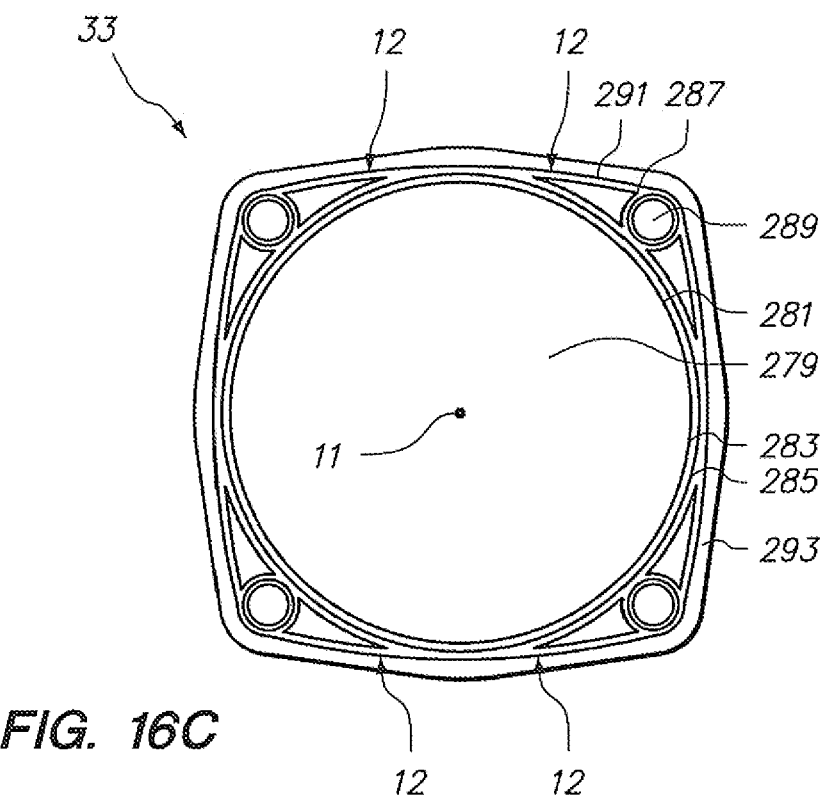
Figure 17A:
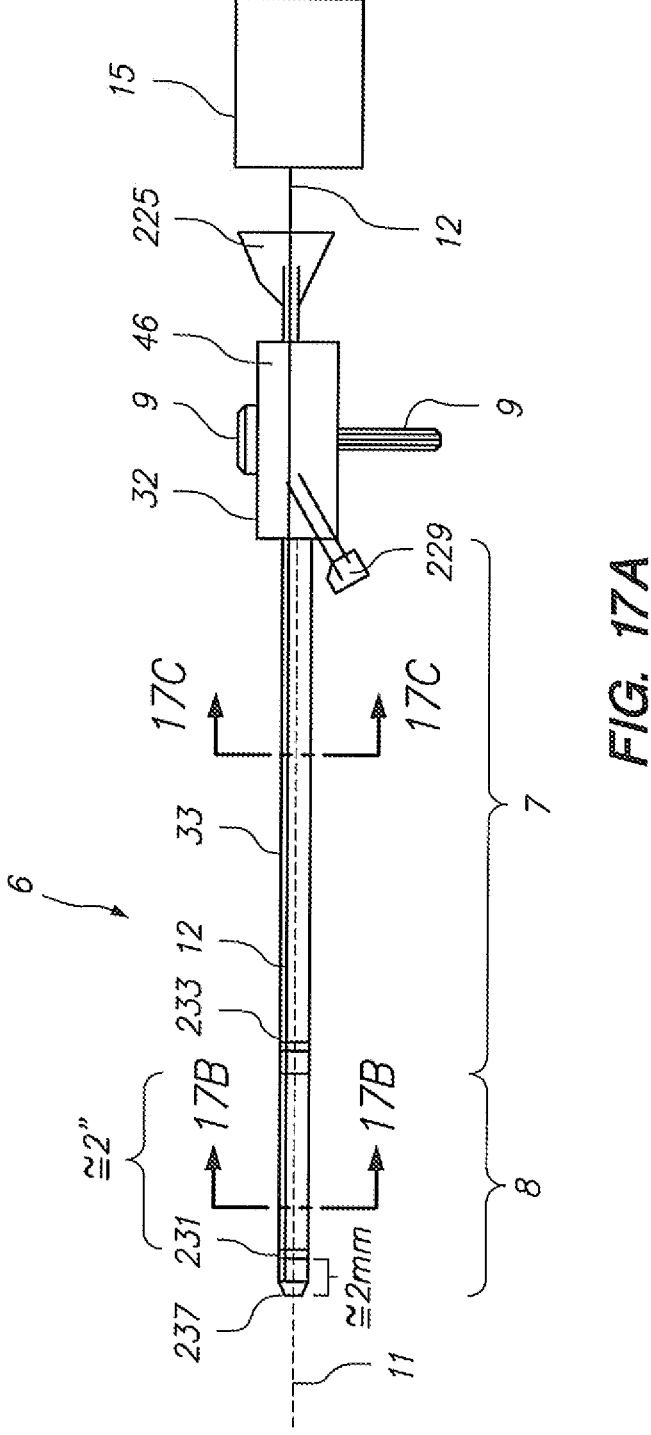
Figure 17B:
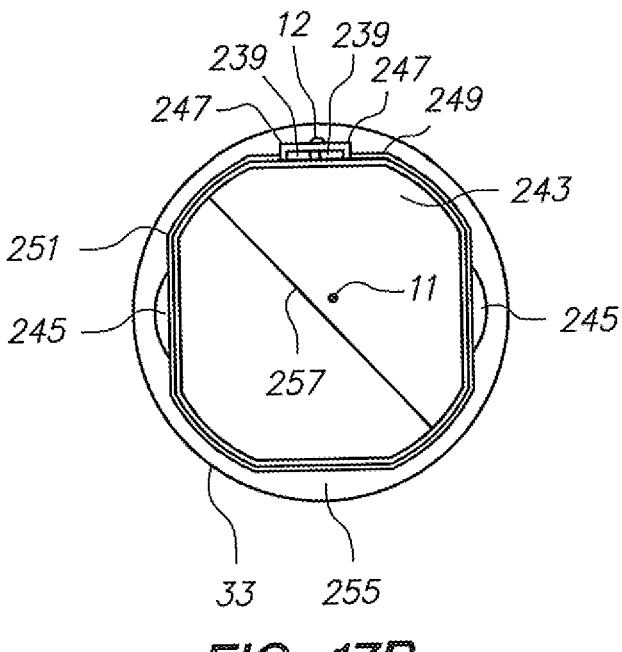
Figure 17C:
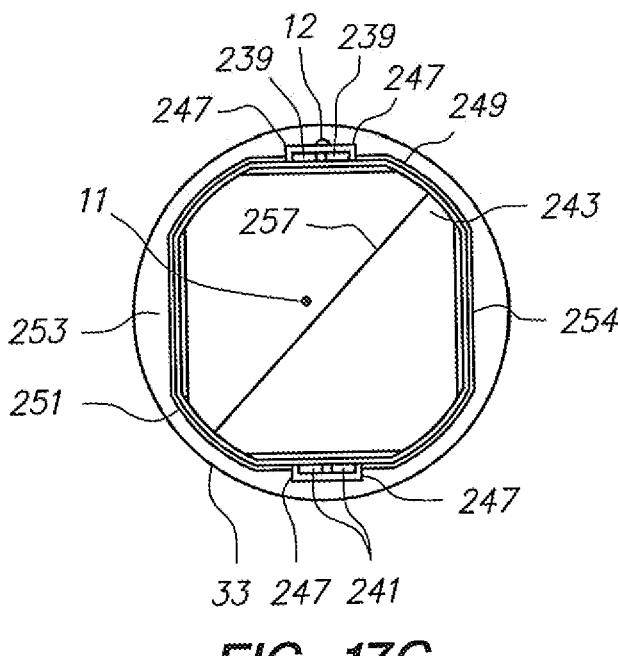
Figure 17D:
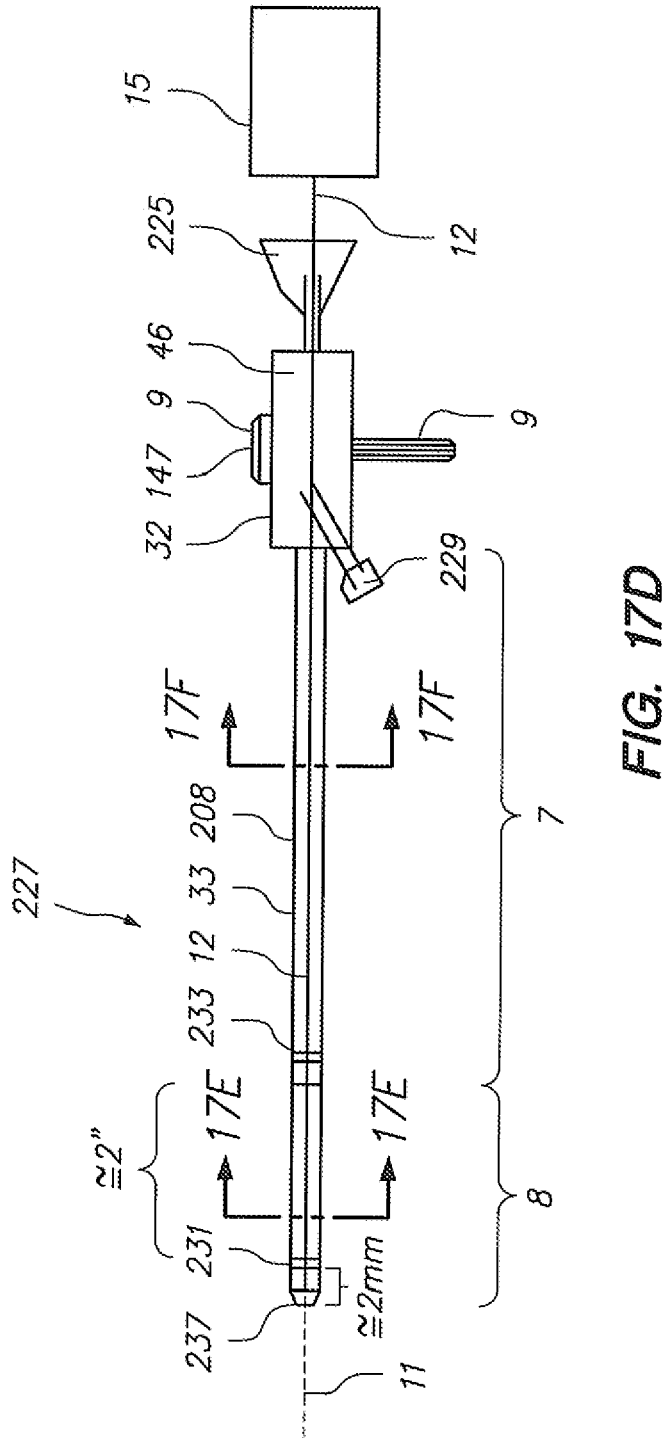
Figures 17E, 17F:
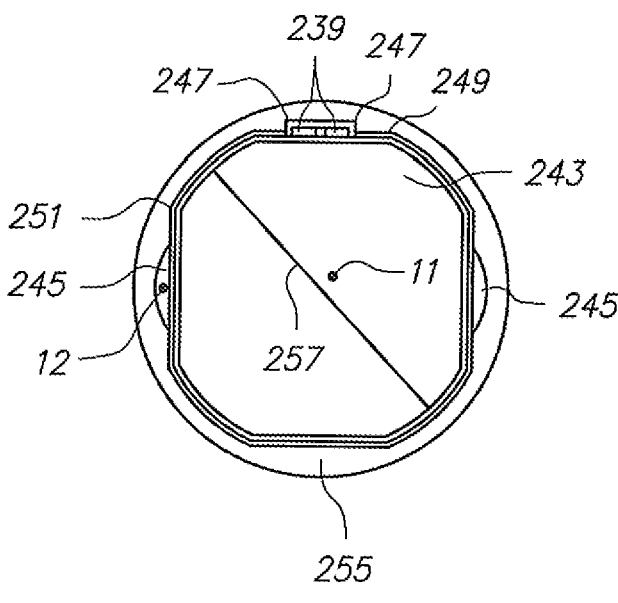

Referring to FIGS. 16A, 16B, and 16D, a catheter-like robotic guide instrument integration embodiment is depicted with three optical fibers (12) and a detector (15) for detecting catheter bending and distal tip position. FIG. 16C depicts and embodiment having four optical fibers (12) for detecting catheter position. FIG. 16D depicts an integration to build such embodiments. As shown in FIG. 16D, in step "E+", mandrels for optical fibers are woven into a braid layer, subsequent to which (step "F") Bragg-grated optical fibers are positioned in the cross sectional space previously occupied by such mandrels (after such mandrels are removed). The geometry of the mandrels relative to the fibers selected to occupy the positions previously occupied by the mandrels after the mandrels are removed preferably is selected based upon the level of constraint desired between the fibers (12) and surrounding catheter body (33) materials. For example, if a highly-constrained relationship, comprising substantial encapsulation, is desired, the mandrels will closely approximate the size of the fibers. If a more loosely-constrained geometric relationship is desired, the mandrels may be sized up to allow for relative motion between the fibers (12) and the catheter body (33) at selected locations, or a tubular member, such as a polyimide or PTFE sleeve, may be inserted subsequent to removal of the mandrel, to provide a "tunnel" with clearance for relative motion of the fiber, and/or simply a layer of protection between the fiber and the materials surrounding it which comprise the catheter or instrument body (33). Similar principles may be applied in embodiments such as those described in reference to FIGS. 17A-17G.

Referring to FIGS. 17A-F, two sheath instrument integrations are depicted, each comprising a single optical fiber (12). FIG. 17G depicts an integration to build such embodiments. As shown in FIG. 16D, in step "B", a mandrel for the optical fiber is placed, subsequent to which (step "K") a Bragg-grated optical fiber is positioned in the cross sectional space previously occupied by the mandrel (after such mandrel is removed).

Figure 18:
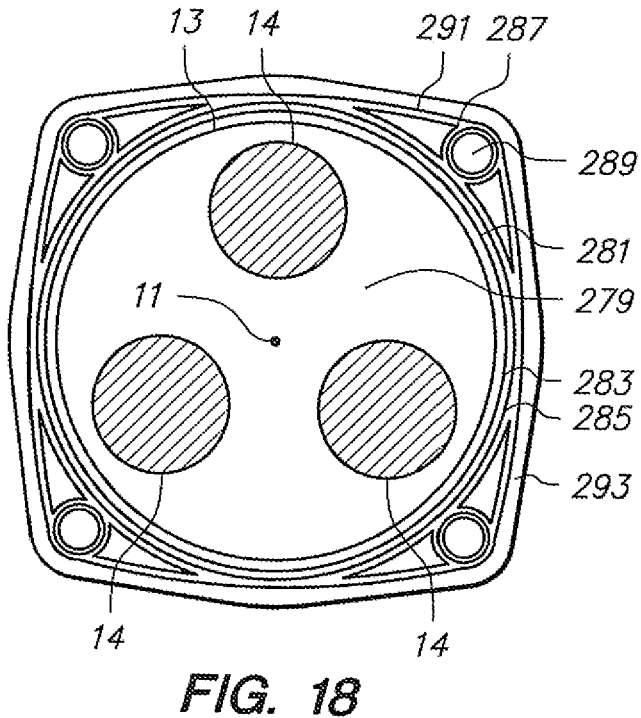
FIG. 18 illustrates a cross sectional view of a bundle of optical fiber within the working lumen of a catheter.

Referring to FIG. 18, in another embodiment, a bundle (13) of fibers (14) may be placed down the working lumen of an off-the-shelf robotic catheter (guide or sheath instrument type) such as that depicted in FIG. 18, and coupled to the catheter in one or more locations, with a selected level of geometric constraint, as described above, to provide 3-D spatial detection.

Tension and compression loads on an elongate instrument may be detected with common mode deflection in radially-outwardly positioned fibers, or with a single fiber along the neutral bending axis. Torque may be detected by sensing common mode additional tension (in addition, for example, to tension and/or compression sensed by, for example, a single fiber coaxial with the neutral bending axis) in outwardly-positioned fibers in configurations such as those depicted in FIGS. 12A-H.

In another embodiment, the tension elements utilized to actuate bending, steering, and/or compression of an elongate instrument, such as a steerable catheter, may comprise optical fibers with gratings, as compared with more conventional metal wires or other structures, and these fiber optic tension elements may be monitored for deflection as they are loaded to induce bending/steering to the instrument. Such monitoring may be used to prevent overstraining of the tension elements, and may also be utilized to detect the position of the instrument as a whole, as per the description above.

Figure 19:
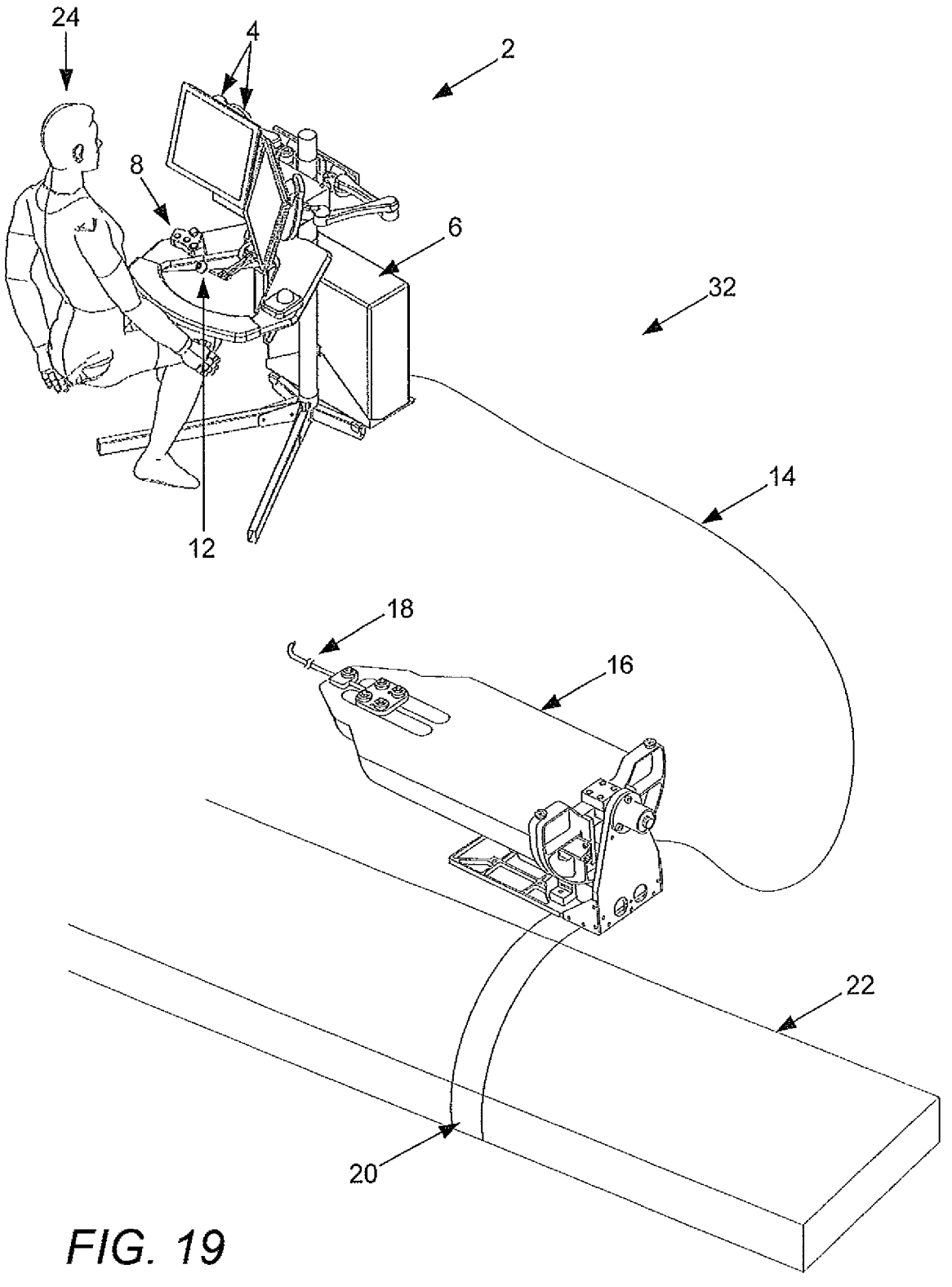
FIG. 19 illustrates a robotic surgical system in accordance with some embodiments.

Referring to FIG. 19, one embodiment of a robotic catheter system 32, includes an operator control station 2 located remotely from an operating table 22, to which a instrument driver 16 and instrument 18 are coupled by a instrument driver mounting brace 20. A communication link 14 transfers signals between the operator control station 2 and instrument driver 16. The instrument driver mounting brace 20 of the depicted embodiment is a relatively simple, arcuate-shaped structural member configured to position the instrument driver 16 above a patient (not shown) lying on the table 22.

Figures 20, 21:
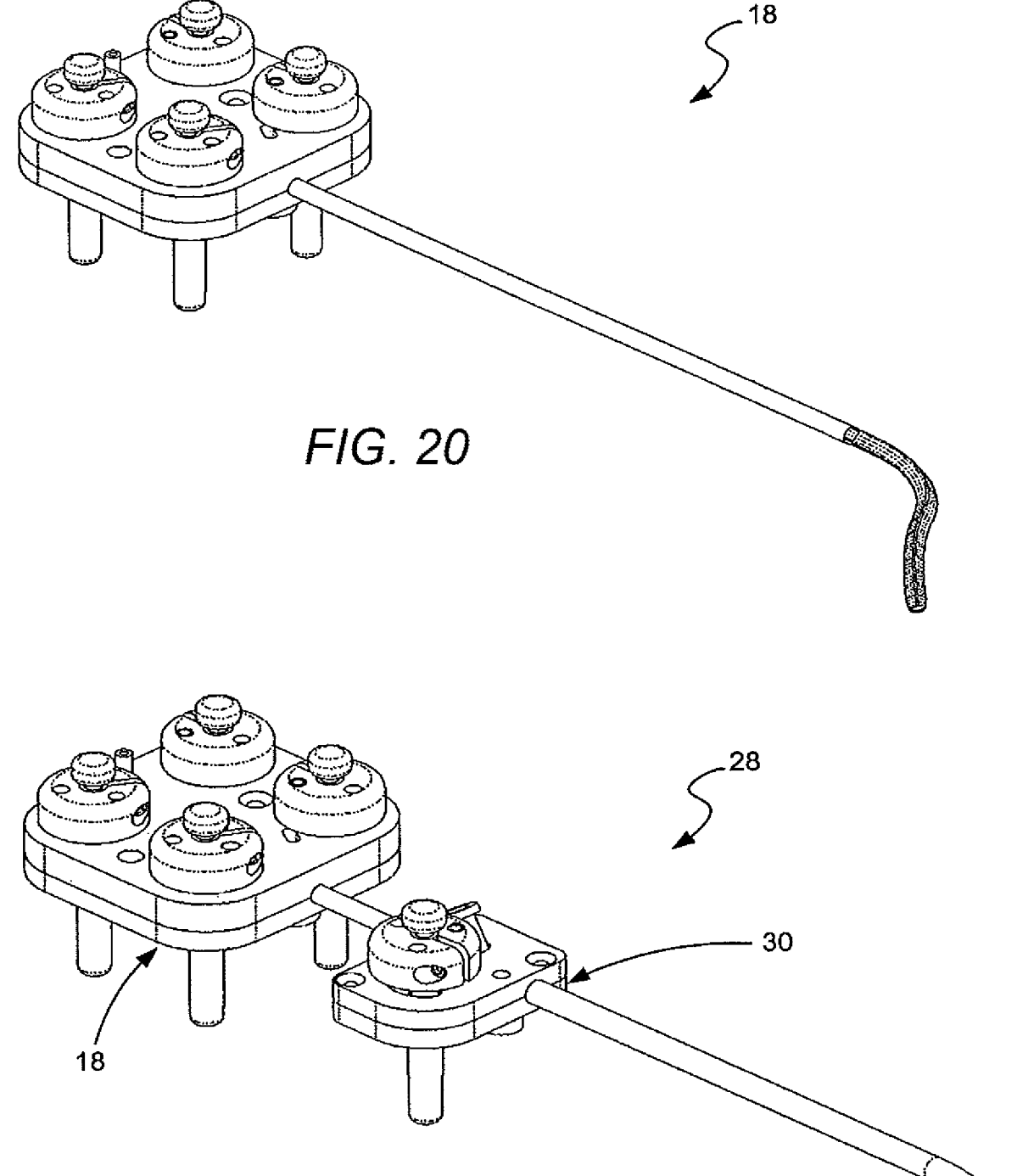
FIG. 20 illustrates an isometric view of an instrument having a guide catheter in accordance with some embodiments.
FIG. 21 illustrates an isometric view of the instrument of FIG. 20, showing the instrument coupled to a sheath instrument in accordance with some embodiments.

FIGS. 20 and 21 depict isometric views of respective embodiments of instruments configured for use with an embodiment of the instrument driver (16), such as that depicted in FIG. 19. FIG. 20 depicts an instrument (18) embodiment without an associated coaxial sheath coupled at its midsection. FIG. 21 depicts a set of two instruments (28), combining an embodiment like that of FIG. 20 with a coaxially coupled and independently controllable sheath instrument (30). To distinguish the non-sheath instrument (18) from the sheath instrument (30) in the context of this disclosure, the "non-sheath" instrument may also be termed the "guide" instrument (18).

Figure 22:
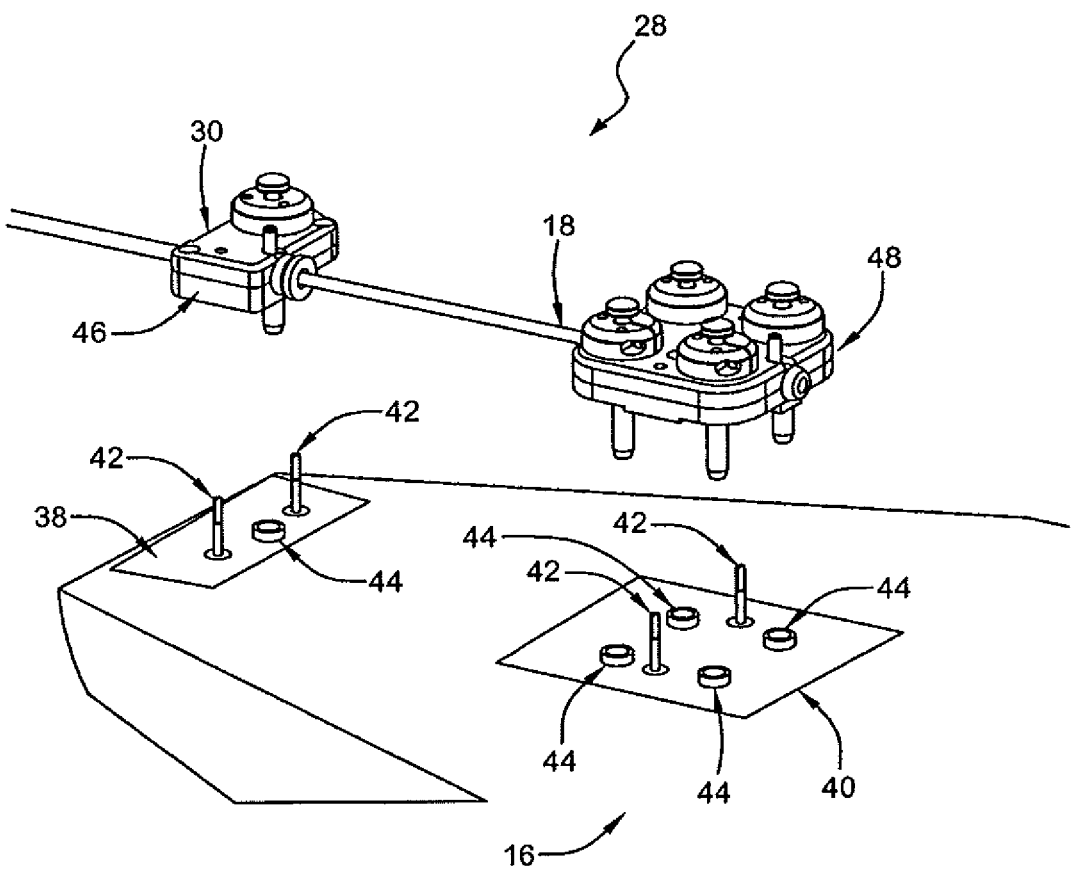
FIG. 22 illustrates an isometric view of a set of instruments for use with an instrument driver in accordance with some embodiments.

Referring to FIG. 22, a set of instruments (28), such as those in FIG. 21, is depicted adjacent an instrument driver (16) to illustrate an exemplary mounting scheme. The sheath instrument (30) may be coupled to the depicted instrument driver (16) at a sheath instrument interface surface (38) having two mounting pins (42) and one interface socket (44) by sliding the sheath instrument base (46) over the pins (42). Similarly, and preferably simultaneously, the guide instrument (18) base (48) may be positioned upon the guide instrument interface surface (40) by aligning the two mounting pins (42) with alignment holes in the guide instrument base (48). As will be appreciated, further steps may be required to lock the instruments (18, 30) into place upon the instrument driver (16).

Figure 23:
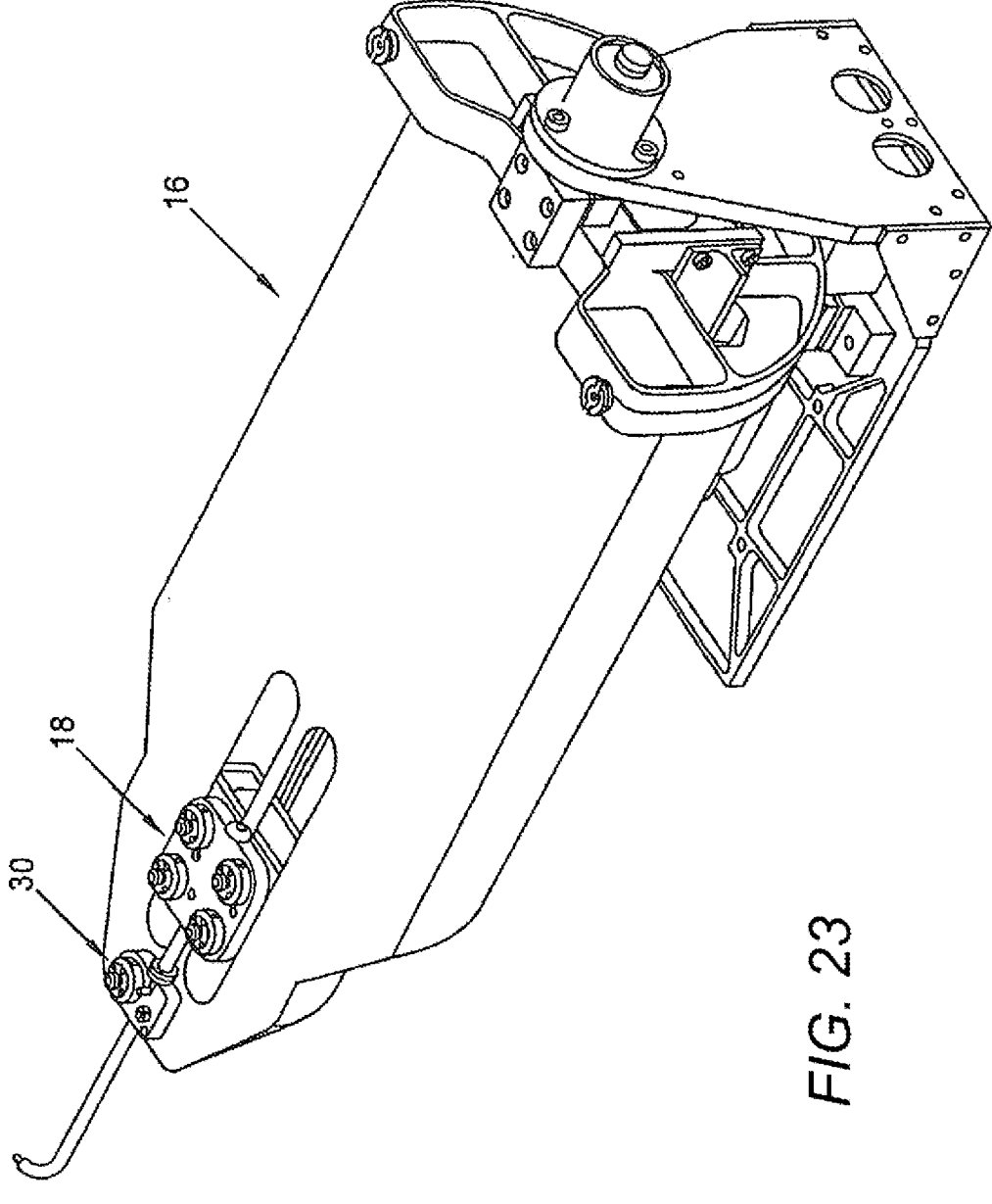
FIG. 23 illustrates an isometric view of an instrument driver coupled with a steerable guide instrument and a steerable sheath instrument in accordance with some embodiments.
Figure 24:
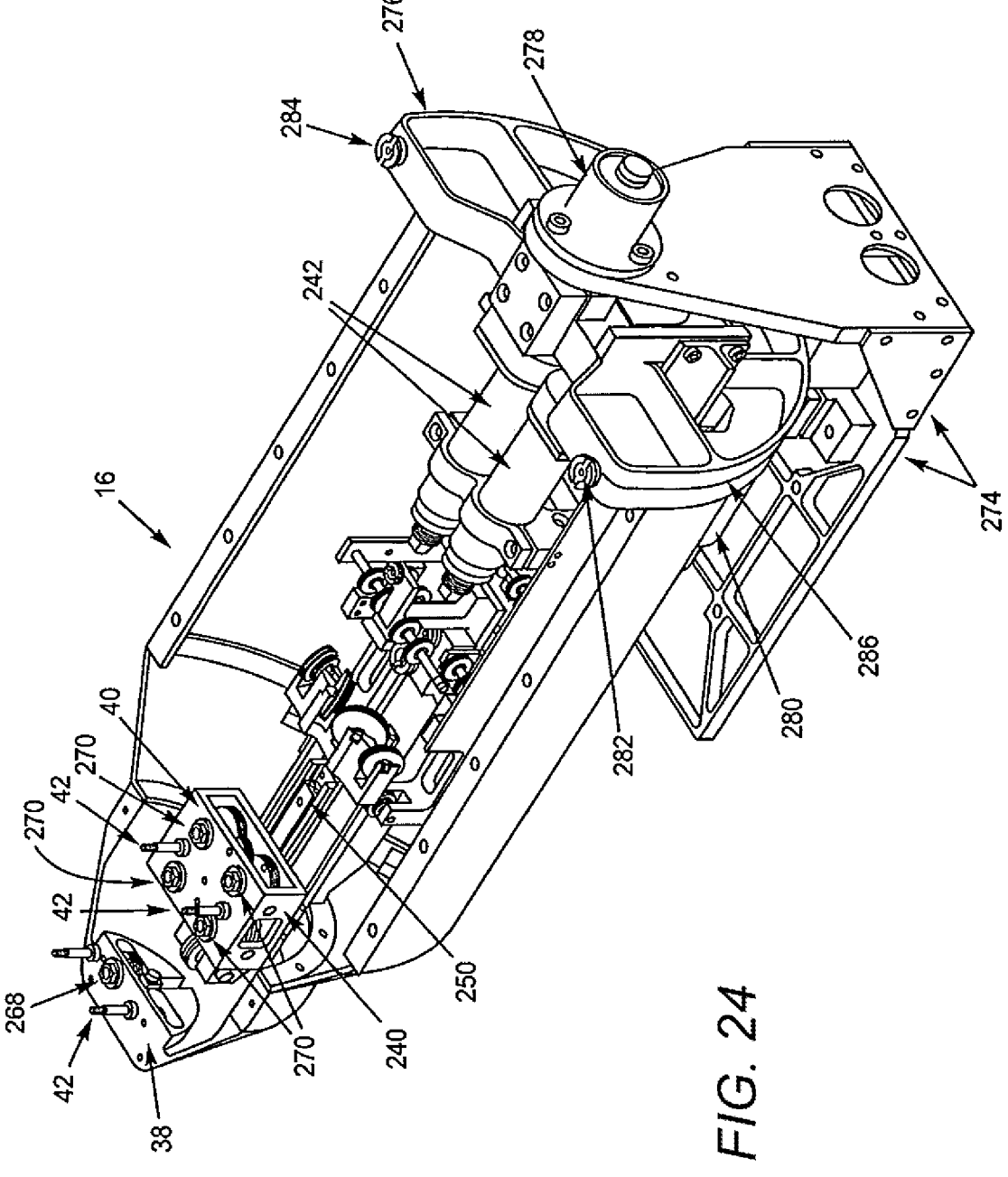
FIG. 24 illustrates components of the instrument driver of FIG. 23 in accordance with some embodiments.

In FIG. 23, an instrument driver (16) is depicted as interfaced with a steerable guide instrument (18) and a steerable sheath instrument (30). FIG. 24 depicts an embodiment of the instrument driver (16), in which the sheath instrument interface surface (38) remains stationary, and requires only a simple motor actuation in order for a sheath to be steered using an interfaced control element via a control element interface assembly (132). This may be accomplished with a simple cable loop about a sheath socket drive pulley (272) and a capstan pulley (not shown), which is fastened to a motor, similar to the two upper motors (242) (visible in FIG. 24). The drive motor for the sheath socket drive schema is hidden under the linear bearing interface assembly.

The drive schema for the four guide instrument interface sockets (270) is more complicated, due in part to the fact that they are coupled to a carriage (240) configured to move linearly along a linear bearing interface (250) to provide for motor-driven insertion of a guide instrument toward the patient relative to the instrument driver, hospital table, and sheath instrument. Various conventional cable termination and routing techniques are utilized to accomplish a preferably high-density instrument driver structure with the carriage (240) mounted forward of the motors for a lower profile patient-side interface.

Figure 25:
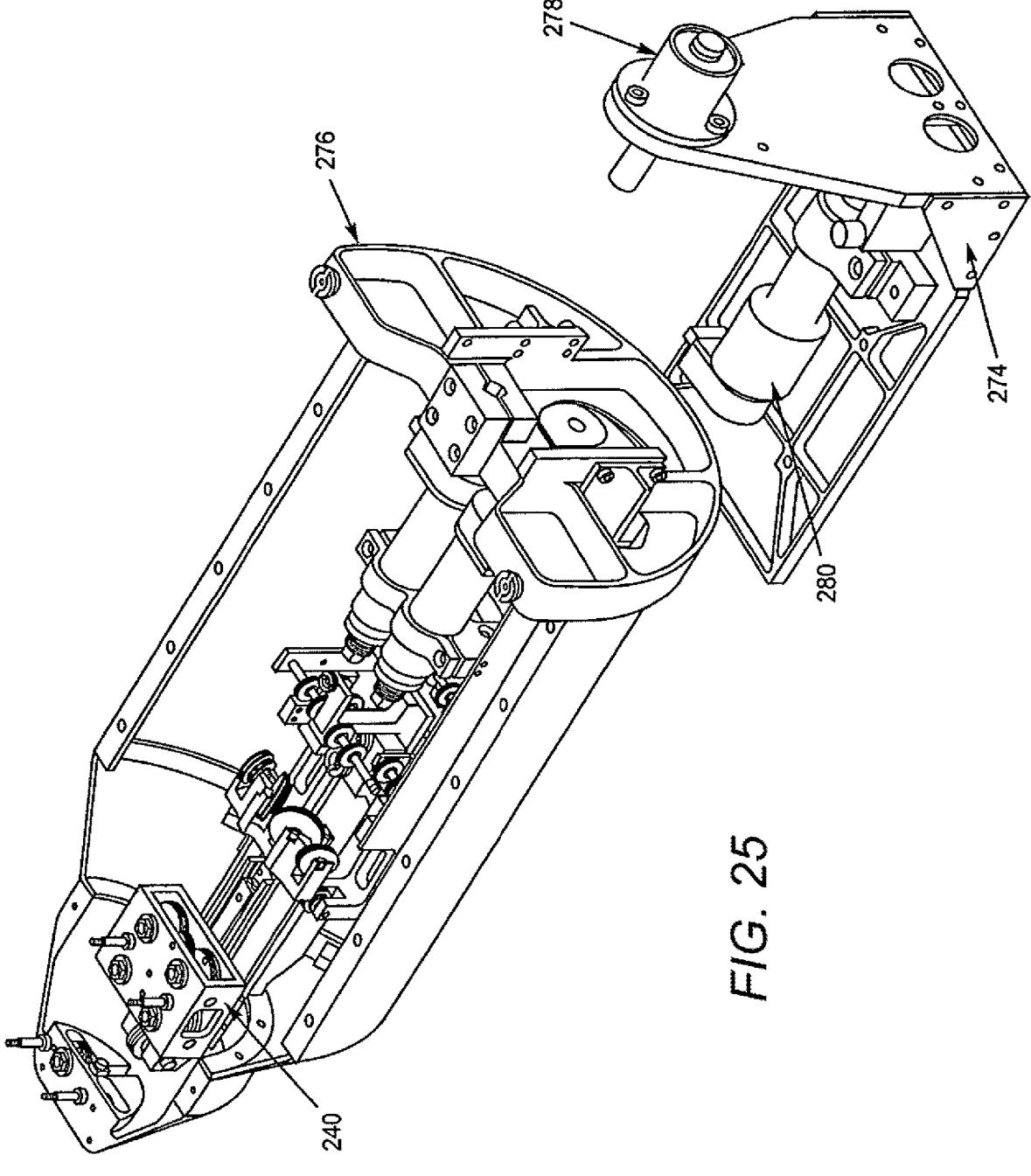
FIG. 25 illustrates the instrument driver of FIG. 24, showing the instrument driver having a roll motor.

Still referring to FIG. 24, the instrument driver (16) is rotatably mounted to an instrument driver base (274), which is configured to interface with an instrument driver mounting brace (not shown), such as that depicted in FIG. 19, or a movable setup joint construct (not shown). Rotation between the instrument driver base (274) and an instrument driver base plate (276) to which it is coupled is facilitated by a heavy-duty flanged bearing structure (278). The flanged bearing structure (278) is configured to allow rotation of the body of the instrument driver (16) about an axis approximately coincident with the longitudinal axis of a guide instrument (not shown) when the guide instrument is mounted upon the instrument driver (16) in a neutral position. This rotation preferably is automated or powered by a roll motor (280) and a simple roll cable loop (286), which extends around portions of the instrument driver base plate and terminates as depicted (282, 284). Alternatively, roll rotation may be manually actuated and locked into place with a conventional clamping mechanism. The roll motor (280) position is more easily visible in FIG. 25.

Figure 26:
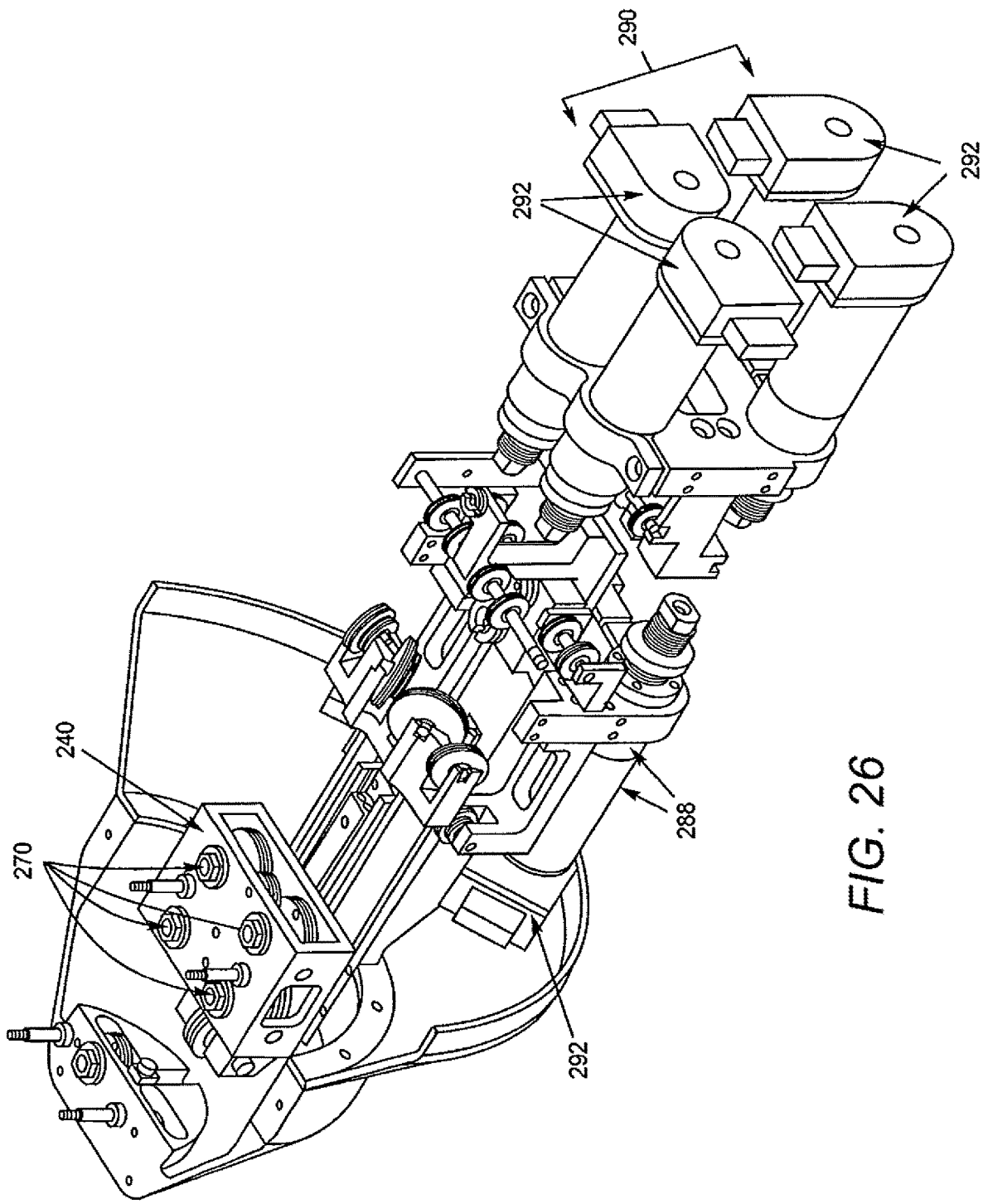
FIG. 26 illustrates components of an instrument driver in accordance with some embodiments, showing the instrument driver having four motors.

FIG. 26 illustrates another embodiment of an instrument driver, including a group of four motors (290). Each motor (290) has an associated high-precision encoder for controls purposes and being configured to drive one of the four guide instrument interface sockets (270), at one end of the instrument driver. Another group of two motors (one hidden, one visible—288) with encoders (292) are configured to drive insertion of the carriage (240) and the sheath instrument interface socket (268).

Figure 27:
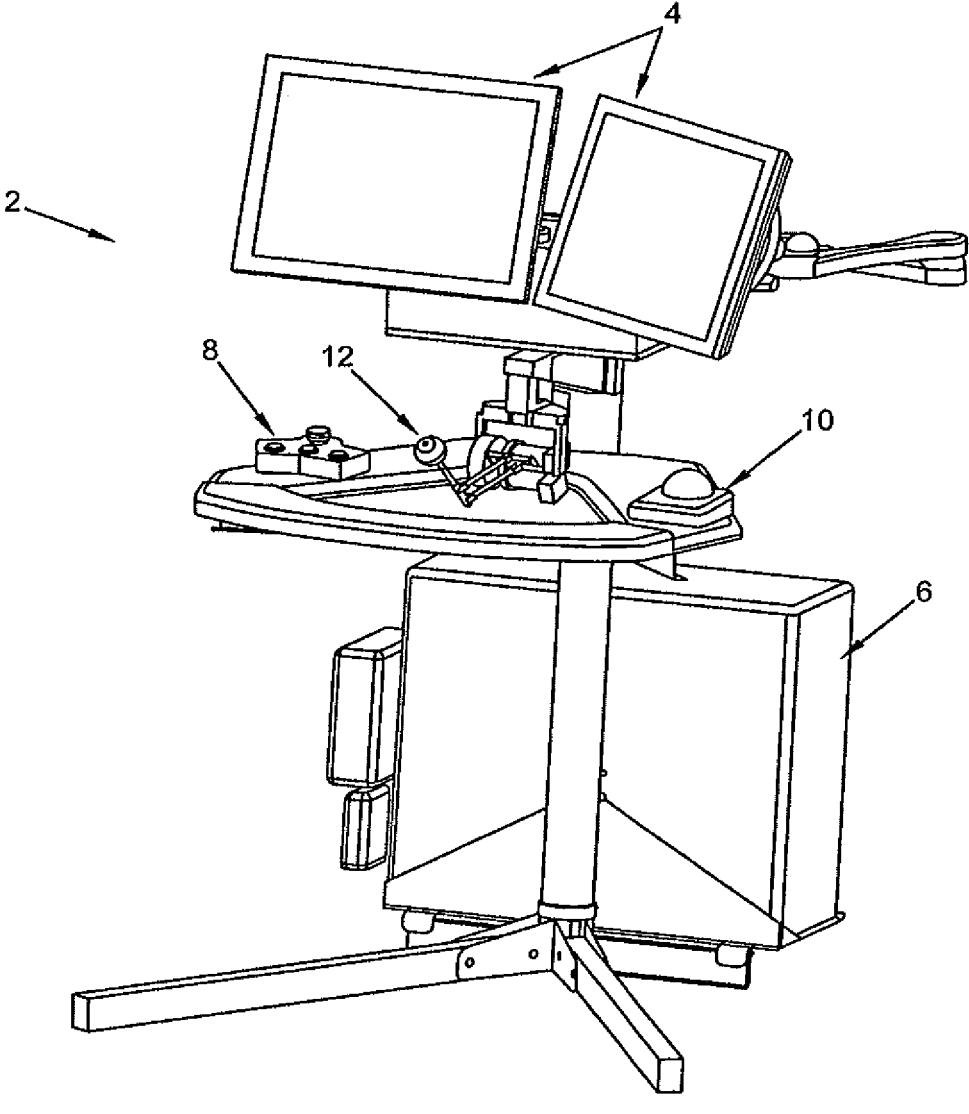
FIG. 27 illustrates an operator control station in accordance with some embodiments.

Referring to FIG. 27, an operator control station is depicted showing a control button console (8), a computer (6), a computer control interface (10), such as a mouse, a visual display system (4) and a master input device (12). In addition to "buttons" on the button console (8) footswitches and other known user control interfaces may be utilized to provide an operator interface with the system controls.

Figure 28A:
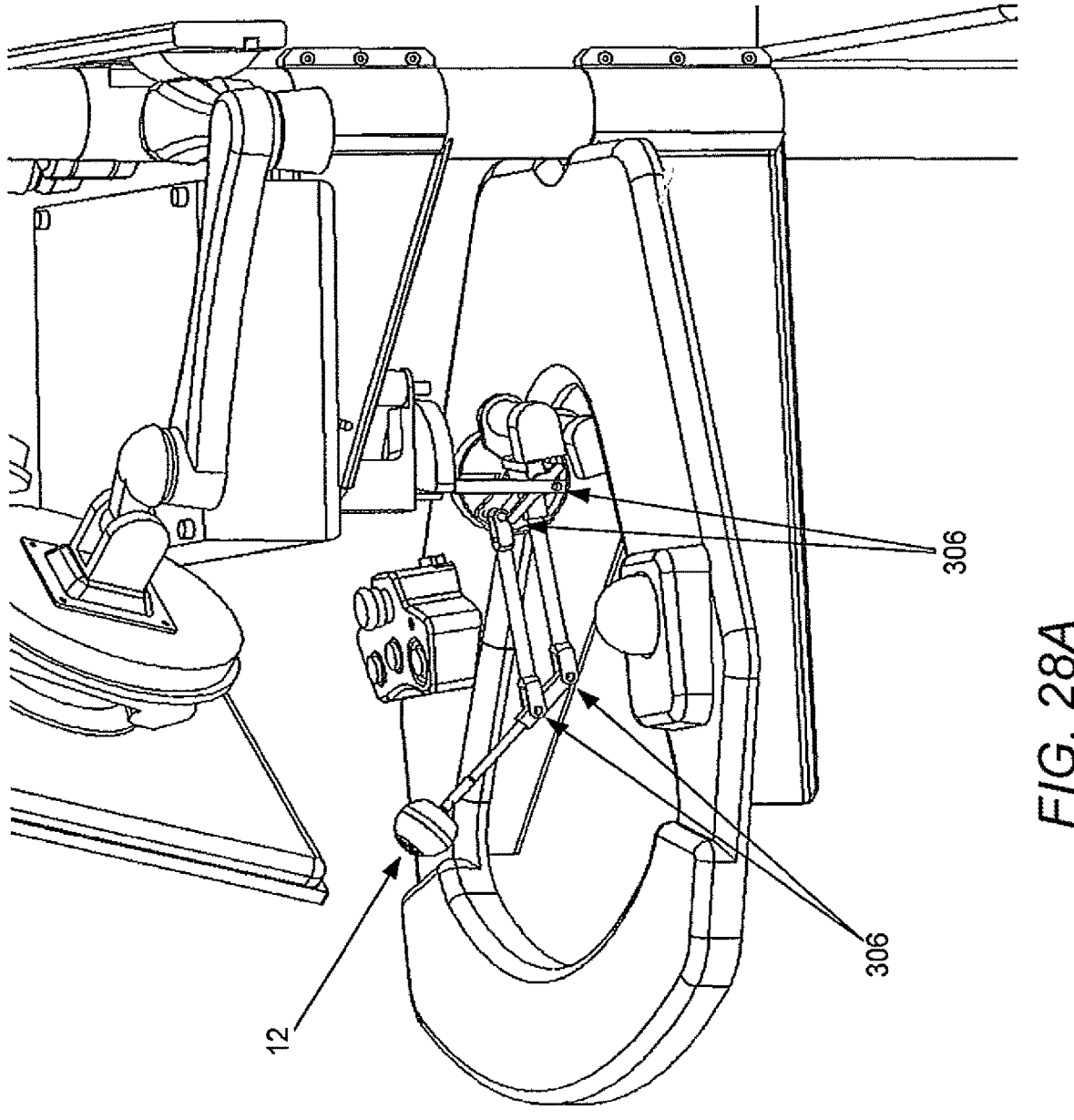
FIG. 28A illustrates a master input device in accordance with some embodiments.

Referring to FIG. 28A, in one embodiment, the master input device (12) is a multi-degree-of-freedom device having multiple joints and associated encoders (306). An operator interface (217) is configured for comfortable interfacing with the human fingers. The depicted embodiment of the operator interface (217) is substantially spherical. Further, the master input device may have integrated haptics capability for providing tactile feedback to the user.

Figure 28B:
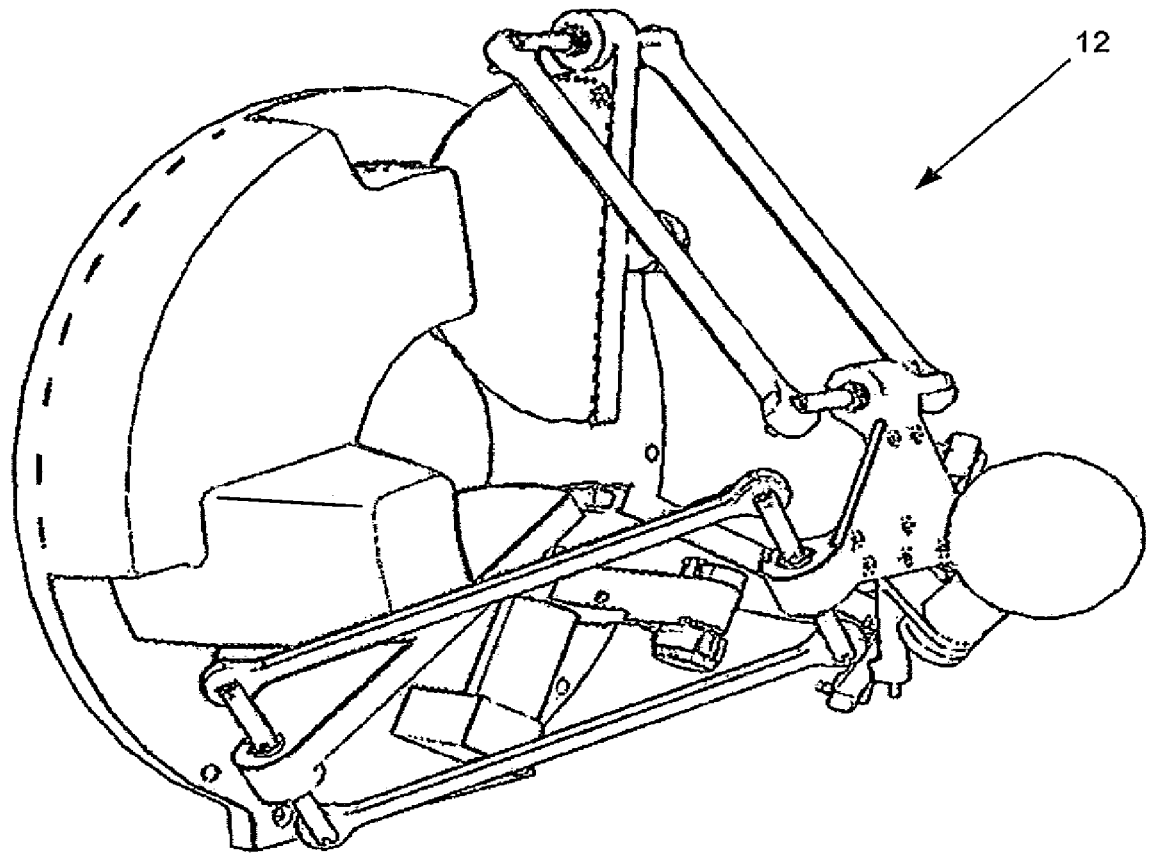
FIG. 28B illustrates a master input device in accordance with other embodiments.

Another embodiment of a master input device (12) is depicted in FIG. 28B having a similarly-shaped operator interface (217). Suitable master input devices are available from manufacturers such as Sensible Devices Corporation under the trade name "Phanto™", or Force Dimension under the trade name "Omega™". In one embodiment featuring an Omega-type master input device, the motors of the master input device are utilized for gravity compensation. In other words, when the operator lets go of the master input device with his hands, the master input device is configured to stay in position, or hover around the point at which is was left, or another predetermined point, without gravity taking the handle of the master input device to the portion of the master input device's range of motion closest to the center of the earth. In another embodiment, haptic feedback is utilized to provide feedback to the operator that he has reached the limits of the pertinent instrument workspace. In another embodiment, haptic feedback is utilized to provide feedback to the operator that he has reached the limits of the subject tissue workspace when such workspace has been registered to the workspace of the instrument (i.e., should the operator be navigating a tool such as an ablation tip with a guide instrument through a 3-D model of a heart imported, for example, from CT data of an actual heart, the master input device is configured to provide haptic feedback to the operator that he has reached a wall or other structure of the heart as per the data of the 3-D model, and therefore help prevent the operator from driving the tool through such wall or structure without at least feeling the wall or structure through the master input device). In another embodiment, contact sensing technologies configured to detect contact between an instrument and tissue may be utilized in conjunction with the haptic capability of the master input device to signal the operator that the instrument is indeed in contact with tissue.

Referring to FIGS. 29-32, the basic kinematics of a catheter with four control elements is reviewed.

Figures 29A, 29B:
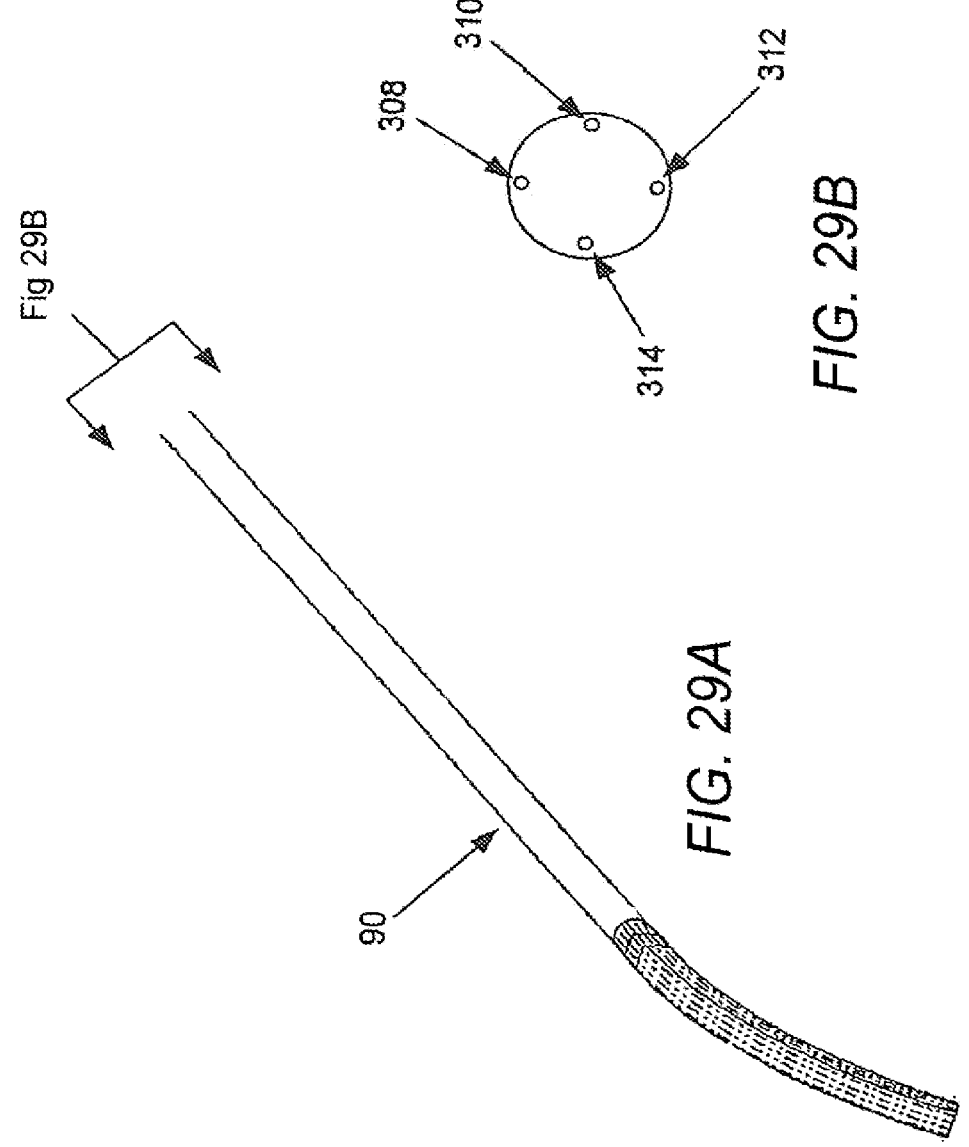
Figures 30A, 30B:
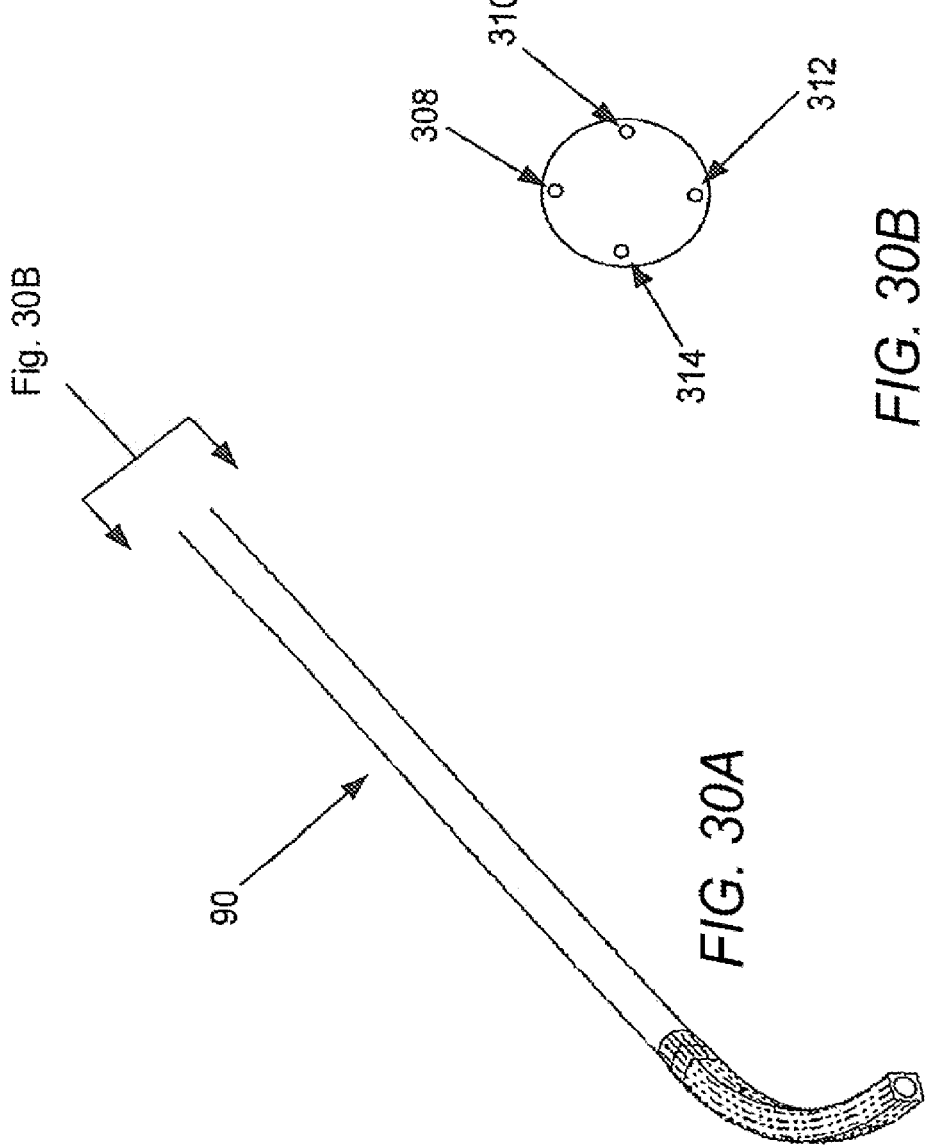
FIG. 30A illustrating a catheter with tension placed upon a left control element, and FIG. 30B illustrating an end view of the catheter of FIG. 30A.
Figures 31A, 31B:
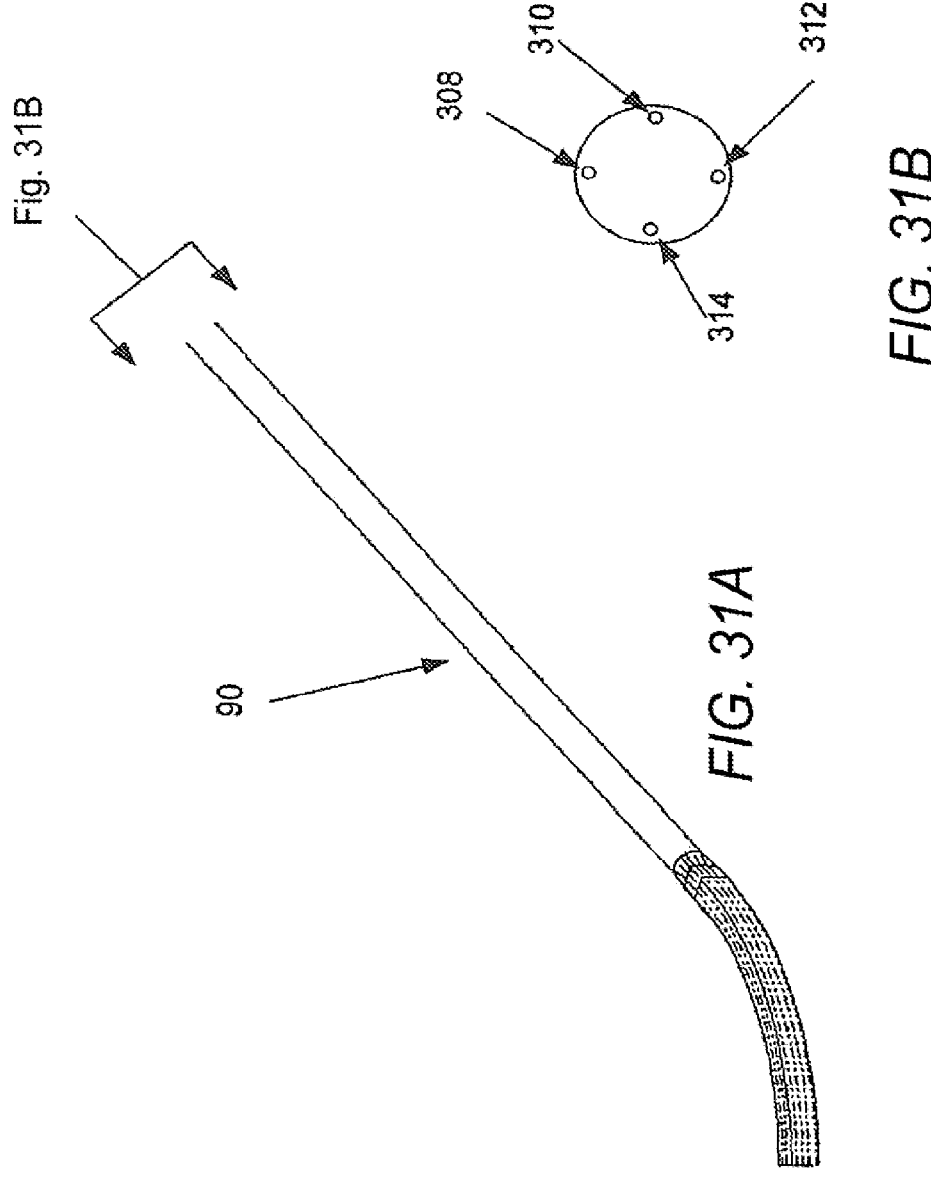
FIG. 31A illustrating a catheter with tension placed upon a right control element, and FIG. 31B illustrating an end view of the catheter of FIG. 31A.
Figures 32A, 32B:
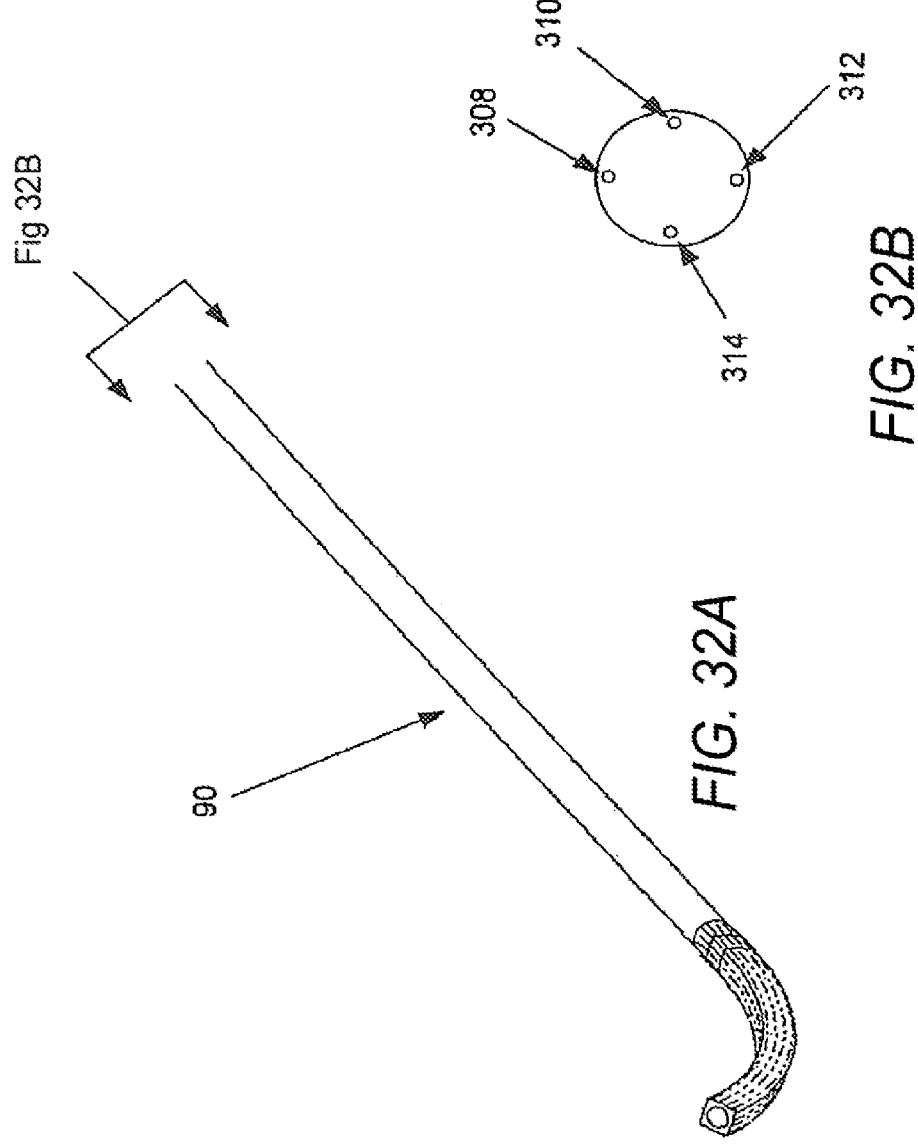
FIG. 32A illustrating a catheter with tension placed upon a top control element, and FIG. 32B illustrating an end view of the catheter of FIG. 32A.

Referring to FIGS. 29A-B, as tension is placed only upon the bottom control element (312), the catheter bends downward, as shown in FIG. 29A. Similarly, pulling the left control element (314) in FIGS. 30A-B bends the catheter left, pulling the right control element (310) in FIGS. 31A-B bends the catheter right, and pulling the top control element (308) in FIGS. 32A-B bends the catheter up. As will be apparent to those skilled in the art, well-known combinations of applied tension about the various control elements results in a variety of bending configurations at the tip of the catheter member (90). One of the challenges in accurately controlling a catheter or similar elongate member with tension control elements is the retention of tension in control elements, which may not be the subject of the majority of the tension loading applied in a particular desired bending configuration. If a system or instrument is controlled with various levels of tension, then losing tension, or having a control element in a slack configuration, can result in an unfavorable control scenario.

Figures 33A, 33B, 33C, 33D, 33E:
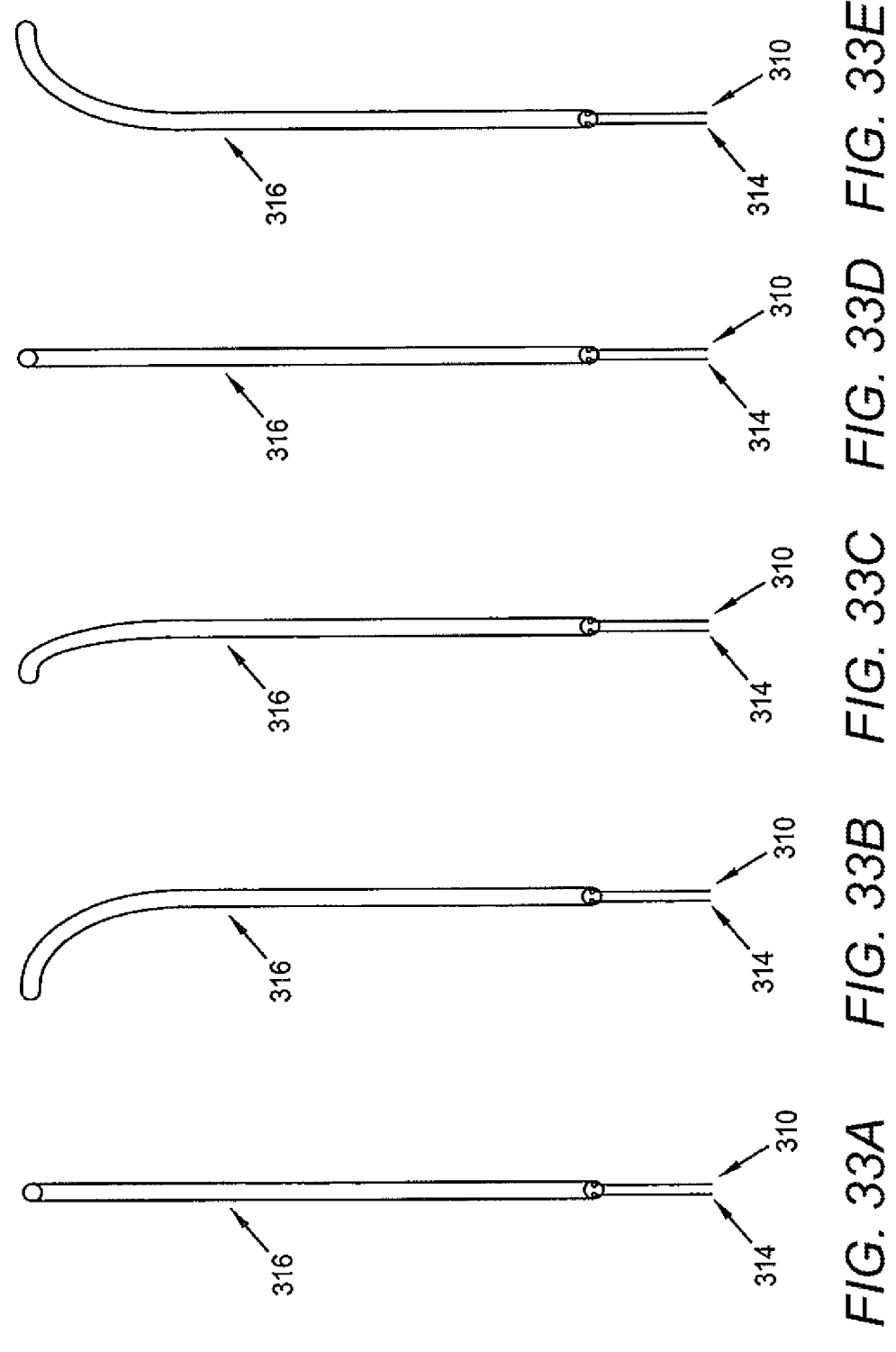
FIGS. 33A-33E illustrates different bending configurations of a catheter in accordance with various embodiments.

Referring to FIGS. 33A-E, a simple scenario is useful in demonstrating this notion. As shown in FIG. 33A, a simple catheter (316) steered with two control elements (314, 310) is depicted in a neutral position. If the left control element (314) is placed into tension greater than the tension, if any, which the right control element (310) experiences, the catheter (316) bends to the left, as shown in FIG. 33B. If a change of direction is desired, this paradigm needs to reverse, and the tension in the right control element (310) needs to overcome that in the left control element (314). At the point of a reversal of direction like this, where the tension balance changes from left to right, without slack or tension control, the right most control element (314) may gather slack which needs to be taken up before precise control can be reestablished. Subsequent to a "reeling in" of slack which may be present, the catheter (316) may be pulled in the opposite direction, as depicted in FIGS. 33C-E, without another slack issue from a controls perspective until a subsequent change in direction.

The above-described instrument embodiments present various techniques for managing tension control in various guide instrument systems having between two and four control elements. For example, in one set of embodiments, tension may be controlled with active independent tensioning of each control element in the pertinent guide catheter via independent control element interface assemblies (132) associated with independently-controlled guide instrument interface sockets (270) on the instrument driver (16). Thus, tension may be managed by independently actuating each of the control element interface assemblies (132) in a four-control-element embodiment, a three-control-element embodiment, or a two-control-element embodiment.

In another set of embodiments, tension may be controlled with active independent tensioning with a split carriage design. For example, a split carriage with two independent linearly movable portions, may be utilized to actively and independently tension each of the two control element interface assemblies (132), each of which is associated with two dimensions of a given degree of freedom. For example, one interface assembly can include + and –pitch, with + and –yaw on the other interface assembly, where slack or tension control provided for pitch by one of the linearly movable portions (302) of the split carriage (296), and slack or tension control provided for yaw by the other linearly movable portion (302) of the split carriage (296).

Similarly, slack or tension control for a single degree of freedom, such as yaw or pitch, may be provided by a single-sided split carriage design, with the exception that only one linearly movable portion would be required to actively tension the single control element interface assembly of an instrument.

In another set of embodiments, tensioning may be controlled with spring-loaded idlers configured to keep the associated control elements out of slack. The control elements preferably are pre-tensioned in each embodiment to prevent slack and provide predictable performance. Indeed, in yet another set of embodiments, pre-tensioning may form the main source of tension management. In the case of embodiments only having pre-tensioning or spring-loaded idler tensioning, the control system may need to be configured to reel in bits of slack at certain transition points in catheter bending, such as described above in relation to FIGS. 33A and 33B.

To accurately coordinate and control actuations of various motors within an instrument driver from a remote operator control station such as that depicted in FIG. 19, an advanced computerized control and visualization system is preferred. While the control system embodiments that follow are described in reference to a particular control systems interface, namely the SimuLink™ and XPC™ control interfaces available from The Mathworks Inc., and PC-based computerized hardware configurations, many other configurations may be utilized, including various pieces of specialized hardware, in place of more flexible software controls running on PC-based systems.

Figure 34:
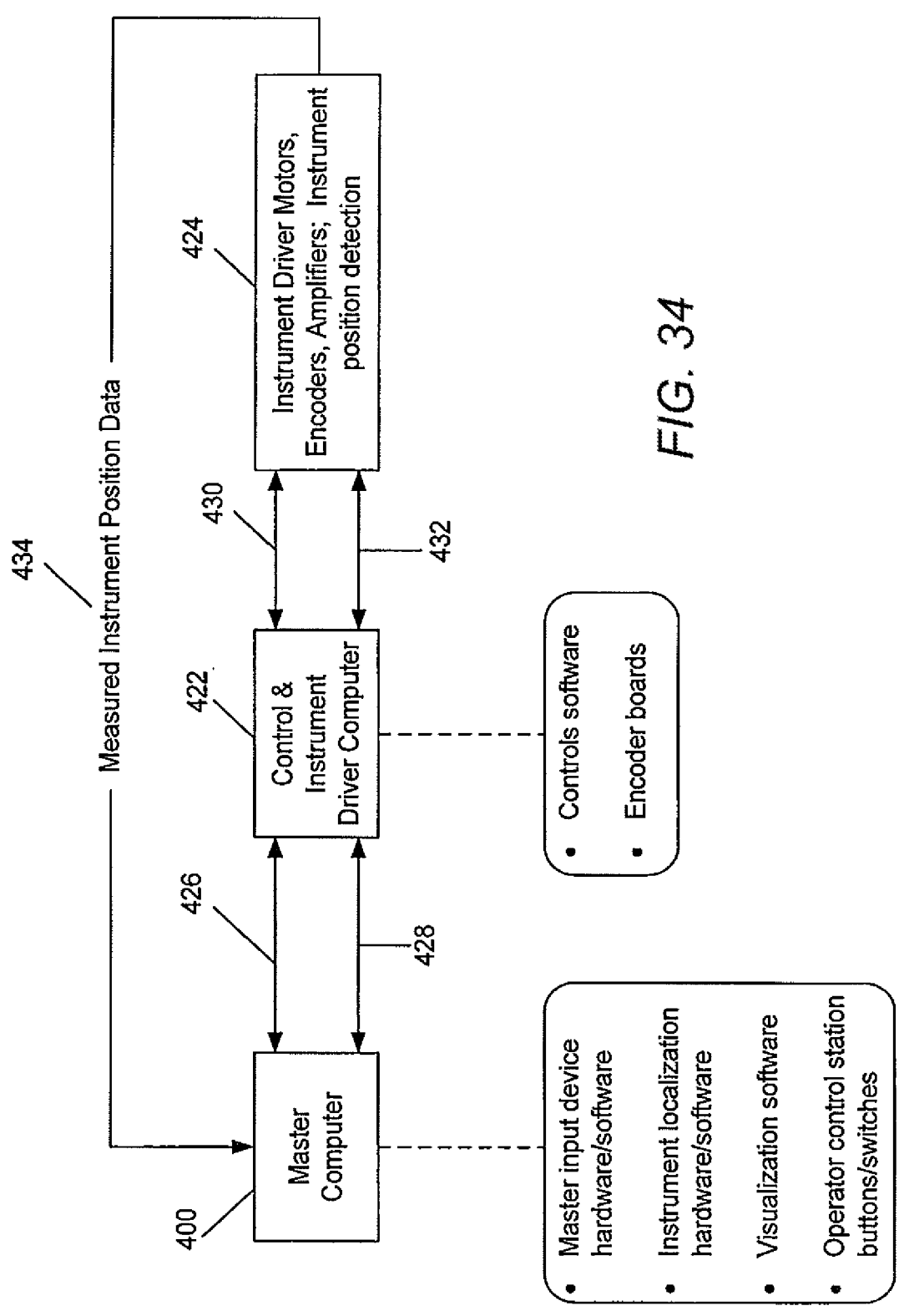
FIG. 34 illustrates a control system in accordance with some embodiments.

Referring to FIG. 34, an overview of an embodiment of a controls system flow is depicted. A master computer (400) running master input device software, visualization software, instrument localization software, and software to interface with operator control station buttons and/or switches is depicted: In one embodiment, the master input device software is a proprietary module packaged with an off-the-shelf master input device system, such as the Phantom™ from Sensible Devices Corporation, which is configured to communicate with the Phantom™ hardware at a relatively high frequency as prescribed by the manufacturer. Other suitable master input devices, such as that (12) depicted in FIG. 28B are available from suppliers such as Force Dimension of Lausanne, Switzerland. The master input device (12) may also have haptics capability to facilitate feedback to the operator, and the software modules pertinent to such functionality may also be operated on the master computer (400). Preferred embodiments of haptics feedback to the operator are discussed in further detail below.

The term "localization" is used in the art in reference to systems for determining and/or monitoring the position of objects, such as medical instruments, in a reference coordinate system. In one embodiment, the instrument localization software is a proprietary module packaged with an off-the-shelf or custom instrument position tracking system, such as those available from Ascension Technology Corporation, Biosense Webster, Inc., Endocardial Solutions, Inc., Boston Scientific (EP Technologies), Medtronic, Inc., and others. Such systems may be capable of providing not only real-time or near real-time positional information, such as X-Y-Z coordinates in a Cartesian coordinate system, but also orientation information relative to a given coordinate axis or system. For example, such systems can employ an electromagnetic based system (e.g., using electromagnetic coils inside a device or catheter body). Information regarding one electromagnetic based system can be found on: http://www.biosensewebster.com/products/navigation/carto3.aspx. The relevant portions of which are incorporated by reference.

Figure 35B:
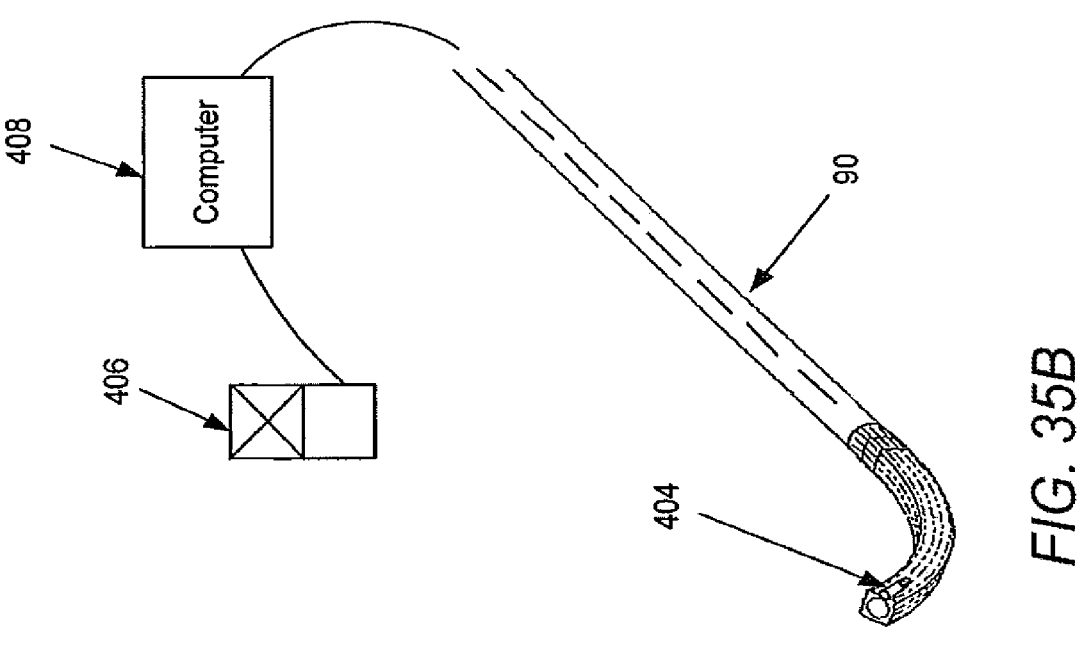
FIG. 35B illustrates a localization sensing system in accordance with other embodiments.
Figure 35A:
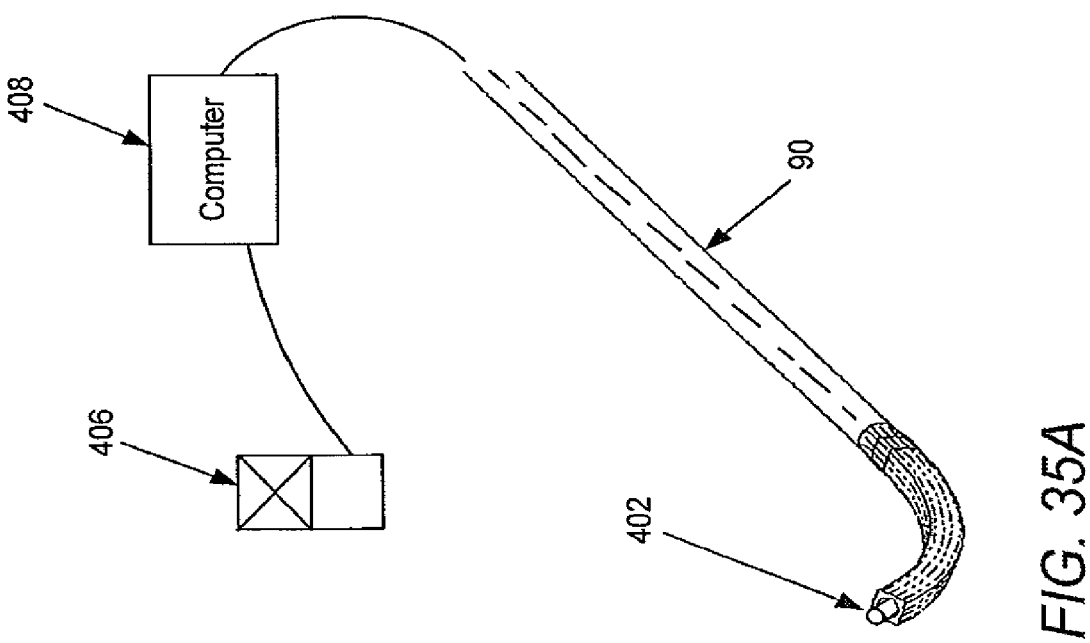
FIG. 35A illustrates a localization sensing system having an electromagnetic field receiver in accordance with some embodiments.

Some of the commercially-available localization systems use electromagnetic relationships to determine position and/or orientation, while others, such as some of those available from Endocardial Solutions, Inc.—St Jude Medical, utilize potential difference or voltage, as measured between a conductive sensor located on the pertinent instrument and conductive portions of sets of patches placed against the skin, to determine position and/or orientation. Referring to FIGS. 35A and 35B, various localization sensing systems may be utilized with the various embodiments of the robotic catheter system disclosed herein. In other embodiments not comprising a localization system to determine the position of various components, kinematic and/or geometric relationships between various components of the system may be utilized to predict the position of one component relative to the position of another. Some embodiments may utilize both localization data and kinematic and/or geometric relationships to determine the positions of various components. Information regarding impedance based systems can be found on: http://www.sjmprofessional.com/Products/US/Mapping-and-Visualization/EnSite-Velocity.aspx. The relevant portions of which are incorporated by reference.

As shown in FIG. 35A, one preferred localization system comprises an electromagnetic field transmitter (406) and an electromagnetic field receiver (402) positioned within the central lumen of a guide catheter (90). The transmitter (406) and receiver (402) are interfaced with a computer operating software configured to detect the position of the detector relative to the coordinate system of the transmitter (406) in real or near-real time with high degrees of accuracy. Referring to FIG. 35B, a similar embodiment is depicted with a receiver (404) embedded within the guide catheter (90) construction. Preferred receiver structures may comprise three or more sets of very small coils spatially configured to sense orthogonal aspects of magnetic fields emitted by a transmitter. Such coils may be embedded in a custom configuration within or around the walls of a preferred catheter construct. For example, in one embodiment, two orthogonal coils are embedded within a thin polymeric layer at two slightly flattened surfaces of a catheter (90) body approximately ninety degrees orthogonal to each other about the longitudinal axis of the catheter (90) body, and a third coil is embedded in a slight polymer-encapsulated protrusion from the outside of the catheter (90) body, perpendicular to the other two coils. Due to the very small size of the pertinent coils, the protrusion of the third coil may be minimized. Electronic leads for such coils may also be embedded in the catheter wall, down the length of the catheter body to a position, preferably adjacent an instrument driver, where they may be routed away from the instrument to a computer running localization software and interfaced with a pertinent transmitter.

In another similar embodiment (not shown), one or more conductive rings may be electronically connected to a potential-difference-based localization/orientation system, along with multiple sets, preferably three sets, of conductive skin patches, to provide localization and/or orientation data utilizing a system such as those available from Endocardial Solutions—St. Jude Medical. The one or more conductive rings may be integrated into the walls of the instrument at various longitudinal locations along the instrument, or set of instruments. For example, a guide instrument may have several conductive rings longitudinally displaced from each other toward the distal end of the guide instrument, while a coaxially-coupled sheath instrument may similarly have one or more conductive rings longitudinally displaced from each other toward the distal end of the sheath instrument—to provide precise data regarding the location and/or orientation of the distal ends of each of such instruments.

Figure 36:
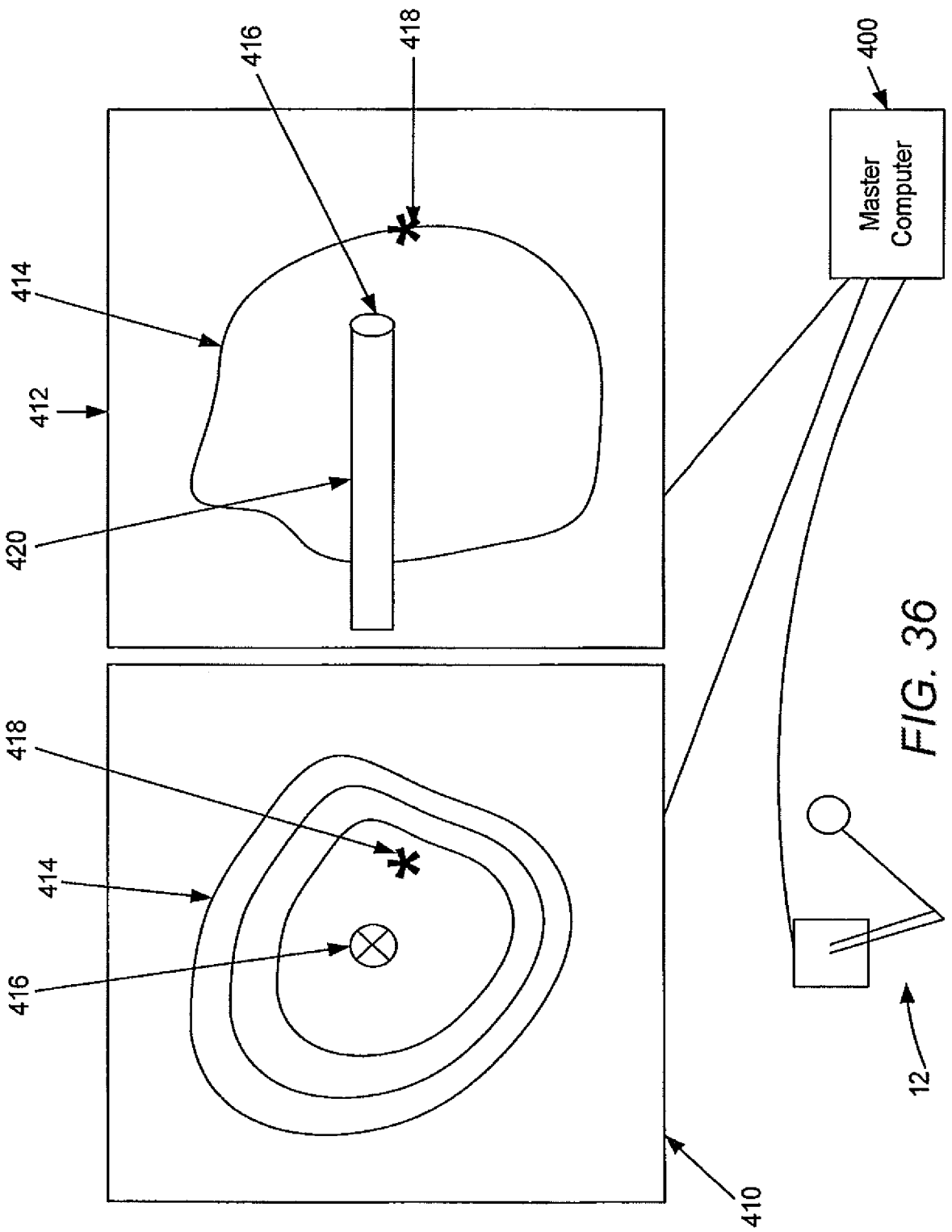
FIG. 36 illustrates a user interface for a master input device in accordance with some embodiments.

Referring back to FIG. 34, in one embodiment, visualization software runs on the master computer (400) to facilitate real-time driving and navigation of one or more steerable instruments. In one embodiment, visualization software provides an operator at an operator control station, such as that depicted in FIG. 19 (2), with a digitized "dashboard" or "windshield" display to enhance instinctive drivability of the pertinent instrumentation within the pertinent tissue structures. Referring to FIG. 36, a simple illustration is useful to explain one embodiment of a preferred relationship between visualization and navigation with a master input device (12). In the depicted embodiment, two display views (410, 412) are shown. One preferably represents a primary (410) navigation view, and one may represent a secondary (412) navigation view. To facilitate instinctive operation of the system, it is preferable to have the master input device coordinate system at least approximately synchronized with the coordinate system of at least one of the two views. Further, it is preferable to provide the operator with one or more secondary views which may be helpful in navigating through challenging tissue structure pathways and geometries.

Using the operation of an automobile as an example, if the master input device is a steering wheel and the operator desires to drive a car in a forward direction using one or more views, his first priority is likely to have a view straight out the windshield, as opposed to a view out the back window, out one of the side windows, or from a car in front of the car that he is operating. The operator might prefer to have the forward windshield view as his primary display view, such that a right turn on the steering wheel takes him right as he observes his primary display, a left turn on the steering wheel takes him left, and so forth. If the operator of the automobile is trying to park the car adjacent another car parked directly in front of him, it might be preferable to also have a view from a camera positioned, for example, upon the sidewalk aimed perpendicularly through the space between the two cars (one driven by the operator and one parked in front of the driven car), so the operator can see the gap closing between his car and the car in front of him as he parks. While the driver might not prefer to have to completely operate his vehicle with the sidewalk perpendicular camera view as his sole visualization for navigation purposes, this view is helpful as a secondary view.

Referring still to FIG. 36, if an operator is attempting to navigate a steerable catheter in order to, for example, contact a particular tissue location with the catheter's distal tip, a useful primary navigation view (410) may comprise a three dimensional digital model of the pertinent tissue structures (414) through which the operator is navigating the catheter with the master input device (12), along with a representation of the catheter distal tip location (416) as viewed along the longitudinal axis of the catheter near the distal tip. This embodiment illustrates a representation of a targeted tissue structure location (418), which may be desired in addition to the tissue digital model (414) information. A useful secondary view (412), displayed upon a different monitor, in a different window upon the same monitor, or within the same user interface window, for example, comprises an orthogonal view depicting the catheter tip representation (416), and also perhaps a catheter body representation (420), to facilitate the operator's driving of the catheter tip toward the desired targeted tissue location (418).

In one embodiment, subsequent to development and display of a digital model of pertinent tissue structures, an operator may select one primary and at least one secondary view to facilitate navigation of the instrumentation. By selecting which view is a primary view, the user can automatically toggle a master input device (12) coordinate system to synchronize with the selected primary view. In an embodiment with the leftmost depicted view (410) selected as the primary view, to navigate toward the targeted tissue site (418), the operator should manipulate the master input device (12) forward, to the right, and down. The right view will provide valued navigation information, but will not be as instinctive from a "driving" perspective.

To illustrate: if the operator wishes to insert the catheter tip toward the targeted tissue site (418) watching only the rightmost view (412) without the master input device (12) coordinate system synchronized with such view, the operator would have to remember that pushing straight ahead on the master input device will make the distal tip representation (416) move to the right on the rightmost display (412). Should the operator decide to toggle the system to use the rightmost view (412) as the primary navigation view, the coordinate system of the master input device (12) is then synchronized with that of the rightmost view (412), enabling the operator to move the catheter tip (416) closer to the desired targeted tissue location (418) by manipulating the master input device (12) down and to the right.

The synchronization of coordinate systems described herein may be conducted using fairly conventional mathematic relationships. For example, in one embodiment, the orientation of the distal tip of the catheter may be measured using a 6-axis position sensor system such as those available from Ascension Technology Corporation, Biosense Webster, Inc., Endocardial Solutions, Inc., Boston Scientific (EP Technologies), and others. A 3-axis coordinate frame, C, for locating the distal tip of the catheter, is constructed from this orientation information. The orientation information is used to construct the homogeneous transformation matrix, $$T_{Gref}^{G0},$$

which transforms a vector in the Catheter coordinate frame "C" to the fixed Global coordinate frame "G" in which the sensor measurements are done (the subscript $G_{ref}$ and superscript $C_{ref}$ are used to represent the O'th, or initial, step). As a registration step, the computer graphics view of the catheter is rotated until the master input and the computer graphics view of the catheter distal tip motion are coordinated and aligned with the camera view of the graphics scene. The 3-axis coordinate frame transformation matrix $T_{Gref}^{G0}$ for the camera position of this initial view is stored (subscripts $G_{ref}$ and superscript $C_{ref}$ stand for the global and camera "reference" views). The corresponding catheter "reference view" matrix for the catheter coordinates is obtained as:

$$T_{Cref}^{C0} = T_{G_0}^{C0} T_{Gref}^{G0} T_{Cref}^{Gref} = \left(T_{C_0}^{G0}\right)^{-1} T_{Gref}^{G0} T_{C1}^{G1}$$

Also note that the catheter's coordinate frame is fixed in the global reference frame G, thus the transformation matrix between the global frame and the catheter frame is the same in all views, i.e., $$T_{C_0}^{G0} = T_{Cref}^{Gref} = T_{Ci}^{Gi}$$

for any arbitrary view i. The coordination between primary view and master input device coordinate systems is achieved by transforming the master input as follows: Given any arbitrary computer graphics view of the representation, e.g. the i'th view, the 3-axis coordinate frame transformation matrix $T_{Gi}^{G0}$ of the camera view of the computer graphics scene is obtained from the computer graphics software. The corresponding catheter transformation matrix is computed in a similar manner as above:

$$T_{Ci}^{C0} = T_{G_0}^{C0} T_{Gi}^{G0} T_{Ci}^{Gi} = \left(T_{C_0}^{G0}\right)^{-1} T_{Gi}^{G0} T_{Ci}^{Gi}$$

The transformation that needs to be applied to the master input which achieves the view coordination is the one that transforms from the reference view that was registered above, to the current ith view, i.e., $T_{Cref}^{Ci}$. Using the previously computed quantities above, this transform is computed as:

$$T_{Cref}^{Ci} = T_{C0}^{Ci} T_{Cref}^{C0}$$

The master input is transformed into the commanded catheter input by application of the transformation $T_{Cref}^{Ci}$. Given a command input $$r_{master} = \begin{bmatrix} x_{master} \\ y_{master} \\ y_{master} \end{bmatrix},$$

one may calculate:

$$r_{catheter} = \begin{bmatrix} x_{catheter} \\ y_{catheter} \\ y_{catheter} \end{bmatrix} = T_{Cref}^{Ci} \begin{bmatrix} x_{master} \\ y_{master} \\ y_{master} \end{bmatrix}$$

$$r_{catheter} = \begin{bmatrix} x_{catheter} \\ y_{catheter} \\ y_{catheter} \end{bmatrix} = T_{Cref}^{Ci} \begin{bmatrix} x_{master} \\ y_{master} \\ y_{master} \end{bmatrix}$$

Under such relationships, coordinate systems of the primary view and master input device may be aligned for instinctive operation.

Referring back to embodiment of FIG. 34, the master computer (400) also comprises software and hardware interfaces to operator control station buttons, switches, and other input devices which may be utilized, for example, to "freeze" the system by functionally disengaging the master input device as a controls input, or provide toggling between various scaling ratios desired by the operator for manipulated inputs at the master input device (12). The master computer (400) has two separate functional connections with the control and instrument driver computer (422): one (426) for passing controls and visualization related commands, such as desired XYZ (in the catheter coordinate system) commands, and one (428) for passing safety signal commands. Similarly, the control and instrument driver computer (422) has two separate functional connections with the instrument and instrument driver hardware (424): one (430) for passing control and visualization related commands such as required-torque-related voltages to the amplifiers to drive the motors and encoders, and one (432) for passing safety signal commands.

In one embodiment, the safety signal commands represent a simple signal repeated at very short intervals, such as every 10 milliseconds, such signal chain being logically read as "system is ok, amplifiers stay active". If there is any interruption in the safety signal chain, the amplifiers are logically toggled to inactive status and the instrument cannot be moved by the control system until the safety signal chain is restored. Also shown in the signal flow overview of FIG. 34 is a pathway (434) between the physical instrument and instrument driver hardware back to the master computer to depict a closed loop system embodiment wherein instrument localization technology, such as that described in reference to FIGS. 35A-B, is utilized to determine the actual position of the instrument to minimize navigation and control error, as described in further detail below.

FIGS. 37-47 depict various aspects of one embodiment of a SimuLink™ software control schema for an embodiment of the physical system, with particular attention to an embodiment of a "master following mode." In this embodiment, an instrument is driven by following instructions from a master input device, and a motor servo loop embodiment, which comprises key operational functionality for executing upon commands delivered from the master following mode to actuate the instrument.

Figure 37:
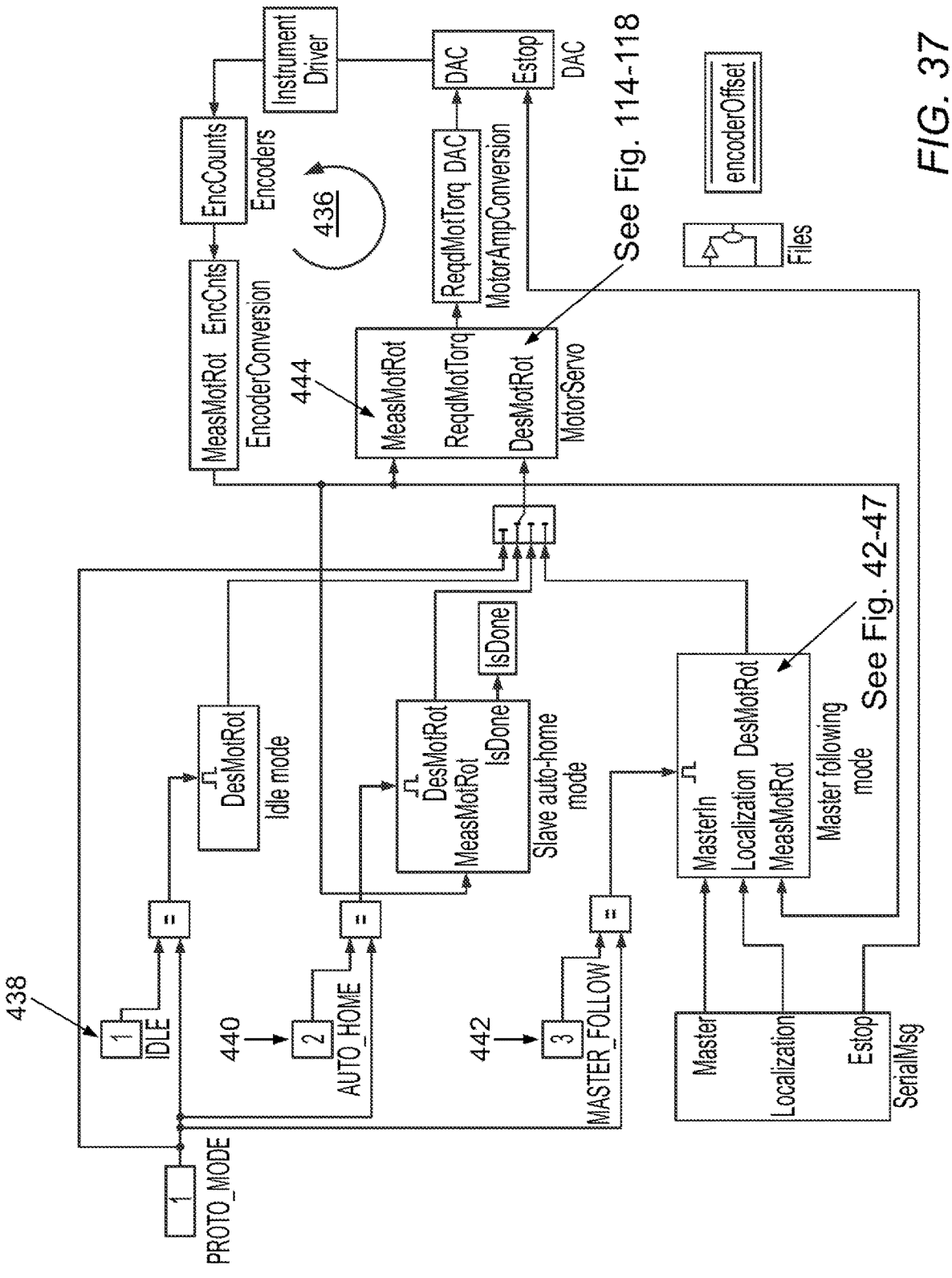
FIGS. 37-47 illustrate software control schema in accordance with various embodiments.

FIG. 37 depicts a high-level view of an embodiment wherein any one of three modes may be toggled to operate the primary servo loop (436). In idle mode (438), the default mode when the system is started up, all of the motors are commanded via the motor servo loop (436) to servo about their current positions, their positions being monitored with digital encoders associated with the motors. In other words, idle mode (438) deactivates the motors, while the remaining system stays active. Thus, when the operator leaves idle mode, the system knows the position of the relative components. In auto home mode (440), cable loops within an associated instrument driver, such as that depicted in FIG. 23, are centered within their cable loop range to ensure substantially equivalent range of motion of an associated instrument in both directions for a various degree of freedom, such as + and − directions of pitch or yaw, when loaded upon the instrument driver. This is a setup mode for preparing an instrument driver before an instrument is engaged.

In master following mode (442), the control system receives signals from the master input device, and in a closed loop embodiment from both a master input device and a localization system, and forwards drive signals to the primary servo loop (436) to actuate the instrument in accordance with the forwarded commands. Aspects of this embodiment of the master following mode (442) are depicted in further detail in FIGS. 42-124. Aspects of the primary servo loop and motor servo block (444) are depicted in further detail in FIGS. 38-41.

Figure 42:
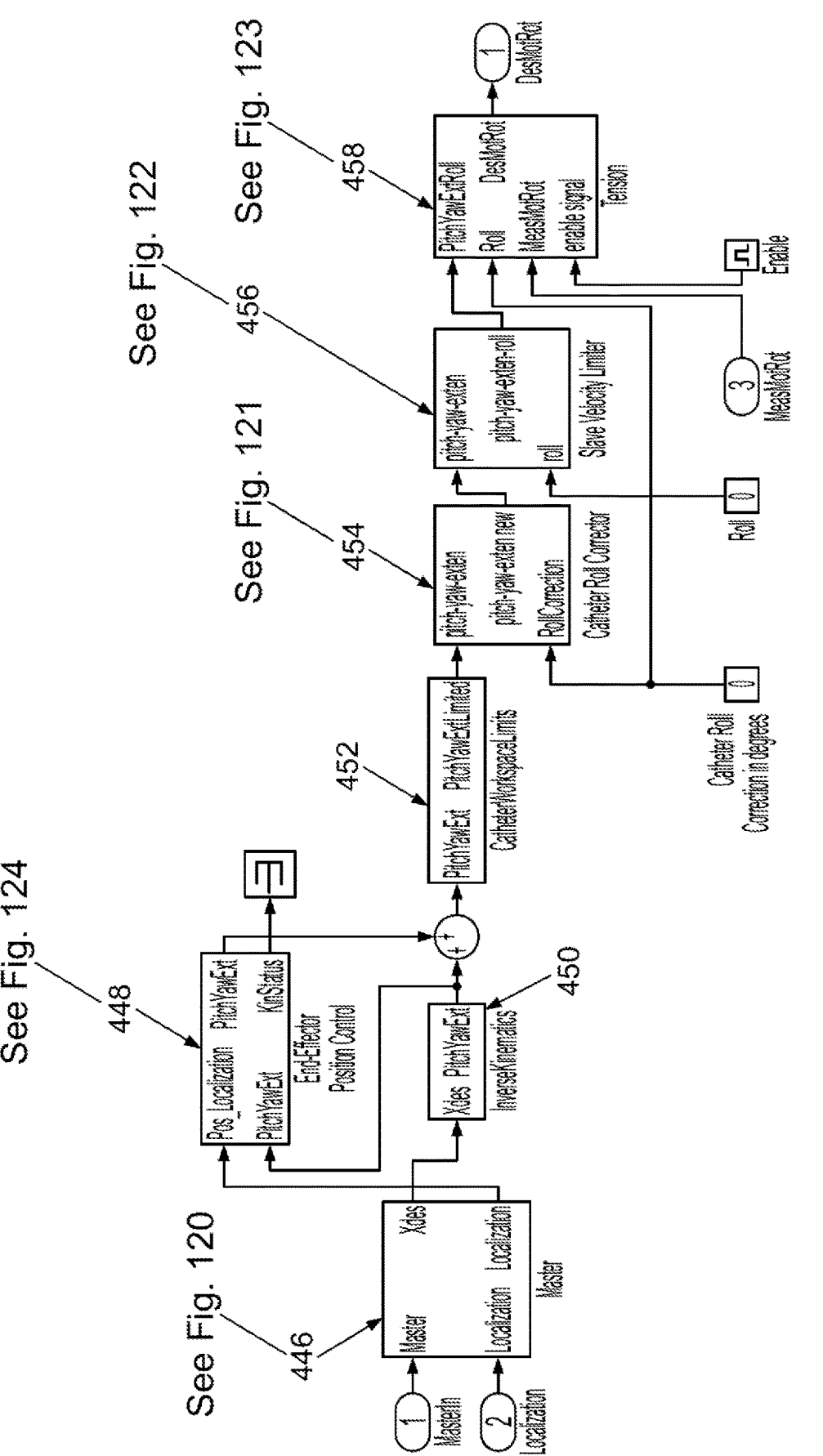
Figure 43:
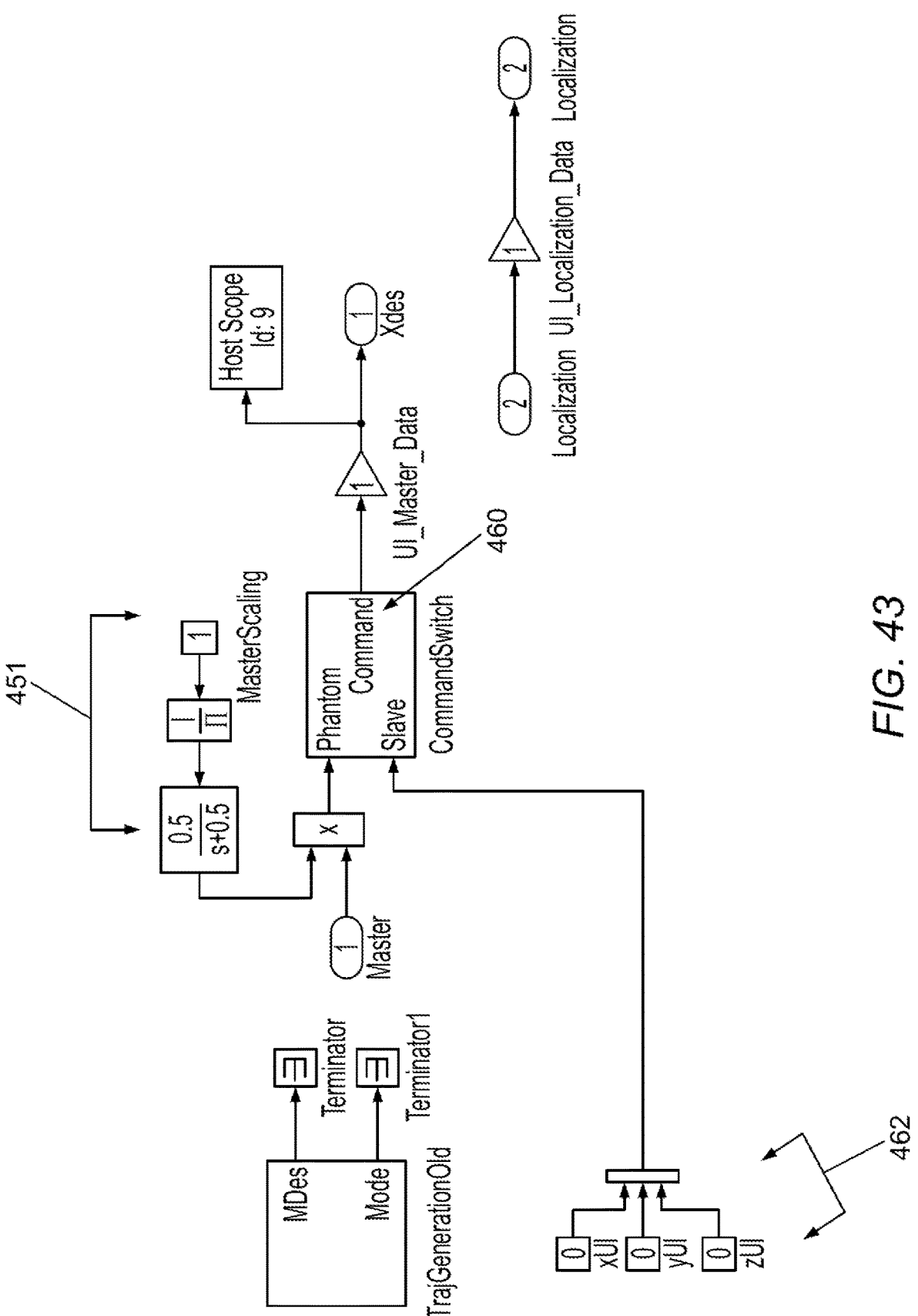

Referring to FIG. 42, a more detailed functional diagram of an embodiment of master following mode (442) is depicted. As shown in FIG. 42, the inputs to functional block (446) are XYZ position of the master input device in the coordinate system of the master input device which, per a setting in the software of the master input device may be aligned to have the same coordinate system as the catheter, and localization XYZ position of the distal tip of the instrument as measured by the localization system in the same coordinate system as the master input device and catheter. Referring to FIG. 43 for a more detailed view of functional block (446) of FIG. 42, a switch (460) is provided at block to allow switching between master inputs for desired catheter position, to an input interface (462) through which an operator may command that the instrument go to a particular XYZ location in space. Various controls features may also utilize this interface to provide an operator with, for example, a menu of destinations to which the system should automatically drive an instrument, etc. Also depicted in FIG. 43 is a master scaling functional block (451) which is utilized to scale the inputs coming from the master input device with a ratio selectable by the operator. The command switch (460) functionality includes a low pass filter to weight commands switching between the master input device and the input interface (462), to ensure a smooth transition between these modes.

Referring back to FIG. 42, desired position data in XYZ terms is passed to the inverse kinematics block (450) for conversion to pitch, yaw, and extension (or "insertion") terms in accordance with the predicted mechanics of materials relationships inherent in the mechanical design of the instrument.

The kinematic relationships for many catheter instrument embodiments may be modeled by applying conventional mechanics relationships. In summary, a control-element-steered catheter instrument is controlled through a set of actuated inputs. In a four-control-element catheter instrument, for example, there are two degrees of motion actuation, pitch and yaw, which both have + and − directions. Other motorized tension relationships may drive other instruments, active tensioning, or insertion or roll of the catheter instrument. The relationship between actuated inputs and the catheter's end point position as a function of the actuated inputs is referred to as the "kinematics" of the catheter.

Figure 49:
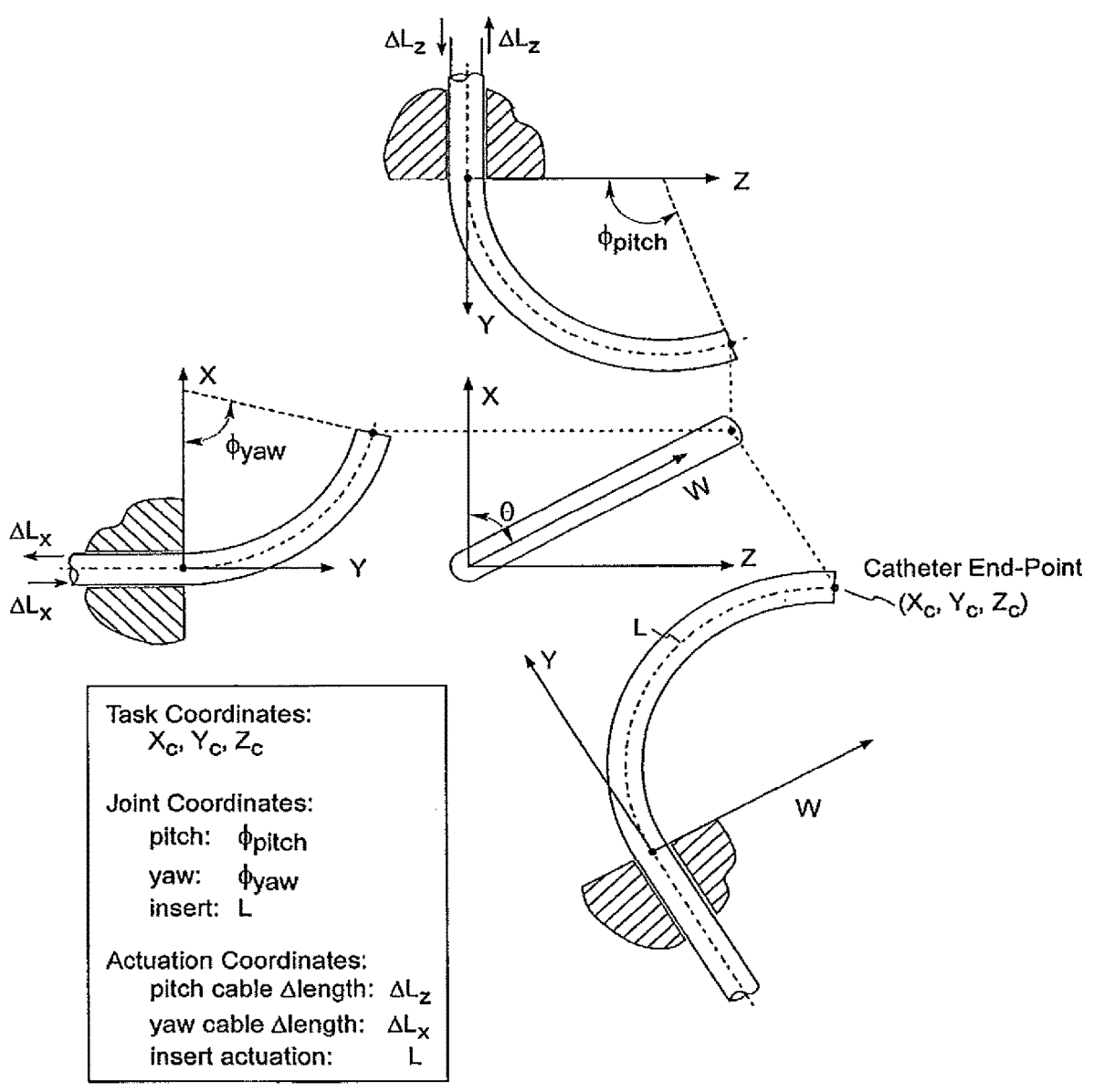
FIG. 49 illustrates task coordinates, joint coordinates, and actuation coordinates in accordance with some embodiments.

Referring to FIG. 48, the "forward kinematics" expresses the catheter's end-point position as a function of the actuated inputs while the "inverse kinematics" expresses the actuated inputs as a function of the desired end-point position. Accurate mathematical models of the forward and inverse kinematics are essential for the control of a robotically controlled catheter system. For clarity, the kinematics equations are further refined to separate out common elements, as shown in FIG. 48. The basic kinematics describes the relationship between the task coordinates and the joint coordinates. In such case, the task coordinates refer to the position of the catheter end-point while the joint coordinates refer to the bending (pitch and yaw, for example) and length of the active catheter. The actuator kinematics describes the relationship between the actuation coordinates and the joint coordinates. The task, joint, and bending actuation coordinates for the robotic catheter are illustrated in FIG. 49. By describing the kinematics in this way we can separate out the kinematics associated with the catheter structure, namely the basic kinematics, from those associated with the actuation methodology.

An inverse kinematic model translates intended device motion into the commands that will adjust the actuator and/or control element to position the shapeable instrument as desired. Referring back to FIG. 1B, the shapeable instrument kinematics are the mathematical relationships between the task space description of the instrument (e.g., tip position) and the configuration space description of the instrument (e.g., shape). Specifically, the inverse kinematics (task to configuration space) are used as part of the chain that translates desired tip positions into actuator commands (leading to displacements of the control elements) that move tip position of the actual device for reaching a desired tip position.

These inverse kinematic algorithms are derived based upon certain assumptions about how the shapeable instrument moves. Examples of these assumptions include but are not limited to: 1) Each catheter segment bends in a constant curvature arc; 2) Each catheter segment bends within a single plane; 3) Some catheter segments have fixed (constant) lengths; 4) Some catheter segments have variable (controllable) lengths.

The development of the catheter's kinematics model is derived using a few essential assumptions. Included are assumptions that the catheter structure is approximated as a simple beam in bending from a mechanics perspective, and that control elements, such as thin tension wires, remain at a fixed distance from the neutral axis and thus impart a uniform moment along the length of the catheter.

Figure 50:
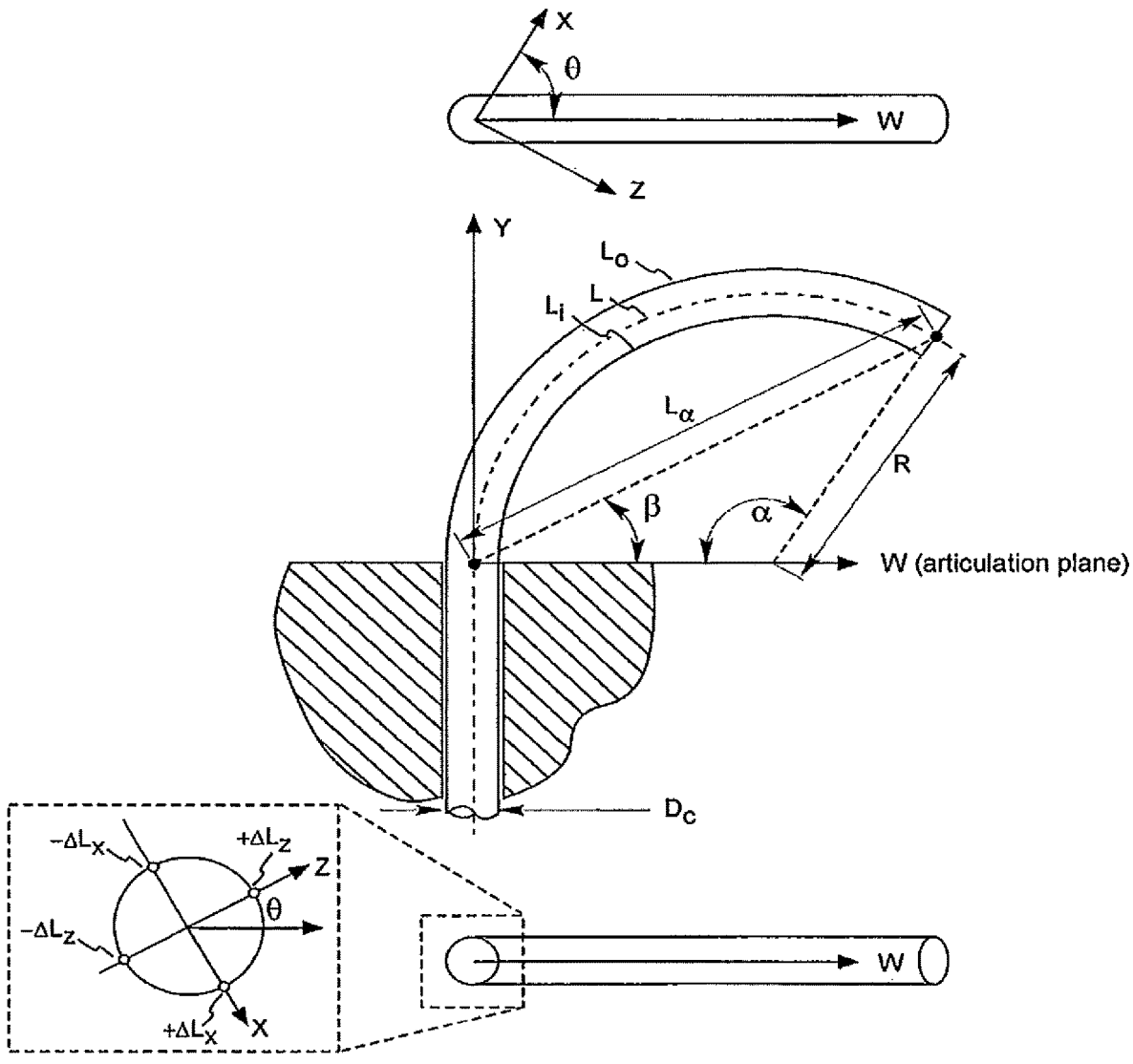
FIG. 50 illustrates variables associated with a geometry of a catheter in accordance with some embodiments.

In addition to the above assumptions, the geometry and variables shown in FIG. 50 are used in the derivation of the forward and inverse kinematics. The basic forward kinematics, relating the catheter task coordinates ($X$, $Y_e$, $Z_e$) to the joint coordinates ($\square_{pitch}$, $\square_{pitch}$, L), is given as follows:

$$X_C = \omega \cos(\theta)$$

$$Y_c = R \sin(\alpha)$$

$$Z_c = \omega \sin(\theta)$$

Where $$\omega = R(1 - \cos(\alpha))$$

$$\alpha = \left[(\phi_{pitch})^2 + (\phi_{yaw})^2\right]^{\frac{1}{2}} \text{ (total bending)}$$

$$R = \frac{L}{\alpha} \text{ (bend radius)}$$

$$\theta = \text{atan2}(\phi_{pitch}, \phi_{yaw}) \text{ (raw angle)}$$

The actuator forward kinematics, relating the joint coordinates ($\square_{pitch}$, $\square_{pitch}$, L) to the actuator coordinates ($\square L_x$, $\square L_z$, L) is given as follows:

$$\phi_{yaw} = \frac{2\Delta L_x}{D_c}$$

As illustrated in FIG. 48, the catheter's end-point position can be predicted given the joint or actuation coordinates by using the forward kinematics equations described above.

Calculation of the catheter's actuated inputs as a function of end-point position, referred to as the inverse kinematics, can be performed numerically, using a nonlinear equation solver such as Newton-Raphson. A more desirable approach, and the one used in this illustrative embodiment, is to develop a closed-form solution which can be used to calculate the required actuated inputs directly from the desired end-point positions.

As with the forward kinematics, we separate the inverse kinematics into the basic inverse kinematics, which relates joint coordinates to the task coordinates, and the actuation inverse kinematics, which relates the actuation coordinates to the joint coordinates. The basic inverse kinematics, relating the joint coordinates ($\square_{pitch}$, $\square_{pitch}$, L), to the catheter task coordinates ($X_c$, $Y_c$, $Z_c$) is given as follows:

$$\phi_{pitch} = \alpha \sin(\theta)$$

$$\phi_{yaw} = \alpha \cos(\theta)$$

$$L = R\alpha$$

$$\theta = \text{atan2}(Z_c, X_c)\beta = \text{atan2}(Y_c, W_c)$$

$$\theta = \text{atan2}(Z_c, X_c)\beta =$$

$$\text{atan2}(Y_c, W_c) \rightarrow \text{where} \rightarrow \rightarrow \begin{array}{l} R = \dfrac{l \sin\beta}{\sin 2\beta} \\ \alpha = \pi - 2\beta \end{array} \rightarrow \begin{array}{l} W_c = (X_c^2 + Z_c^2)^{1/2} \\ l = (W_c^2 + Y_c^2)^{1/2} \end{array}$$

The actuator inverse kinematics, relating the actuator coordinates ($\square L_x$, $\square L_z$, L) to the joint coordinates ($\square_{pitch}$, $\square_{pitch}$, L) is given as follows:

$$\Delta L_x = \frac{D_c \phi_{yaw}}{2}$$

$$\Delta L_T = \frac{D_c \phi_{pitch}}{2}$$

Figure 47:
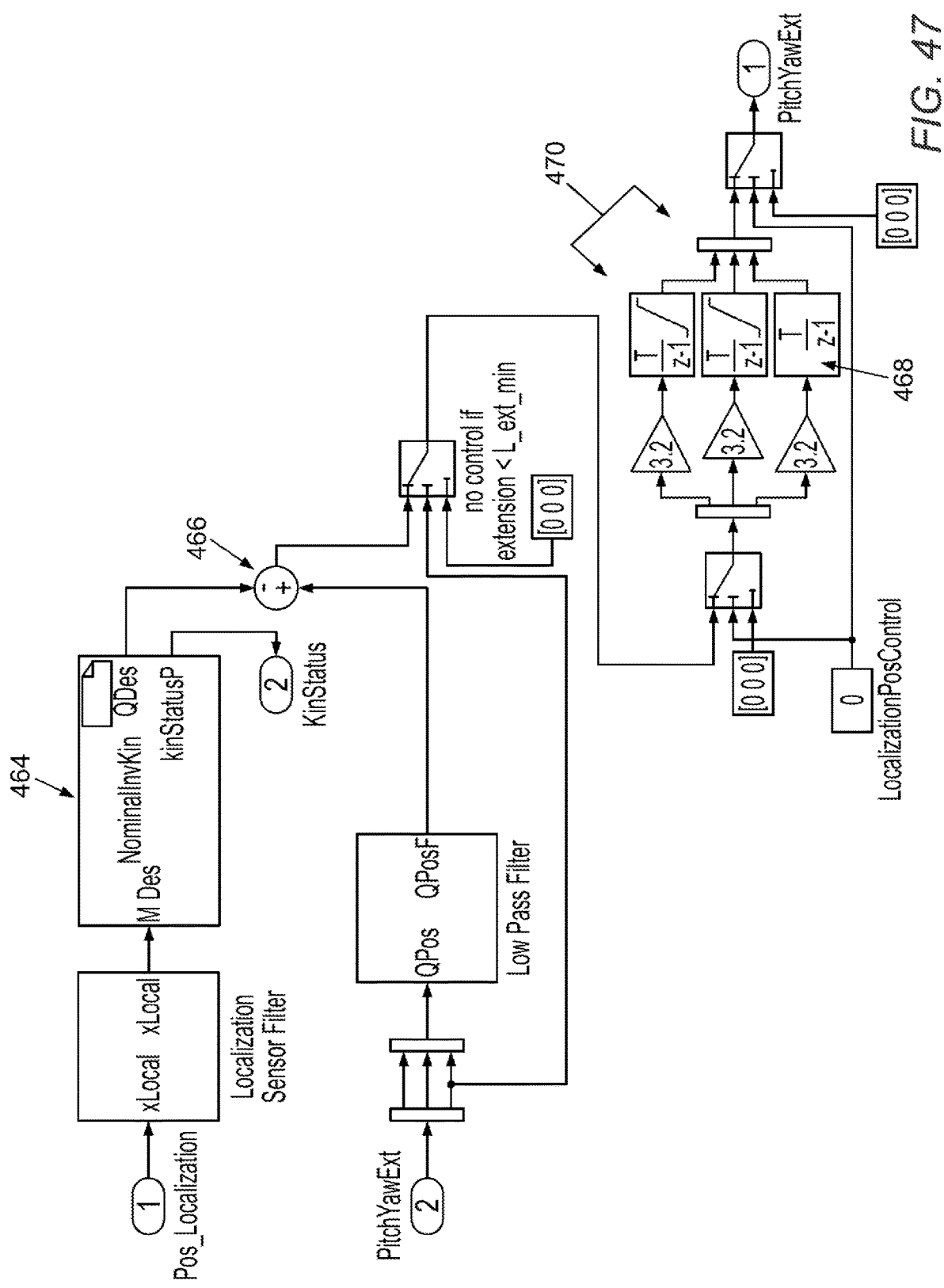

Referring back to FIG. 42, pitch, yaw, and extension commands are passed from the inverse kinematics (450) to a position control block (448) along with measured localization data. FIG. 47 provides a more detailed view of the position control block (448). After measured XYZ position data comes in from the localization system, it goes through a inverse kinematics block (464) to calculate the pitch, yaw, and extension the instrument needs to have in order to travel to where it needs to be. Comparing (466) these values with filtered desired pitch, yaw, and extension data from the master input device, integral compensation is then conducted with limits on pitch and yaw to integrate away the error. In this embodiment, the extension variable does not have the same limits (468), as do pitch and yaw (470). As will be apparent to those skilled in the art, having an integrator in a negative feedback loop forces the error to zero. Desired pitch, yaw, and extension commands are next passed through a catheter workspace limitation (452), which may be a function of the experimentally determined physical limits of the instrument beyond which componentry may fail, deform undesirably, or perform unpredictably or undesirably. This workspace limitation essentially defines a volume similar to a cardioid-shaped volume about the distal end of the instrument. Desired pitch, yaw, and extension commands, limited by the workspace limitation block, are then passed to a catheter roll correction block (454).

Figure 44:
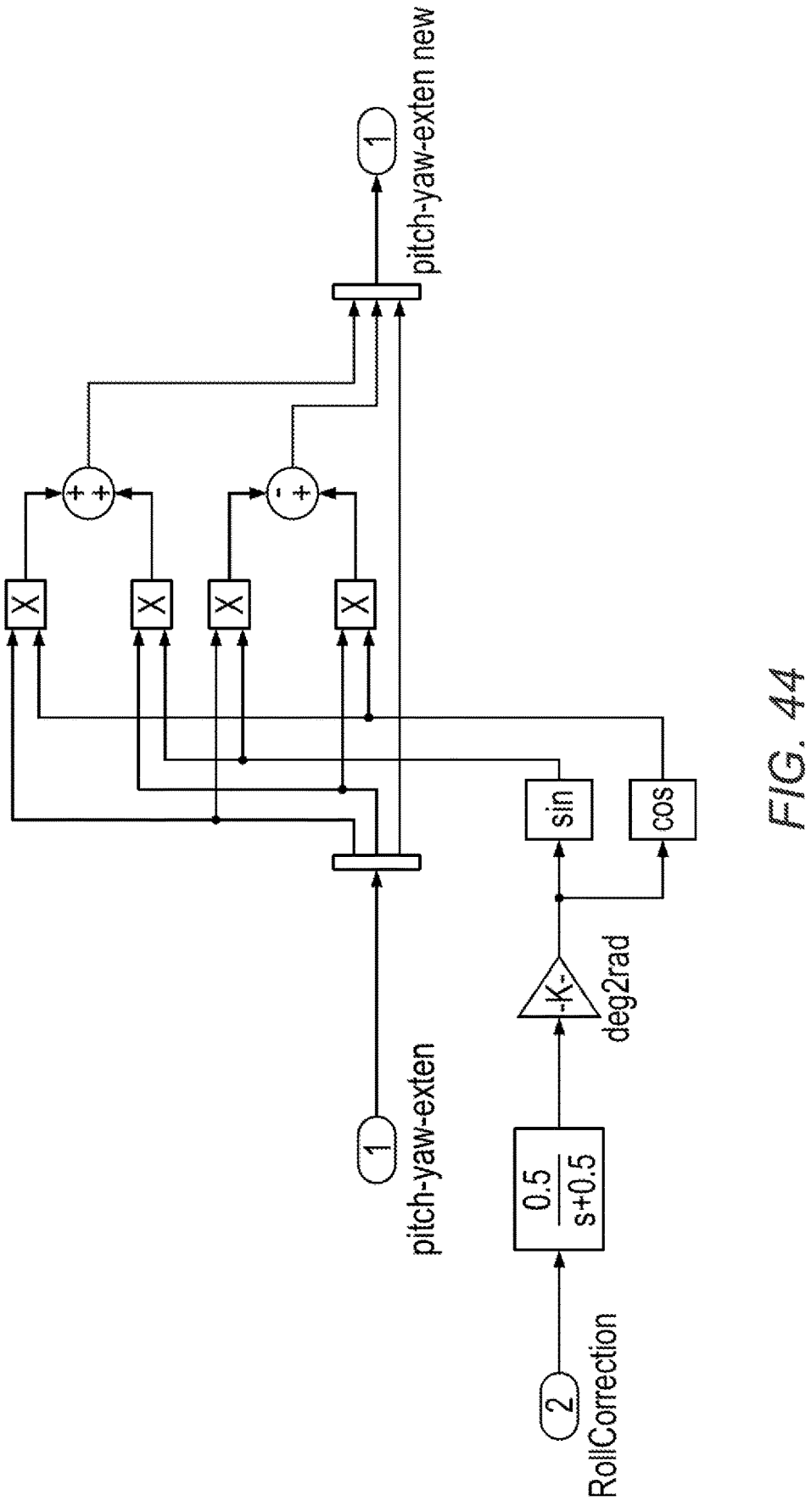

This functional block is depicted in further detail in FIG. 44, and essentially comprises a rotation matrix for transforming the pitch, yaw, and extension commands about the longitudinal, or "roll", axis of the instrument—to calibrate the control system for rotational deflection at the distal tip of the catheter that may change the control element steering dynamics. For example, if a catheter has no rotational deflection, pulling on a control element located directly up at twelve o'clock should urge the distal tip of the instrument upward. If, however, the distal tip of the catheter has been rotationally deflected by, say, ninety degrees clockwise, to get an upward response from the catheter, it may be necessary to tension the control element that was originally positioned at a nine o'clock position. The catheter roll correction schema depicted in FIG. 44 provides a means for using a rotation matrix to make such a transformation, subject to a roll correction angle, such as the ninety degrees in the above example, which is input, passed through a low pass filter, turned to radians, and put through rotation matrix calculations.

In one embodiment, the roll correction angle is determined through experimental experience with a particular instrument and path of navigation. In another embodiment, the roll correction angle may be determined experimentally in-situ using the accurate orientation data available from the preferred localization systems. In other words, with such an embodiment, a command to, for example, bend straight up can be executed, and a localization system can be utilized to determine at which angle the deflection actually went—to simply determine the in-situ roll correction angle.

Figure 45:
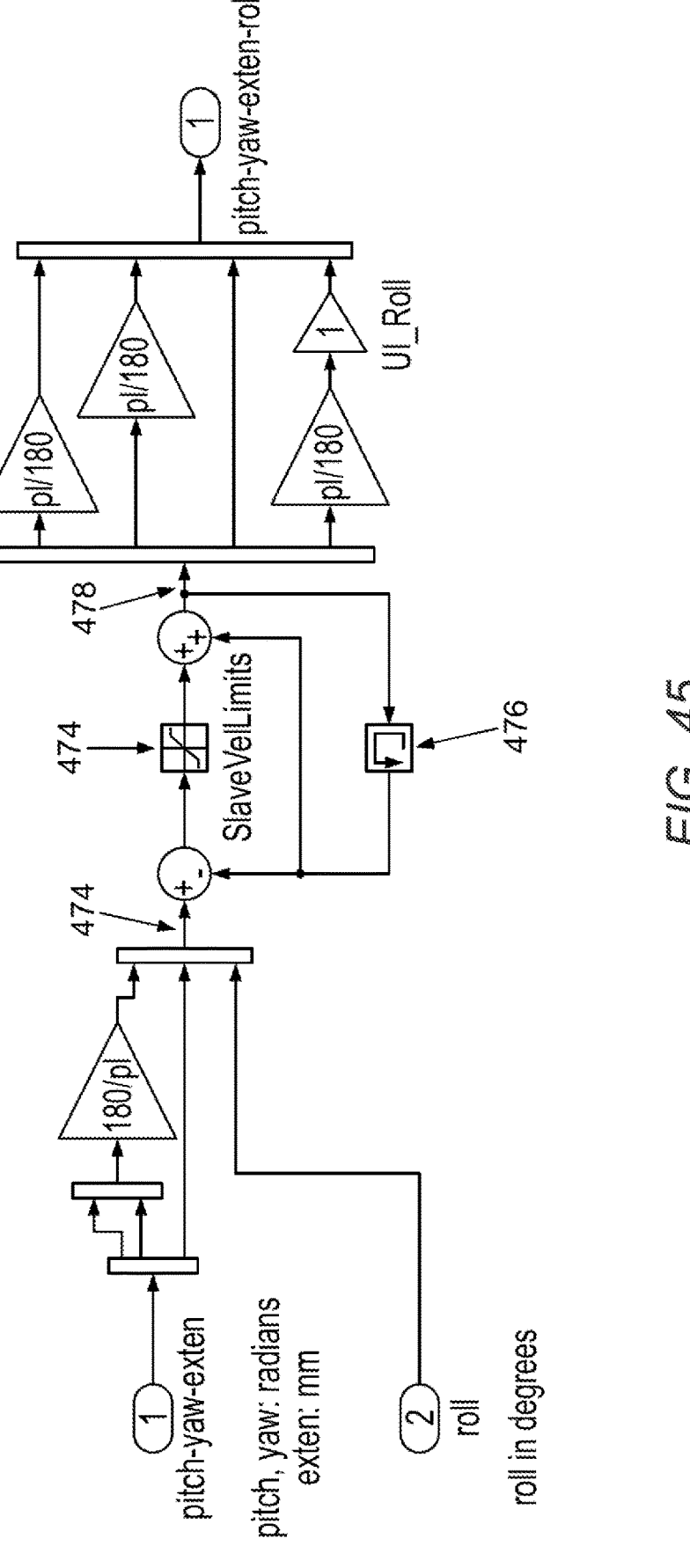

Referring briefly back to FIG. 42, roll corrected pitch and yaw commands, as well as unaffected extension commands, are output from the roll correction block (454) and may optionally be passed to a conventional velocity limitation block (456). Referring to FIG. 45, pitch and yaw commands are converted from radians to degrees, and automatically controlled roll may enter the controls picture to complete the current desired position (472) from the last servo cycle. Velocity is calculated by comparing the desired position from the previous servo cycle, as calculated with a conventional memory block (476) calculation, with that of the incoming commanded cycle. A conventional saturation block (474) keeps the calculated velocity within specified values, and the velocity-limited command (478) is converted back to radians and passed to a tension control block (458).

Figure 46:
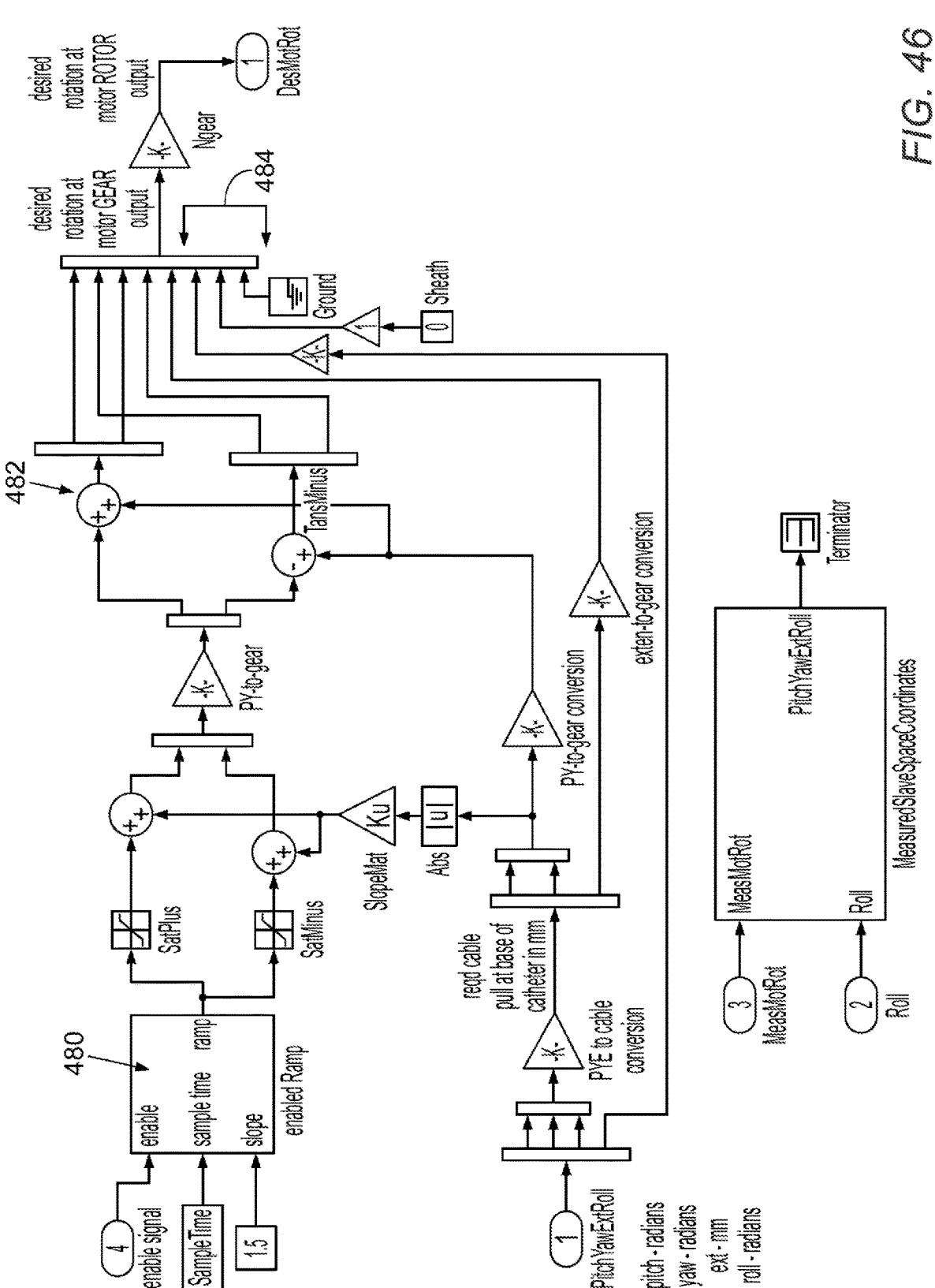

Tension within control elements may be managed depending upon the particular instrument embodiment, as described above in reference to the various instrument embodiments and tension control mechanisms. As an example, FIG. 46 depicts a pre-tensioning block (480) with which a given control element tension is ramped to a present value. An adjustment is then added to the original pre-tensioning based upon a preferably experimentally-tuned matrix pertinent to variables, such as the failure limits of the instrument construct and the incoming velocity-limited pitch, yaw, extension, and roll commands. This adjusted value is then added (482) to the original signal for output, via gear ratio adjustment, to calculate desired motor rotation commands for the various motors involved with the instrument movement. In this embodiment, extension, roll, and sheath instrument actuation (484) have no pre-tensioning algorithms associated with their control. The output is then complete from the master following mode functionality, and this output is passed to the primary servo loop (436).

Referring back to FIG. 37, incoming desired motor rotation commands from either the master following mode (442), auto home mode (440), or idle mode (438) in the depicted embodiment are fed into a motor servo block (444), which is depicted in greater detail in FIGS. 38-41.

Figure 38:
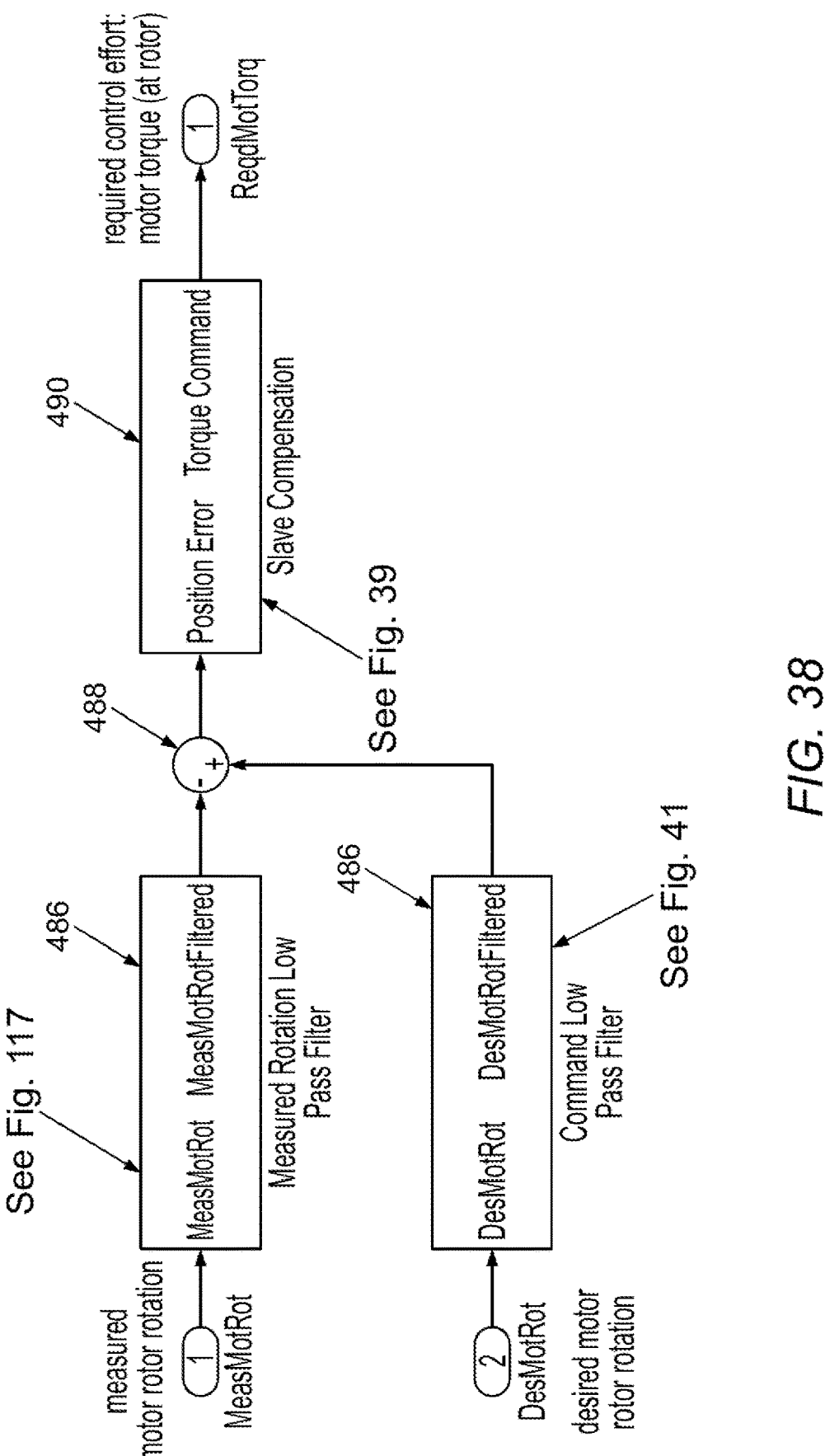
Figure 40:
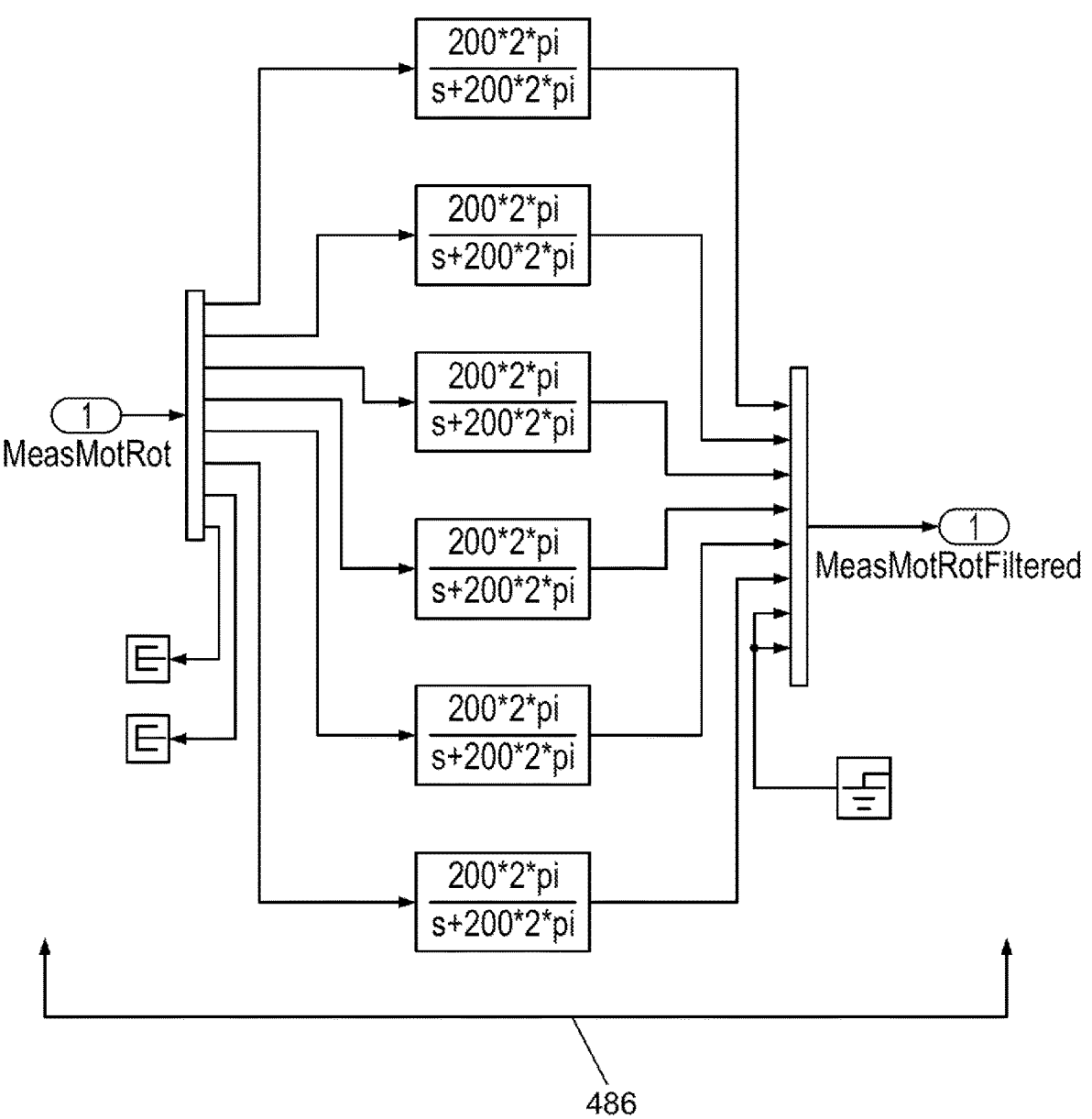
Figure 41:
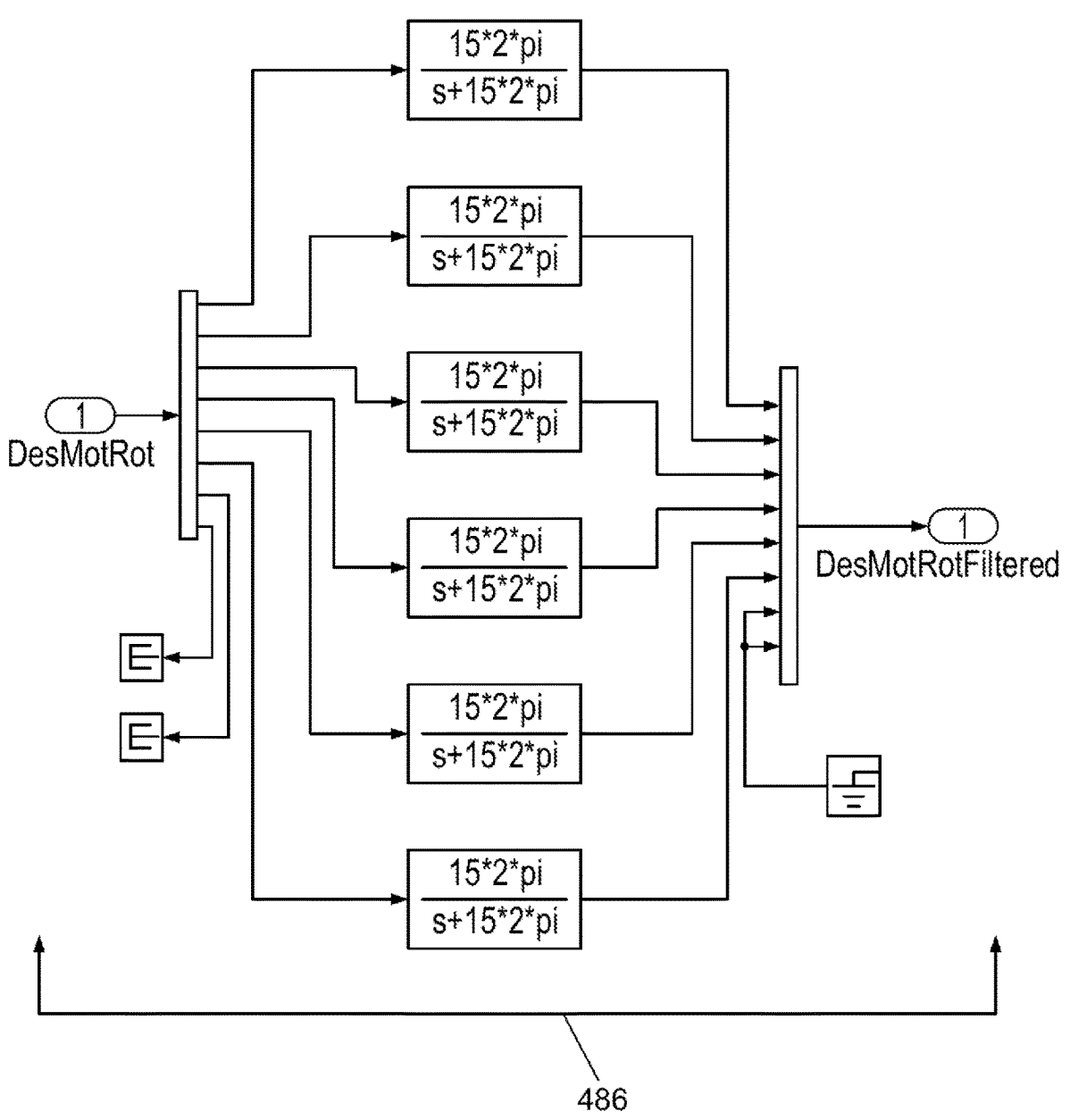

Referring to FIG. 38, incoming measured motor rotation data from digital encoders and incoming desired motor rotation commands are filtered using conventional quantization noise filtration at frequencies selected for each of the incoming data streams to reduce noise while not adding undue delays which may affect the stability of the control system. As shown in FIGS. 40 and 41, conventional quantization filtration is utilized on the measured motor rotation signals at about 200 hertz in this embodiment, and on the desired motor rotation command at about 15 hertz. The difference (488) between the quantization filtered values forms the position error which may be passed through a lead filter, the functional equivalent of a proportional derivative ("PD")+low pass filter. In another embodiment, conventional PID, lead/lag, or state space representation filter may be utilized. The lead filter of the depicted embodiment is shown in further detail in FIG. 39.

Figure 39:
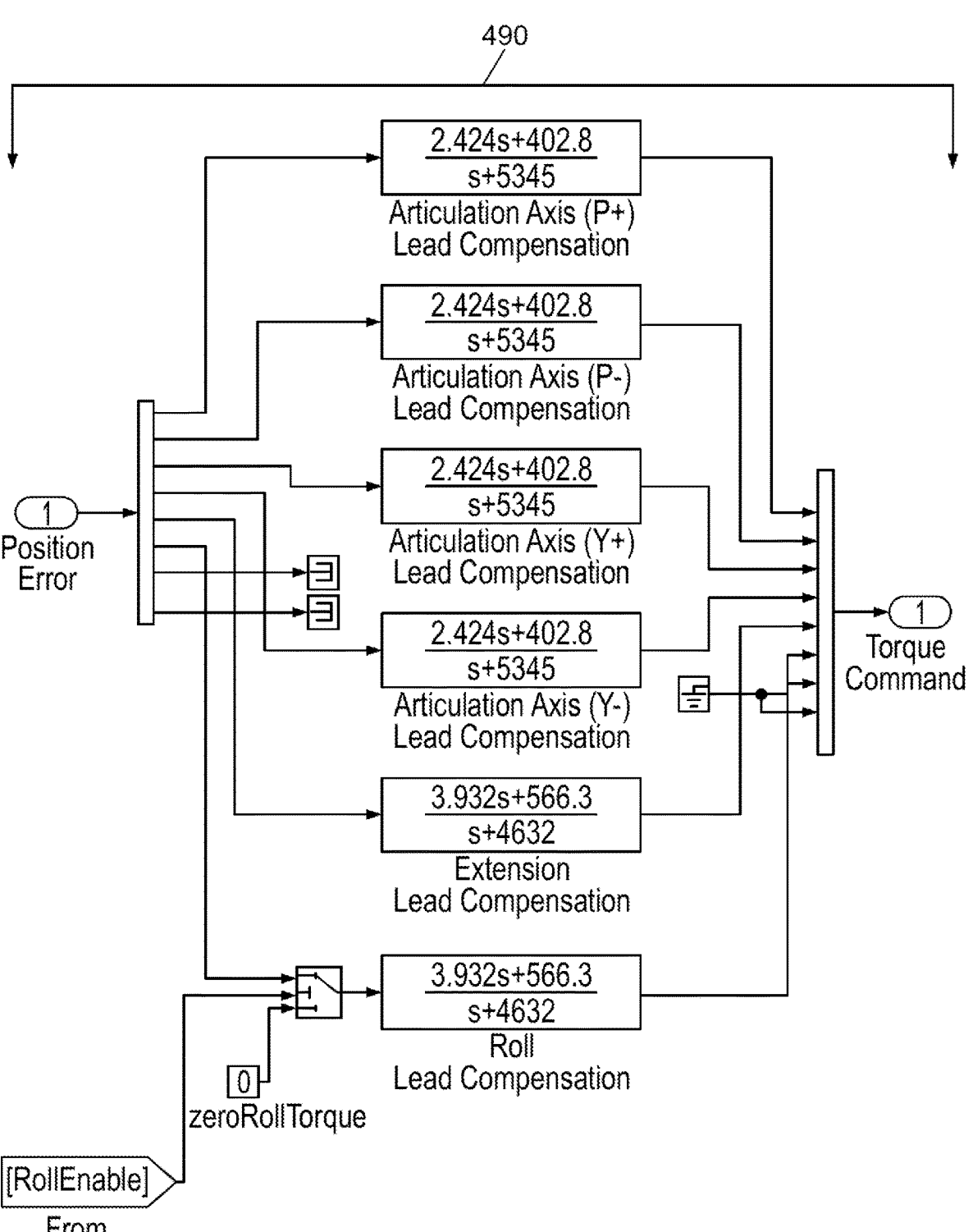

In particular, the lead filter embodiment in FIG. 39 comprises a variety of constants selected to tune the system to achieve desired performance. The depicted filter addresses the needs of one embodiment of a 4-control element guide catheter instrument with independent control of each of four control element interface assemblies for .+−.pitch and .+−.yaw, and separate roll and extension control. As demonstrated in the depicted embodiment, insertion and roll have different inertia and dynamics as opposed to pitch and yaw controls, and the constants selected to tune them is different. The filter constants may be theoretically calculated using conventional techniques and tuned by experimental techniques, or wholly determined by experimental techniques, such as setting the constants to give a sixty degree or more phase margin for stability and speed of response, a conventional phase margin value for medical control systems.

In an embodiment where a tuned master following mode is paired with a tuned primary servo loop, an instrument and instrument driver, such as those described above, may be "driven" accurately in three-dimensions with a remotely located master input device. Other preferred embodiments incorporate related functionalities, such as haptic feedback to the operator, active tensioning with a split carriage instrument driver, navigation utilizing direct visualization and/or tissue models acquired in-situ and tissue contact sensing, and enhanced navigation logic.

Figures 51, 52:
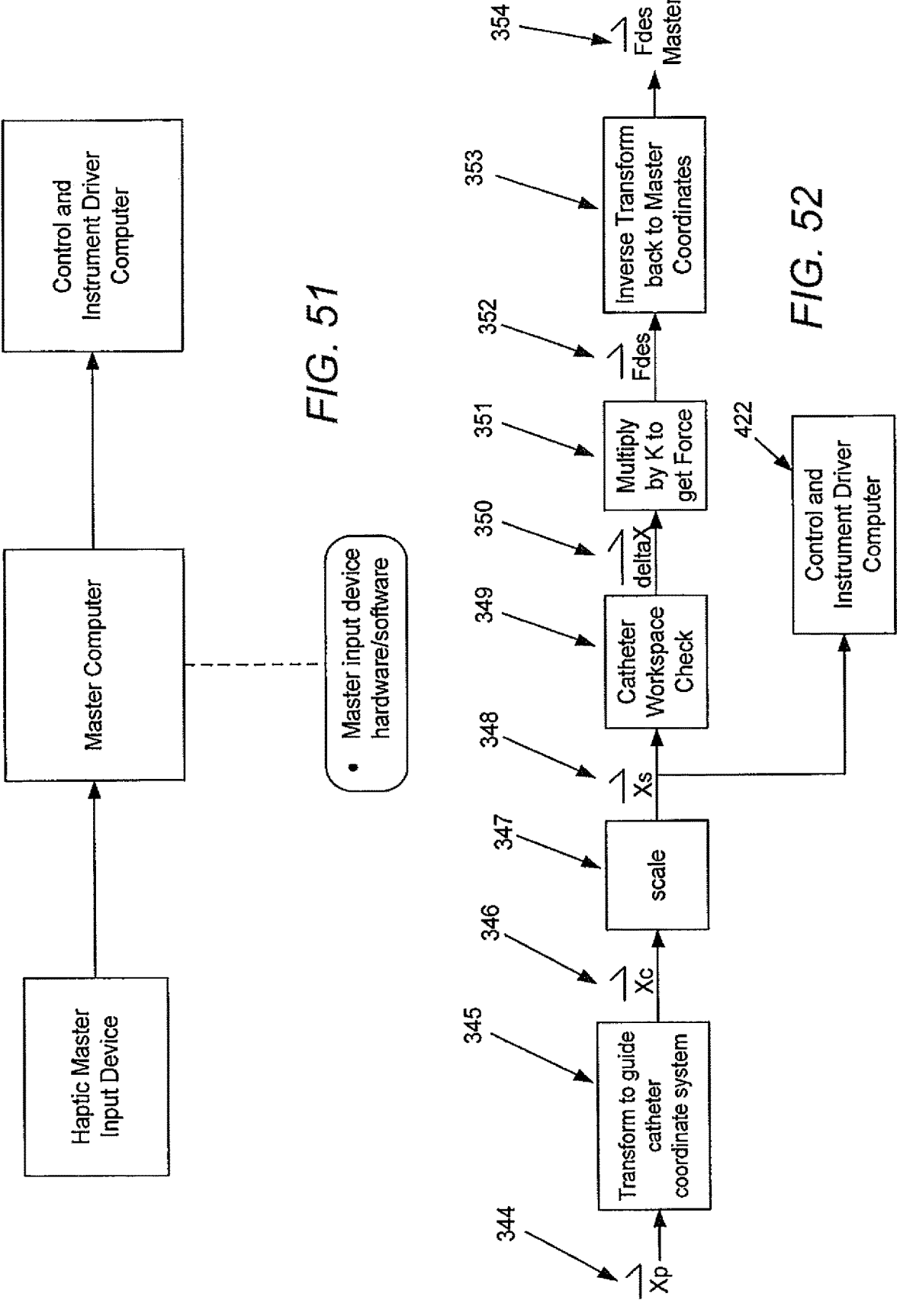
FIG. 51 illustrates a block diagram of a system having a haptic master input device.
FIG. 52 illustrates a method for generating a haptic signal in accordance with some embodiments.

Referring to FIG. 51, in one embodiment, the master input device may be a haptic master input device, such as those available from Sensible Devices, Inc., under the trade name Phantom™, and the hardware and software required for operating such a device may at least partially reside on the master computer. The master XYZ positions measured from the master joint rotations and forward kinematics are generally passed to the master computer via a parallel port or similar link and may subsequently be passed to a control and instrument driver computer. With such an embodiment, an internal servo loop for the Phantom™ generally runs at a much higher frequency in the range of 1,000 Hz, or greater, to accurately create forces and torques at the joints of the master.

Referring to FIG. 52, a sample flowchart of a series of operations leading from a position vector applied at the master input device to a haptic signal applied back at the operator is depicted. A vector (344) associated with a master input device move by an operator may be transformed into an instrument coordinate system, and in particular to a catheter instrument tip coordinate system, using a simple matrix transformation (345). The transformed vector (346) may then be scaled (347) per the preferences of the operator, to produce a scaled-transformed vector (348). The scaled-transformed vector (348) may be sent to both the control and instrument driver computer (422) preferably via a serial wired connection, and to the master computer for a catheter workspace check (349) and any associated vector modification (350). this is followed by a feedback constant multiplication (351) chosen to produce preferred levels of feedback, such as force, in order to produce a desired force vector (352), and an inverse transform (353) back to the master input device coordinate system for associated haptic signaling to the operator in that coordinate system (354).

A conventional Jacobian may be utilized to convert a desired force vector (352) to torques desirably applied at the various motors comprising the master input device, to give the operator a desired signal pattern at the master input device. Given this embodiment of a suitable signal and execution pathway, feedback to the operator in the form of haptics, or touch sensations, may be utilized in various ways to provide added safety and instinctiveness to the navigation features of the system, as discussed in further detail below.

Figure 53:
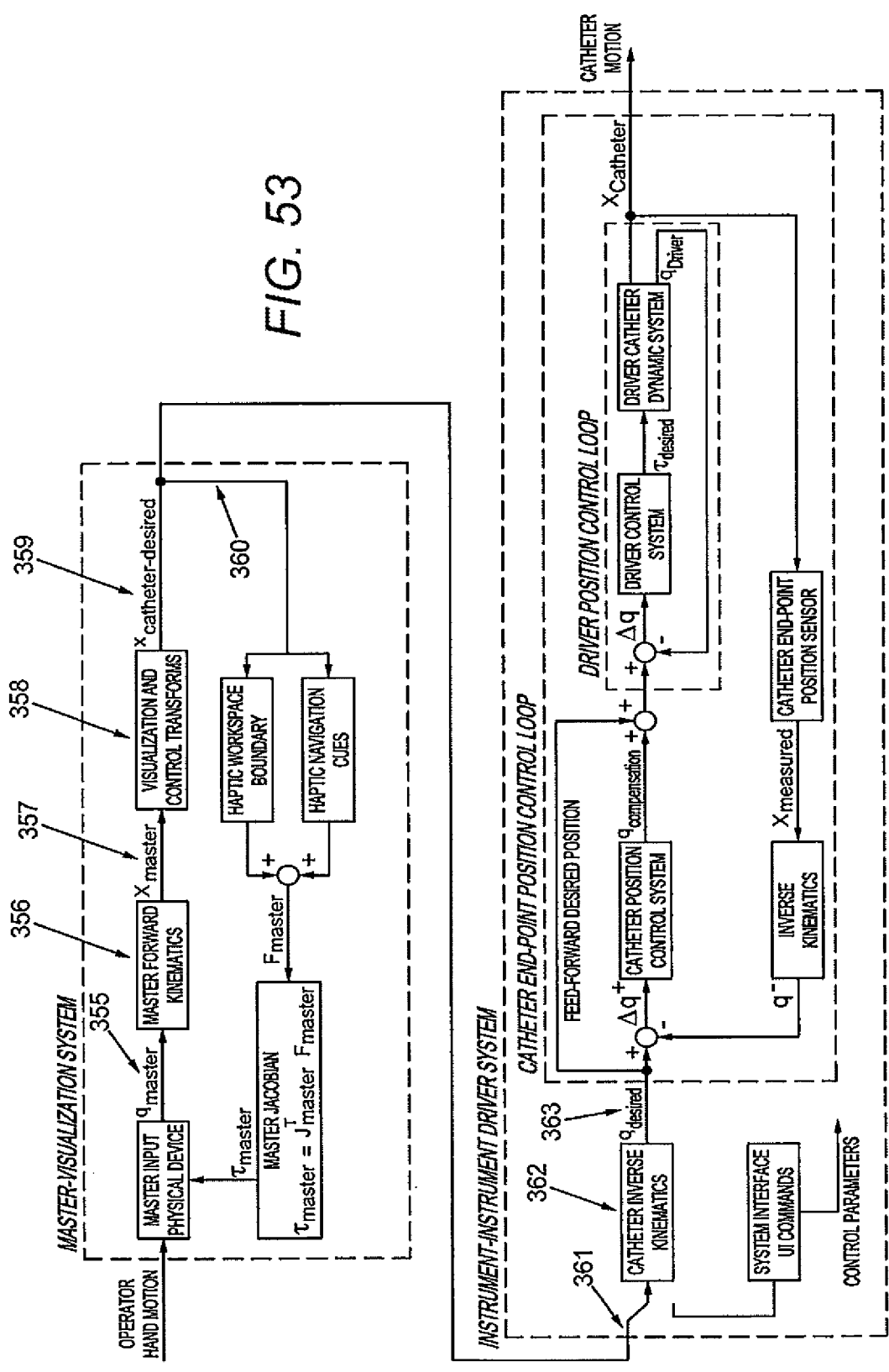
FIG. 53 illustrates a method for converting an operator hand motion to a catheter motion in accordance with some embodiments.

FIG. 53 is a system block diagram including haptics capability. As shown in summary form in FIG. 53, encoder positions on the master input device, changing in response to motion at the master input device, are measured (355), sent through forward kinematics calculations (356) pertinent to the master input device to get XYZ spatial positions of the device in the master input device coordinate system (357), then transformed (358) to switch into the catheter coordinate system and (perhaps) transform for visualization orientation and preferred controls orientation, to facilitate "instinctive driving."

The transformed desired instrument position (359) may then be sent down one or more controls pathways to, for example, provide haptic feedback (360) regarding workspace boundaries or navigation issues, and provide a catheter instrument position control loop (361) with requisite catheter desired position values, as transformed utilizing inverse kinematics relationships for the particular instrument (362) into yaw, pitch, and extension, or "insertion", terms (363) pertinent to operating the particular catheter instrument with open or closed loop control.

As discussed above, a system that controls a shapeable instrument can be improved using a shape measurement. The shape measurement relies upon a localization system as described above. In most cases the localization system generates a plurality of data defining real-time or near real-time positional information, such as X-Y-Z coordinates in a Cartesian coordinate system, orientation information relative to a given coordinate axis or system. Typically, the reference of the coordinate system can be taken from one or more points along the shapeable instrument. In additional variations, the reference of the coordinate system can be taken from one or more points on the anatomy, on the robotic control system, and/or on any other point as required by the particular application. As noted herein, the methods, systems, and device described herein are useful for device shape sensing that uses the shape data to improved catheter control, estimation, visualization, and diagnosis.

Figure 54:
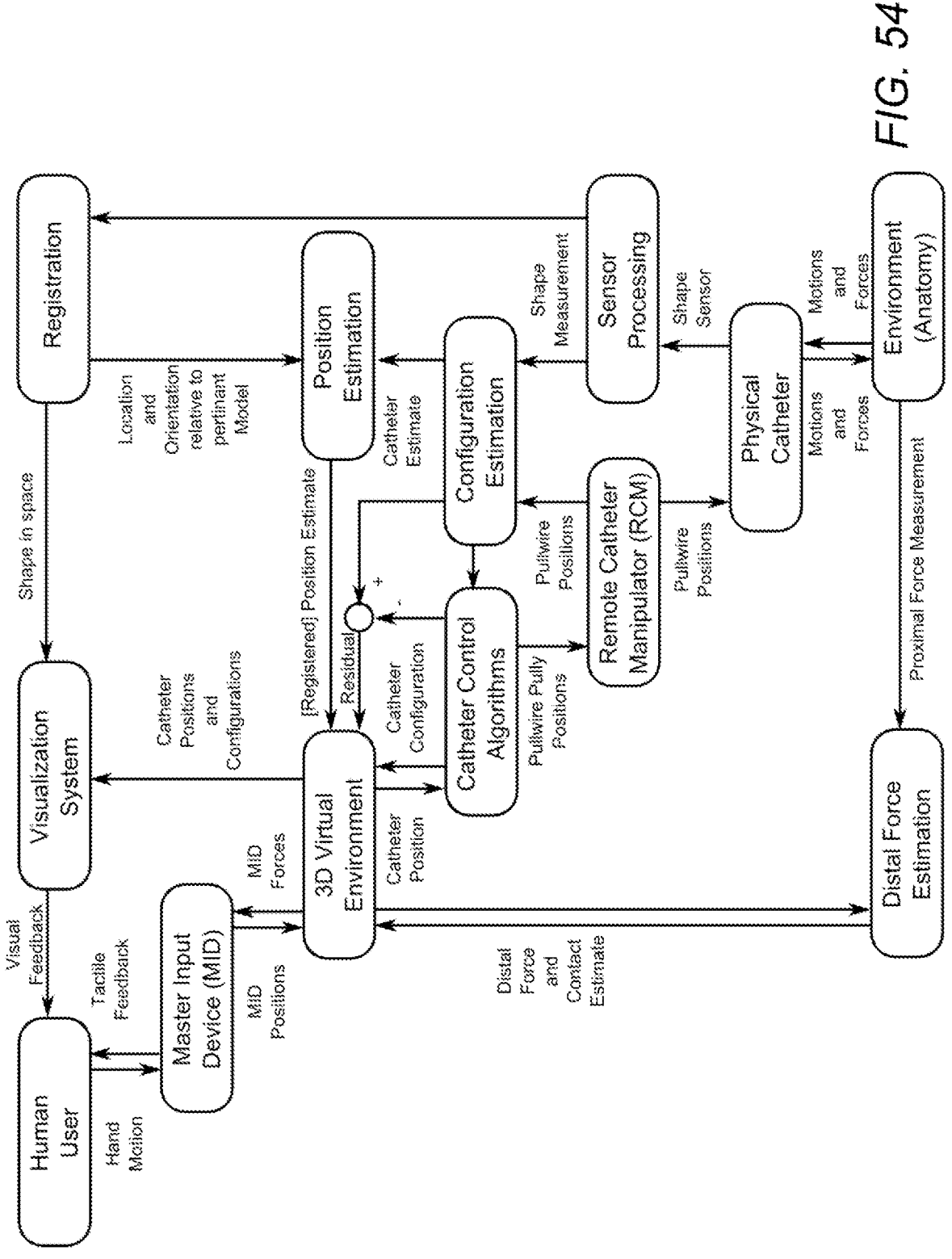
FIG. 54 shows a diagram of where shape information can be integrated into one example of a robotic control topology.

FIG. 54 shows a diagram of where shape information can be integrated into one example of a robotic control topology. As shown, applications for shape sensing can be categorized into three general groups based upon where the shape information is fed into the control algorithm. In a first example, the shape information is fed back into the catheter control algorithms in order to achieve improved catheter control. However, as shown, the shape information can also be fed to a virtual environment or to estimate a position of the catheter.

Figure 55A:
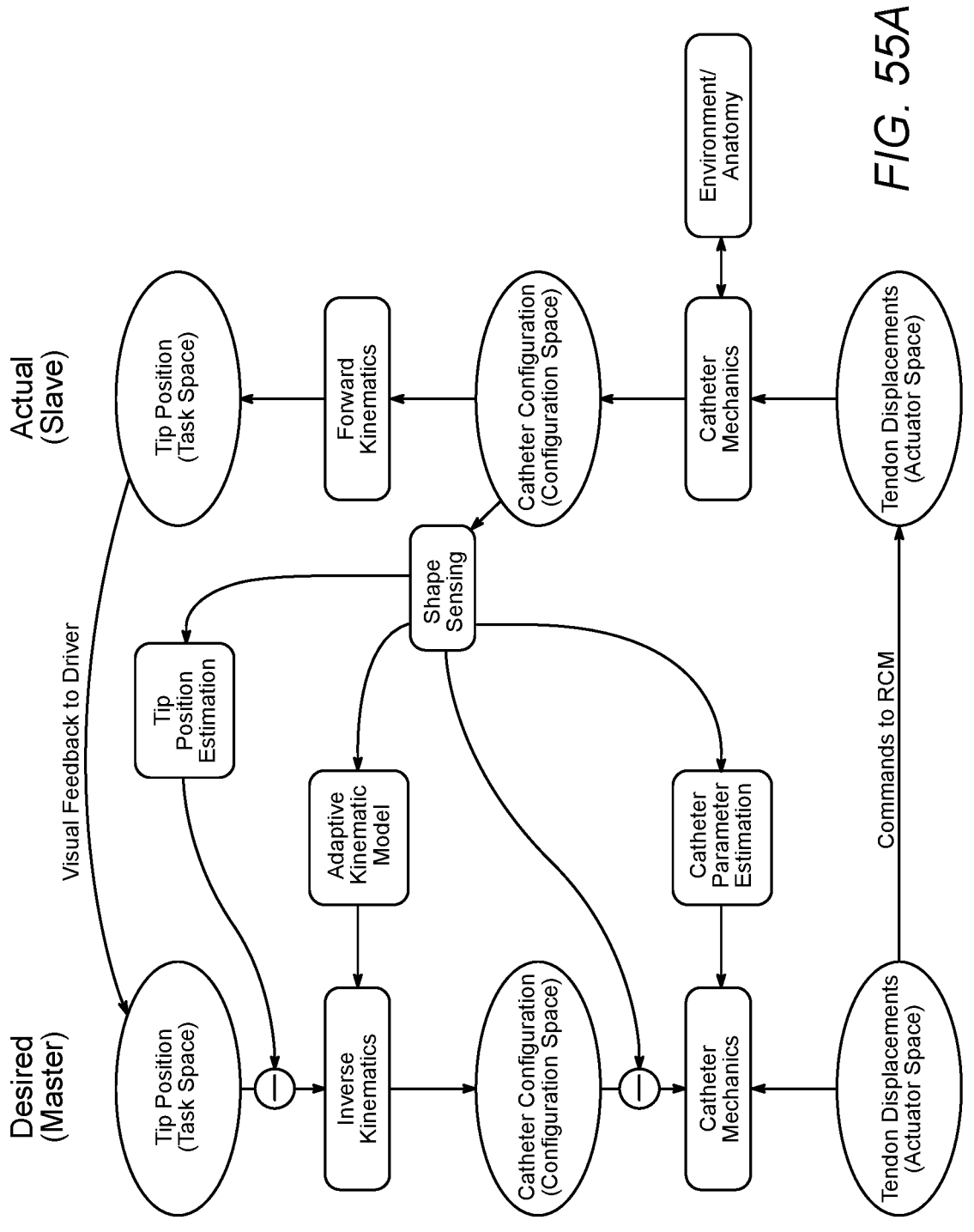
FIG. 55A shows an example of a control topology augmented by shape information at several possible locations.

FIG. 55A shows an example of a catheter control topology similar to that shown in FIG. 1B. However, in this example, the control topology is augmented by shape information at several possible locations. As noted above, the shape information (528) can be used for tip position estimation (530), adaptive kinematic modeling (532), and/or catheter parameter estimation (534). There are numerous ways in which this additional data can be used to close feedback loops that do not rely upon the human operator. It should be noted that there are multiple discrete points along the control algorithm in which shape information can be used to improve the robotic system.

Figures 55B, 55C:
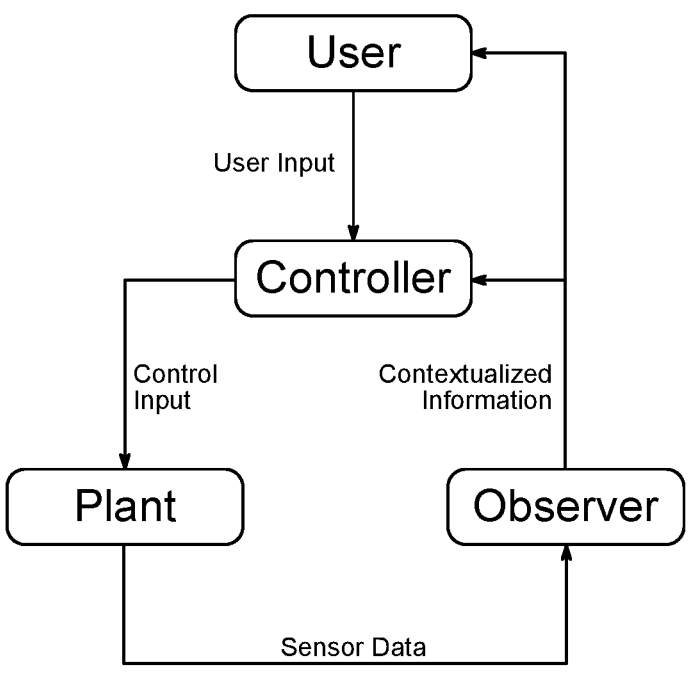
FIG. 55B shows a control topology with shape sensing using an observer.
FIG. 55C provides an example of information needed to estimate other elements of the set.

Shape sensing is one observation into the state of a flexible device. FIG. 55B shows a basic control topology. Without measured shape information, important positions along the flexible device must be estimated and controlled using other information. In its most general form, shape sensing is an observer as shown in FIG. 55B. In this context, observer refers to a control element that collects and uses sensor data from the plant to provide contextualized information to the controller and/or the user.

The following disclosure includes combining different pieces of information (e.g., position) with shape to estimate other unknowns (e.g., tissue contact). Shape is a very important piece of information for a flexible robot. Also, shape value increases when combined with other information channels. For example, shape combined with a solid mechanics model of the flexible section can be used to calculate possible forces acting on the device. More simply, with the position of the base and the shape, the position of the tip is known. This is described further below.

FIG. 55C provides an example of information needed (in columns) to estimate other elements of the set (in the rows). Tip position refers to a position registered to an external reference frame. An internal reference frame in which a device is actuated is assumed.

For simple flexible devices, shape can be estimated, albeit correctly only in near ideal scenarios, with tip position and orientation, base position and orientation and a model of the device. To effectively estimate shape, position and orientation information is needed at multiple points in the device. Corresponding to the complexity of estimating shape, it is useful for estimating other things. If the device should follow a perfect arc (a simple model), knowing the tip and base orientations and the path length (a subset of full position information) is sufficient information to estimate shape from simple geometric principles.

Tissue contact is useful for constructing geometric models of the environment or safely traversing constrained volumes. Contact can be inferred from shape deflection from the intended shape. However, analog forces may also be inferred from this difference in shape. We would like to simplify the estimate requirements to the most straightforward or smallest subset. Thus, we can say tip contact can be estimated from distal forces (which might be measured with local strain gauges or also inferred from IntelliSense measurements). If a three-dimensional model already exists, measured position registered to the model should indicate whether the device is in contact near the measurement.

If shape base position and base orientation are known, tip position and orientation are straightforward to calculate. Considering that tip position and orientation may be measured directly with off-the-shelf products (NavX, Carto), it may be more useful to consider the case with shape and tip position and orientation measurements. Base position and orientation can be calculated with shape and tip information. Further, position and orientation at any point along the path of the device are also known. With a geometric model of the environment, knowledge of the entire device position can be used to prevent or reduce contact or plan paths.

Since a device model (along with known actuator inputs) should allow estimation of ideal device shape, real shape could be used to adapt the model to achieve closer agreement between expected and measured shape. Device contact with the environment is important because it will cause its own shape deflection and thus the model adaptation could ignore data when in contact or include contact forces in the estimation (as discussed further below).

Distal forces can be estimated from shape, a solid mechanics device model and knowledge of contact. If the device is inserted straight but the measured shape indicates a bend, the amount and point of application of force must be estimated. The device will bend differently if force is applied at the middle of the bisected length than if force is applied at the tip. The shape of the bends along with their degree and the solid mechanics model will indicate external forces applied to the device. More detailed descriptions of the estimation of force and the use of force data will be described below.

Knowledge of contact can be used to create a model of the environment in the internal reference frame. Position information registered to an external reference frame allows such a model to also be registered. Shape is not indicated in the table for estimating a geometric environment model, but shape is important for estimating contact.

Finally, positioning element tension (and other internal device forces) can be estimated using shape and the solid-mechanics model of the device (assuming no contact). Positioning element tension may also be used in estimating or improving estimates of other items of this set, but shape is more important or useful.

Task Space Feedback

A task space application involves those situations where a robotic system attempts to position a working end of a shapeable device at a target region or goal. Applying shape feedback information to a task spaced application can assist in producing the desired task space positions and motions.

Figure 56A:
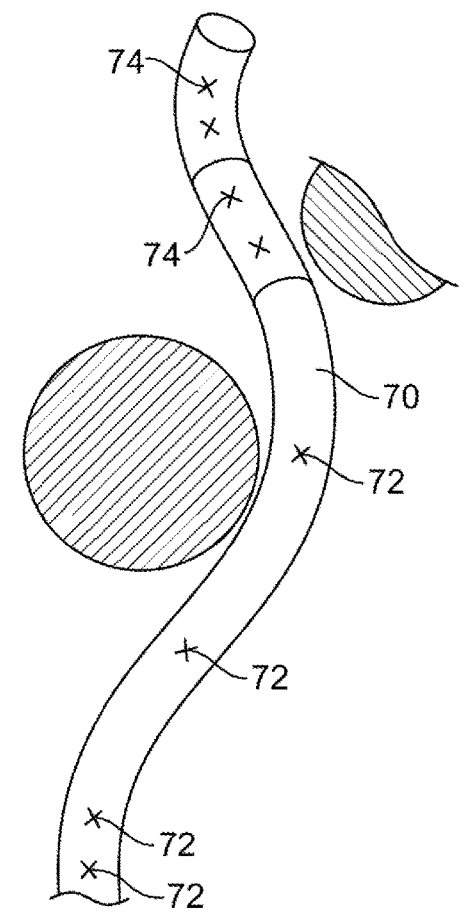
FIG. 56A represents a shapeable instrument when navigated through an environment.

The shape of a catheter, when given some reference, can be integrated to yield position or orientation, such as tip position estimation (530) represented in FIG. 55A. There are multiple other methods for measuring positions and orientations for points along the length of a catheter. Points of particular interest can be the termination of positioning elements on a control ring, termination of pressure vessels or any other actuator, or transitions in catheter stiffness. FIG. 56A represents a shapeable instrument (70) when navigated through an environment. In such a case, some points of interest might include intermediate points (72) along a lengthy section where inflections in curvature are likely to occur and the resulting effects on the tip portion or points (74) adjacent to the tip. The location of these points can be determined experimentally by observing shapeable instrument or a similar model in the relevant anatomy that can indicate appropriate sampling frequency to capture the observed bending state. Alternatively, modeling of the shapeable instruments mechanics can be used to determine those points that should be measured.

The task space can be specified in terms of the distal tip motion; however a given task may be concerned with intermediate proximal points as well to traverse a path. Therefore, task space control can include the explicit control of one or more positions and orientations along the length of the flexible device. In the simplest case, the model assumes free motion of all sections (such as in an open heart chamber) where the system controls the distal tip position to apply some therapy such as ablation. In this case, the system feeds an estimated tip position and orientation and compares against an input reference position as seen in FIG. 56B.

This error signal can then go through some compensator (550) such as a time derivative and gain to yield a command such as a tip velocity. The forward kinematics can then be inverted differentially (552), (e.g., via Jacobian pseudo-inverse or other non-linear constrained optimization techniques) that translates the velocity command into an actuator command (such as displacement or tensioning of a positioning element). These actuator commands in turn put a force on the instrument and as it interacts with the environment (captured together as plant (554)), the sensor will read the new position/orientation for further feedback. If the sensor were not available, the feedback could simply be the model forward kinematics (556) that would at least prevent integration error in this scheme.

Figure 56B:
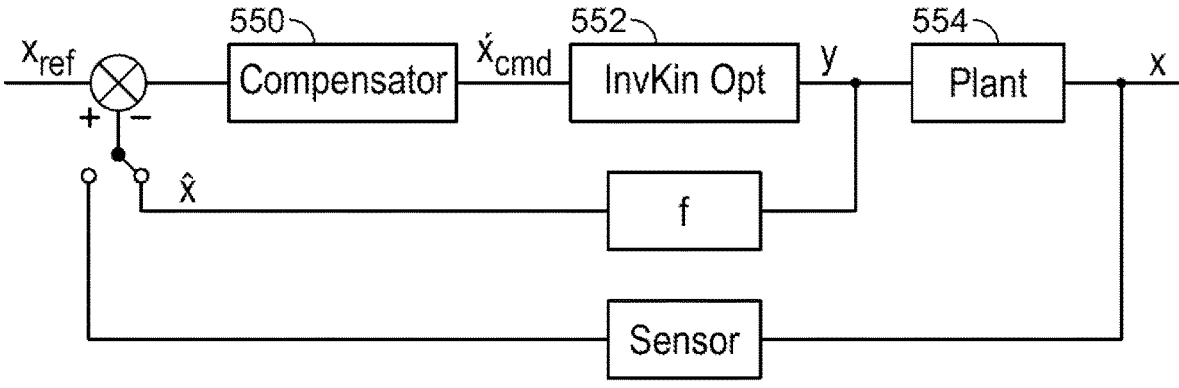
FIG. 56B shows an example of feeding an estimated tip position and orientation and comparing against an input reference position.

One example of task space feedback control using the scheme shown in FIG. 56B is to control an automated ablation inside the heart. In such an example, a 3-D geometrical model of the heart can be used in combination with the known location of the instrument (in this case a catheter) in the model to carry out a circular ablation around the pulmonary veins. A user could define points around the pulmonary vein. The system would then calculate a spline in between these defined points to further define the path of the catheter. The real catheter position would then be measured, and the difference between this position and the initial ablation point would be the error signal sent into the compensator (550). The inverse kinematics (552) then transforms the distal tip position error into commands that drive actuators to adjust positioning elements in the instrument to produce desired displacements. In some cases, the system can optimize for low force in the positioning elements. The catheter tip would then move towards the initial ablation position and the real position would be measured once again. Once the catheter is detected to be within some threshold of this initial ablation position (i.e., the error signal is sufficiently low), the commanded position would then begin to move along the ablation path. The user could adjust the speed of motion, as well as the position error threshold by which the catheter should stop moving if it exceeds.

The preceding example only uses the measured tip position as a means of generating an error signal. However, the sensor feedback can be used for other purposes. For example, the Jacobian (or inverse kinematics) can be adaptive based on shape or angle, or other feedback as described previously. This can be important because the inverse kinematics themselves assume a known configuration of the catheter and updated information would be beneficial. The adaptive component could be as simple as updating configuration parameters such as angle and curvature, or could be as complex as a learning algorithm that adapts over time to learn the mapping from commanded to achieved velocity.

An even simpler form of distal tip feedback control is simply to run the normal inverse kinematics as in FIG. 55A but with the tip position estimation used to feed in an error signal. In this case, the original position command into the inverse kinematics will now be an error signal with a gain term (and potentially integration, differentiation, or other operations), which should move the catheter in the desired direction. This method of operation could also benefit from adaptive kinematics to aid with directionalities. It could also benefit from lower level configuration feedback control as described previously so the assumed shape is more likely to be correct.

These methods for controlling the distal tip position and orientation could also be applied to more intermediate points of interest provided sufficient degrees of freedom. In some variations, it may be necessary to specify weightings or some other criteria on specific task goals if the dimension of the task space is greater than the dimension of the actuator space. In variations where the system controls multiple points simultaneously, the system might select directions that align axially with the local point so as to move along the present path. Alternatively, the system can place emphasis to distal degrees of freedom since proximal motions have large effects on distal points due to the moment arm from proximal constraints. These trade-offs motivate lower level control of the device in configuration space.

Configuration Space Feedback

Figure 57A:
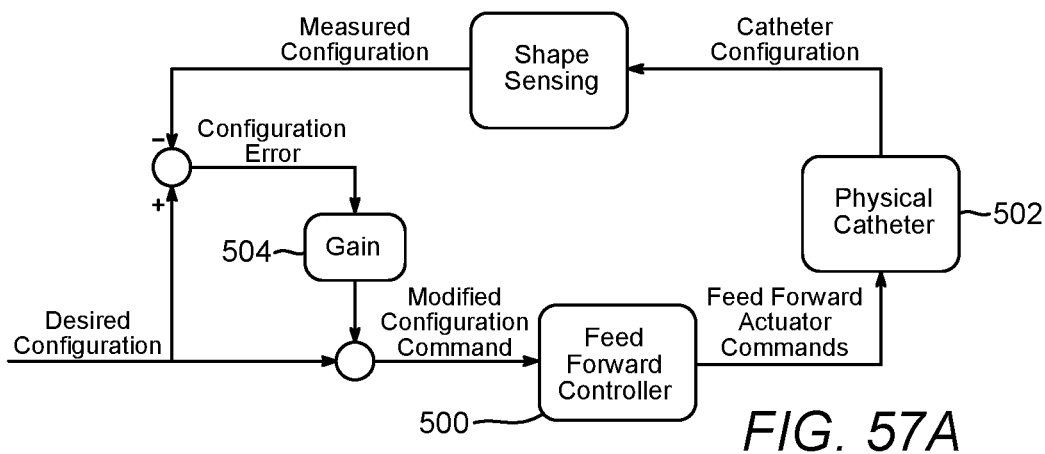
FIG. 57A illustrates an example of a modification to apply shape feedback information into an existing closed loop system to alter a feed forward signal.

Shape can describe the configuration of a device better than feedback of a single position or orientation. Having the capability to obtain shape information allows for the current shape of a device (including angle, curvature, profile, torsion, etc.) to be fed back into a controller. The controller can then process a command to actuate the device into a desired shape. FIG. 57A illustrates one example of a modification to apply shape feedback information into an existing closed loop system to alter a position control signal. As shown, shape sensing provides a measured configuration (via localization data) of a real shape of the shapeable device. This measured configuration is then compared to a desired configuration. Where the desired configuration is either modeled data or a known ideal configuration such that a differential between the real and desired shape can be quantified. Here, the feedback system uses the difference between the measured and desired catheter configuration to produce a configuration error, error signal, or signal that is then applied to a feed-back controller (500) to modify the configuration command sent to a feed forward control element that effects a response in the shapeable instrument or catheter (502). The difference between the measured and desired configuration can be applied through a gain element (504) as shown. The gain element can include a multitude of control elements such as proportional, derivative, or integral terms. This illustrated configuration uses shape data to alter a feed forward command that drives the shapeable instrument to a desired target.

Figure 57B:
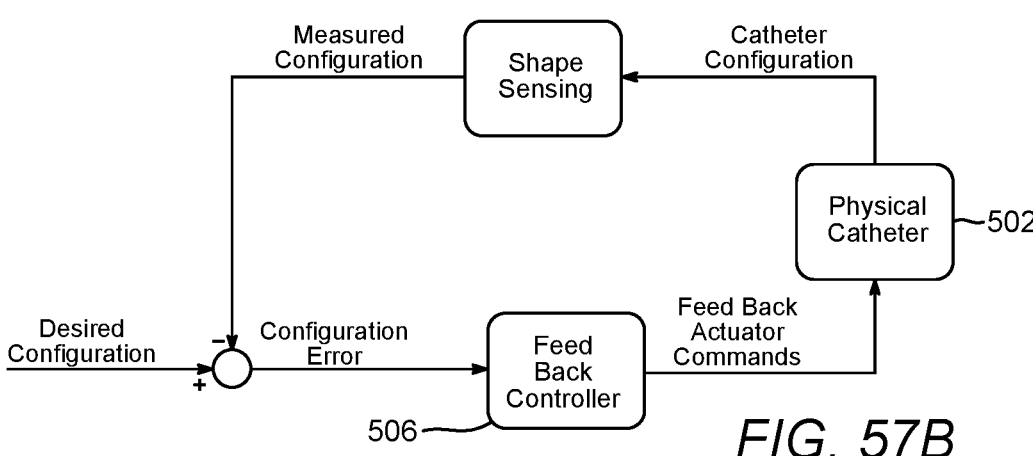
FIG. 57B illustrates an alterative closed loop control configuration for a pure feedback control form that uses an error between the measured or real shape data and the desired shape.

FIG. 57B illustrates an alterative closed loop control configuration for a pure feedback control form that uses an error between the measured or real shape data and the desired shape. This error is then fed as an input to the feed back controller (506) to generate a feed back signal to control the shapeable instrument (502). This configuration does not depend upon a model-based feedoforward control element (sometimes referred to as model-based control). However, a pure feedback controller as shown here may require integrator terms internally in order to achieve steady-state error requirements.

Figure 57C:
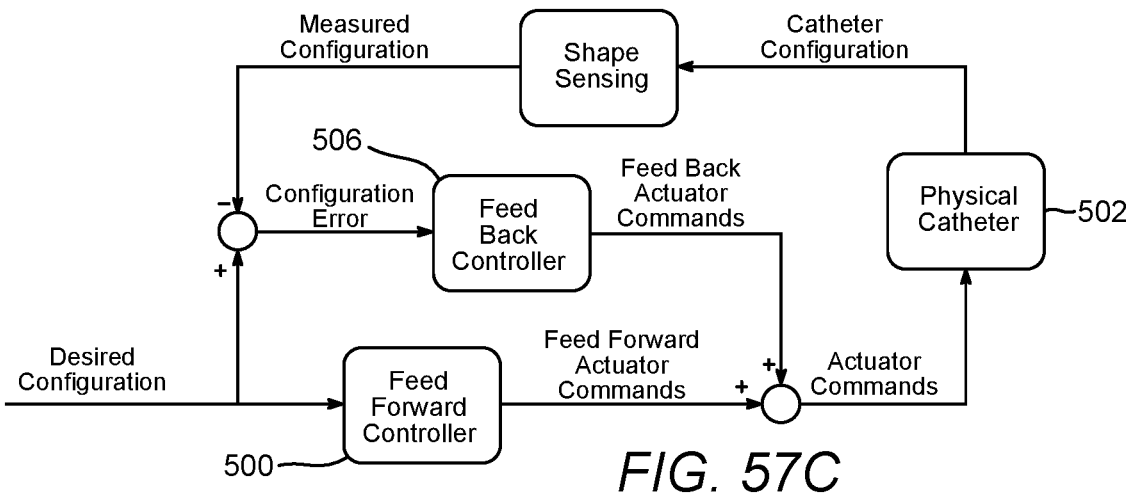
FIGS. 57C to 57E illustrate examples of a feed back controller combined with a feed forward controller to apply shape data.

Because both pure feed forward and pure feedback topologies have clearly identifiable advantages and disadvantages, the topologies can be combined as shown in FIG. 57C to realize the benefits of both feed forward and pure feedback configurations. As shown, the feed forward control element (500) uses its detailed model knowledge to improve transient tracking and to reduce dependence upon large integrator terms. The feedback control element (506) can help reject environmental disturbances or modeling errors by modifying the actuator commands coming from the (hopefully dominant) feed forward control element (506).

Figures 57D, 57E:
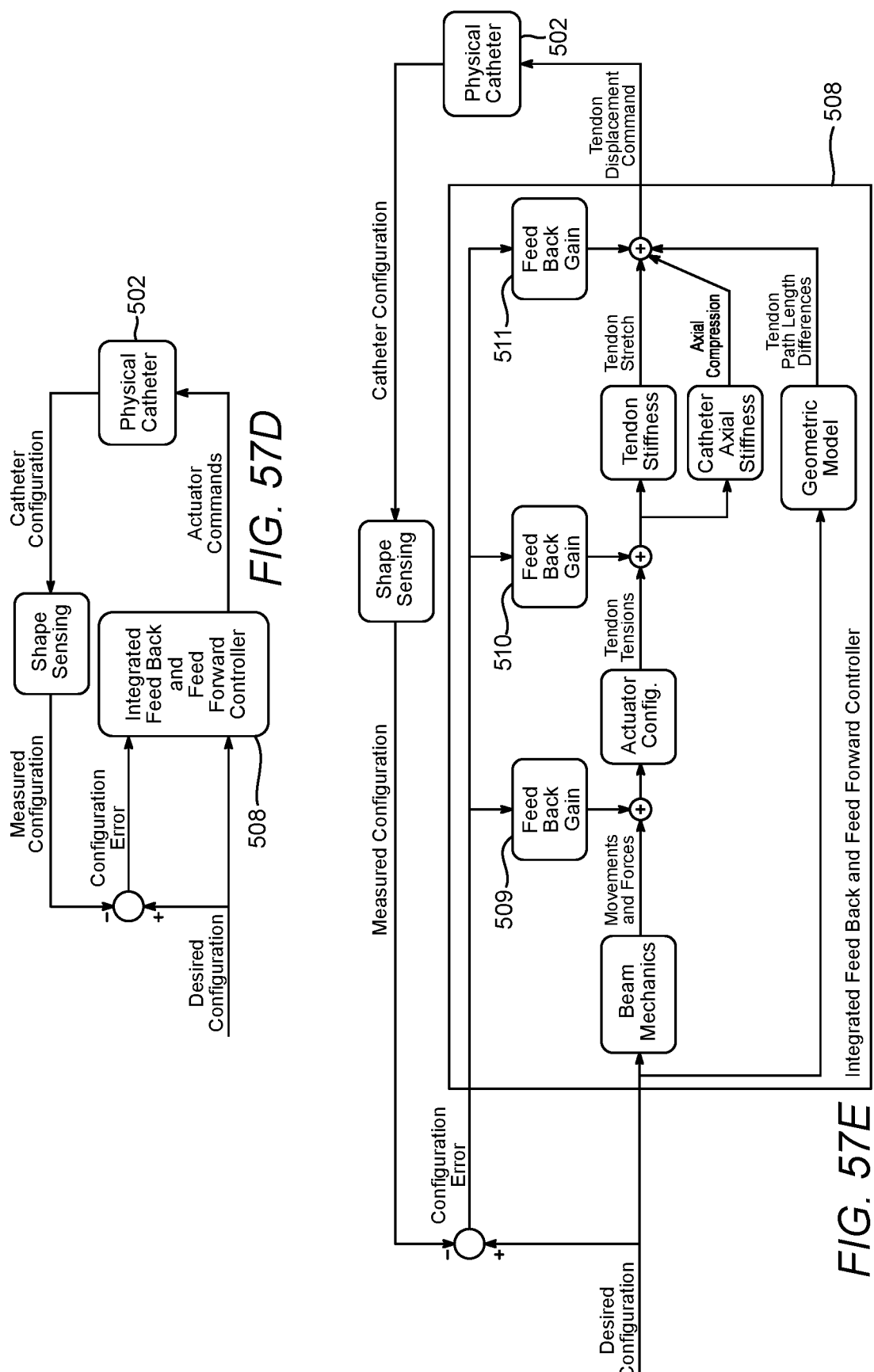

FIG. 57D shows another variation of a control system using an integrated feed back and feed forward controller. This allows the feed back controller to exercise control authority at one or more points within the feed forward controller.

FIG. 57E shows one example of an integrated feedback and feed forward controller. As shown, in the integrated controller (508), feedback terms are inserted into the existing (model based) feed forward control algorithms. In this example, configuration error, once mapped through appropriate gain elements (509), (510), (511), can be injected as feedback terms into the existing model-control pathway at several discrete locations. In the illustrated example, the configuration error, is used to modify the moments and forces coming from the beam mechanics model, the individual tendon tension commands, or the final tendon displacement commands. However, any of these methods can also apply to alternative actuation methods such as remote micro actuators (voltage command), fluid channels (pressure command), thrusters (ejection speed), magnets (orientation or shield duty cycle), etc.

Tracking with Shape Information

In an additional variation, systems, methods and devices using shape information can be used to track advancement of a shapeable instrument through an anatomic path. The anatomic path can include a path through a vessel, organ, or between organs. For example, the anatomic path can include a path through one or more vessels to access the heart. Alternatively, the path can include navigation through bronchial passages or the digestive tract. The robotic system then monitors the shape of the instrument for any changes in shape that would indicate the need for a corrective action.

Figure 58A:
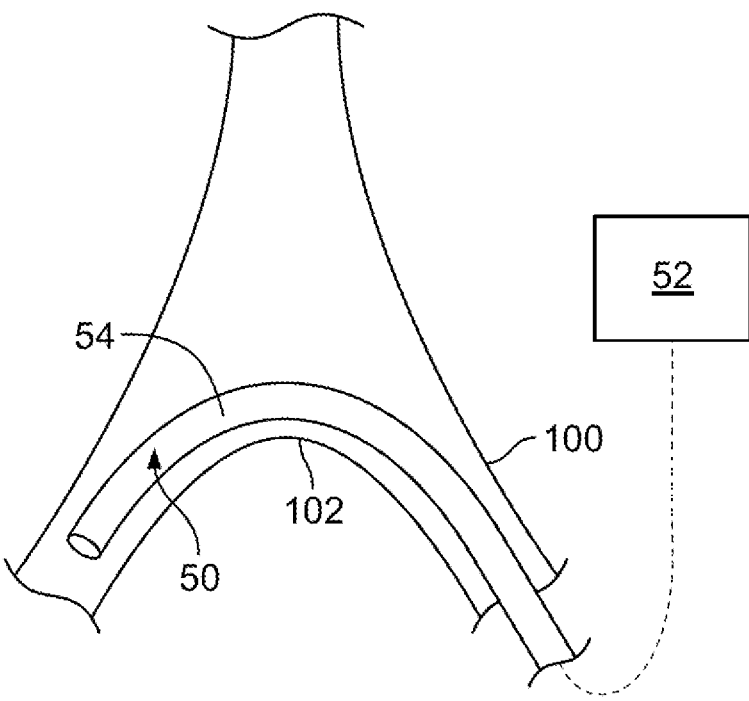
FIGS. 58A and 58B show examples of using shape data for tracking of a shapeable instrument in the anatomy.
Figure 58B:
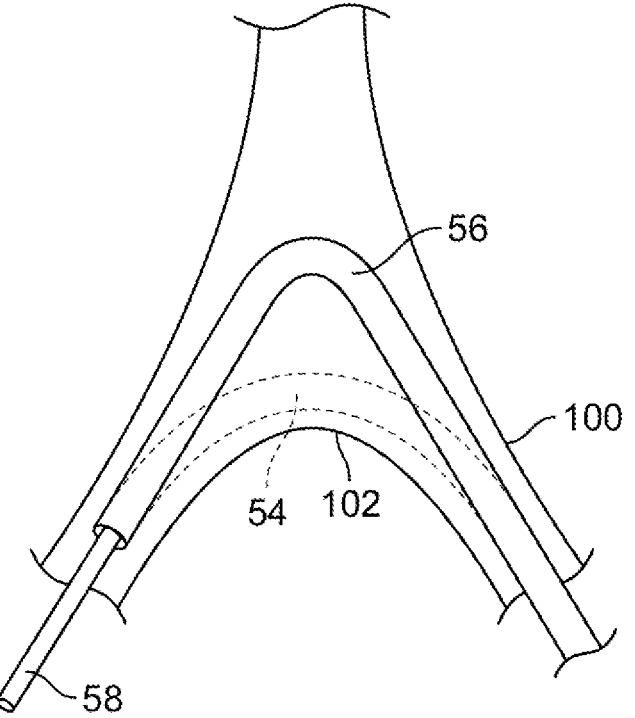

FIG. 58A illustrates an example of endovascular tracking of a shapeable instrument. In this example, the shapeable instrument (50) is advanced through an iliac artery (100) using a robotic system (52) that monitors shape information to adjust advancement of the instrument (50). FIG. 58A illustrates a desired shape (54) of the instrument (50) when advanced into the iliac artery (100) and across the aorta (102). As shown, if the shapeable instrument (50) advances as desired it will naturally assume the shape of the anatomy. During insertion, it is desired that the distal tip of the catheter advance in the direction it is facing. However, as shown in FIG. 58B, if the instrument (50) fails to advance in the desired path, the instrument (50) assumes a shape (54) that varies from the desired shape (52). In this example, the instrument (50) assumes a sharp bend as it backs into the aorta due to the lack of any constraining anatomy. In this situation, the distal tip of the instrument (50) either ceases advancing, or even backs further into the aorta. This motion in the opposite direction of intended could be a major problem for a robotic system (52) that is supposed to be intuitive.

To protect against this situation, the robotic system (52) monitors the shape of one or more portions of the instrument (50) to detect for the expected shape or to monitor for unexpected shapes such as the sharp bend (56) shown in FIG. 58B. In some variations, the robotic system saves a present or natural shape of the instrument (50) as a reference indicative of the shape of that anatomy. The robotic system (52) could even save a shape of the anatomy as a reference. During insertion, the progressing instrument (50) should approximately follow the reference if tracking is occurring successfully. If a sufficiently large deviation is detected in the present instrument (50) shape (56) with the reference or a desired shape (54), the robotic system (52) ceases instrument (50) insertion to prevent backup into the aorta. In an additional variation, using knowledge of the location of the deviation, the instrument (50) can be actuated near that location to attempt to break friction with the wall and descend in the direction of intended tracking. Alternatively, the instrument (50) can be withdrawn and advanced in a different manner to prevent the backup. This procedure, or similar actuation scheme, may be repeated along with continued insertion to resume tracking. Alternatively, if the shape detects tracking failure, a guide (58) could be inserted out of the distal tip of the instrument (50) as far as possible to obtain purchase (or stability). This guide (58) could then be left in the anatomy to provide a track for continued tracking of the catheter.

Although tracking of shape is beneficial when advanced using a robotic system, tracking of shape can also benefit procedures in which the instrument is manually advanced or advancement is assisted via a robotic system. In such cases, the instrument will be coupled to a system that can provide information to the operator regarding the shape of the instrument as described above.

Reduced Model Control

One of the primary benefits of feedback control is avoiding reliance on models and their associated errors. The less data that is available, the more important a model becomes. With full state feedback of some combination of shape, position, orientation, or deformation over a sufficient history, the relationships between actuator and position or shape can be learned. For example, during a procedure the robotic system can use shape data to correlate a map between force on one or more positioning elements and multi-section bending of the instrument. This map can be inferred from many measurements. For a particular region, this map may depend on the anatomical constraints and may need to be refreshed (or continuously updated) if conditions are significantly altered. To supplement the data, a model could be used for the anatomy to estimate its presence and characteristics as it interacts with the catheter. This mapping could at one extreme serve as a black box within the controller (508) in FIG. 57D where the user input is first related to some description of the state of the shapeable element and the mapping is used to find the actuator commands. In this example, there is very little modeling, mostly on the high-level user interface relating the user's intentions to instrument state. Otherwise, the sensor data can be used in place of a model and continuously updated.

A simple use of reduced model control could be to monitor the mapping between proximal instrument insertion and distal tip motion. A distal tip of the instrument can move in almost any direction under proximal insertion depending on distal contact with anatomy. Therefore, knowing this mapping between proximal insert and distal motion is of critical importance in maintaining intuitive robotic control. In the simplest form, the user could request a calibration where the proximal insertion would be dithered, and the distal tip motion measured. Subsequent movements of the master input device in the measured direction would then map to distal insertion and preserve intuitive driving.

To further reduce the model, it might be possible to instrument a non-robotic catheter with shape sensing for a given procedure or sub-routine of a procedure. The specific goals of each part of the procedure could be stated and associated with the measured catheter state. This association could provide the basis for a mapping between user intent and catheter result that could be applied to a robotic system. The user could then simply operate the robotic system in supervisory fashion where the user provides a command such as cannulate the carotid and this command is then translated to catheter shape, then actuator commands: This process could be largely based on data history and not be overly reliant on complex models.

Different device and control architectures, shape sensing accuracies, and device configurations requires different modeling trade-offs. A less accurate shape sensor may require more device modeling to achieve accurate control. Thus, models are useful in many scenarios. Kinematic models of robotic devices are very useful. The strong geometric basis of kinematic models is well informed by shape. As discussed below, systems and methods use shape information to adjust or inform kinematic models.

Applying Shape Information to Kinematic Models

Due in large part to the open-loop nature of the existing instrument control, the instrument mechanics algorithms can be dependent upon an accurate kinematic model that represents the mechanical and physical characteristics and parameters of the instrument. Some of the parameters in this model are "tuned" at development/design time while others are characterized on an individual device basis or lot-by-lot basis as part of the manufacturing process. A partial list of these model parameters includes: segment length, overall lengths, diameter, bending stiffness, axial stiffnesses, and control positioning element stiffness, etc.

Figure 59A:
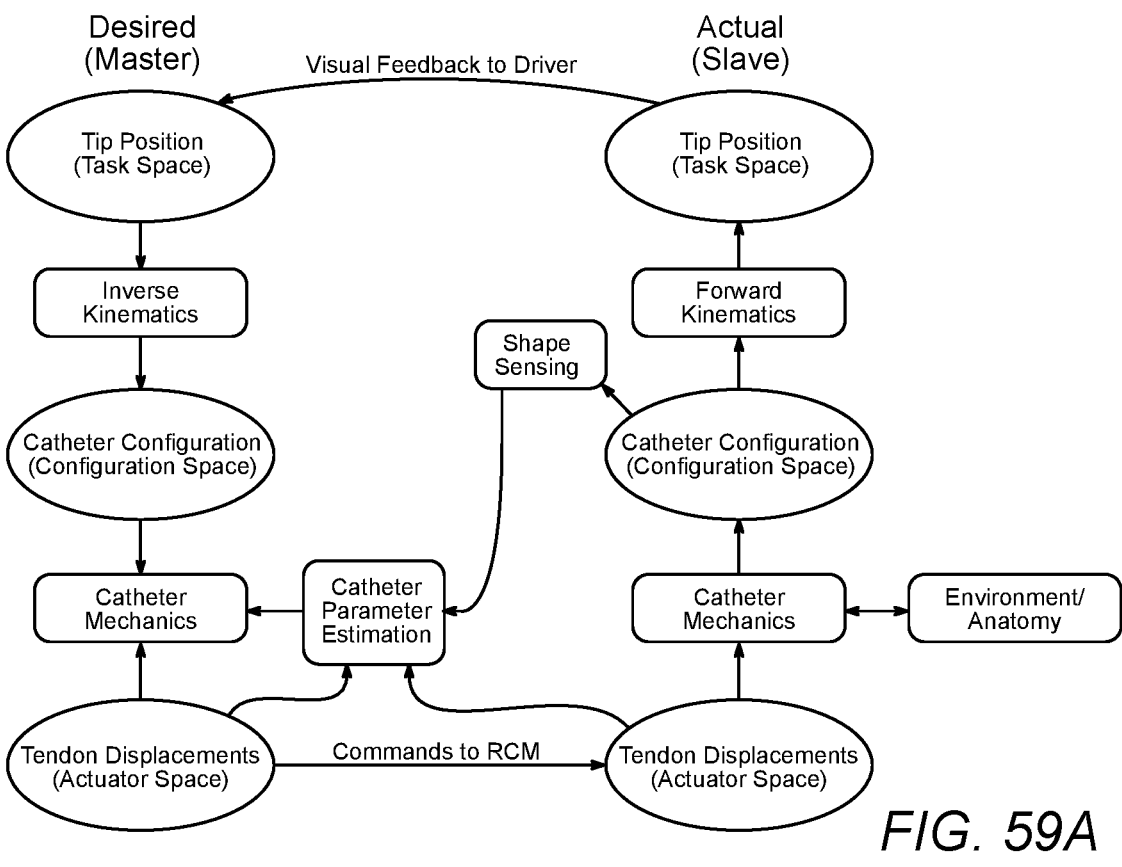
FIGS. 59A and 59B represent examples control relationship where shape sensing occurs after the real instrument is positioned to adjust catheter mechanics or adapt a kinematic model of the instrument.

In one variation, systems and methods disclosed herein can use an instruments measured shape data in combination with commanded shape, commanded tendon displacements, measured tendon displacements, and any other available sensor data (e.g., measured tendon tensions) to estimate improved parameters for the instrument model used by the instrument mechanics algorithms. This combination can modify an instrument's configuration control algorithms as discussed below. Alternatively, or in combination, the combination can allow for new parameter values that make the control model more accurately match the specific instrument being manipulated. The estimation of these improved parameters can be accomplished with existing model-fitting, machine learning, or adaptive control techniques. FIG. 59A represents an example control relationship where shape sensing occurs after the real instrument is positioned. The resulting shape sensing data is fed to an estimation of the catheter parameter along with virtual catheter configuration as well as virtual and actual tendon displacement. The resulting error or difference can be used to update the catheter mechanics in the catheter model for improving future commands generated by the robot control system.

Figure 59B:
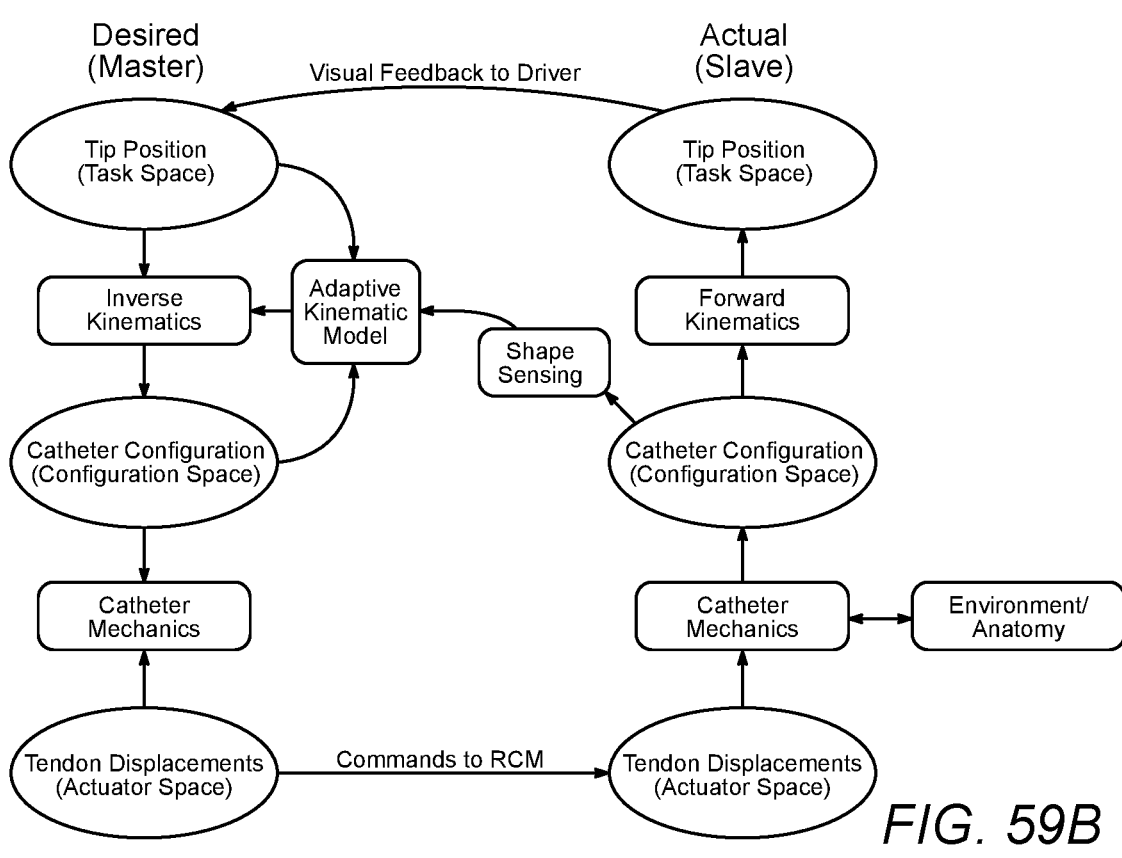

Another application of applying shape sensing data involves improving a performance of the instrument driving when a mismatch occurs between an assumed and a real kinematic relationship. For example, as shown in FIG. 59B, when measuring a real or actual shape of an instrument, the control system can adapt the inverse kinematic algorithms, if necessary, to more closely match how the real catheter actually moves based on the error between the desired instrument configuration and the obtained shape data. Thus, the inverse kinematic model becomes updated or improved based on real correlation of the movement of the instrument. This allows for the robotic control system to generate commands an improved inverse kinematic model that contains a more realistic set of inverse kinematic relationships. As a result, an actual tip position of the instrument should more closely track a desired tip position.

In a general implementation, the adaptive kinematics module will likely combine measured shape information with knowledge about the commanded shape, actuator commands, and any other sensory information that may be available (e.g., measured pullwire or positioning element tensions). Several more specific algorithmic implementations are listed below.

One variation of an adaptation scheme includes a "trial and error" type approach. This approach requires an initial guess as to instrument position with a subsequent collection of the shape data to determine the actual result. The control system then compares the initial guessed position or shape with the actual measured resulting shape and uses the measured error signal to improve correlation to learn from the error. In this sense, the control system uses an original or idealized inverse kinematic model to compute the initial robot control commands whenever the user starts driving in a new portion of the anatomy or driving in a previously unexplored direction. Because of this, the instruments response to the user's first motion commands should contain the greatest error. As the user makes repeated efforts to access a target, the response of the control system to manipulate the instrument should increase in accuracy.

In another variation, an adaption scheme could include the use of building a lookup table of commanded catheter configurations vs. actually achieved catheter shapes and their corresponding tip positions relative to the base coordinate frame.

In one example, adapting a kinematic model can benefit on a temporary basis. For example, if the shapeable instrument encounters an anatomic constraint during navigation the behavior of the instrument will be affected as long as it encounters the constraint. For instance, a common occurrence is where a shapeable instrument comprises a catheter where a proximal portion of the catheter is largely constrained by a blood vessel and only' a distal portion of the catheter is free to articulate. In this case, adapting the kinematic model can be as simple as estimating a new effective articulation length based upon sorting the length of the catheter into a section that, upon measuring shape, is observed to move freely and a section that generally is not changing shape (or encounters significant resistive force when changing shape).

In another example of adapting a kinematic model, a measured shape of an instrument can be used to compute curvature as a function of arc length along the instrument. By analyzing the shape data for sharp transitions or discontinuities the assumed articulating length of the catheter can be broken up into several subsections that may be behaving differently from each other, but within each subsection the behavior more accurately matches the assumed constant curvature arcs. Based upon this auto-segmentation, the inverse kinematics can be computed as a chain of several smaller subsections that each can be accurately computed with the traditional kinematic models.

Figure 60:
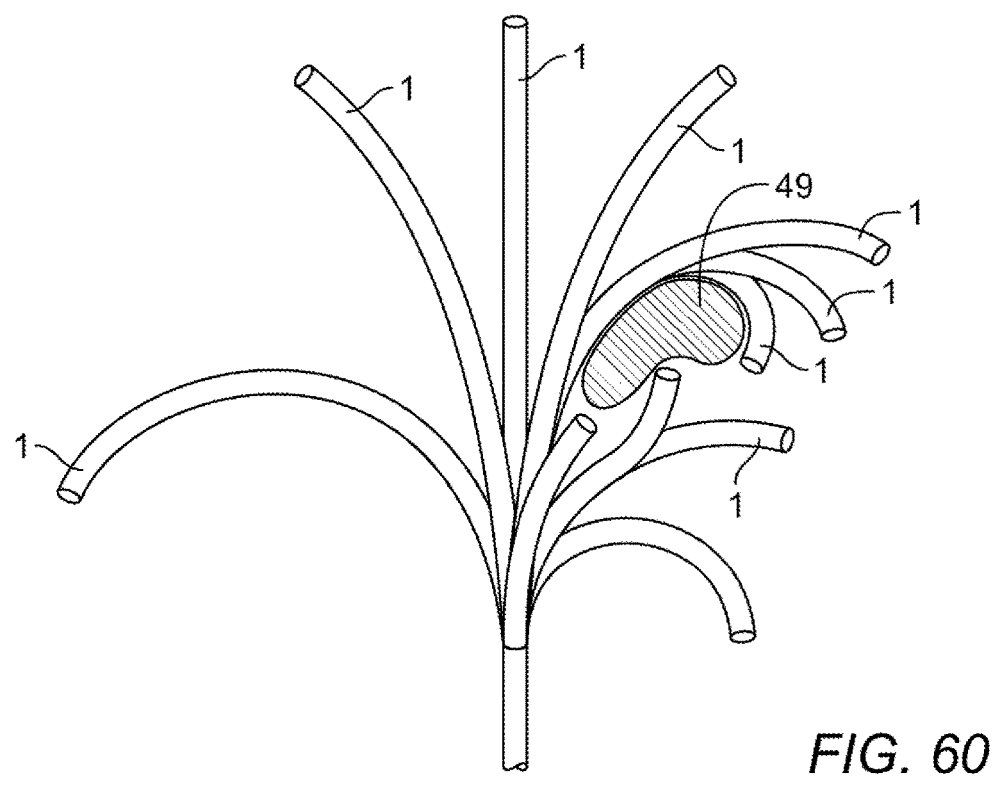
FIG. 60 shows an example of overlaying shape data to assess a local environment.

In another variation, shape data can be overlayed, as shown in FIG. 60. As illustrated, the shapeable instrument (1) is articulated or repositioned (either automatically by the robotic control system or manually by an operator). In doing so, the instrument (1) could use a threshold resistance value so that when encountering the resistance, the instrument moves to another position. Once a period of time passes, the system assess all of the shapes collected during the window, typically during intervals. The system can then look for voids or regions where the instrument was forced to avoid. These void spaces will likely represent some sort of environment constraint (obstruction) that can be included in the computation of the inverse kinematics. Once the system identifies these environmental obstacles, the system can apply a wide range of existing path planning algorithms to help solve for desired instrument shapes that achieve a desired tip position while avoiding the identified obstacles. Furthermore, the information shown in FIG. 60 can be provided in a graphical form for observation by the operator.

Improved Kinematic Models

An initial or existing inverse kinematic model is typically based upon a parametric model that describes the number and nature (length, degrees of freedom, coupling, etc.) of bending segments of the shapeable instrument. One variation of improving the kinematic model is to adapt the model via a model fitting exercise. The system or an operator can engage the robotic system to perform a training routine in which the shapeable instrument moves through a series of locations and shapes. Once sufficient training data is collected on the observed correlation between instrument configuration (shape) and tip position, one or more model fitting techniques can find the parameter set for the kinematic model that produces predictions that best match observations or that produces the predictions desired for the particular application. This best fit model is then used to compute the inverse kinematics for future iterations.

In yet another variation of adapting the model, an implementation of an adaptive kinematics module could use some intelligent combination of several of the concepts described herein. Keep in mind, that while all of these approaches deal with the translation of commands from task space to configuration space, they do not necessarily all employ the exact same description of the catheter in joint space.

Adaptive Jacobian

Another approach to adapting kinematics is to solve the inverse kinematics based on velocity rather than position. Typically, at each time step the system solves for an instrument configuration that achieves a desired tip position. Instead, the system can solve for the change in shape of the instrument, relative to its current configuration or shape, where the change produces a desired incremental movement or velocity of the instrument's tip change in catheter configuration mathematically, the general relationship between velocities is a derivative of the kinematic relationships between positions this relationship is referred to as the Jacobian. One significant benefit of an adaptive Jacobian model is that exact kinematic relationships between positions are not needed. The model could simply infer, estimate, or learn the Jacobian from the sensed shape information. However, when combined with other methods, determining the relationships would be required.

One example of a very simple adaptive Jacobian approach is in a modified control architecture where a configuration space command is a measure of how hard the system is trying to bend or direct the shapeable instrument in a particular direction. Using a measurement of the shape of the instrument and its associated tip orientation, the adaptive Jacobian approach translates a tip velocity command into a configuration commands as follows:

1) To move the tip laterally (relative to the tip orientation) in the direction of the catheter bend, apply more bending effort to the catheter segment.
2) To move the tip laterally (relative to the tip orientation) in the direction opposite the catheter bend, apply less bending effort to the catheter segment.
3) To move the tip in the direction it is pointed, insert the catheter segment.
4) To move the tip in the opposite direction than it is pointed, retract the catheter segment.

As noted above, one advantage to this control model is to reduced dependence upon accurately modeling all aspects of the catheter and the environment with which it interacts. The model simply relies on moving the shapeable instrument and its tip from its current position to a desired position.

Real Shape Display

Figure 61A:
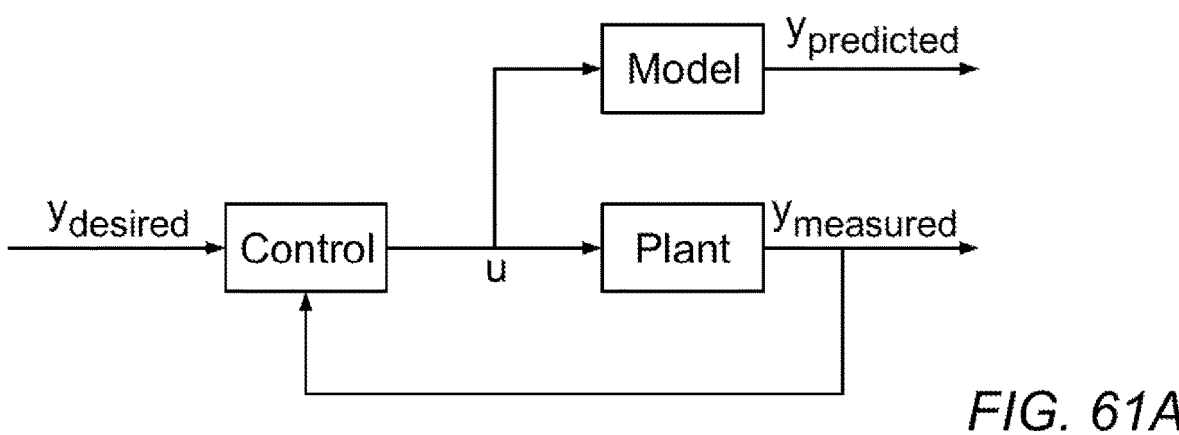
FIG. 61A illustrates a general system block diagram for adaption to minimize the differences between predicted and measured positions.

Estimation of an instrument's mechanical parameter can be performed post manufacturing to be set statically for the procedure. Alternatively, or in combination, mechanical and other parameters can be updated intraoperatively to improve control. When the properties of a flexible section are used to determine control inputs, system feedback can be used to estimate those properties. As a basic example, the stiffness of a section of the instrument can be used to decide how much to displace positioning elements (e.g., pull tension wires) to produce a desired configuration. If the bulk bending stiffness of a section is different than the existing stiffness parameters, then the section will not bend or bend too much and not produce the desired configuration. Using shape data to assess the shape of the instrument, a new bending stiffness can be continuously updated based on the degree to which the positioning elements are displaced and the resulting actual bending. A recursive-least-squares technique can be used to quickly recalculate a new bending stiffness as new data is measured. However, any number of other methods of adapting parameters can also be used. FIG. 61A illustrates a general system block diagram where the goal of adaptation is to choose the characteristics of the model that minimize the difference between $y_{measured}$ and $y_{predicted}$.

Figure 61B:
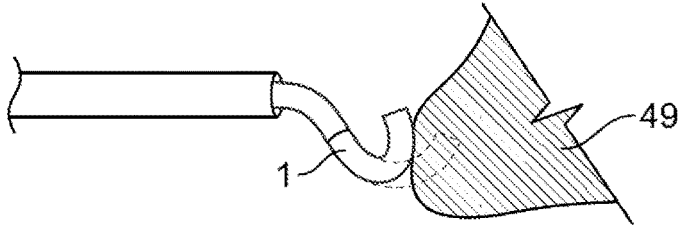
FIG. 61B illustrates an instrument that is prevented from bending as far as expected due to contact with an external object.

However, in adapting the actual instrument parameters, it will be useful to determine if the instrument is in contact with the environment. When the instrument is operated in free space, the parameters can be adapted to reduce the difference between the desired configurations versus the predicted configuration. However, if the instrument (1) is not bending as far as expected due to contact with an external object (49), as shown in FIG. 61B, then updating the bending stiffness parameters should not be updated unless the instrument (1) is to be operated while engaging the object (49). Accordingly, this model will benefit from measuring external forces on the instrument (1) prior to altering mechanical parameters.

One instrument state that is difficult to observe in practice is a compression or extension along a longitudinal axis of the shapeable instrument. Knowledge of the compression or extension of the instrument is important in the control of the instrument because the actuators often act in series with this axial mode. For example, positioning elements or tendon actuation can be used to control an instrument by routing the positioning elements through a conduit along a length of the instrument. The control elements can be terminated at the distal end and actuated proximally to alter a shape of the instrument. In this case, compression of the instrument also affects the positioning elements and could even lead to slack. Therefore, the axial compression ore extension should be known or estimated to maintain improved control authority. In addition, the axial deformation can be important if some other member is routed co-axially with the shapeable instrument. For example, an ablation catheter can be routed down a central through lumen. If the instrument compresses, the ablation catheter becomes further exposed. Clinically, this exposure, or protrusion, can cause difficulty in performing articulations in small spaces since the uncontrolled ablation catheter will be sticking out further and occupying significant volume.

Ideally, an observer or a localization system could provide complete deformation information for the entire length of the device (similar to Finite Element Method results), including the axial deformation. In reality, measurements only of select states are practical, each potentially requiring its own unique sensor. In the case of axial deformation, there are a number of potential methods to sense the desired information. For example, in FIG. 62A, an optical fiber (12) can be incorporated into a shapeable instrument (1) as described above. However, in this variation, one or more the optical fibers (12) are configured in a helix within the instrument (1). The helices of the optical fiber or fibers (12) provide mechanical flexibility and can provide for estimating compression of the instrument (1).

Alternatively, as shown in FIG. 62B a longitudinal multi-core fiber (12) could be allowed to float either along the centroid of the shapeable instrument (1), or at some other distance from the centroid. At the proximal end (17) the fiber (12), compression or extension of the instrument (1) causes the fiber to move relative to the instrument since it is free-floating. Axial deformation or expansion can be measured by measuring the movement of the fiber (17).

This linear motion of the fiber (17) can be measured by a linear encoder or similar method. Since the bending can be calculated using the Bragg Gratings or another localization system, the manipulator's axial compression can be found from this proximal linear motion of the fiber. Additional variations of this configuration allow for any other flexible element to be used instead of the freely floating fiber. Such flexible elements include, but are not limited to: a wire, coil tube, or actuation element so long as its own axial deformation is observable or reasonably assumed to be negligible. If such axial deformation is predicted to be significant, the force on the elongate element could be measured to estimate its own axial deformation. Similarly, the force of all actuation elements could be measured or modeled to estimate the total axial deformation of the flexible manipulator itself.

Given information of axial deformation, there are various steps that can be taken to make use of this information. For example, as shown in FIG. 62B, an ablation catheter could be controlled to axially adjust so that the amount exposed at the distal end of the shapeable instrument (1) is controlled. Similar to that shown in FIG. 62B, in an architecture with multiple concentric manipulators (such as the Artisan inner and outer guides manufactured by Hansen Medical), inner and outer guide insert positions can be adjusted to account for axial deformation as well. In fact, the axial deformation could be used for manipulation of the devices to achieve a desired axial motion. This axial motion could be useful for extending reach, dithering out tendon friction, ablation catheter friction, or otherwise. Another use of active axial deformation control would be to pre-load the manipulator by a quantity sufficient to hold constant compression over the range of articulations. Then the ablation catheter would appear to stay fixed with respect to the guide catheter.

As previously mentioned, the axial deformation can be important simply for maintaining control authority as it affects the actuators. For example, if the axial deformation were accurately known, that quantity could be adjusted via the actuators that drive the positioning elements in addition to the amount due to bending and deformation of the positioning elements themselves. Furthermore, with accurate knowledge of the axial deformation combined with some knowledge of bending, the ab solute angle of a point on the catheter may be identifiable with respect to the robot. For example, if the total force on the catheter is measured or modeled, we can infer the axial deformation based on stiffness.

An alternative way to measure the axial deformation would be to obtain localization data (from sensor, image processing, etc.) of the ablation catheter differenced from the inner guide catheter. Cumulative bending and axial deformation can also be obtained by the amount which a coil tube (60) (which is axially rigid and allowed to float in the catheter) displaces out of the proximal end of the instrument (I). The coil tube (60) displacement less the axial deformation estimate yields pure bend information that indicates the angle of deflection A of the distal coil tube termination with respect to the robot as shown in FIG. 62C. This angle information could be considered part of the shape sensing feedback where it can feedback to the user, high level control, or low level control. For instrument control as in FIG. 62C, the angular information gleaned from axial deformation could be used for tip pose feedback, in an adaptive model by updating directionalities, or in catheter parameter estimation for updating stiffness and more.

Pre-Tensioning

When a shapeable instrument is coupled to a robotic control mechanism there is typically an unknown amount of slack in positioning element. If the catheter is to be effectively controlled by position (rather than tension) controlling each of the positioning elements, this unknown positioning element slack must be removed by finding appropriate position offsets for each positioning element. Pre-tensioning is the process of finding out how much slack is in each tendon and removing it.

Several sources of initial slack in the tendons are illustrated in FIGS. 63A to 63C. As shown in FIG. 63A, the lengths of positioning elements (62) can inconsistent due to manufacturing tolerances. Additionally, as shown in FIGS. 63B and 63C, any bends in the proximal (non-articulating) or distal (articulating) portions of the shapeable instrument (1) will also contribute to an offset in the position of the positioning elements (62) due to different path lengths along the inside and outside of the bends. One way in which we deal with is to slowly drive the articulation axes until the operator "feels" (by monitoring motor currents or sensed wire tensions) the positioning elements (62) pull taught. Without shape sensing, this procedure is dependent upon two critical assumptions: 1) The articulating portion of the catheter is straight when pre-tensioning occurs; and 2) The non-articulating portion of the catheter does not change shape after pre-tensioning occurs.

The first assumption is important because by pre-tensioning is intended to find the "zero-point" for the control element displacements. It is from this "zero point" that control element commands are added to displace the control element to control the shapeable device. If the articulating portion of the catheter is in fact bent during pre-tensioning, this will introduce an un-modeled disturbance to the catheter control algorithms and result in degraded tracking of user commands. In theory, this assumption could be relaxed to require that the articulating portion of the catheter is in any known configuration during pre-tensioning. However, without shape sensing, a straight catheter (held there by the catheter's internal bending stiffness) is the most practical configuration to assume.

The second assumption comes from the fact that any motion in the non-articulating portion of the instrument (1) introduces additional offsets to the positions of the positioning elements (62). Because the configuration of the non-articulating portion of the instrument (1) is neither modeled nor (without shape sensing) sensed, the instrument (1) control algorithms are unaware of these changes in the positioning element (62) displacements, therefore resulting in degraded tracking of user commands. Conventionally, pre-tensioning the instrument (1) occurs after it has been inserted into the patient and taken the shape of the patient's anatomy. If subsequent significant changes to the shape of the non-articulating portion of the instrument (1) occur, the operator must straighten out the articulating portion and re-execute pre-tensioning to account for these changes.

Shape sensing provides an opportunity to relax both of these assumptions. The articulating portion of the instrument (1) could be pre-tensioned in any configuration by using the shape sensing system to measure the configuration of the catheter at the completion of pre-tensioning. The measured pretension offsets are then corrected by computing the deviation in position of the positioning element (62) due to the measured configuration. This computation itself if very similar to portions of the existing instrument (1) control algorithms.

The non-articulating portion of the instrument (1) can also be allowed to move after pre-tensioning by continually or periodically measuring the shape of the non-articulating portion. The pretension offsets can then be corrected by computing the deviation in tendon position due to the measured change in the shape of the non-articulating portion of the instrument (1).

Reaction Force

While contact deflection can disturb catheter parameter adaptation, use of shape data allows contact deflection to be used to estimate the contact force. If the bending stiffness of a section is known or has been adapted before coming in contact with an obstruction (49), the deviation between a predicted shape and an actual shape as measured can reveal where the instrument (1) makes contact and the degree of force with the environment or obstruction (49). If the estimate of bending stiffness, calculated simply from tendon positions and shape, were to rapidly change in conjunction with commanded movement, the device could be assumed to have come into contact with its environment. The new bending stiffness should be ignored in lieu of that calculated prior to the rapid change. Next, since the shape is dependent on the control inputs, device properties and the force from the environment. The force from the environment can be determined or estimated since the control inputs and device properties are known. For example, as shown in FIG. 61B, when the shapeable instrument (1) encounters an obstruction (49), the change in shape is measured and the control inputs as well as the device properties are know. Therefore, the system can calculate the force required to deflect the instrument (1) into its real position.

Estimating Force Applied to Anatomy with Shape Information

With no interaction with the environment, a flexible device will have a default shape for a sequence of actuator inputs. If the flexible device contacts with the environment, the device (or a portion) will deflect in shape along portions of the device again as shown in FIG. 61B. A correct estimation of contact forces applied against the shapeable instrument in a solid-mechanics model can minimize the difference between the estimated shape and measured shape that results from contact. However, there can be multiple combinations forces that will achieve the solution. The reaction force can be presumed to occur at specific locations based on the expected shape of the device. The device will often contact the environment at the tip with a reaction force perpendicular to the tip. The device may also contact along the body. To solve for body contact, a force can be applied to a beam model of the device at various locations along the length of the device model. The resulting deflected model that best matches the measured shape can be selected as best describing the reaction force.

Also, if there are multiple possible shapes for a set input configurations (i.e., path dependence), the previous configuration may also need to be considered in solving the forces.

If shape is not tracking the command, it could be in contact with tissue. Constantly observing the error between commanded shape and actual shape allows rapid detection of contact. An obvious metric for this error is the norm of the distance between measured and commanded positions along the path of the catheter (any number of norms could be used). However, this metric would amplify disturbances in curvature at one point (since such a disturbance is integrated to position). Another metric includes the mean square error between commanded and measured curvature at each point. This weights the points more evenly and attributes error properly at the afflicted location rather than the effect of the error on other points, as distance does.

Once contact is made, there are several possible actions depending on the severity of tissue contact. If no tissue contact is tolerable, the controller generates a signal or stops the instrument from moving and an alarm notice may be posted for the operator. In another variation, the control system may issue commands to automatically retrace motion to move away from the contact by a set distance.

If contact should merely be limited, there are more possibilities. For example, haptic feedback such as a vibration or force can be applied to the input device to indicate contact. Vibration is useful if the location or direction of contact is unknown. However, a reasonable guess of direction is the vector of motion when contact occurred. Force could be added to resist motion in that direction on the input device. Also, slave movement could be de-scaled when in contact.

If force is estimated as previously described, a haptic force could be applied to the input device proportional to the estimated force. The direction of the master haptic force should be that which will reduce the reaction force in the slave.

Use of Force Data for Path Planning

If the environment geometry is known, the forces can be estimated for all actual instrument configurations. Two sub-cases are described where the goal is either known or unknown.

If a goal position in the environment is known, the path to that point can be planned given knowledge of the environment geometry. The best path will depend on the cost associated with forces applied to the instrument (1). For example, one example constraint could be that distal tip forces must be below one threshold and body forces must be below another (this could be to effectively limit the pressure on tissue). These two conditions constrain the possible path to the goal. In fact, there may be no path and this could be communicated to the operator allowing the operator to change threshold or reposition the starting point. If there is one path that meets the constraints, it is likely there are many. Haptic forces or visual shading may be used to guide the operator to stay in the set of acceptable paths. Also, the path which minimizes peak forces (or sum-of-square forces) may be calculated and light haptic forces could be used to guide the operator to drive directly along that path. Similarly, that path may be automatically driven by the robot.

Figure 64B:
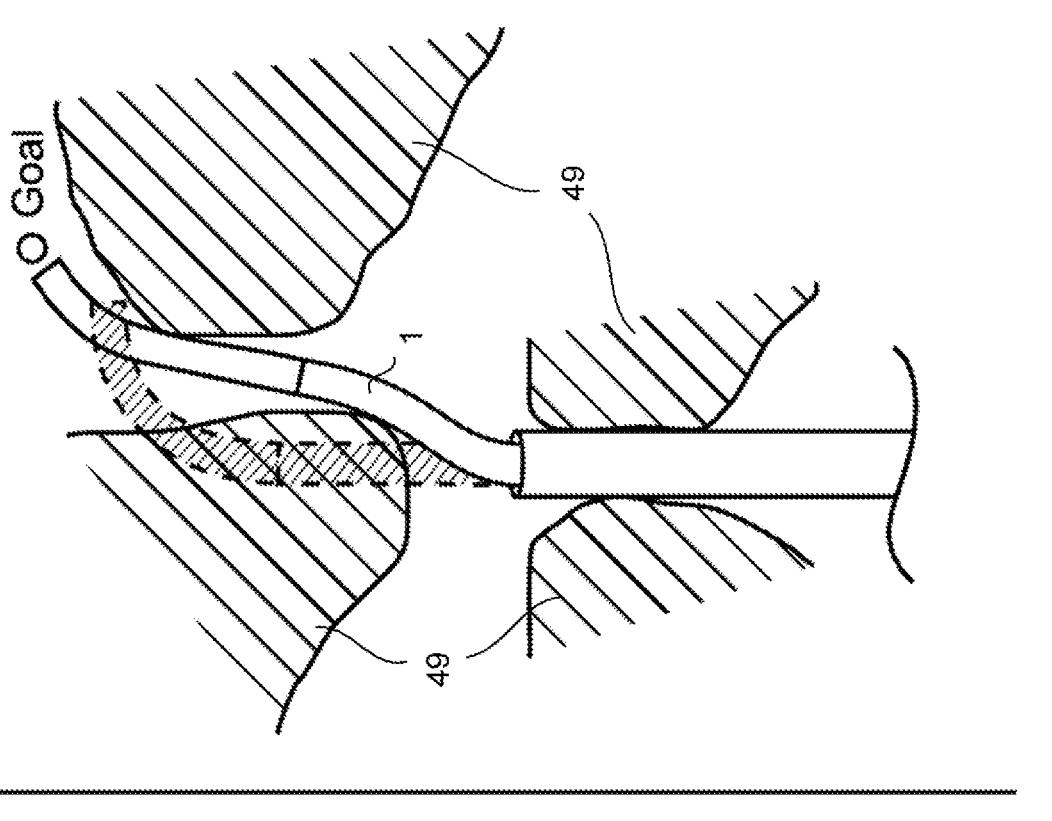
FIGS. 64A and 64B illustrate examples of using force data on a shapeable instrument for path planning.
Figure 64A:
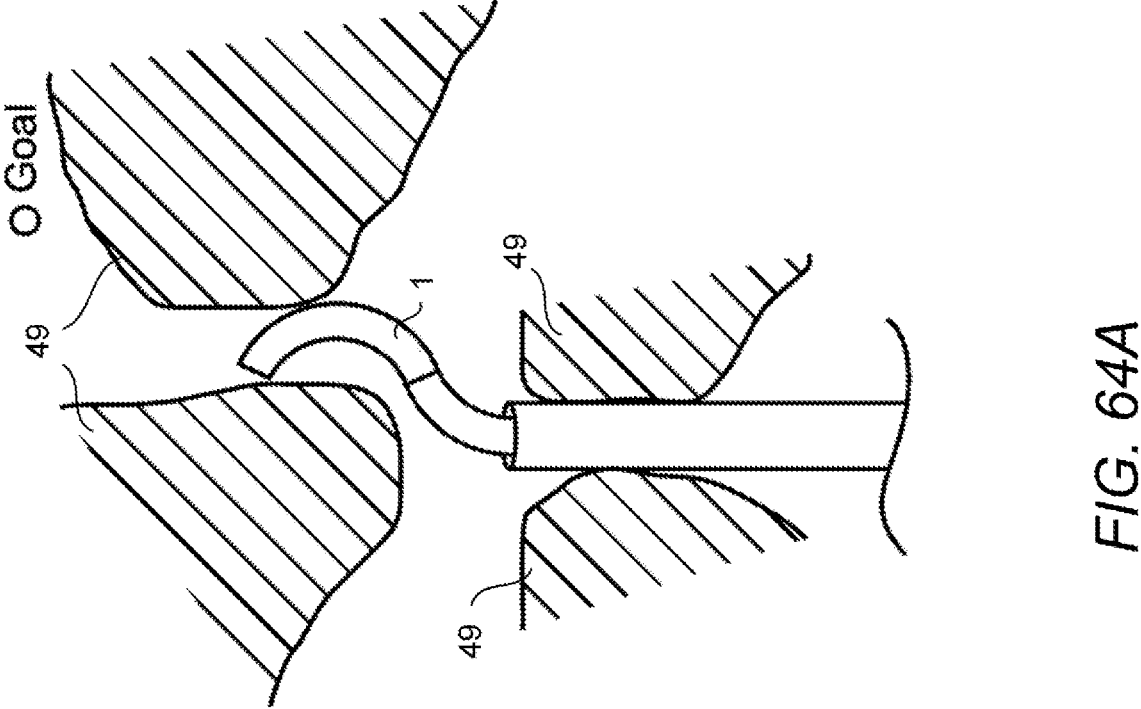

If the goal is unknown, there may still be a predictable set of acceptable paths through the environment. If the operator is interested in two distinct modes—maneuvering to a specific area then applying treatment in that area, the user interface can provide an interface to switch between the two modes. In the maneuvering mode, the path planner will try to keep the treatment tip and catheter body away from tissue and minimize forces along potential paths. As shown in FIGS. 64A and 64B, use of contact force and shape data to reach desired points (a), the system can guide the operator along paths with low forces that can lead to other areas of the geometry. As shown in FIG. 64B, switching to treatment mode, the system will allow the treatment tip to approach anatomy while controlling the shape to minimize interaction forces (pressures) along the body of the instrument (1).

Mechanical Failure and Structural Integrity of the Instrument

The use of shape information also allows for determining different types of mechanical failure. FIG. 65A shows a shapeable instrument (1) assuming a particular configuration. Generally, shapeable instruments that include positioning elements that apply tension but not compressive force have two main sources of mechanical failures modes that can be diagnosed with measurement of shape. The first mode includes fracture of positioning element that results in a failure to properly position the instrument (1). The second failure mode includes a fracture in the structure of the shapeable instrument (1) as noted by area (92). The ability to measure shape of the instrument (1) allows for an immediate indication of a mechanical failure of the instrument (1).

In the case of a fracture in the structure, bending with non-zero force around the point of fracture results in higher than normal curvature. The curvature may be higher than expected for a device and lead to an immediate failure diagnosis simply monitoring each point along the path of the device. An example of a block diagram to assess such a failure is shown in FIG. 65C. The high value shown in (520) can be pre-determined using the bending characteristics of the device.

Figures 65D, 66A, 66B:
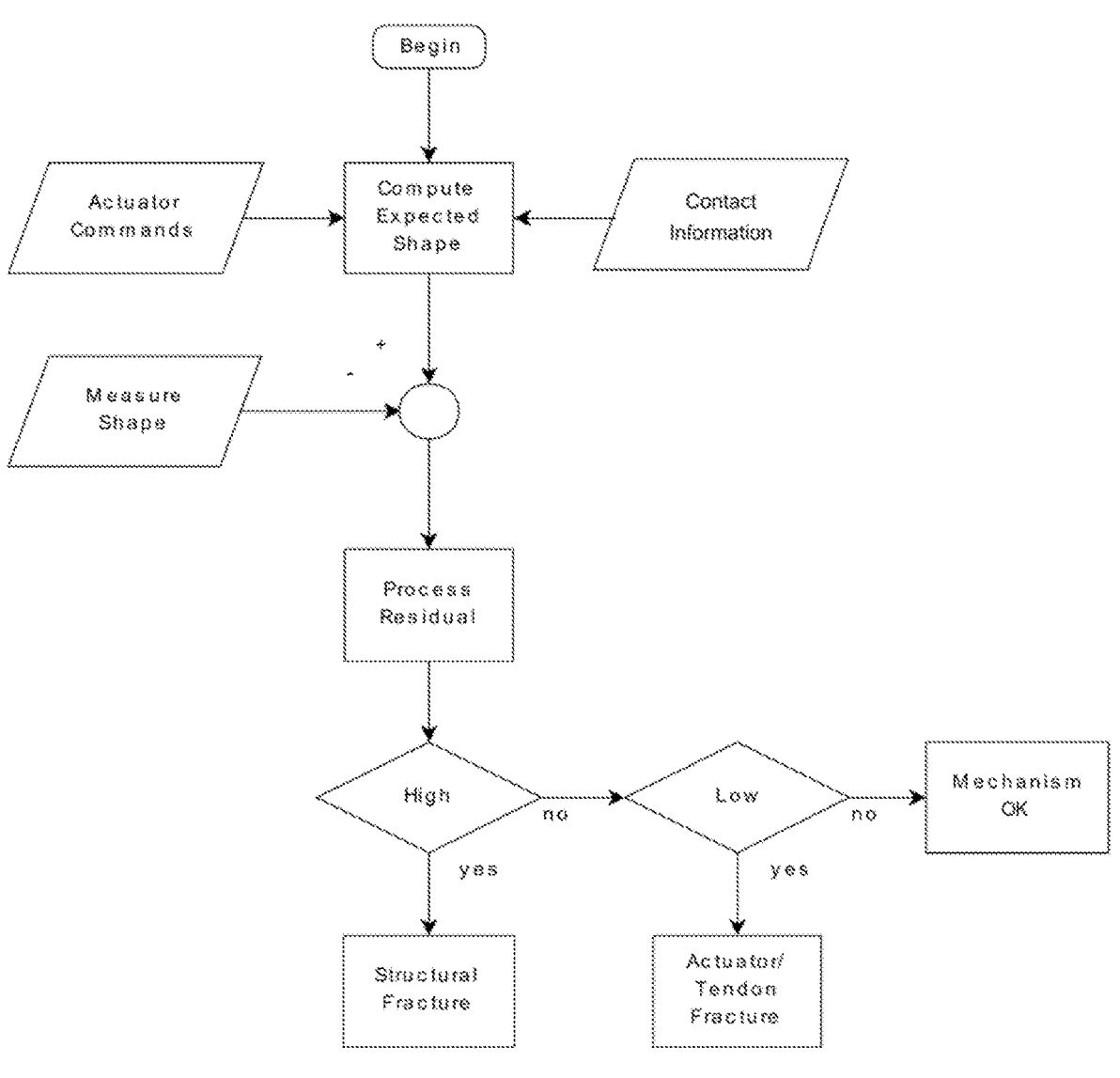
FIG. 65D shows an example of a block diagram to assess fracture or failure of a shapeable instrument.
FIGS. 66A and 66B show examples of visual indicators of different failure modes.

For a more subtle partial fracture, the curvature could be compared to an expected curvature generated by a model and a diagnosis made based on the cumulative residual (e.g., integral of norm of distance between expected and measured shapes), diagramed in FIG. 65D.

A simple model might be a minimum smoothness of curvature such that a discontinuity at any point gives rise to indicate a mechanical failure. The expected shape of a device could also be generated by a solid mechanics model taking into account the actuator inputs. The expected curvature for each point would be compared to the measurement of curvature at that point, iterating along the path of the device.

In the case of fracture of actuating tendons, the curvature would be less than expected for a given level of actuation. If the flexible section defaults to a zero-force position, the curvature must be compared to a modeled curvature. The flowchart in FIG. 65D describes differentiating between a case of a structural fracture with a high curvature and a positioning element fracture that give rise to a low curvature.

As discussed above, contact with the environment will alter the shape from that expected when the instrument is actuated in free space. Such environmental factors can be considered when comparing measured curvature to expected curvature to prevent a false indication of failure. The diagnostic algorithm can simply ignore shape measurements when in the shapeable instrument (1) contacts an obstruction. If distal force is measured, it can be included in models that estimate shape.

Dynamics can be used to assess the instrument for failure modes while it is in contact with the environment, meaning when there is an error between the desired shape and measured shapes. To detect a quick mechanical fracture (such as a break or tear), the measured curvature at each point along the device could be compared with a low-pas filtered version of itself. If the two differ greatly, a fracture may have occurred. The bandwidth of the filter would have to be faster than the bandwidth of actuation.

Following, the actuator inputs could be considered and applied to a current estimate of catheter shape. The shape estimate would filter the measured shape to accommodate contact deflection and apply the actuation relatively to the estimate. A beneficial by-product of this shape estimate would be an estimate of when the device makes contact with its environment.

Display of Fracture Information

When a fracture is detected, it is important to convey the failure to the automated system and user. When the control system is notified of a mechanical fracture, tension on tendons should be configured to freeze the actuator state or reduce passive applied force which would likely be the relaxed tendon positions. In an additional variation, the user interface could provide haptic feedback to the operator by changing the force characteristics on the master device (e.g., turn off force-feedback, centering, gravity compensation, etc.). Also, the system could display a visual indicator of device failure. Visual notification could be simply textual. Alternatively, the visual notification can be information rich. If the system has a visual depiction of the instrument, the depiction of the instrument could be altered in shape, color, and/or other representative features to reflect the failure. Thus, if the instrument structure fractures, then the operator interface display could show a displacement of material at the suspected point of fracture on the corresponding depiction. If the actual fracture mode is not visually compelling to demonstrate the degree of corresponding mechanical problem that will result from the failure, the main display could show an icon near the area, magnify the area and show the fracture or highlight the area with contrasting colors. Simulating a colored semi-transparent light illuminating the fractured section would imitate other alarms such as police revolving lights to give operators an intuitive reaction.

Communicating the point of failure and type if possible is important in those cases where stopping treatment or operation of the device is not the chosen fail-safe response to a failure. If the instrument remains functional (albeit impaired), then the system could permit a user with the option of continuing in a reduced workspace or reduced functionality. In such a case, showing the old and new workspace as well as the fracture point will aid an operator in safely performing their tasks or exiting the workspace. FIGS. 66A and 66B illustrate two examples of visual indication of a failure mode. For example, FIG. 66A shows a condition where a positioning element fails causing low curvature. As shown, the real shape of the device is shown with a phantom desired shape. Also, the fracture is represented by a failure indicator. FIG. 66B illustrates another example where the device remains operable but the fracture (92) is indicated by a visual fracture indicator (96). Clearly, any number of additional variations are within the scope of this disclosure.

Active Secondary Diagnostic

Because of variation in devices and operating conditions, there is often some overlap between acceptable and unacceptable failures in a given diagnostic metric. Thus, there may be what are statistically called Type I or Type II errors for the hypothesis that there is a failure (false failures/positive or false passes/negative, respectively). To avoid false passes in critical diagnostics, the pass-fail criteria may be biased to report failures when the behavior is questionable due to operating condition. As one example, if a positioning element fractures while a default-straight device is nearly straight it will be difficult to diagnose with the small change in movement from nearly straight to straight. The system may request an operator perform a specific maneuver or input in order to verify the failure behavior. In the positioning element fractures situation, the system will request the operator move in the direction the positioning element in question would normally pull. A lack of motion with such intentional motion would clearly indicate a fracture which could be reported with confidence to the user.

Structural Integrity of the Instrument

One aspect of using any flexing material is that the bulk properties of flexible sections change over time as the section is repeatedly flexed. Materials may fatigue, slightly surpass their elastic regions or in the case of composites experience slip on the micro-scale between materials. In extreme cases, these behaviors qualify as a fracture of the material. However, in many cases, less significant changes allow continued use of the flexible section but alter the flexural properties of the flexing material and therefore of the shapeable device. If the degradation is fairly continuous and smoothly progressing in time, knowledge of the level of degradation could be useful to the system operator. This "state of the health" of the flexible section as well as other adapted properties are useful information for users and extra-control subsystems.

The state of health could be conveyed to the user as numerical percentage of original life or with an icon such as a battery level type indicator. The state of health can be calculated by comparing measured behavior to behavior predicted from a model of the device populated with parameters from the initial manufactured properties. It could also be calculated by comparing the behavior to models populated with parameters of known fatigued devices. This second technique would also provide an estimate of the device properties which may be used to in place of the initial parameters improve control of the device. Finally, the device properties may be adapted directly by minimizing the residual by varying the value of the target property.

Sensor Integrity

In order to diagnose failures of a flexible robotic mechanism, the integrity of the shape sensor must be known. Differentiating between a failure of the sensor and a failure of that which is sensed can be complicated depending on the type of sensor used for the measurement.

The first diagnostic of sensor integrity can be based on the physics of the sensor itself. First, the range of reasonable outputs of the sensor should be bounded to enable detection of disconnected wiring. For example, if curvature at point x along the flexible path S is measured as an electrical potential between 1 and 4 Volts, the electrical system should be capable of measuring between 0 and 5 Volts. Thus, a measurement of 0.5 Volts would lead to obvious diagnosis of a sensor fault. The physics of the sensor and measuring system can be considered in designing this level of diagnostic. When the sensor is measuring outside the realm of physically reasonable, information about the robot cannot be known.

If more subtle failures of the sensor are possible, a scalar error for example, lack of sensor integrity could easily be confused for a mechanical failure. If the sensor registers an extremely large curvature at one point, that would seem to indicate a fractured structure. If such errors are possible in the sensor though, other information may be considered to differentiate sensor integrity from mechanical integrity. This is important in order to properly inform the user what component has failed for repair or replacement and for the control system to implement a fail-safe response.

In this case, model based diagnostics may be used to combine other sources of information to decide which component has failed.

If tip position is measured, a sudden movement of the tip position could indicate a real fracture. If the shape sensor measures a change that should move the tip position, but no tip motion is detected, the sensor may be faulted.

The current shape and tip position of the device can be predicted based on a model of the device, the previous shape measurement and the previous tip position measurement. Thus, the measured shape and tip position may be compared to their predicted values to produce residuals. These residuals may be the output of a Kalman filter or other such estimator. The residuals may then be analyzed to decide which failure to report. They may each simply be compared to a threshold, the residual may be integrated then compared to a threshold, or the residuals may be incorporated with operating conditions in a Bayesian network trained with operating and failed components.

Tip orientation can be used analogously or combined with to tip position.

If a measured shape has been registered to a hollow geometric environment model, the device should pass through the model surface boundaries. If the sensor measurement leaves the model, the sensor is probably erroneous.

If the measured device shape changes rapidly but there is no change in actuating wire-tensions, the device probably did not fracture and thus the sensor is probably erroneous.

Similarly, if the device is held in a state with natural potential energy by actuators connected with a back drivable drive train and the measured shape changes but the actuator effort does not, the device probably did not fracture and thus the sensor is probably erroneous.

The systems described herein can predict the current shape and other properties the device and actuators based on a model of the device, the previous shape measurement and other estimates of previous properties. Thus, comparing measured shape and other measurements to their predicted values provides residuals. These residuals may be the output of a Kalman filter or other such estimator. The residuals may then be analyzed to decide which failure to report. They may each simply be compared to a threshold, the residual may be dynamically transformed then compared to a threshold, or the residuals may be incorporated with operating conditions in a Bayesian network trained with operating and failed components.

While multiple embodiments and variations of the many aspects of the invention have been disclosed and described herein, such disclosure is provided for purposes of illustration only. Many combinations and permutations of the disclosed system are useful in minimally invasive medical intervention and diagnosis, and the system is configured to be flexible. The foregoing illustrated and described embodiments of the invention are susceptible to various modifications and alternative forms, and it should be understood that the invention generally, as well as the specific embodiments described herein, are not limited to the particular forms or methods disclosed, but also cover all modifications, equivalents and alternatives falling within the scope of the appended claims. Further, the various features and aspects of the illustrated embodiments may be incorporated into other embodiments, even if not so described herein, as will be apparent to those skilled in the art.

We claim:

1. A surgical system, comprising:
a shapeable instrument, wherein the shapeable instrument includes:
  a distal end, and
  one or more positioning elements that move the shapeable instrument; and
a computer configured to perform a method comprising:
  obtaining a plurality of localization data to determine a measured shape of at least a first portion of the shapeable instrument,
  pretensioning the shapeable instrument by incrementally actuating at least one actuator, thereby causing a movement of the first portion of the shapeable instrument from an initial position to a pretensioned shape, and
  manipulating one or more of the positioning elements to reposition the distal end or the first portion of the shapeable instrument, the manipulating of the one or more of the positioning elements being based on at least one actuation command that accounts for the movement.

2. The system of claim 1, wherein the shapeable instrument comprises a proximal non-articulating portion and a distal articulating portion, wherein the distal articulating portion includes the distal end, wherein the first portion of the shapeable instrument includes the proximal non-articulating portion or the distal articulating portion, wherein the computer is configured to advance the shapeable instrument into an anatomic path within a body such that the non-articulating portion assumes a profile as a result of the anatomic path; and
  wherein the computer is configured to obtain the plurality of localization data after advancing the shapeable instrument into the anatomic path; and wherein the computer is configured to pretension the shapeable instrument after obtaining the plurality of localization data.

3. The system of claim 2, wherein the measured shape is a first measured shape of the non-articulating portion, and wherein the computer is further configured to obtain a second plurality of localization data to determine a second measured shape of the non-articulating portion.

4. The system of claim 3, wherein the computer is configured to monitor a change between the first measured shape and the second measured shape of the non-articulating portion for a minimum value, and wherein the computer is further configured to further pre-tension the shapeable instrument if the change exceeds a pre-determined level, wherein the further pre-tensioning includes causing a second movement of the first portion of the shapeable instrument.

5. The system of claim 1, wherein the computer is configured such that the movement of the first portion of the shapeable instrument from the initial position to the pretensioned shape reduces a slack in the shapeable instrument.

6. The system of claim 5, wherein the computer is configured to determine an amount of the slack in the shapeable instrument.

7. The system of claim 1, wherein the computer is configured to determine a path for the shapeable instrument between a first position and a second position, wherein determining the path includes determining a force associated with a movement of the shapeable instrument between the first and second positions.

8. The system of claim 1, wherein the computer is configured to determine a magnitude of a force associated with a contact of the shapeable instrument with an environment of the shapeable instrument.

9. The system of claim 8, wherein determining the magnitude of the force includes matching the measured shape of the shapeable instrument to a model of the shapeable instrument.

10. The system of claim 1, wherein the computer is configured to detect a contact of the shapeable instrument based upon a difference between a commanded shape of the shapeable instrument and the measured shape of the shapeable instrument.

11. The system of claim 10, wherein detecting the contact includes determining a mean square error between the commanded shape of the shapeable instrument and the measured shape of the shapeable instrument.

12. The system of claim 1, wherein the computer is configured to provide the movement to a controller including a master input device.

13. The system of claim 12, wherein the controller accounts for the movement in the at least one actuation command where the at least one actuation command manipulates the one or more of the positioning elements to reposition the distal end or the first portion of the shapeable instrument.

14. The system of claim 13, wherein the movement reduces slack in the shapeable instrument.

15. A non-transitory computer readable medium storing instructions operable to configure a surgical system to perform a set of steps comprising:

pretensioning a shapeable instrument by incrementally actuating at least one actuator, thereby causing a movement of a first portion of the shapeable instrument from an initial position to a pretensioned shape;

obtaining localization data to measure the pretensioned shape of the first portion of the shapeable instrument; and manipulating one or more positioning elements of the shapeable instrument to reposition a distal end or the first portion of the shapeable instrument based at least in part on the measured pretensioned shape.

16. The medium of claim 15, wherein the instructions are operable such that the movement of the first portion of the shapeable instrument from the initial position to the pretensioned shape reduces a slack in the shapeable instrument.

17. A surgical system, comprising:

a shapeable instrument comprising:

an elongate body, one or more tendons coupled to the elongate body and configured to actuate the elongate body, and a sensor coupled to the elongate body and configured to obtain measurements of the elongate body; and a computer configured to perform a method comprising:

pretensioning the shapeable instrument by incrementally actuating the one or more tendons, obtaining localization data from the sensor, the localization data including a measured configuration of at least a portion of the elongate body at completion of the pretensioning of the shapeable instrument, and manipulating the one or more tendons to thereby control the elongate body, the control of the elongate body being based at least in part on the measured configuration.

18. The surgical system of claim 17, wherein the method performed by the computer comprises:

determining one or more position offsets based on the pretensioning of the shapeable instrument, the one or more position offsets corresponding to the one or more tendons; and correcting the one or more position offsets based on the measured configuration.

19. The surgical system of claim 17, wherein:

the portion of the elongate body is a distal articulating portion of the elongate body, and the measured configuration includes a measured shape of the distal articulating portion.

20. The surgical system of claim 17, wherein:

the portion of the elongate body is a proximal non-articulating portion of the elongate body, and the measured configuration includes a measured shape of the proximal non-articulating portion.

* * * * *